(12) United States Patent
Schultheiss et al.

(10) Patent No.: US 10,231,397 B2
(45) Date of Patent: Mar. 19, 2019

(54) FUNGAL RESISTANT PLANTS EXPRESSING EIN2

(71) Applicant: BASF PLANT SCIENCE COMPANY GMBH, Ludwigshafen (DE)

(72) Inventors: Holger Schultheiss, Boehl-Iggelhiem (DE); Ralf Flachmann, Limburgerhof (DE); Tobias Mentzel, Roemerberg (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 0 days.

(21) Appl. No.: 14/763,630

(22) PCT Filed: Jan. 17, 2014

(86) PCT No.: PCT/EP2014/050879
§ 371 (c)(1),
(2) Date: Jul. 27, 2015

(87) PCT Pub. No.: WO2014/118018
PCT Pub. Date: Aug. 7, 2014

(65) Prior Publication Data
US 2015/0353956 A1 Dec. 10, 2015

(30) Foreign Application Priority Data
Jan. 29, 2013 (EP) .................................. 13152968

(51) Int. Cl.
*C12N 15/82* (2006.01)
*A01H 5/10* (2018.01)
*C07K 14/415* (2006.01)

(52) U.S. Cl.
CPC ............. *A01H 5/10* (2013.01); *C07K 14/415* (2013.01); *C12N 15/8282* (2013.01); *C12N 15/8291* (2013.01)

(58) Field of Classification Search
None
See application file for complete search history.

(56) References Cited

U.S. PATENT DOCUMENTS 5,955,652 A * 9/1999 Ecker ..................... A01H 1/04
435/320.1

FOREIGN PATENT DOCUMENTS

| WO | WO-98/41083 A1 | 9/1998 |
| WO | WO-03/088738 A1 | 10/2003 |
| WO | WO-2012/172498 A1 | 12/2012 |
| WO | WO-2013/001435 A1 | 1/2013 |
| WO | WO-2013/092275 A2 | 6/2013 |
| WO | WO-2013/093738 A1 | 6/2013 |
| WO | WO-2013/149801 A1 | 10/2013 |
| WO | WO-2013/149804 A1 | 10/2013 |
| WO | WO-2013/152917 A1 | 10/2013 |
| WO | WO-2014/024079 A2 | 2/2014 |
| WO | WO-2014/024090 A2 | 2/2014 |
| WO | WO-2014/024102 A1 | 2/2014 |
| WO | WO-2014/041444 A1 | 3/2014 |
| WO | WO-2014/076614 A1 | 5/2014 |
| WO | WO-2014/076659 A1 | 5/2014 |
| WO | WO-2014/117988 A1 | 8/2014 |
| WO | WO-2014/117990 A1 | 8/2014 |
| WO | WO-2014/118018 A1 | 8/2014 |
| WO | WO-2014/135682 A1 | 9/2014 |

OTHER PUBLICATIONS

Friedberg. Bioinformatics. 7: 225-242, 2006.*
Hill et al. Biochem. Biophys. Res. Comm. 244:573-577, 1998.*
Guo et al. Proc. Natl. Acad. Sci. USA 101:9205-9210, 2004.*
Fourgoux-Nicol et al. Plant Molecular Biology 40: 857-872, 1999.*
Alonso et al., "EIN2, a bifunctional transducer of ethylene and stress responses in *Arabidopsis*", *Science*, 284: 2148-52 (1999).
Alonso et al., "The ethylene signaling pathway", *Science*, 306: 1513-5 (2004).
Bisson et al., "New paradigm in ethylene signaling: EIN2, the central regulator of the signaling pathway, interacts directly with the upstream receptors", *Plant Signal Behav.* 6(1): 164-6 (2011).
European Search Report for Application No. 13 15 2968 dated May 15, 2013.
Godoy et al., "Diagrammatic scale for assessment of soybean rust severity", *Fitopatol. Bras.* 31(1): 63-8 (2006).
Heath, "Cellular interactions between biotrophic fungal pathogens and host or nonhost plants", *Can. J. Plant Pathol.* 24: 259-64 (2002).
International Search Report and Written Opinion for Application No. PCT/EP2014/050879 dated Mar. 25, 2014.
Neu et al., "Cytological and molecular analysis of the *Hordeum vulgare-Puccinia triticina* nonhost interaction", *MPMI*, 16(7): 626-33 (2003).
Penmetsa et al., "The *Medicago truncatula* ortholog of *Arabidopsis* EIN2, sickle, is a negative regulator of symbiotic and pathogenic microbial associations", *Plant J.* 55: 580-95 (2008).
Rytter et al., "Additional alternative hosts of *Phakopsora pachyrhizi*, causal agent of soybean rust", *Plant Dis.* 68(9): 818-9 (1984).
Sinclair et al., *Proceedings of the rust workshop* (1995), National Soybean Research Laboratory, (1996).
Smith et al., "Known host crops of *Phakopsora pachyrhizi* causal agent of soybean rust (SBR)", 1-6 (2006).
Thomma et al, "Requirement of functional ethylene-insensitive 2 gene for efficient resistance of *Arabidopsis* to infection by *Botrytis cinerea*", *Plant Physiol.* 121: 1093-101 (1999).

* cited by examiner

*Primary Examiner* — Medina A Ibrahim
(74) *Attorney, Agent, or Firm* — Marshall, Gerstein & Borun LLP

(57) ABSTRACT

The present invention relates to a method of increasing resistance against fungal pathogens of the family Phacopsoraceae in plants and/or plant cells. This is achieved by increasing the expression of an EIN2 protein or fragment thereof in a plant, plant part and/or plant cell in comparison to wild type plants, wild type plant parts and/or wild type plant cells. Furthermore, the invention relates to transgenic plants, plant parts, and/or plant cells having an increased resistance against fungal pathogens, in particular, pathogens of the family Phacopsoraceae, and to recombinant expression vectors comprising a sequence that is identical or homologous to a sequence encoding an EIN2 protein.

24 Claims, 25 Drawing Sheets

Figure 1:
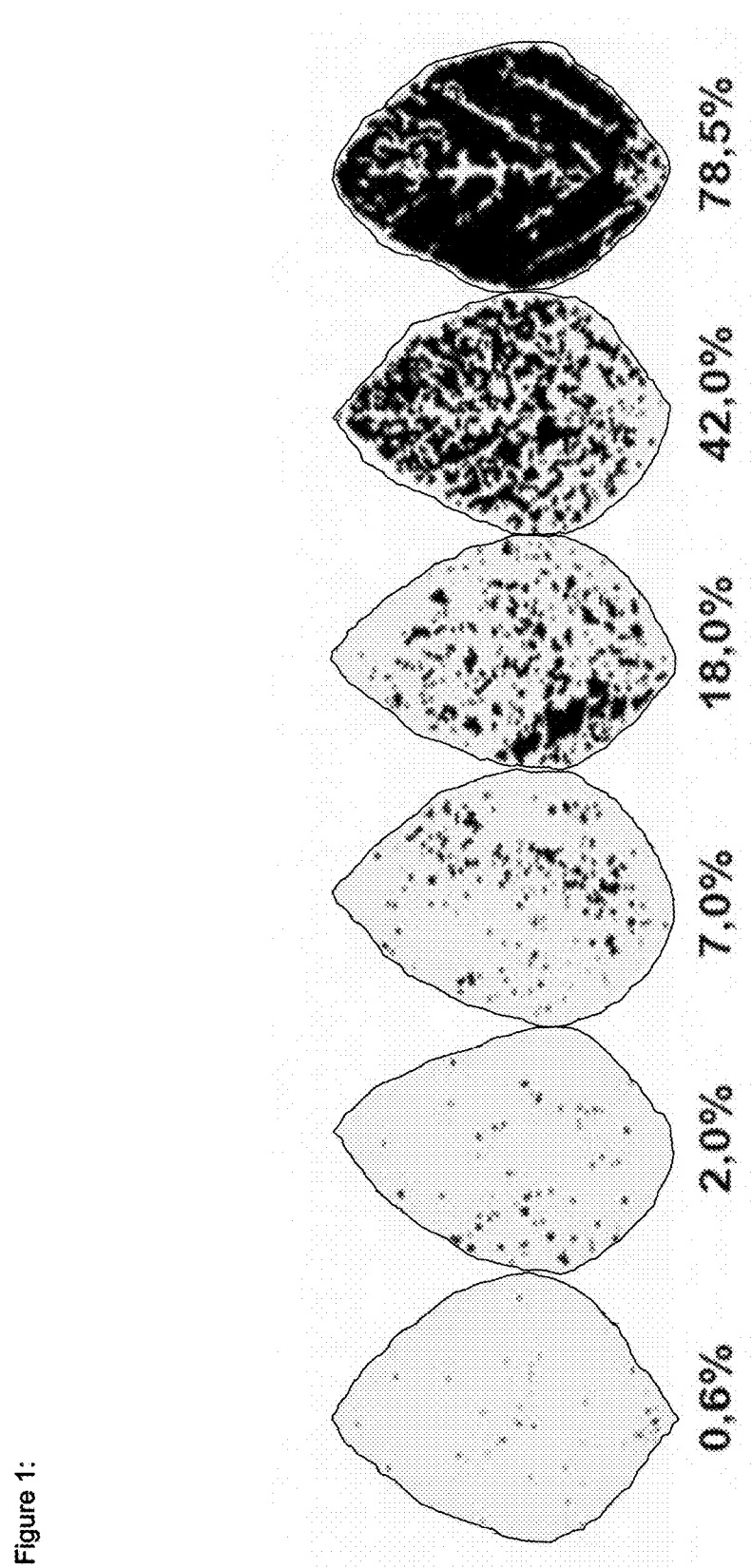

Specification includes a Sequence Listing.

Figure 3:

```
                             SEQ-ID1_EIN2-fragment     (1) ------------------------------------------------------------  60
                        SEQ-ID2_EIN2-fragment-CDS     (1) ------------------------------------------------------------
                                 SEQ-ID4_EIN2-CDS     (1) ------------------------------------------------------------
                             SEQ-ID6_EIN2-genomic     (1) ATCTCTCTCTTCGATGGAACTGAGCTCTTCTCTCTTCTCCTCTCTTCTTTCTCTCTCTAT
                                                          61                                                         120
                             SEQ-ID1_EIN2-fragment     (1) ------------------------------------------------------------
                        SEQ-ID2_EIN2-fragment-CDS     (1) ------------------------------------------------------------
                                 SEQ-ID4_EIN2-CDS     (1) ------------------------------------------------------------
                             SEQ-ID6_EIN2-genomic    (61) CTCTATCTCTCGTAGCTTGATAAGAGTTTCTCTCTCTTTTGAAGATCCGTTCTCTCTCTCT
                                                          121                                                        180
                             SEQ-ID1_EIN2-fragment     (1) ------------------------------------------------------------
                        SEQ-ID2_EIN2-fragment-CDS     (1) ------------------------------------------------------------
                                 SEQ-ID4_EIN2-CDS     (1) ------------------------------------------------------------
                             SEQ-ID6_EIN2-genomic   (121) CACTGAGACTATTGTTGTTAGGTCAACTTGCGATCATGGCGATTTCGAAGGTGACTTCTT
                                                          181                                                        240
                             SEQ-ID1_EIN2-fragment     (1) ------------------------------------------------------------
                        SEQ-ID2_EIN2-fragment-CDS     (1) ------------------------------------------------------------
                                 SEQ-ID4_EIN2-CDS     (1) ------------------------------------------------------------
                             SEQ-ID6_EIN2-genomic   (181) TCAAAAAACCCTAATCCTCTGTTTTTTTTTTTTTTATTTTGCTGGGGGGCTTTGTACGGACTTT
                                                          241                                                        300
                             SEQ-ID1_EIN2-fragment     (1) ------------------------------------------------------------
                        SEQ-ID2_EIN2-fragment-CDS     (1) ------------------------------------------------------------
                                 SEQ-ID4_EIN2-CDS     (1) ------------------------------------------------------------
                             SEQ-ID6_EIN2-genomic   (241) CATGGGGTTTTTTGTAGCTTTTCCCTCGGCTTTTGCGCAAATGAGACTTTCTGGGTTTTTTT
                                                          301                                                        360
                             SEQ-ID1_EIN2-fragment     (1) ------------------------------------------------------------
                        SEQ-ID2_EIN2-fragment-CDS     (1) ------------------------------------------------------------
                                 SEQ-ID4_EIN2-CDS     (1) ------------------------------------------------------------
                             SEQ-ID6_EIN2-genomic   (301) TCCAGCTTTTTATAATTTCATCAGGTGGATCGAATTCGTAGTTTCAGCTTAGATCTCTCT
                                                          361                                                        420
                             SEQ-ID1_EIN2-fragment     (1) ------------------------------------------------------------
                        SEQ-ID2_EIN2-fragment-CDS     (1) ------------------------------------------------------------
                                 SEQ-ID4_EIN2-CDS     (1) ------------------------------------------------------------
                             SEQ-ID6_EIN2-genomic   (361) CCCTCTTCATTATCTGGACTTTCCAGACTTGGAGTTCTTCGGGATTGTTTCGGTTTCTG
```

Figure 3 continued:

```
                            421                                                          480
SEQ-ID1_EIN2-fragment   (1) ------------------------------------------------------------
SEQ-ID2_EIN2-fragment-CDS (1) ------------------------------------------------------------
SEQ-ID4_EIN2-CDS        (1) ------------------------------------------------------------
SEQ-ID6_EIN2-genomic  (421) GGTTTTGTTTTAATTGCGAGATTTAAGCTTTTTTCTTTTTACTACTGTACTTGGTTTGT
                            481                                                          540
SEQ-ID1_EIN2-fragment   (1) ------------------------------------------------------------
SEQ-ID2_EIN2-fragment-CDS (1) ------------------------------------------------------------
SEQ-ID4_EIN2-CDS        (1) ------------------------------------------------------------
SEQ-ID6_EIN2-genomic  (481) GGTTGACCTTTTTTTTTCCTTGAAGATCTGAATGCGTAGATCATACGGGATCTTTGCATTT
                            541                                                          600
SEQ-ID1_EIN2-fragment   (1) ------------------------------------------------------------
SEQ-ID2_EIN2-fragment-CDS (1) ------------------------------------------------------------
SEQ-ID4_EIN2-CDS        (1) ------------------------------------------------------------
SEQ-ID6_EIN2-genomic  (541) TTGTTGCTTTTCGTCAGCGTTACGATTCTTTTAGCTTCAGTTTAGTTGAAATTTGTATTT
                            601                                                          660
SEQ-ID1_EIN2-fragment   (1) ------------------------------------------------------------
SEQ-ID2_EIN2-fragment-CDS (1) ------------------------------------------------------------
SEQ-ID4_EIN2-CDS        (1) ------------------------------------------------------------
SEQ-ID6_EIN2-genomic  (601) TTTTTGAGCTTATCTTCTTTTTGTTGCTGCTTCATACTAAGATCAATTATTGATTTGTAA
                            661                                                          720
SEQ-ID1_EIN2-fragment   (1) ------------------------------------------------------------
SEQ-ID2_EIN2-fragment-CDS (1) ------------------------------------------------------------
SEQ-ID4_EIN2-CDS        (1) ------------------------------------------------------------
SEQ-ID6_EIN2-genomic  (661) TACTACTGTATCTGAAGATTTTCACCATAAAAAAAATTCAGGTCTGAAGCTGATTTCG
                            721                                                          780
SEQ-ID1_EIN2-fragment   (1) ------------------------------------------------------------
SEQ-ID2_EIN2-fragment-CDS (1) ------------------------------------------------------------
SEQ-ID4_EIN2-CDS        (1) ------------------------------------------------------------
SEQ-ID6_EIN2-genomic  (721) AATGGTTTGGAGAGATATCCGTAGTGGTTAAGCATATGGAAGTCTATGTTCTGCTCTTGGTT
                            781                                                          840
SEQ-ID1_EIN2-fragment   (1) ------------------------------------------------------------
SEQ-ID2_EIN2-fragment-CDS (1) ------------------------------------------------------------
SEQ-ID4_EIN2-CDS        (1) ------------------------------------------------------------
SEQ-ID6_EIN2-genomic  (781) GCTCTGTTAGGGCTTCCTCCTCCATTGGACCAACTTAGCTGATGTTGTATGATCTCTCTCC
```

Figure 3 continued:

```
                          841                                                                      900
SEQ-ID1_EIN2-fragment      (1) --------------------------------------------------------------------
SEQ-ID2_EIN2-fragment-CDS  (1) --------------------------------------------------------------------
SEQ-ID4_EIN2-CDS           (1) --------------------------------------------------------------------
SEQ-ID6_EIN2-genomic     (841) TTGAAGCAGCAAATAAGAAGAAGGTCTGGTCCTTAACTTAACATCTGGTTACTAGAGGAA
                                                                                                   960
SEQ-ID1_EIN2-fragment      (1) --------------------------------------------------------------------
SEQ-ID2_EIN2-fragment-CDS  (1) --------------------------------------------------------------------
SEQ-ID4_EIN2-CDS           (1) --------------------------------------------------------------------
SEQ-ID6_EIN2-genomic     (901) ACTTCAGCTATTATTAGGTAAAGAAGACTGTACAGAGTTGTATAACAAGTAAGCGTTAG
                                                                                                  1020
SEQ-ID1_EIN2-fragment      (1) --------------------------------------------------------------------
SEQ-ID2_EIN2-fragment-CDS  (1) --------------------------------------------------------------------
SEQ-ID4_EIN2-CDS           (1) --------------------------------------------------------------------
SEQ-ID6_EIN2-genomic     (961) AGTGGCTTTGTTTGCCTCGGTGATAGAAGAACCGACTGATTCGTTGTGTGTTAGCTT
                                                                                                  1080
SEQ-ID1_EIN2-fragment      (1) --------------------------------------------------------------------
SEQ-ID2_EIN2-fragment-CDS  (1) --------------------------------------------------------------------
SEQ-ID4_EIN2-CDS           (1) --------------------------------------------------------------------
SEQ-ID6_EIN2-genomic    (1021) TGGAGGGAATCAGATTTCGCGAGGGAAGGTGTTTTAGATCAAATCTGTGAATTTTACTCA
                                                                                                  1140
SEQ-ID1_EIN2-fragment      (1) --------------------------------------------------------------------
SEQ-ID2_EIN2-fragment-CDS  (1) --------------------------------------------------------------------
SEQ-ID4_EIN2-CDS           (1) --------------------------------------------------------------------
SEQ-ID6_EIN2-genomic    (1081) ACTGAGGCTTTTAGTGAACCACGACTGAGAGTTGACCTTGAATCCTACTCTGAGTAATT
                                                                                                  1200
SEQ-ID1_EIN2-fragment      (1) --------------------------------------------------------------------
SEQ-ID2_EIN2-fragment-CDS  (1) --------------------------------------------------------------------
SEQ-ID4_EIN2-CDS           (1) --------------------------------------------------------------------
SEQ-ID6_EIN2-genomic    (1141) ATATTATCAGATAGATTTAGCTTGAAGCTTGAATTCTGAATGTGAACTTCAGCTTAGG
                                                                                                  1260
SEQ-ID1_EIN2-fragment      (1) --------------------------------------------------------------------
SEQ-ID2_EIN2-fragment-CDS  (1) --------------------------------------------------------------------
SEQ-ID4_EIN2-CDS          (40) TTATCAGCAGCATGCTCGTGCTGTCCCTGTCCTACTCCCTTTGGTTCTGCGGATATAT
SEQ-ID6_EIN2-genomic    (1201) TTATCAGCAGCATGCTCGTGCTGTCCCTGTCCTACTCCCTTTGGTTCTGCGGATATAT
```

Figure 3 continued:

Figure 3 continued:

```
                                      1681                                                              1740
SEQ-ID1_EIN2-fragment    (1)    ----------------------------------------------------------
SEQ-ID2_EIN2-fragment-CDS (1)   ----------------------------------------------------------
SEQ-ID4_EIN2-CDS       (337)    ----------------------------------------------------------
SEQ-ID6_EIN2-genomic  (1681)    TATGTGATGATAAATTTGATTCCTCTGACTTGAGCTTCTCTATTATAAACAGTTTTGGAA
                                      1741                                                             1800
SEQ-ID1_EIN2-fragment    (1)    ----------------------------------------------------------
SEQ-ID2_EIN2-fragment-CDS (1)   ----------------------------------------------------------
SEQ-ID4_EIN2-CDS       (346)    CTTGCAATGCACTAACCTTTTGTCGCGTGAGTTACCACTGGAGTGTTTTGGCT
SEQ-ID6_EIN2-genomic  (1741)    CTTGCAATGCACTAACCTTTTGTCGCGTGAGTTACCACTGGAGTGTTTTGGCT
                                      1801                                                             1860
SEQ-ID1_EIN2-fragment    (1)    ----------------------------------------------------------
SEQ-ID2_EIN2-fragment-CDS (1)   ----------------------------------------------------------
SEQ-ID4_EIN2-CDS       (406)    GCCATGCATGCGTTTTATTTGTTTTGCCTCTTTTCCTTGTATGACTGGTCTTCCTG
SEQ-ID6_EIN2-genomic  (1801)    GCCATGCATGCGTTTTATTTGTTTTGCCTCTTTTCCTTGTATGACTGGTCTTCCTG
                                      1861                                                             1920
SEQ-ID1_EIN2-fragment    (1)    ----------------------------------------------------------
SEQ-ID2_EIN2-fragment-CDS (1)   ----------------------------------------------------------
SEQ-ID4_EIN2-CDS       (448)    ----------------------------------------------------------
SEQ-ID6_EIN2-genomic  (1861)    TCTTGTTTTTTTTCTCCACGTTCTTGAAATAGCATTATTGAAATTAGCTGACATGCATA
                                      1921                                                             1980
SEQ-ID1_EIN2-fragment    (1)    ----------------------------------------------------------
SEQ-ID2_EIN2-fragment-CDS (1)   ----------------------------------------------------------
SEQ-ID4_EIN2-CDS       (448)    GAAATTGTATTGCAATACGTATTCATTACTTGCACCGCTTGT
SEQ-ID6_EIN2-genomic  (1921)    CAATTTCTGACACGAAATTGTATTGCAATACGTATTCATTACTTGCACCGCTTGT
                                      1981                                                             2040
SEQ-ID1_EIN2-fragment    (1)    ----------------------------------------------------------
SEQ-ID2_EIN2-fragment-CDS (1)   ----------------------------------------------------------
SEQ-ID4_EIN2-CDS       (495)    ATTACTTCATGTATCCAATGTACTGCGCTTGCTGAATCACTCGAGAACCGATCGTATGAA
SEQ-ID6_EIN2-genomic  (1981)    ATTACTTCATGTATCCAATGTACTGCGCTTGCTGAATCACTCGAGAACCGATCGTATGAA
                                      2041                                                             2100
SEQ-ID1_EIN2-fragment    (1)    ----------------------------------------------------------
SEQ-ID2_EIN2-fragment-CDS (1)   ----------------------------------------------------------
SEQ-ID4_EIN2-CDS       (555)    TGGAGTGTTGACTCGGTAAGTGGATTGATCGATGACTGTGAGTTCTTTGGCGC
SEQ-ID6_EIN2-genomic  (2041)    TGGAGTGTTGACTCGGTAAGTGGATTGATCGATGACTGTGAGTTCTTTGGCGC
```

Figure 3 continued:

```
                                            2101                                                            2160
SEQ-ID1_EIN2-fragment        (1) ----------------------------------------------------------
SEQ-ID2_EIN2-fragment-CDS    (1) ----------------------------------------------------------
SEQ-ID4_EIN2-CDS           (615) AACATCGTTTCCACAATTTTATATCCATTCTATTTCTCTGG-----------------
SEQ-ID6_EIN2-genomic      (2101) AACATCGTTTCCACAATTCTATATCCATTCTATTTCTCTGGGTACCTTTTTCTC 2161                                                            2220
SEQ-ID1_EIN2-fragment        (1) ----------------------------------------------------------
SEQ-ID2_EIN2-fragment-CDS    (1) ----------------------------------------------------------
SEQ-ID4_EIN2-CDS           (661) ----------------------------------------------------------
SEQ-ID6_EIN2-genomic      (2161) TTTATATGTATCTCTCTTTTCTGTTAAGAAGCAATAATTATACTAAGCAGTGAACGCTCT 2221                                                            2280
SEQ-ID1_EIN2-fragment        (1) ----------------------------------------------------------
SEQ-ID2_EIN2-fragment-CDS    (1) ----------------------------------------------------------
SEQ-ID4_EIN2-CDS           (661) ------GAAGTACAATTCTGTTCTGTTATTCAGAAGACAGCTTGTCTAAAGACA-------
SEQ-ID6_EIN2-genomic      (2221) ATTACAGGAAGTACAATTCTGTTCTGTTATTCAGAAGACAGCTTGTCTAAAGACA 2281                                                            2340
SEQ-ID1_EIN2-fragment        (1) ----------------------------------------------------------
SEQ-ID2_EIN2-fragment-CDS    (1) ----------------------------------------------------------
SEQ-ID4_EIN2-CDS           (714) GTTCGCCATCTTGTGTGTTTCAGCGGACTGCTACTGTAATTATTGATGATGCT
SEQ-ID6_EIN2-genomic      (2281) GTTCGCCATCTTGTGTGTTTCAGCGGACTGCTACTGTAATTATTGATGATGCT 2341                                                            2400
SEQ-ID1_EIN2-fragment        (1) ----------------------------------------------------------
SEQ-ID2_EIN2-fragment-CDS    (1) ----------------------------------------------------------
SEQ-ID4_EIN2-CDS           (774) AGCAACTAATTGTTTCACAGCTACTGGCCTGTGCTACTGTTCAGATGCCTGTC
SEQ-ID6_EIN2-genomic      (2341) AGCAACTAATTGTTTCACAGCTACTGGCCTGTGCTACTGTTCAGATGCCTGTC 2401                                                            2460
SEQ-ID1_EIN2-fragment        (1) ----------------------------------------------------------
SEQ-ID2_EIN2-fragment-CDS    (1) ----------------------------------------------------------
SEQ-ID4_EIN2-CDS           (834) ACTAATGCAGCAG--------------------------------------------
SEQ-ID6_EIN2-genomic      (2401) ACTAATGCAGCAGAGTTTGTTCTGACGGTTTTATGTTCGTATTAGTCTATAATTCATTTT 2461                                                            2520
SEQ-ID1_EIN2-fragment        (1) ----------------------------------------------------------
SEQ-ID2_EIN2-fragment-CDS    (1) ----------------------------------------------------------
SEQ-ID4_EIN2-CDS           (847) ----------------------------------------------------------
SEQ-ID6_EIN2-genomic      (2461) AGGGAAAATGTTCAGAAATCTCTCGTGATTAATTATCTTGTTCTTGATTGTTGATCA
```

```
SEQ-ID1_EIN2-fragment         (2428) CTTGTAGAAAAGGCCGACCGGTGCAGGTGATGTGCTTTCCCAAGGGGAAAG
SEQ-ID2_EIN2-fragment-CDS     (2351) CTTGTAGAAAAGGCCGACCGGTGCAGGTGATGTGCTTTCCCAAGGGGAAAG
SEQ-ID4_EIN2-CDS              (3707) CTTGTAGAAAAGGCCGACCGGTGCAGGTGATGTGCTTTCCCAAGGGGAAAG
SEQ-ID6_EIN2-genomic          (5461) CTTGTAGAAAAGGCCGACCGGTGCAGGTGATGTGCTTTCCCAAGGGGAAAG
                                     5461                                              5520

SEQ-ID1_EIN2-fragment         (2488) AGAATTTGGCTTCCGGTTTGAAGCGGTCGGTATAAACGGTATCGAATAAACCAGTAGGTA
SEQ-ID2_EIN2-fragment-CDS     (2411) AGAATTTGGCTTCCGGTTTGAAGCGGTCGGTATAAACGGTATCGAATAAACCAGTAGGTA
SEQ-ID4_EIN2-CDS              (3767) AGAATTTGGCTTCCGGTTTGAAGCGGTCGGTATAAACGGTATCGAATAAACCAGTAGGTA
SEQ-ID6_EIN2-genomic          (5521) AGAATTTGGCTTCCGGTTTGAAGCGGTCGGTATAAACGGTATCGAATAAACCAGTAGGTA
                                     5521                                              5580

SEQ-ID1_EIN2-fragment         (2548) TGAATCAGGATGGACCCGGTTCAAGAAAAACCTGACTGCGTACGGATCATTGGGTTGA
SEQ-ID2_EIN2-fragment-CDS     (2471) TGAATCAGGATGGACCCGGTTCAAGAAAAACCTGACTGCGTACGGATCATTGGGTTGA
SEQ-ID4_EIN2-CDS              (3827) TGAATCAGGATGGACCCGGTTCAAGAAAAACCTGACTGCGTACGGATCATTGGGTTGA
SEQ-ID6_EIN2-genomic          (5581) TGAATCAGGATGGACCCGGTTCAAGAAAAACCTGACTGCGTACGGATCATTGGGTTGA
                                     5581                                              5640

SEQ-ID1_EIN2-fragment         (2607) --------------------------------------------------
SEQ-ID2_EIN2-fragment-CDS     (2530) --------------------------------------------------
SEQ-ID4_EIN2-CDS              (3886) --------------------------------------------------
SEQ-ID6_EIN2-genomic          (5641) GAAGAAGAACATTGTGAGAAATCTCATGATCAAAGTGACGTCGAGAGGGAAGCCGAAGAA
                                     5641                                              5700

SEQ-ID1_EIN2-fragment         (2607) --------------------------------------------------
SEQ-ID2_EIN2-fragment-CDS     (2530) --------------------------------------------------
SEQ-ID4_EIN2-CDS              (3886) --------------------------------------------------
SEQ-ID6_EIN2-genomic          (5701) TCAAAACTCTCGCTTTTGATTGCTCCCTCTGCTTCGTTAATTGTGTATTAAGAAAAGAAGA
                                     5701                                              5760

SEQ-ID1_EIN2-fragment         (2607) --------------------------------------------------
SEQ-ID2_EIN2-fragment-CDS     (2530) --------------------------------------------------
SEQ-ID4_EIN2-CDS              (3886) --------------------------------------------------
SEQ-ID6_EIN2-genomic          (5761) AAAAAATGGATTTTGCTTCAGAATTTTTCGCTCTTTTTTTCTTAATTGGTTGTA
                                     5761                                              5820

SEQ-ID1_EIN2-fragment         (2607) --------------------------------------------------
SEQ-ID2_EIN2-fragment-CDS     (2530) --------------------------------------------------
SEQ-ID4_EIN2-CDS              (3886) --------------------------------------------------
SEQ-ID6_EIN2-genomic          (5821) ATGTTATGTTTATATACATATATCATCATCATAGGACCATAGCTACAAACCGAATCCGGT
                                     5821                                              5880
```

Figure 3 continued:

```
SEQ-ID1_EIN2-fragment    (2607)
SEQ-ID2_EIN2-fragment-CDS (2530)
SEQ-ID4_EIN2-CDS         (3886)
SEQ-ID6_EIN2-genomic     (5881) TTGTGTAATTCTATGCGGAATCATAAAGAAATCGTCGGTTTGAAATGTT  5929
```

Figure 4:

```
                                    1                                                    50
SEQ-ID3_EIN2-fragment-protein  (1)
   SEQ-ID5_EIN2-protein        (1) MEAEIVNVRPQLGFIQRMVPALLPVLLVSVGYIDPGKWVANIEGGARFGY
                                   51                                                   100
SEQ-ID3_EIN2-fragment-protein  (1)
   SEQ-ID5_EIN2-protein       (51) DLVAITLLFNFAAILCQYVAARISVVTGKHLAQICNEEYDRWTCMFLGIQ
                                   101                                                  150
SEQ-ID3_EIN2-fragment-protein  (1)
   SEQ-ID5_EIN2-protein      (101) AEFSAILLDLTMVVGVAHALNLLFGVELSTGVFLAAMDAFLFPVFASFLE
                                   151                                                  200
SEQ-ID3_EIN2-fragment-protein  (1)
   SEQ-ID5_EIN2-protein      (151) NGMANTVSIYSAGLVLLLYVSGVLLSQSEIPLSMNGVLTRLNGESAFALM
                                   201                                                  250
SEQ-ID3_EIN2-fragment-protein  (1)
   SEQ-ID5_EIN2-protein      (201) GLLGASIVPHNFYIHSYFAGESTSSSDVDKSSLCQDHLFAIFGVFSGLSL
                                   251                                                  300
SEQ-ID3_EIN2-fragment-protein  (1)
   SEQ-ID5_EIN2-protein      (251) VNYVLMNAAANVFHSTGLVVLTFHDALSLMEQVFMSPLIPVVFLMLLFFS
                                   301                                                  350
SEQ-ID3_EIN2-fragment-protein  (1)
   SEQ-ID5_EIN2-protein      (301) SQITALAWAFGGEVVLHDFLKIEIPAWLHRATIRILAVAPALYCVWTSGA
                                   351                                                  400
SEQ-ID3_EIN2-fragment-protein  (1)
   SEQ-ID5_EIN2-protein      (351) DGIYQLLIFTQVLVAMMLPCSVIPLFRIASSRQIMGVHKIPQVGEFLALT
                                   401                                                  450
SEQ-ID3_EIN2-fragment-protein  (1)
   SEQ-ID5_EIN2-protein      (401) TFLGFLGLNVVFVVEMVFGSSDWAGGLRWNTVMGTSIQYTTLLVSSCASL
```

Figure 4 continued:

| | | |
|---|---|---|
| SEQ-ID3_EIN2-fragment-protein | (1) | ------------------------------------------------- 500 |
| SEQ-ID5_EIN2-protein | (451) | CILRLAATPLKSASNRAEAQIWNNDAQNALSYPSVQEEIERTETRRNE 550 |
| SEQ-ID3_EIN2-fragment-protein | (49) | SESTVRLESRVAQLIDTMTVTSSVYDLPENILMDQEIRSSPPEERELDY |
| SEQ-ID5_EIN2-protein | (501) | SESTVRLESRVAQLIDTMTVTSSVYDLPENILMTDQEIRSSPPEERELDY 600 |
| SEQ-ID3_EIN2-fragment-protein | (99) | KYTSTSQVYSSLAEDSDVKSQSVYLQSTVVNEVSDKDLIVETKMAKIEPNSPY |
| SEQ-ID5_EIN2-protein | (551) | KYTSTSQVYSSLREDSDVKSQSVYLQSTVVNREVSDKDLIVETRMAKIEPNSPY 650 |
| SEQ-ID3_EIN2-fragment-protein | (149) | EKIVSMENNSKFIEKDVYEGVSWETEEATREAAPTSNFTVGSDGPPSPRSLS |
| SEQ-ID5_EIN2-protein | (601) | EKIVSMENNSKFIEKDVYEGVSWETEEATKAAPTSNFTVGSDGPPSPRSLS 700 |
| SEQ-ID3_EIN2-fragment-protein | (199) | GHGGSGTGSLSRLQGLGRALRPHLSAILDEFWGHLKDFHGQLVRRARAKK |
| SEQ-ID5_EIN2-protein | (651) | GHGGSGTGSLSRLQGLGRAAPRHLSAILDEFWGHLKDFHGQLVAEARAKK 750 |
| SEQ-ID3_EIN2-fragment-protein | (249) | LDQLFGTDQRSASSMKARSFGRDISSGYCMSPTAKGMSQMTSSLIDSLK |
| SEQ-ID5_EIN2-protein | (701) | LDQLFGTDQRSASSMKARSFGRDISSGYCMSPTAKGMSQMTSSLIDSLK 800 |
| SEQ-ID3_EIN2-fragment-protein | (299) | QQRTPGSIDSLYGLQRSSSPSFLVRMQMLGAVGNTTMNRNAYELSERHY |
| SEQ-ID5_EIN2-protein | (751) | QQRTPGSIDSLYGLQRSSSPSFLVNRMQMLGAVGNTTMNRNAYELSERHY 850 |
| SEQ-ID3_EIN2-fragment-protein | (349) | SSLRAPSSSEGWHEDQPATVHGYQMKSYTDNLAKTRLRALQSRGEIPTSR |
| SEQ-ID5_EIN2-protein | (801) | SSLRAPSSSEGWHEDQPATVHGYQMKSYTDNLAKTRLRALQSRGEIPTSR 900 |
| SEQ-ID3_EIN2-fragment-protein | (399) | SMALGTLSTTQQLALALHQSSPWGLTPGFAPGFHNFAGSPSISQSESSY |
| SEQ-ID5_EIN2-protein | (851) | SMALGTLSTTQQLALALHQSSPWGLTPGFAPGFHNFAGSPSISQSESSY 950 |
| SEQ-ID3_EIN2-fragment-protein | (449) | YGVFSSGNTDTVGAAVANEKYSSMPDISGLSMSAANNELPNNKSGYNDP |
| SEQ-ID5_EIN2-protein | (901) | YGVFSSGNTDTVGAAVANEKYSSMPDISGLSMSAANNELPNNKSGYNDP 1000 |
| SEQ-ID3_EIN2-fragment-protein | (499) | SSGGGGYGASYGRLSMESSLISHLGSRVGVPSTYDISQSRGGYRDAYSL |
| SEQ-ID5_EIN2-protein | (951) | SSGGGGYGASYGRLSMESSLISHLGSRVGVPSTYDISQSRGGYRDAYSL 1050 |
| SEQ-ID3_EIN2-fragment-protein | (549) | PQSAMTGTGSLWSNQPTRQPSYARNGAVGELRNNSSPTINDNNASSNY |
| SEQ-ID5_EIN2-protein | (1001) | PQSAMTGTGSLWSNQPTRQPSYARNGAVGELRNNSSPTINDNNASSNY |

Figure 4 continued:

```
SEQ-ID3_EIN2-fragment-protein  (599)  DAEAKLLQSFRECILKLIKLEGSEWLFGQSDGVDEELIDRVAAREKFIYE
         SEQ-ID5_EIN2-protein (1051) DAEAKLLQSFRECILKLIKLEGSEWLFGQSDGVDEELIDRVAAREKFIYE  1100

SEQ-ID3_EIN2-fragment-protein  (649) AEAREINQVGHMGEPLISSVPNCGDGCVWRADLIVSFGVWCIHRVIDLSL
         SEQ-ID5_EIN2-protein (1101) AEAREINQVGHMGEPLISSVPNCGDGCVWRADLIVSFGVWCIHRVIDLSL  1150

SEQ-ID3_EIN2-fragment-protein  (699) MESRPELWGKYTYVLNRLQGVIDPAFSKLRTPMTECFCLQIPASHQRASP
         SEQ-ID5_EIN2-protein (1151) MESRPELWGKYTYVLNRLQGVIDPAFSKLRTPMTECFCLQIPASHQRASP  1200

SEQ-ID3_EIN2-fragment-protein  (749) TSANGMLPPAAKPAKGKCTTAVTLLDLIKDVEMAISCREKGRTGTAAGDVA
         SEQ-ID5_EIN2-protein (1201) TSANGMLPPAAKPAKGKCTTAVTLLDLIKDVEMAISCREKGRTGTAAGDVA  1250

SEQ-ID3_EIN2-fragment-protein  (799) FPKGKENLASVTLKRTKRRLSNKFVGMNQDGPGSRRNTTAYGSLG-
         SEQ-ID5_EIN2-protein (1251) FPKGKENLASVTLKRTKRRLSNKFVGMNQDGPGSRRNTTAYGSLG-  1295
```

Figure 5:

```
   1 ATGCTCTGGC TGGCAGCCAC GCCGCTGAAA TCTGCGAGTA ACAGAGCGGA
  51 AGCTCAAATA TGGAACATGG ATGCTCAAAA TGCTTTATCT TATCCATCTG
 101 TTCAAGAAGA GGAAATTGAA AGAACAGAAA CAAGGAGGAA CGAAGACGAA
 151 TCAATAGTGC GGTTGGAAAG CAGGGTAAAG GATCAGTTGG ATACTACGTC
 201 TGTTACTAGC TCGGTCTATG ATTTGCCAGA GAACATTCTA ATGACGGATC
 251 AAGAAATCCG TTCGAGCCCT CCAGAGGAAA GAGAGTTGGA TGTAAAGTAC
 301 TCTACCTCTC AAGTTAGTAG TCTTAAGGAA GACTCTGATG TAAAGGAACA
 351 GTCTGTATTG CAGTCAACAG TGGTTAATGA GGTCAGTGAT AAGGATCTGA
 401 TTGTTGAAAC AAAGATGGCG AAAATTGAAC CAATGAGTCC TGTGGAGAAG
 451 ATTGTTAGCA TGGAGAATAA CAGCAAGTTT ATTGAAAAGG ATGTTGAAGG
 501 GGTTTCATGG GAAACAGAAG AAGCTACCAA AGCTGCTCCT ACAAGCAACT
 551 TTACTGTCGG ATCTGATGGT CCTCCTTCAT TCCGCAGCTT AAGTGGGGAA
 601 GGGGGAAGTG GGACTGGAAG CCTTTCACGG TTGCAAGGTT TGGGACGTGC
 651 TGCCCGGAGA CACTTATCTG CGATCCTTGA TGAATTTTGG GGACATTTAT
 701 ATGATTTTCA TGGGCAATTG GTTGCTGAAG CCAGGGCAAA GAAACTAGAT
 751 CAGCTGTTTG GCACTGATCA AAAGTCAGCC TCTTCTATGA AAGCAGATTC
 801 GTTTGGAAAA GACATTAGCA GTGGATATTG CATGTCACCA ACTGCGAAGG
 851 GAATGGATTC ACAGATGACT TCAAGTTTAT ATGATTCACT GAAGCAGCAG
 901 AGGACACCGG GAAGTATCGA TTCGTTGTAT GGATTACAAA GAGGTTCGTC
 951 ACCGTCACCG TTGGTCAACC GTATGCAGAT GTTGGGTGCA TATGGTAACA
1001 CCACTAATAA TAATAATGCT TACGAATTGA GTGAGAGAAG ATACTCTAGC
1051 CTGCGTGCTC CATCATCTTC AGAGGGTTGG GAACACCAAC AACCAGCTAC
1101 AGTTCACGGA TACCAGATGA AGTCATATGT AGACAATTTG GCAAAAGAAA
1151 GGCTTGAAGC CTTACAATCC CGTGGAGAGA TCCCGACATC GAGATCTATG
1201 GCGCTTGGTA CATTGAGCTA TACACAGCAA CTTGCTTTAG CCTTGAAACA
1251 GAAGTCCCAG AATGGTCTAA CCCCTGGACC AGCTCCTGGG TTTGAGAATT
1301 TTGCTGGGTC TAGAAGCATA TCGCGACAAT CTGAAAGATC TTATTACGGT
1351 GTTCCATCTT CTGGCAATAC TGATACTGTT GGCGCAGCAG TAGCCAATGA
1401 GAAAAAATAT AGTAGCATGC CAGATATCTC AGGATTGTCT ATGTCCGCAA
1451 GGAACATGCA TTTACCAAAC AACAAGAGTG GATACTGGGA TCCGTCAAGT
1501 GGAGGAGGAG GGTATGGTGC GTCTTATGGT CGGTTAAGCA ATGAATCATC
1551 GTTATATTCT AATTTGGGGT CACGGGTGGG AGTACCCTCG ACTTATGATG
1601 ACATTTCTCA ATCAAGAGGA GGCTACAGAG ATGCCTACAG TTTGCCACAG
1651 AGTGCAACAA CAGGGACCGG ATCGCTTTGG TCCAGACAGC CCTTTGAGCA
1701 GTTTGGTGTA GCGGAGAGGA ATGGTGCTGT TGGTGAGGAG CTCAGGAATA
1751 GATCGAATCC GATCAATATA GACAACAACG CTTCTTCTAA TGTTGATGCA
1801 GAGGCTAAGC TTCTTCAGTC GTTCAGGCAC TGTATTCTAA AGCTTATTAA
1851 ACTTGAAGGA TCCGAGTGGT TGTTTGGACA AAGCGATGGA GTTGATGAAG
1901 AACTGATTGA CCGGGTAGCT GCACGAGAGA AGTTTATCTA TGAAGCTGAA
1951 GCTCGAGAAA TAAACCAGGT GGGTCACATG GGGGAGCCAC TAATTTCATC
2001 GGTTCCTAAC TGTGGAGATG GTTGCGTTTG GAGAGCTGAT TTGATTGTGA
2051 GCTTTGGAGT TTGGTGCATT CACCGTGTCC TTGACTTGTC TCTCATGGAG
2101 AGTCGGCCTG AGCTTTGGGG AAAGTACACT TACGTTCTCA ACCGCCTACA
2151 GGTAACAAAA ACCGCAGTAG TTCATTGAAA ATCACAGTTT TGCAGTTTGA
2201 AAATATTGAC ATGTATGGAT TTAAACAGGG AGTGATTGAT CCGGCGTTCT
2251 CAAAGCTGCG GACACCAATG ACACCGTGCT TTTGCCTTCA GATTCCAGCG
2301 AGCCACCAGA GAGCGAGTCC GACTTCAGCT AACGGAATGT TACCTCCGGC
2351 TGCAAAACCG GCTAAAGGCA AATGCACAAC CGCAGTCACA CTTCTTGATC
2401 TAATCAAAGA CGTTGAAATG GCAATCTCTT GTAGAAAAGG CCGAACCGGT
2451 ACAGCTGCAG GTGATGTGGC TTTCCCAAAG GGGAAAGAGA ATTTGGCTTC
2501 GGTTTTGAAG CGGTATAAAC GTCGGTTATC GAATAAACCA GTAGGTATGA
2551 ATCAGGATGG ACCCGGTTCA AGAAAAAACG TGACTGCGTA CGGATCATTG
2601 GGTTGA
```

Figure 6:

```
MLWLAATPLKSASNRAEAQIWNMDAQNALSYPSVQEEEIERTETRRNEDE  50
SIVRLESRVKDQLDTTSVTSSVYDLPENILMTDQEIRSSPPEERELDVKY 100
STSQVSSLKEDSDVKEQSVLQSTVVNEVSDKDLIVETKMAKIEPMSPVEK 150
IVSMENNSKFIEKDVEGVSWETEEATKAAPTSNFTVGSDGPPSFRSLSGE 200
GGSGTGSLSRLQGLGRAARRHLSAILDEFWGHLYDFHGQLVAEARAKKLD 250
QLFGTDQKSASSMKADSFGKDISSGYCMSPTAKGMDSQMTSSLYDSLKQQ 300
RTPGSIDSLYGLQRGSSPSPLVNRMQMLGAYGNTTNNNNAYELSERRYSS 350
LRAPSSSEGWEHQQPATVHGYQMKSYVDNLAKERLEALQSRGEIPTSRSM 400
ALGTLSYTQQLALALKQKSQNGLTPGPAPGFENFAGSRSISRQSERSYYG 450
VPSSGNTDTVGAAVANEKKYSSMPDISGLSMSARNMHLPNNKSGYWDPSS 500
GGGGYGASYGRLSNESSLYSNLGSRVGVPSTYDDISQSRGGYRDAYSLPQ 550
SATTGTGSLWSRQPFEQFGVAERNGAVGEELRNRSNPINIDNNASSNVDA 600
EAKLLQSFRHCILKLIKLEGSEWLFGQSDGVDEELIDRVAAREKFIYEAE 650
AREINQVGHMGEPLISSVPNCGDGCVWRADLIVSFGVWCIHRVLDLSLME 700
SRPELWGKYTYVLNRLQGVIDPAFSKLRTPMTPCFCLQIPASHQRASPTS 750
ANGMLPPAAKPAKGKCTTAVTLLDLIKDVEMAISCRKGRTGTAAGDVAFP 800
KGKENLASVLKRYKRRLSNKPVGMNQDGPGSRKNVTAYGSLG*
```

Figure 7:

```
   1 ATGGAAGCTG AAATTGTGAA TGTGAGACCT CAGCTAGGGT TTATCCAGAG
  51 AATGGTTCCT GCTCTACTTC CTGTCCTTTT GGTTTCTGTC GGATATATTG
 101 ATCCCGGGAA ATGGGTTGCA AATATCGAAG GAGGTGCTCG TTTCGGGTAT
 151 GACTTGGTGG CAATTACTCT GCTTTTCAAT TTTGCCGCCA TCTTATGCCA
 201 ATATGTTGCA GCTCGCATAA GCGTTGTGAC TGGTAAACAC TTGGCTCAGA
 251 TCTGCAATGA AGAATATGAC AAGTGGACGT GCATGTTCTT GGGCATTCAG
 301 GCGGAGTTCT CAGCAATTCT GCTCGACCTT ACCATGGTTG TGGGAGTTGC
 351 GCATGCACTT AACCTTTTGT TTGGGGTGGA GTTATCCACT GGAGTGTTTT
 401 TGGCCGCCAT GGATGCGTTT TTATTTCCTG TTTTCGCCTC TTTCCTTGAA
 451 AATGGTATGG CAAATACAGT ATCCATTTAC TCTGCAGGCC TGGTATTACT
 501 TCTCTATGTA TCTGGCGTCT GCTGAGTCA GTCTGAGATC CCACTCTCTA
 551 TGAATGGAGT GTTAACTCGG TTAAATGGAG AGAGCGCATT CGCACTGATG
 601 GGTCTTCTTG GCGCAAGCAT CGTCCCTCAC AATTTTTATA TCCATTCTTA
 651 TTTTGCTGGG GAAAGTACAT CTTCGTCTGA TGTCGACAAG AGCAGCTTGT
 701 GTCAAGACCA TTTGTTCGCC ATCTTTGGTG TCTTCAGCGG ACTGTCACTT
 751 GTAAATTATG TATTGATGAA TGCAGCAGCT AATGTGTTTC ACAGTACTGG
 801 CCTTGTGGTA CTGACTTTTC ACGATGCCTT GTCACTAATG GAGCAGGTAT
 851 TTATGAGTCC GCTCATTCCA GTGGTCTTTT TGATGCTCTT GTTCTTCTCT
 901 AGTCAAATTA CCGCACTAGC TTGGGCTTTC GGTGGAGAGG TCGTCCTGCA
 951 TGACTTCCTG AAGATAGAAA TACCCGCTTG GCTTCATCGT GCTACAATCA
1001 GAATTCTTGC AGTTGCTCCT GCGCTTTATT GTGTATGGAC ATCTGGTGCA
1051 GACGGAATAT ACCAGTTACT TATATTCACC CAGGTCTTGG TGGCAATGAT
1101 GCTTCCTTGC TCGGTAATAC CGCTTTTCCG CATTGCTTCG TCGAGACAAA
1151 TCATGGGTGT CCATAAAATC CCTCAGGTTG GCGAGTTCCT CGCACTTACA
1201 ACGTTTTGG GATTTCTGGG GTTGAATGTT GTTTTTGTTG TTGAGATGGT
1251 ATTTGGGAGC AGTGACTGGG CTGGTGGTTT GAGATGGAAT ACCGTGATGG
1301 GCACCTCGAT TCAGTACACC ACTCTGCTTG TATCGTCATG TGCATCCTTA
1351 TGCCTGATAC TCTGGCTGGC AGCCACGCCG CTGAAATCTG CGAGTAACAG
1401 AGCGGAAGCT CAAATATGGA ACATGGATGC TCAAAATGCT TTATCTTATC
1451 CATCTGTTCA AGAAGAGGAA ATTGAAAGAA CAGAAACAAG GAGGAACGAA
1501 GACGAATCAA TAGTGCGGTT GGAAAGCAGG GTAAAGGATC AGTTGGATAC
1551 TACGTCTGTT ACTAGCTCGG TCTATGATTT GCCAGAGAAC ATTCTAATGA
1601 CGGATCAAGA AATCCGTTCG AGCCCTCCAG AGGAAAGAGA GTTGGATGTA
1651 AAGTACTCTA CCTCTCAAGT TAGTAGTCTT AAGGAAGACT CTGATGTAAA
1701 GGAACAGTCT GTATTGCAGT CAACAGTGGT TAATGAGGTC AGTGATAAGG
```

Figure 7 continued:

```
1751 ATCTGATTGT TGAAACAAAG ATGGCGAAAA TTGAACCAAT GAGTCCTGTG
1801 GAGAAGATTG TTAGCATGGA GAATAACAGC AAGTTTATTG AAAAGGATGT
1851 TGAAGGGGTT TCATGGGAAA CAGAAGAAGC TACCAAAGCT GCTCCTACAA
1901 GCAACTTTAC TGTCGGATCT GATGGTCCTC CTTCATTCCG CAGCTTAAGT
1951 GGGGAAGGGG GAAGTGGGAC TGGAAGCCTT TCACGGTTGC AAGGTTTGGG
2001 ACGTGCTGCC CGGAGACACT TATCTGCGAT CCTTGATGAA TTTTGGGGAC
2051 ATTTATATGA TTTTCATGGG CAATTGGTTG CTGAAGCCAG GGCAAAGAAA
2101 CTAGATCAGC TGTTTGGCAC TGATCAAAAG TCAGCCTCTT CTATGAAAGC
2151 AGATTCGTTT GGAAAAGACA TTAGCAGTGG ATATTGCATG TCACCAACTG
2201 CGAAGGGAAT GGATTCACAG ATGACTTCAA GTTTATATGA TTCACTGAAG
2251 CAGCAGAGGA CACCGGGAAG TATCGATTCG TTGTATGGAT TACAAAGAGG
2301 TTCGTCACCG TCACCGTTGG TCAACCGTAT GCAGATGTTG GGTGCATATG
2351 GTAACACCAC TAATAATAAT AATGCTTACG AATTGAGTGA GAGAAGATAC
2401 TCTAGCCTGC GTGCTCCATC ATCTTCAGAG GGTTGGGAAC ACCAACAACC
2451 AGCTACAGTT CACGGATACC AGATGAAGTC ATATGTAGAC AATTTGGCAA
2501 AAGAAAGGCT TGAAGCCTTA CAATCCCGTG GAGAGATCCC GACATCGAGA
2551 TCTATGGCGC TTGGTACATT GAGCTATACA CAGCAACTTG CTTTAGCCTT
2601 GAAACAGAAG TCCCAGAATG GTCTAACCCC TGGACCAGCT CCTGGGTTTG
2651 AGAATTTTGC TGGGTCTAGA AGCATATCGC GACAATCTGA AAGATCTTAT
2701 TACGGTGTTC CATCTTCTGG CAATACTGAT ACTGTTGGCG CAGCAGTAGC
2751 CAATGAGAAA AAATATAGTA GCATGCCAGA TATCTCAGGA TTGTCTATGT
2801 CCGCAAGGAA CATGCATTTA CCAAACAACA AGAGTGGATA CTGGGATCCG
2851 TCAAGTGGAG GAGGAGGGTA TGGTGCGTCT TATGGTCGGT TAAGCAATGA
2901 ATCATCGTTA TATTCTAATT TGGGGTCACG GGTGGGAGTA CCCTCGACTT
2951 ATGATGACAT TTCTCAATCA AGAGGAGGCT ACAGAGATGC CTACAGTTTG
3001 CCACAGAGTG CAACAACAGG GACCGGATCG CTTTGGTCCA GACAGCCCTT
3051 TGAGCAGTTT GGTGTAGCGG AGAGGAATGG TGCTGTTGGT GAGGAGCTCA
3101 GGAATAGATC GAATCCGATC AATATAGACA ACAACGCTTC TTCTAATGTT
3151 GATGCAGAGG CTAAGCTTCT TCAGTCGTTC AGGCACTGTA TTCTAAAGCT
3201 TATTAAACTT GAAGGATCCG AGTGGTTGTT TGGACAAAGC GATGGAGTTG
3251 ATGAAGAACT GATTGACCGG GTAGCTGCAC GAGAGAAGTT TATCTATGAA
3301 GCTGAAGCTC GAGAAATAAA CCAGGTGGGT CACATGGGGG AGCCACTAAT
3351 TTCATCGGTT CCTAACTGTG GAGATGGTTG CGTTTGGAGA GCTGATTTGA
3401 TTGTGAGCTT TGGAGTTTGG TGCATTCACC GTGTCCTTGA CTTGTCTCTC
3451 ATGGAGAGTC GGCCTGAGCT TTGGGGAAAG TACACTTACG TTCTCAACCG
3501 CCTACAGGGA GTGATTGATC CGGCGTTCTC AAAGCTGCGG ACACCAATGA
3551 CACCGTGCTT TTGCCTTCAG ATTCCAGCGA GCCACCAGAG AGCGAGTCCG
3601 ACTTCAGCTA ACGGAATGTT ACCTCCGGCT GCAAAACCGG CTAAAGGCAA
3651 ATGCACAACC GCAGTCACAC TTCTTGATCT AATCAAAGAC GTTGAAATGG
3701 CAATCTCTTG TAGAAAAGGC CGAACCGGTA CAGCTGCAGG TGATGTGGCT
3751 TTCCCAAAGG GGAAAGAGAA TTTGGCTTCG GTTTTGAAGC GGTATAAACG
3801 TCGGTTATCG AATAAACCAG TAGGTATGAA TCAGGATGGA CCCGGTTCAA
3851 GAAAAAACGT GACTGCGTAC GGATCATTGG GTTGA
```

Figure 8:

```
MEAEIVNVRPQLGFIQRMVPALLFVLLVSVGYIDPGKWVANIEGGARFGY      50
DLVAITLLFNFAAILCQYVAARISVVTGKHLAQICNEEYDKWTCMFLGIQ     100
AEFSAILLDLTMVVGVAHALNLLFGVELSTGVFLAAMDAFLFPVFASFLE     150
NGMANTVSIYSAGLVLLLYVSGVLLSQSEIPLSMNGVLTRLNGESAFALM     200
GLLGASIVPHNFYIHSYFAGESTSSSDVDKSSLCQDHLFAIFGVFSGLSL     250
VNYVLMNAAANVFHSTGLVVLTFHDALSLMEQVFMSPLIPVVFLMLLFFS     300
SQITALAWAFGGEVVLHDFLKIEIPAWLHRATIRILAVAPALYCVWTSGA     350
DGIYQLLIFTQVLVAMMLPCSVIPLFRIASSRQIMGVHKIPQVGEFLALT     400
TFLGFLGLNVVFVVEMVFGSSDWAGGLRWNTVMGTSIQYTTLLVSSCASL     450
CLILWLAATPLKSASNRAEAQIWNMDAQNALSYPSVQEEEIERTETRRNE     500
DESIVRLESRVKDQLDTTSVTSSVYDLPENILMTDQEIRSSPPEERELDV     550
KYSTSQVSSLKEDSDVKEQSVLQSTVVNEVSDKDLIVETKMAKIEPMSPV     600
EKIVSMENNSKFIEKDVEGVSWETEEATKAAPTSNFTVGSDGPPSFRSLS     650
GEGGSGTGSLSRLQGLGRAARRHLSAILDEFWGHLYDFHGQLVAEARAKK     700
LDQLFGTDQKSASSMKADSFGKDISSGYCMSPTAKGMDSQMTSSLYDSLK     750
QQRTPGSIDSLYGLQRGSSPSPLVNRMQMLGAYGNTTNNNNAYELSERRY     800
SSLRAPSSSEGWEHQQPATVHGYQMKSYVDNLAKERLEALQSRGEIPTSR     850
SMALGTLSYTQQLALALKQKSQNGLTPGPAPGFENFAGSRSISRQSERSY     900
YGVPSSGNTDTVGAAVANEKKYSSMPDISGLSMSARNMHLPNNKSGYWDP     950
SSGGGGYGASYGRLSNESSLYSNLGSRVGVPSTYDDISQSRGGYRDAYSL    1000
PQSATTGTGSLWSRQPFEQFGVAERNGAVGEELRNRSNPINIDNNASSNV    1050
DAEAKLLQSFRHCILKLIKLEGSEWLFGQSDGVDEELIDRVAAREKFIYE    1100
AEAREINQVGHMGEPLISSVPNCGDGCVWRADLIVSFGVWCIHRVLDLSL    1150
MESRPELWGKYTYVLNRLQGVIDPAFSKLRTPMTPCFCLQIPASHQRASP    1200
TSANGMLPPAAKPAKGKCTTAVTLLDLIKDVEMAISCRKGRTGTAAGDVA    1250
FPKGKENLASVLKRYKRRLSNKPVGMNQDGPGSRKNVTAYGSLG*
```

Figure 9:

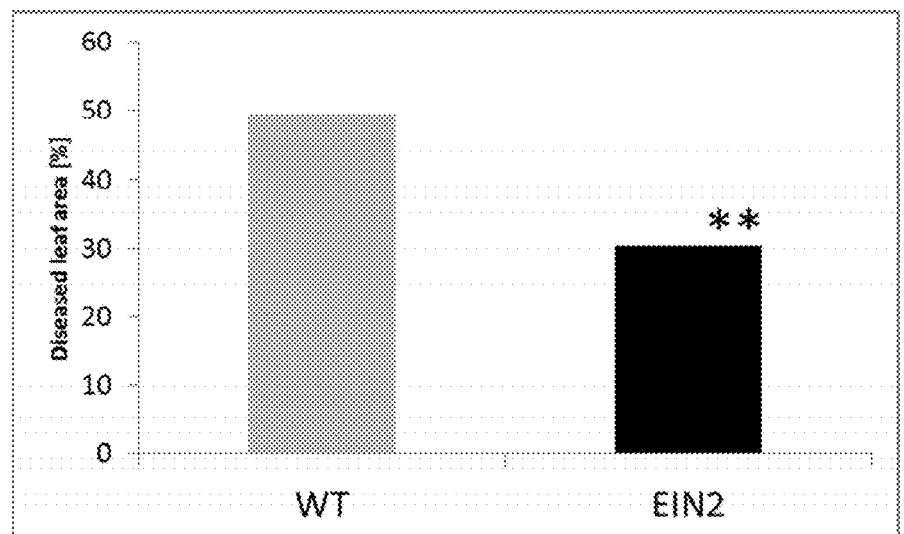

Figure 10:

| SEQ ID NO: | Description of the sequence listing |
|---|---|
| 1 | Nucleotide sequence of EIN2 C-terminal fragment; Arabidopsis thaliana |
| 2 | Nucleotide sequence of EIN2 C-terminal fragment (Alonso et al. (1999) Science 284(5423):2148-52); Arabidopsis thaliana |
| 3 | Amino acid sequence of EIN2 C-terminal fragment protein; Arabidopsis thaliana |
| 4 | Nucleotide sequence of full-length EIN2 sequence, putative CDS (accession No. NM_120406); Arabidopsis thaliana |
| 5 | Amino acid sequence of full-length EIN2 protein, NP_195948; Arabidopsis thaliana |
| 6 | Nucleotide sequence of the genomic sequence around the region which codes for EIN2 (AT5G03280, TAIR accession No 4515110756); Arabidopsis thaliana |
| 7 | EIN2 forward primer 1 |
| 8 | EIN2 reverse primer 1 |
| 9 | EIN2 forward primer 2 |
| 10 | EIN2 reverse primer 2 |
| 11 | Nucleotide sequence EIN2, variant 1 |
| 12 | Amino acid sequence EIN2, variant 1 |
| 13 | Nucleotide sequence EIN2, variant 2 |
| 14 | Amino acid sequence EIN2, variant 2 |
| 15 | Nucleotide sequence EIN2, variant 3 |
| 16 | Amino acid sequence EIN2, variant 3 |
| 17 | Nucleotide sequence EIN2, variant 4 |
| 18 | Amino acid sequence EIN2, variant 4 |
| 19 | Nucleotide sequence EIN2, variant 5 |
| 20 | Amino acid sequence EIN2, variant 5 |
| 21 | Nucleotide sequence EIN2, variant 6 |
| 22 | Amino acid sequence EIN2, variant 6 |
| 23 | Nucleotide sequence EIN2, variant 7 |
| 24 | Amino acid sequence EIN2, variant 7 |
| 25 | Nucleotide sequence EIN2, variant 8 |
| 26 | Amino acid sequence EIN2, variant 8 |
| 27 | Nucleotide sequence EIN2, variant 9 |
| 28 | Nucleotide sequence EIN2, variant 10 |
| 29 | Nucleotide sequence EIN2, variant 11 |

Figure 10 continued:

| 30 | Nucleotide sequence EIN2, variant 12 |
|----|--------------------------------------|
| 31 | Nucleotide sequence EIN2, variant 13 |
| 32 | Nucleotide sequence EIN2, variant 14 |
| 33 | Nucleotide sequence EIN2, variant 15 |
| 34 | Nucleotide sequence EIN2, variant 16 |

SEQUENCE LISTING

```
<160> NUMBER OF SEQ ID NOS: 34

<210> SEQ ID NO 1
<211> LENGTH: 2606
<212> TYPE: DNA
<213> ORGANISM: Arabidopsis thaliana
<220> FEATURE:
<221> NAME/KEY: source
<222> LOCATION: 1..2606
<223> OTHER INFORMATION: /organism="Arabidopsis thaliana"
      /note="Nucleotide sequence of EIN2 C-terminal fragment"
      /mol_type="unassigned DNA"

<400> SEQUENCE: 1
atgctctggc tggcagccac gccgctgaaa tctgcgagta acagagcgga agctcaaata      60
tggaacatgg atgctcaaaa tgctttatct tatccatctg ttcaagaaga ggaaattgaa     120
agaacagaaa caaggaggaa cgaagacgaa tcaatagtgc ggttggaaag cagggtaaag     180
gatcagttgg atactacgtc tgttactagc tcggtctatg atttgccaga gaacattcta     240
atgacggatc aagaaatccg ttcgagccct ccagaggaaa gagagttgga tgtaaagtac     300
tctacctctc aagttagtag tcttaaggaa gactctgatg taaaggaaca gtctgtattg     360
cagtcaacag tggttaatga ggtcagtgat aaggatctga ttgttgaaac aaagatggcg     420
aaaattgaac caatgagtcc tgtggagaag attgttagca tggagaataa cagcaagttt     480
attgaaaagg atgttgaagg ggtttcatgg gaaacagaag aagctaccaa agctgctcct     540
acaagcaact ttactgtcgg atctgatggt cctccttcat tccgcagctt aagtggggaa     600
gggggaagtg ggactggaag cctttcacgg ttgcaaggtt tgggacgtgc tgcccggaga     660
cacttatctg cgatccttga tgaattttgg ggacatttat atgattttca tgggcaattg     720
gttgctgaag ccagggcaaa gaaactagat cagctgtttg gcactgatca aaagtcagcc     780
tcttctatga aagcagattc gtttggaaaa gacattagca gtggatattg catgtcacca     840
actgcgaagg gaatggattc acagatgact tcaagtttat atgattcact gaagcagcag     900
```

```
aggacaccgg gaagtatcga ttcgttgtat ggattacaaa gaggttcgtc accgtcaccg    960
ttggtcaacc gtatgcagat gttgggtgca tatggtaaca ccactaataa taataatgct   1020
tacgaattga gtgagagaag atactctagc ctgcgtgctc catcatcttc agagggttgg   1080
gaacaccaac aaccagctac agttcacgga taccagatga agtcatatgt agacaatttg   1140
gcaaaagaaa ggcttgaagc cttacaatcc cgtggagaga tcccgacatc gagatctatg   1200
gcgcttggta cattgagcta tacacagcaa cttgctttag ccttgaaaca gaagtcccag   1260
aatggtctaa cccctggacc agctcctggg tttgagaatt ttgctgggtc tagaagcata   1320
tcgcgacaat ctgaaagatc ttattacggt gttccatctt ctggcaatac tgatactgtt   1380
ggcgcagcag tagccaatga gaaaaaatat agtagcatgc cagatatctc aggattgtct   1440
atgtccgcaa ggaacatgca tttaccaaac aacaagagtg gatactggga tccgtcaagt   1500
ggaggaggag ggtatggtgc gtcttatggt cggttaagca atgaatcatc gttatattct   1560 aatttgggt cacgggtggg agtaccctcg acttatgatg acatttctca atcaagagga   1620
ggctacagag atgcctacag tttgccacag agtgcaacaa cagggaccgg atcgctttgg   1680
tccagacagc cctttgagca gtttggtgta gcggagagga atggtgctgt tggtgaggag   1740
ctcaggaata gatcgaatcc gatcaatata gacaacaacg cttcttctaa tgttgatgca   1800
gaggctaagc ttcttcagtc gttcaggcac tgtattctaa gcttattaa acttgaagga   1860 tccgagtggt tgtttggaca aagcgatgga gttgatgaag aactgattga ccgggtagct   1920
gcacgagaga gtttatcta tgaagctgaa gctcgagaaa taaaccaggt gggtcacatg   1980
ggggagccac taatttcatc ggttcctaac tgtgagatg gttgcgtttg agagctgat   2040 ttgattgtga gctttggagt ttggtgcatt caccgtgtcc ttgacttgtc tctcatggag   2100
agtcggcctg agctttgggg aaagtacact tacgttctca accgcctaca ggtaacaaaa   2160
accgcagtag ttcattgaaa atcacagttt tgcagtttga aaatattgac atgtatggat   2220
ttaaacaggg agtgattgat ccggcgttct caaagctgcg gacaccaatg acaccgtgct   2280
tttgccttca gattccagcg agccaccaga gagcgagtcc gacttcagct aacggaatgt   2340
tacctccggc tgcaaaaccg gctaaaggca aatgcacaac cgcagtcaca cttcttgatc   2400
taatcaaaga cgttgaaatg gcaatctctt gtagaaaagg ccgaaccggt acagctgcag   2460
gtgatgtggc tttcccaaag gggaaagaga atttggcttc ggttttgaag cggtataaac   2520
gtcggttatc gaataaacca gtaggtatga atcaggatgg acccggttca agaaaaaacg   2580
tgactgcgta cggatcattg ggttga                                        2606
```

<210> SEQ ID NO 2
<211> LENGTH: 2529
<212> TYPE: DNA
<213> ORGANISM: Arabidopsis thaliana
<220> FEATURE:
<221> NAME/KEY: source
<222> LOCATION: 1..2529
<223> OTHER INFORMATION: /organism="Arabidopsis thaliana"
      /note="Nucleotide sequence of EIN2 C-terminal fragment (Alonso et
      al. (1999) Science 284(5423):2148-52)"
      /mol_type="unassigned DNA"

<400> SEQUENCE: 2

```
atgctctggc tggcagccac gccgctgaaa tctgcgagta acagagcgga agctcaaata    60
tggaacatgg atgctcaaaa tgctttatct tatccatctg ttcaagaaga ggaaattgaa   120
agaacagaaa caaggaggaa cgaagacgaa tcaatagtgc ggttggaaag cagggtaaag   180
```

```
gatcagttgg atactacgtc tgttactagc tcggtctatg atttgccaga gaacattcta    240
atgacggatc aagaaatccg ttcgagccct ccagaggaaa gagagttgga tgtaaagtac    300
tctacctctc aagttagtag tcttaaggaa gactctgatg taaaggaaca gtctgtattg    360
cagtcaacag tggttaatga ggtcagtgat aaggatctga ttgttgaaac aaagatggcg    420
aaaattgaac caatgagtcc tgtggagaag attgttagca tggagaataa cagcaagttt    480
attgaaaagg atgttgaagg ggtttcatgg gaaacagaag aagctaccaa agctgctcct    540
acaagcaact ttactgtcgg atctgatggt cctccttcat tccgcagctt aagtggggaa    600
gggggaagtg ggactggaag cctttcacgg ttgcaaggtt gggacgtgc tgcccggaga    660 cacttatctg cgatccttga tgaattttgg ggacatttat atgattttca tgggcaattg    720
gttgctgaag ccagggcaaa gaaactagat cagctgtttg gcactgatca aaagtcagcc    780
tcttctatga aagcagattc gtttggaaaa gacattagca gtggatattg catgtcacca    840
actgcgaagg gaatggattc acagatgact tcaagtttat atgattcact gaagcagcag    900
aggacaccgg gaagtatcga ttcgttgtat ggattacaaa gaggttcgtc accgtcaccg    960
ttggtcaacc gtatgcagat gttgggtgca tatggtaaca ccactaataa taataatgct   1020
tacgaattga gtgagagaag atactctagc ctgcgtgctc catcatcttc agagggttgg   1080
gaacaccaac aaccagctac agttcacgga taccagatga agtcatatgt agacaatttg   1140
gcaaaagaaa ggcttgaagc cttacaatcc cgtggagaga tcccgacatc gagatctatg   1200
gcgcttggta cattgagcta tacacagcaa cttgctttag ccttgaaaca gaagtcccag   1260
aatggtctaa cccctggacc agctcctggg tttgagaatt ttgctgggtc tagaagcata   1320
tcgcgacaat ctgaaagatc ttattacggt gttccatctt ctggcaatac tgatactgtt   1380
ggcgcagcag tagccaatga gaaaaaatat agtagcatgc cagatatctc aggattgtct   1440
atgtccgcaa ggaacatgca tttaccaaac aacaagagtg gatactggga tccgtcaagt   1500
ggaggaggag ggtatggtgc gtcttatggt cggttaagca tgaatcatc gttatattct   1560 aatttggggt cacgggtggg agtaccctcg acttatgatg acatttctca atcaagagga   1620
ggctacagag atgcctacag tttgccacag agtgcaacaa cagggaccgg atcgctttgg   1680
tccagacagc cctttgagca gtttggtgta gcggagagga atggtgctgt tggtgaggag   1740
ctcaggaata gatcgaatcc gatcaatata gacaacaacg cttcttctaa tgttgatgca   1800
gaggctaagc ttcttcagtc gttcaggcac tgtattctaa agcttattaa acttgaagga   1860
tccgagtggt tgtttggaca aagcgatgga ggttgatgaag aactgattga ccgggtagct   1920
gcacgagaga agtttatcta tgaagctgaa gctcgagaaa taaaccaggt gggtcacatg   1980
ggggagccac taatttcatc ggttcctaac tgtggagatg gttgcgtttg gagagctgat   2040
ttgattgtga gctttggagt ttggtgcatt caccgtgtcc ttgacttgtc tctcatggag   2100
agtcggcctg agctttgggg aaagtacact tacgttctca accgcctaca gggagtgatt   2160
gatccggcgt tctcaaagct gcggacacca atgacaccgt gcttttgcct tcagattcca   2220
gcgagccacc agagagcgag tccgacttca gctaacggaa tgttacctcc ggctgcaaaa   2280
ccggctaaag gcaaatgcac aaccgcagtc acacttcttg atctaatcaa agacgttgaa   2340
atggcaatct cttgtagaaa aggccgaacc ggtacagctg caggtgatgt ggctttccca   2400 aagggggaaag agaatttggc ttcggttttg aagcggtata acgtcggtt atcgaataaa   2460 ccagtaggta tgaatcagga tggacccggt tcaagaaaaa acgtgactgc gtacggatca   2520
```

```
ttgggttga                                                           2529
```

<210> SEQ ID NO 3
<211> LENGTH: 842
<212> TYPE: PRT
<213> ORGANISM: Arabidopsis thaliana
<220> FEATURE:
<223> OTHER INFORMATION: Amino acid sequence of EIN2 C-terminal fragment protein

<400> SEQUENCE: 3

```
Met Leu Trp Leu Ala Ala Thr Pro Leu Lys Ser Ala Ser Asn Arg Ala
1               5                   10                  15

Glu Ala Gln Ile Trp Asn Met Asp Ala Gln Asn Ala Leu Ser Tyr Pro
            20                  25                  30

Ser Val Gln Glu Glu Ile Glu Arg Thr Glu Thr Arg Arg Asn Glu
        35                  40                  45

Asp Glu Ser Ile Val Arg Leu Glu Ser Arg Val Lys Asp Gln Leu Asp
    50                  55                  60

Thr Thr Ser Val Thr Ser Ser Val Tyr Asp Leu Pro Glu Asn Ile Leu
65                  70                  75                  80

Met Thr Asp Gln Glu Ile Arg Ser Ser Pro Pro Glu Glu Arg Glu Leu
                85                  90                  95

Asp Val Lys Tyr Ser Thr Ser Gln Val Ser Ser Leu Lys Glu Asp Ser
            100                 105                 110

Asp Val Lys Glu Gln Ser Val Leu Gln Ser Thr Val Asn Glu Val
        115                 120                 125

Ser Asp Lys Asp Leu Ile Val Glu Thr Lys Met Ala Lys Ile Glu Pro
    130                 135                 140

Met Ser Pro Val Glu Lys Ile Val Ser Met Glu Asn Asn Ser Lys Phe
145                 150                 155                 160

Ile Glu Lys Asp Val Glu Gly Val Ser Trp Glu Thr Glu Glu Ala Thr
                165                 170                 175

Lys Ala Ala Pro Thr Ser Asn Phe Thr Val Gly Ser Asp Gly Pro Pro
            180                 185                 190

Ser Phe Arg Ser Leu Ser Gly Glu Gly Ser Gly Thr Gly Ser Leu
        195                 200                 205

Ser Arg Leu Gln Gly Leu Gly Arg Ala Ala Arg Arg His Leu Ser Ala
    210                 215                 220

Ile Leu Asp Glu Phe Trp Gly His Leu Tyr Asp Phe His Gly Gln Leu
225                 230                 235                 240

Val Ala Glu Ala Arg Ala Lys Lys Leu Asp Gln Leu Phe Gly Thr Asp
                245                 250                 255

Gln Lys Ser Ala Ser Ser Met Lys Ala Asp Ser Phe Gly Lys Asp Ile
            260                 265                 270

Ser Ser Gly Tyr Cys Met Ser Pro Thr Ala Lys Gly Met Asp Ser Gln
        275                 280                 285

Met Thr Ser Ser Leu Tyr Asp Ser Leu Lys Gln Gln Arg Thr Pro Gly
    290                 295                 300

Ser Ile Asp Ser Leu Tyr Gly Leu Gln Arg Gly Ser Ser Pro Ser Pro
305                 310                 315                 320

Leu Val Asn Arg Met Gln Met Leu Gly Ala Tyr Gly Asn Thr Thr Asn
                325                 330                 335

Asn Asn Asn Ala Tyr Glu Leu Ser Glu Arg Arg Tyr Ser Leu Arg
            340                 345                 350
```

```
Ala Pro Ser Ser Ser Glu Gly Trp Glu His Gln Gln Pro Ala Thr Val
            355                 360                 365

His Gly Tyr Gln Met Lys Ser Tyr Val Asp Asn Leu Ala Lys Glu Arg
    370                 375                 380

Leu Glu Ala Leu Gln Ser Arg Gly Glu Ile Pro Thr Ser Arg Ser Met
385                 390                 395                 400

Ala Leu Gly Thr Leu Ser Tyr Thr Gln Gln Leu Ala Leu Ala Leu Lys
                405                 410                 415

Gln Lys Ser Gln Asn Gly Leu Thr Gly Pro Ala Pro Gly Phe Glu
            420                 425                 430

Asn Phe Ala Gly Ser Arg Ser Ile Ser Arg Gln Ser Glu Arg Ser Tyr
        435                 440                 445

Tyr Gly Val Pro Ser Ser Gly Asn Thr Asp Thr Val Gly Ala Ala Val
    450                 455                 460

Ala Asn Glu Lys Lys Tyr Ser Ser Met Pro Asp Ile Ser Gly Leu Ser
465                 470                 475                 480

Met Ser Ala Arg Asn Met His Leu Pro Asn Asn Lys Ser Gly Tyr Trp
                485                 490                 495

Asp Pro Ser Ser Gly Gly Gly Tyr Gly Ala Ser Tyr Gly Arg Leu
            500                 505                 510

Ser Asn Glu Ser Ser Leu Tyr Ser Asn Leu Gly Ser Arg Val Gly Val
        515                 520                 525

Pro Ser Thr Tyr Asp Asp Ile Ser Gln Ser Arg Gly Gly Tyr Arg Asp
    530                 535                 540

Ala Tyr Ser Leu Pro Gln Ser Ala Thr Thr Gly Thr Gly Ser Leu Trp
545                 550                 555                 560

Ser Arg Gln Pro Phe Glu Gln Phe Gly Val Ala Glu Arg Asn Gly Ala
                565                 570                 575

Val Gly Glu Glu Leu Arg Asn Arg Ser Asn Pro Ile Asn Ile Asp Asn
            580                 585                 590

Asn Ala Ser Ser Asn Val Asp Ala Glu Ala Lys Leu Leu Gln Ser Phe
        595                 600                 605

Arg His Cys Ile Leu Lys Leu Ile Lys Leu Glu Gly Ser Glu Trp Leu
    610                 615                 620

Phe Gly Gln Ser Asp Gly Val Asp Glu Glu Leu Ile Asp Arg Val Ala
625                 630                 635                 640

Ala Arg Glu Lys Phe Ile Tyr Glu Ala Glu Ala Arg Glu Ile Asn Gln
                645                 650                 655

Val Gly His Met Gly Glu Pro Leu Ile Ser Ser Val Pro Asn Cys Gly
            660                 665                 670

Asp Gly Cys Val Trp Arg Ala Asp Leu Ile Val Ser Phe Gly Val Trp
        675                 680                 685

Cys Ile His Arg Val Leu Asp Leu Ser Leu Met Glu Ser Arg Pro Glu
    690                 695                 700

Leu Trp Gly Lys Tyr Thr Tyr Val Leu Asn Arg Leu Gln Gly Val Ile
705                 710                 715                 720

Asp Pro Ala Phe Ser Lys Leu Arg Thr Pro Met Thr Pro Cys Phe Cys
                725                 730                 735

Leu Gln Ile Pro Ala Ser His Gln Arg Ala Ser Pro Thr Ser Ala Asn
            740                 745                 750

Gly Met Leu Pro Pro Ala Ala Lys Pro Ala Lys Gly Lys Cys Thr Thr
        755                 760                 765

Ala Val Thr Leu Leu Asp Leu Ile Lys Asp Val Glu Met Ala Ile Ser
```

```
                770              775             780
Cys Arg Lys Gly Arg Thr Gly Thr Ala Ala Gly Asp Val Ala Phe Pro
785                 790                 795                 800

Lys Gly Lys Glu Asn Leu Ala Ser Val Leu Lys Arg Tyr Lys Arg Arg
                805                 810                 815

Leu Ser Asn Lys Pro Val Gly Met Asn Gln Asp Gly Pro Gly Ser Arg
            820                 825                 830

Lys Asn Val Thr Ala Tyr Gly Ser Leu Gly
            835                 840

<210> SEQ ID NO 4
<211> LENGTH: 3885
<212> TYPE: DNA
<213> ORGANISM: Arabidopsis thaliana
<220> FEATURE:
<221> NAME/KEY: source
<222> LOCATION: 1..3885
<223> OTHER INFORMATION: /organism="Arabidopsis thaliana"
      /note="Nucleotide sequence of full-length EIN2 sequence, putative
      CDS (accession No. NM_120406)"
      /mol_type="unassigned DNA"

<400> SEQUENCE: 4
atggaagctg aaattgtgaa tgtgagacct cagctagggt ttatccagag aatggttcct      60
gctctacttc ctgtcctttt ggtttctgtc ggatatattg atcccgggaa atgggttgca     120
aatatcgaag gaggtgctcg tttcgggtat gacttggtgg caattactct gcttttcaat     180
tttgccgcca tcttatgcca atatgttgca gctcgcataa gcgttgtgac tggtaaacac     240
ttggctcaga tctgcaatga agaatatgac aagtggacgt gcatgttctt gggcattcag     300
gcggagttct cagcaattct gctcgacctt accatggttg tgggagttgc gcatgcactt     360
aaccttttgt ttggggtgga gttatccact ggagtgtttt tggccgccat ggatgcgttt     420
ttatttcctg ttttcgcctc tttccttgaa atggtatgg caaatacagt atccatttac      480
tctgcaggcc tggtattact tctctatgta tctggcgtct gctgagtca gtctgagatc     540 ccactctcta tgaatggagt gttaactcgg ttaaatggag agagcgcatt cgcactgatg     600
ggtcttcttg gcgcaagcat cgtccctcac aattttttata tccattctta ttttgctggg     660
gaaagtacat cttcgtctga tgtcgacaag agcagcttgt gtcaagacca tttgttcgcc     720
atctttggtg tcttcagcgg actgtcactt gtaaattatg tattgatgaa tgcagcagct     780
aatgtgtttc acagtactgg ccttgtggta ctgactttc acgatgcctt gtcactaatg     840
gagcaggtat ttatgagtcc gctcattcca gtggtctttt tgatgctctt gttcttctct     900
agtcaaatta ccgcactagc ttgggctttc ggtggagagg tcgtcctgca tgacttcctg     960
aagatagaaa tacccgcttg gcttcatcgt gctacaatca gaattcttgc agttgctcct    1020
gcgctttatt gtgtatggac atcggtgca gacggaatat accagttact tatattcacc     1080
caggtcttgg tggcaatgat gcttccttgc tcggtaatac cgcttttccg cattgcttcg    1140
tcgagacaaa tcatgggtgt ccataaaatc cctcaggttg gcgagttcct cgcacttaca    1200 acgttttttgg gatttctggg gttgaatgtt gttttgttg ttgagatggt atttgggagc    1260
agtgactggg ctggtggttt gagatggaat accgtgatgg gcacctcgat tcagtacacc    1320
actctgcttg tatcgtcatg tgcatcctta tgcctgatac tctggctggc agccacgccg    1380
ctgaaatctg cgagtaacag agcggaagct caaatatgga acatggatgc tcaaaatgct    1440
ttatcttatc catctgttca agaagaggaa attgaaagaa cagaaacaag gaggaacgaa    1500
```

```
gacgaatcaa tagtgcggtt ggaaagcagg gtaaaggatc agttggatac tacgtctgtt    1560
actagctcgg tctatgattt gccagagaac attctaatga cggatcaaga aatccgttcg    1620
agccctccag aggaaagaga gttggatgta aagtactcta cctctcaagt tagtagtctt    1680
aaggaagact ctgatgtaaa ggaacagtct gtattgcagt caacagtggt taatgaggtc    1740
agtgataagg atctgattgt tgaaacaaag atggcgaaaa ttgaaccaat gagtcctgtg    1800
gagaagatta ttagcatgga gaataacagc aagtttattg aaaaggatgt tgaaggggtt    1860
tcatgggaaa cagaagaagc taccaaagct gctcctacaa gcaactttac tgtcggatct    1920
gatggtcctc cttcattccg cagcttaagt ggggaagggg gaagtgggac tggaagcctt    1980
tcacggttgc aaggtttggg acgtgctgcc cggagacact tatctgcgat ccttgatgaa    2040
ttttggggac atttatatga ttttcatggg caattggttg ctgaagccag ggcaaagaaa    2100
ctagatcagc tgtttggcac tgatcaaaag tcagcctctt ctatgaaagc agattcgttt    2160
ggaaaagaca ttagcagtgg atattgcatg tcaccaactg cgaagggaat ggattcacag    2220
atgacttcaa gtttatatga ttcactgaag cagcagagga caccgggaag tatcgattcg    2280
ttgtatggat tacaaagagg ttcgtcaccg tcaccgttgg tcaaccgtat gcagatgttg    2340
ggtgcatatg gtaacaccac taataataat aatgcttacg aattgagtga gagaagatac    2400
tctagcctgc gtgctccatc atcttcagag ggttgggaac accaacaacc agctacagtt    2460
cacggatacc agatgaagtc atatgtagac aatttggcaa agaaaggct tgaagcctta    2520 caatcccgtg agagatccc gacatcgaga tctatggcgc ttggtacatt gagctataca    2580
cagcaacttg ctttagcctt gaaacagaag tcccagaatg gtctaacccc tggaccagct    2640
cctgggtttg agaattttgc tgggtctaga agcatatcgc gacaatctga aagatcttat    2700
tacggtgttc catcttctgg caatactgat actgttggcg cagcagtagc caatgagaaa    2760
aaatatagta gcatgccaga tatctcagga ttgtctatgt ccgcaaggaa catgcattta    2820
ccaaacaaca agagtggata ctgggatccg tcaagtggag gaggaggta tggtgcgtct    2880 tatggtcggt taagcaatga atcatcgtta tattctaatt tggggtcacg ggtgggagta    2940
ccctcgactt atgatgacat ttctcaatca agaggaggct acagagatgc ctacagtttg    3000
ccacagagtg caacaacagg gaccggatcg ctttggtcca gacagccctt tgagcagttt    3060
ggtgtagcgg agaggaatgg tgctgttggt gaggagctca ggaatagatc gaatccgatc    3120
aatatagaca acaacgcttc ttctaatgtt gatgcagagg ctaagcttct tcagtcgttc    3180
aggcactgta ttctaaagct tattaaactt gaaggatccg agtggttgtt tggacaaagc    3240
gatggagttg atgaagaact gattgaccgg gtagctgcac gagagaagtt tatctatgaa    3300
gctgaagctc gagaaataaa ccaggtgggt cacatggggg agccactaat ttcatcggtt    3360
cctaactgtg gagatggttg cgtttggaga gctgatttga ttgtgagctt tggagtttgg    3420
tgcattcacc gtgtccttga cttgtctctc atggagagtc ggcctgagct ttggggaaag    3480
tacacttacg ttctcaaccg cctacaggga gtgattgatc cggcgttctc aaagctgcgg    3540
acaccaatga caccgtgctt ttgccttcag attccagcga gccaccagag agcgagtccg    3600
acttcagcta acggaatgtt acctccggct gcaaaccgg ctaaaggcaa atgcacaacc    3660
gcagtcacac ttcttgatct aatcaaagac gttgaaatgg caatctcttg tagaaaaggc    3720
cgaaccggta cagctgcagg tgatgtggct ttcccaaagg ggaaagagaa tttggcttcg    3780
gttttgaagc ggtataaacg tcggttatcg aataaaccag taggtatgaa tcaggatgga    3840
cccggttcaa gaaaaaacgt gactgcgtac ggatcattgg gttga    3885
```

```
<210> SEQ ID NO 5
<211> LENGTH: 1294
<212> TYPE: PRT
<213> ORGANISM: Arabidopsis thaliana
<220> FEATURE:
<223> OTHER INFORMATION: Amino acid sequence of full-length EIN2
      protein, NP_195948

<400> SEQUENCE: 5
```

Met Glu Ala Glu Ile Val Asn Val Arg Pro Gln Leu Gly Phe Ile Gln
1               5                   10                  15

Arg Met Val Pro Ala Leu Leu Pro Val Leu Leu Val Ser Val Gly Tyr
            20                  25                  30

Ile Asp Pro Gly Lys Trp Val Ala Asn Ile Glu Gly Gly Ala Arg Phe
        35                  40                  45

Gly Tyr Asp Leu Val Ala Ile Thr Leu Leu Phe Asn Phe Ala Ala Ile
    50                  55                  60

Leu Cys Gln Tyr Val Ala Ala Arg Ile Ser Val Val Thr Gly Lys His
65                  70                  75                  80

Leu Ala Gln Ile Cys Asn Glu Glu Tyr Asp Lys Trp Thr Cys Met Phe
                85                  90                  95

Leu Gly Ile Gln Ala Glu Phe Ser Ala Ile Leu Leu Asp Leu Thr Met
            100                 105                 110

Val Val Gly Val Ala His Ala Leu Asn Leu Leu Phe Gly Val Glu Leu
        115                 120                 125

Ser Thr Gly Val Phe Leu Ala Ala Met Asp Ala Phe Leu Phe Pro Val
    130                 135                 140

Phe Ala Ser Phe Leu Glu Asn Gly Met Ala Asn Thr Val Ser Ile Tyr
145                 150                 155                 160

Ser Ala Gly Leu Val Leu Leu Tyr Val Ser Gly Val Leu Leu Ser
                165                 170                 175

Gln Ser Glu Ile Pro Leu Ser Met Asn Gly Val Leu Thr Arg Leu Asn
            180                 185                 190

Gly Glu Ser Ala Phe Ala Leu Met Gly Leu Leu Gly Ala Ser Ile Val
        195                 200                 205

Pro His Asn Phe Tyr Ile His Ser Tyr Phe Ala Gly Glu Ser Thr Ser
    210                 215                 220

Ser Ser Asp Val Asp Lys Ser Ser Leu Cys Gln Asp His Leu Phe Ala
225                 230                 235                 240

Ile Phe Gly Val Phe Ser Gly Leu Ser Leu Val Asn Tyr Val Leu Met
                245                 250                 255

Asn Ala Ala Ala Asn Val Phe His Ser Thr Gly Leu Val Val Leu Thr
            260                 265                 270

Phe His Asp Ala Leu Ser Leu Met Glu Gln Val Phe Met Ser Pro Leu
        275                 280                 285

Ile Pro Val Val Phe Leu Met Leu Leu Phe Phe Ser Ser Gln Ile Thr
    290                 295                 300

Ala Leu Ala Trp Ala Phe Gly Gly Glu Val Val Leu His Asp Phe Leu
305                 310                 315                 320

Lys Ile Glu Ile Pro Ala Trp Leu His Arg Ala Thr Ile Arg Ile Leu
                325                 330                 335

Ala Val Ala Pro Ala Leu Tyr Cys Val Trp Thr Ser Gly Ala Asp Gly
            340                 345                 350

Ile Tyr Gln Leu Leu Ile Phe Thr Gln Val Leu Val Ala Met Met Leu

```
            355                 360                 365
Pro Cys Ser Val Ile Pro Leu Phe Arg Ile Ala Ser Ser Arg Gln Ile
370                 375                 380

Met Gly Val His Lys Ile Pro Gln Val Gly Glu Phe Leu Ala Leu Thr
385                 390                 395                 400

Thr Phe Leu Gly Phe Gly Leu Asn Val Phe Val Val Glu Met
                    405                 410                 415

Val Phe Gly Ser Ser Asp Trp Ala Gly Gly Leu Arg Trp Asn Thr Val
                    420                 425                 430

Met Gly Thr Ser Ile Gln Tyr Thr Thr Leu Leu Val Ser Ser Cys Ala
                    435                 440                 445

Ser Leu Cys Leu Ile Leu Trp Leu Ala Ala Thr Pro Leu Lys Ser Ala
                    450                 455                 460

Ser Asn Arg Ala Glu Ala Gln Ile Trp Asn Met Asp Ala Gln Asn Ala
465                 470                 475                 480

Leu Ser Tyr Pro Ser Val Gln Glu Glu Ile Glu Arg Thr Glu Thr
                    485                 490                 495

Arg Arg Asn Glu Asp Glu Ser Ile Val Arg Leu Glu Ser Arg Val Lys
                    500                 505                 510

Asp Gln Leu Asp Thr Thr Ser Thr Ser Val Tyr Asp Leu Pro
                    515                 520                 525

Glu Asn Ile Leu Met Thr Asp Gln Glu Ile Arg Ser Ser Pro Pro Glu
530                 535                 540

Glu Arg Glu Leu Asp Val Lys Tyr Ser Thr Ser Gln Val Ser Ser Leu
545                 550                 555                 560

Lys Glu Asp Ser Asp Val Lys Glu Gln Ser Val Leu Gln Ser Thr Val
                    565                 570                 575

Val Asn Glu Val Ser Asp Lys Asp Leu Ile Val Glu Thr Lys Met Ala
                    580                 585                 590

Lys Ile Glu Pro Met Ser Pro Val Lys Ile Val Ser Met Glu Asn
                    595                 600                 605

Asn Ser Lys Phe Ile Glu Lys Asp Val Glu Gly Val Ser Trp Glu Thr
                    610                 615                 620

Glu Glu Ala Thr Lys Ala Ala Pro Thr Ser Asn Phe Thr Val Gly Ser
625                 630                 635                 640

Asp Gly Pro Pro Ser Phe Arg Ser Leu Ser Gly Glu Gly Gly Ser Gly
                    645                 650                 655

Thr Gly Ser Leu Ser Arg Leu Gln Gly Leu Gly Arg Ala Ala Arg Arg
                    660                 665                 670

His Leu Ser Ala Ile Leu Asp Glu Phe Trp Gly His Leu Tyr Asp Phe
                    675                 680                 685

His Gly Gln Leu Val Ala Glu Ala Arg Ala Lys Lys Leu Asp Gln Leu
                    690                 695                 700

Phe Gly Thr Asp Gln Lys Ser Ala Ser Ser Met Lys Ala Asp Ser Phe
705                 710                 715                 720

Gly Lys Asp Ile Ser Ser Gly Tyr Cys Met Ser Pro Thr Ala Lys Gly
                    725                 730                 735

Met Asp Ser Gln Met Thr Ser Ser Leu Tyr Asp Ser Leu Lys Gln Gln
                    740                 745                 750

Arg Thr Pro Gly Ser Ile Asp Ser Leu Tyr Gly Leu Gln Arg Gly Ser
                    755                 760                 765

Ser Pro Ser Pro Leu Val Asn Arg Met Gln Met Leu Gly Ala Tyr Gly
770                 775                 780
```

```
Asn Thr Thr Asn Asn Asn Ala Tyr Glu Leu Ser Glu Arg Arg Tyr
785                 790                 795                 800

Ser Ser Leu Arg Ala Pro Ser Ser Glu Gly Trp Glu His Gln Gln
            805                 810                 815

Pro Ala Thr Val His Gly Tyr Gln Met Lys Ser Tyr Val Asp Asn Leu
            820                 825                 830

Ala Lys Glu Arg Leu Glu Ala Leu Gln Ser Arg Gly Glu Ile Pro Thr
            835                 840                 845

Ser Arg Ser Met Ala Leu Gly Thr Leu Ser Tyr Thr Gln Gln Leu Ala
850                 855                 860

Leu Ala Leu Lys Gln Lys Ser Gln Asn Gly Leu Thr Pro Gly Pro Ala
865                 870                 875                 880

Pro Gly Phe Glu Asn Phe Ala Gly Ser Arg Ser Ile Ser Arg Gln Ser
                885                 890                 895

Glu Arg Ser Tyr Tyr Gly Val Pro Ser Ser Gly Asn Thr Asp Thr Val
            900                 905                 910

Gly Ala Ala Val Ala Asn Glu Lys Lys Tyr Ser Ser Met Pro Asp Ile
            915                 920                 925

Ser Gly Leu Ser Met Ser Ala Arg Asn Met His Leu Pro Asn Asn Lys
            930                 935                 940

Ser Gly Tyr Trp Asp Pro Ser Ser Gly Gly Gly Tyr Gly Ala Ser
945                 950                 955                 960

Tyr Gly Arg Leu Ser Asn Glu Ser Ser Leu Tyr Ser Asn Leu Gly Ser
                965                 970                 975

Arg Val Gly Val Pro Ser Thr Tyr Asp Asp Ile Ser Gln Ser Arg Gly
            980                 985                 990

Gly Tyr Arg Asp Ala Tyr Ser Leu Pro Gln Ser Ala Thr Thr Gly Thr
            995                 1000                1005

Gly Ser Leu Trp Ser Arg Gln Pro Phe Glu Gln Phe Gly Val Ala Glu
    1010                1015                1020

Arg Asn Gly Ala Val Gly Glu Glu Leu Arg Asn Arg Ser Asn Pro Ile
1025                1030                1035                1040

Asn Ile Asp Asn Asn Ala Ser Ser Asn Val Asp Ala Glu Ala Lys Leu
            1045                1050                1055

Leu Gln Ser Phe Arg His Cys Ile Leu Lys Leu Ile Lys Leu Glu Gly
            1060                1065                1070

Ser Glu Trp Leu Phe Gly Gln Ser Asp Gly Val Asp Glu Glu Leu Ile
    1075                1080                1085

Asp Arg Val Ala Ala Arg Glu Lys Phe Ile Tyr Glu Ala Glu Ala Arg
    1090                1095                1100

Glu Ile Asn Gln Val Gly His Met Gly Glu Pro Leu Ile Ser Ser Val
1105                1110                1115                1120

Pro Asn Cys Gly Asp Gly Cys Val Trp Arg Ala Asp Leu Ile Val Ser
            1125                1130                1135

Phe Gly Val Trp Cys Ile His Arg Val Leu Asp Leu Ser Leu Met Glu
            1140                1145                1150

Ser Arg Pro Glu Leu Trp Gly Lys Tyr Thr Tyr Val Leu Asn Arg Leu
    1155                1160                1165

Gln Gly Val Ile Asp Pro Ala Phe Ser Lys Leu Arg Thr Pro Met Thr
    1170                1175                1180

Pro Cys Phe Cys Leu Gln Ile Pro Ala Ser His Gln Arg Ala Ser Pro
1185                1190                1195                1200
```

```
Thr Ser Ala Asn Gly Met Leu Pro Pro Ala Ala Lys Pro Ala Lys Gly
                1205                1210                1215

Lys Cys Thr Thr Ala Val Thr Leu Leu Asp Leu Ile Lys Asp Val Glu
        1220                1225                1230

Met Ala Ile Ser Cys Arg Lys Gly Arg Thr Gly Thr Ala Ala Gly Asp
            1235                1240                1245

Val Ala Phe Pro Lys Gly Lys Glu Asn Leu Ala Ser Val Leu Lys Arg
        1250                1255                1260

Tyr Lys Arg Arg Leu Ser Asn Lys Pro Val Gly Met Asn Gln Asp Gly
1265                1270                1275                1280

Pro Gly Ser Arg Lys Asn Val Thr Ala Tyr Gly Ser Leu Gly
                1285                1290

<210> SEQ ID NO 6
<211> LENGTH: 5929
<212> TYPE: DNA
<213> ORGANISM: Arabidopsis thaliana
<220> FEATURE:
<221> NAME/KEY: source
<222> LOCATION: 1..5929
<223> OTHER INFORMATION: /organism="Arabidopsis thaliana"
      /note="Nucleotide sequence of the genomic sequence around the
      region which codes for EIN2 (AT5G03280, TAIR accession No
      4515110756)"
      /mol_type="genomic DNA"

<400> SEQUENCE: 6
atctctctct ttcgatggaa ctgagctctt tctctctttc ctcttctttt ctctctctat      60
ctctatctct cgtagcttga taagagtttc tctcttttga agatccgttt ctctctctct     120
cactgagact attgttgtta ggtcaacttg cgatcatggc gatttcgaag gtgacttctt     180
tcaaaaaccc taatcctctg ttttttttttt tattttgctg gggggctttg tacggacttt     240
catgggtttt tgtagctttt ccctcggctt ttgcgcaaat gagactttct gggtttttt      300 tccagctttt tataatttca tcaggtggat cgaattcgta gtttcagctt agatctctct     360
ccctcttcat tatctggact ttccagactt ggagttcttc gggattgttt tcggtttctg     420
ggttttgttt taattgcgag atttaagctt tttttctttttt tactactgta cttggtttgt     480
ggttgacctt tttttttcctt gaagatctga atgcgtagat catacgggat ctttgcattt     540
ttgttgcttt tcgtcagcgt tacgattctt ttagcttcag tttagttgaa atttgtattt     600
tttttgagct tatcttctttt ttgttgctgc ttcatactaa gatcaattat tgatttgtaa     660
tactactgta tctgaagatt ttcaccataa aaaaaaaatt caggtctgaa gctgatttcg     720
aatggtttgg agatatccgt agtggttaag catatggaag tctatgttct gctcttggtt     780
gctctgttag ggcttcctcc atttggacca acttagctga atgttgtatg atctctctcc     840
ttgaagcagc aaataagaag aaggtctggt ccttaactta acatctggtt actagaggaa     900
acttcagcta ttattaggta agaaagact gtacagagtt gtataacaag taagcgttag     960
agtggctttg tttgcctcgg tgatagaaga accgactgat tcgttgttgt gtgttagctt    1020
tggagggaat cagatttcgc gagggaaggt gttttagatc aaatctgtga attttactca    1080
actgaggctt ttagtgaacc acgactgtag agttgacctt gaatcctact ctgagtaatt    1140
atattatcag atagatttag gatggaagct gaaattgtga atgtgagacc tcagctaggg    1200
tttatccaga gaatggttcc tgctctactt cctgtccttt tggtttctgt cggatatatt    1260
gatcccggga aatgggttgc aaatatcgaa ggaggtgctc gtttcgggta tgacttggtg    1320
gcaattactc tgcttttcaa ttttgccgcc atcttatgcc aatatgttgc agctcgcata    1380
```

```
agcgttgtga ctggtaaaca cttggctcag gtaaacattt ttctgatctc taaagaacaa    1440
acttttaaa ataacaaact gggctctgtg gttgtcttgt cactttctca aagtggaatt     1500
ctactaacca ccttctctat ttttctaaca ttttaatgtt ctttactggg acagatctgc    1560
aatgaagaat atgacaagtg gacgtgcatg ttccttgggca ttcaggcgga gttctcagca   1620
attctgctcg accttaccat ggtagttact tacaatcttt gctgttctta attttttat    1680
tatgtgataa aattttgatt cctctgactt gagcttctct attataaaca ggttgtggga    1740
gttgcgcatg cacttaacct tttgtttggg gtggagttat ccactggagt gttttttggcc  1800
gccatggatg cgttttttatt tcctgttttc gcctctttcc ttgtatgact ggtcttcctg   1860
tcttgttttt tttctccacg ttcttgaaat agcattattg gaaattagct gacatgcata    1920
caatttctga caggaaaatg gtatggcaaa tacagtatcc atttactctg caggcctggt    1980
attacttctc tatgtatctg gcgtcttgct gagtcagtct gagatcccac tctctatgaa    2040
tggagtgtta actcggttaa atggagagag cgcattcgca ctgatgggtc ttcttggcgc    2100
aagcatcgtc cctcacaatt tttatatcca ttcttatttt gctgggtac ctttttctc     2160
tttatatgta tctctctttt ctgttaagaa gcaataatta tactaagcag tgaacgctct    2220
attacaggaa agtacatctt cgtctgatgt cgacaagagc agcttgtgtc aagaccattt    2280
gttcgccatc tttggtgtct tcagcggact gtcacttgta aattatgtat tgatgaatgc    2340
agcagctaat gtgtttcaca gtactggcct tgtggtactg acttttcacg atgccttgtc    2400
actaatggag caggttttgt ctgacggttt tatgttcgta ttagtctata attcattttt    2460
agggaaaatg ttcagaaatc tctcgtgatt attaattatc ttgttcttga ttgttgatca    2520
caggtattta tgagtccgct cattccagtg gtctttttga tgctcttgtt cttctctagt    2580
caaattaccg cactagcttg ggctttcggt ggagaggtcg tcctgcatga cttcctgaag    2640
atagaaatac ccgcttggct tcatcgtgct acaatcagaa ttcttgcagt tgctcctgcg    2700
cttttattgtg tatggacatc tggtgcagac ggaatatacc agttacttat attcacccag   2760
gtcttggtgg caatgatgct tccttgctcg gtaataccgc ttttccgcat tgcttcgtcg    2820
agacaaatca tgggtgtcca taaaatccct caggttggcg agttcctcgc acttacaacg    2880
tttttgggat ttctggggtt gaatgttgtt tttgttgttg agatggtatt tgggagcagt    2940
gactgggctg gtggtttgag atggaatacc gtgatgggca cctcgattca gtacaccact    3000
ctgcttgtat cgtcatgtgc atccttatgc ctgatactct ggctggcagc cacgccgctg    3060
aaatctgcga gtaacagagc ggaagctcaa atatggaaca tggatgctca aaatgcttta    3120
tcttatccat ctgttcaaga agaggaaatt gaaagaacag aaacaaggag gaacgaagac    3180
gaatcaatag tgcggttgga aagcagggta aaggatcagt tggatactac gtctgttact    3240
agctcggtct atgatttgcc agagaacatt ctaatgacgg atcaagaaat ccgttcgagc    3300
cctccagagg aaagagagtt ggatgtaaag tactctacct ctcaagttag tagtcttaag    3360
gaagactctg atgtaaagga acagtctgta ttgcagtcaa cagtggttaa tgaggtcagt    3420
gataaggatc tgattgttga aacaaagatg gcgaaaattg aaccaatgag tcctgtggag    3480
aagattgtta gcatggagaa taacagcaag tttattgaaa aggatgttga aggggtttca    3540
tgggaaacag aagaagctac caaagctgct cctacaagca actttactgt cggatctgat    3600
ggtcctcctt cattccgcag cttaagtggg aaggggggaa gtgggactgg aagcctttca    3660
cggttgcaag gtttgggacg tgctgcccgg agacacttat ctgcgatcct tgatgaattt    3720
```

```
tggggacatt tatatgattt tcatgggcaa ttggttgctg aagccagggc aaagaaacta      3780
gatcagctgt ttggcactga tcaaaagtca gcctcttcta tgaaagcaga ttcgtttgga      3840
aaagacatta gcagtggata ttgcatgtca ccaactgcga agggaatgga ttcacagatg      3900
acttcaagtt tatatgattc actgaagcag cagaggacac cgggaagtat cgattcgttg      3960
tatggattac aaagaggttc gtcaccgtca ccgttggtca accgtatgca gatgttgggt      4020
gcatatggta acaccactaa taataataat gcttacgaat tgagtgagag aagatactct      4080
agcctgcgtg ctccatcatc ttcagagggt tgggaacacc aacaaccagc tacagttcac      4140
ggataccaga tgaagtcata tgtagacaat ttggcaaaag aaaggcttga agccttacaa      4200
tcccgtggag agatcccgac atcgagatct atggcgcttg gtacattgag ctatacacag      4260
caacttgctt tagccttgaa acagaagtcc cagaatggtc taaccccctgg accagctcct      4320 gggtttgaga attttgctgg gtctagaagc atatcgcgac aatctgaaag atcttattac      4380
ggtgttccat cttctggcaa tactgatact gttggcgcag cagtagccaa tgagaaaaaa      4440
tatagtagca tgccagatat ctcaggattg tctatgtccg caaggaacat gcatttacca      4500
aacaacaaga gtggatactg ggatccgtca agtggaggag agggtatgg tgcgtcttat       4560 ggtcggttaa gcaatgaatc atcgttatat tctaatttgg ggtcacgggt gggagtaccc      4620
tcgacttatg atgacatttc tcaatcaaga ggaggctaca gagatgccta cagtttgcca      4680
cagagtgcaa caacagggac cggatcgctt tggtccagac agccctttga gcagtttggt      4740
gtagcggaga ggaatggtgc tgttggtgag gagctcagga atagatcgaa tccgatcaat      4800
atagacaaca acgcttcttc taatgttgat gcagaggcta agcttcttca gtcgttcagg      4860
cactgtattc taaagcttat taaacttgaa ggatccgagt ggttgtttgg acaaagcgat      4920
ggagttgatg aagaactgat tgaccgggta gctgcacgag agaagtttat ctatgaagct      4980
gaagctcgag aaataaaacca ggtgggtcac atgggggagc cactaatttc atcggttcct      5040
aactgtggag atggttgcgt ttggagagct gatttgattg tgagctttgg agtttggtgc      5100
attcaccgtg tccttgactt gtctctcatg gagagtcggc ctgagctttg gggaaagtac      5160
acttacgttc tcaaccgcct acaggtaaca aaaaccgcag tagttcattg aaaatcacag      5220
ttttgcagtt tgaaaatatt gacatgtatg gatttaaaca gggagtgatt gatccggcgt      5280
tctcaaagct gcggacacca atgacaccgt gcttttgcct tcagattcca gcagccacc       5340 agagagcgag tccgacttca gctaacggaa tgttacctcc ggctgcaaaa ccggctaaag      5400
gcaaatgcac aaccgcagtc acacttcttg atctaatcaa agacgttgaa atggcaatct      5460
cttgtagaaa aggccgaacc ggtacagctg caggtgatgt ggctttccca aaggggaaag      5520
agaatttggc ttcggttttg aagcggtata acgtcggtt atcgaataaa ccagtaggta       5580
tgaatcagga tggacccggt tcaagaaaaa acgtgactgc gtacggatca ttgggttgaa      5640
gaagaagaac attgtgagaa atctcatgat caaagtgacg tcgagaggga agccgaagaa      5700
tcaaaactct cgcttttgat tgctcctctg cttcgttaat tgtgtattaa gaaaagaaga      5760
aaaaaaatgg attttgttg cttcagaatt tttcgctctt tttttcttaa tttggttgta       5820
atgttatgtt tatatacata tatcatcatc ataggaccat agctacaaac cgaatccggt      5880
ttgtgtaatt ctatgcggaa tcataaagaa atcgtcggtt tgaaatgtt                  5929
```

<210> SEQ ID NO 7
<211> LENGTH: 33
<212> TYPE: DNA
<213> ORGANISM: Artificial Sequence

```
<220> FEATURE:
<221> NAME/KEY: source
<222> LOCATION: 1..33
<223> OTHER INFORMATION: /organism="Artificial Sequence"
      /note="EIN 2 forward primer 1"
      /mol_type="unassigned DNA"

<400> SEQUENCE: 7
cctatgcggc cgcccatgct ctggctggca gcc                              33

<210> SEQ ID NO 8
<211> LENGTH: 40
<212> TYPE: DNA
<213> ORGANISM: Artificial Sequence
<220> FEATURE:
<221> NAME/KEY: source
<222> LOCATION: 1..40
<223> OTHER INFORMATION: /organism="Artificial Sequence"
      /note="EIN2 reverse primer 1"
      /mol_type="unassigned DNA"

<400> SEQUENCE: 8
cctatggcgc gcccttcttc ttcaacccaa tgatccgtac                       40

<210> SEQ ID NO 9
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /organism="Artificial Sequence"
      /note="EIN2 forward primer 2"
      /mol_type="unassigned DNA"

<400> SEQUENCE: 9
aattaattaa ccatgctctg gctggcagc                                   29

<210> SEQ ID NO 10
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /organism="Artificial Sequence"
      /note="EIN2 reverse primer 2"
      /mol_type="unassigned DNA"

<400> SEQUENCE: 10
ttggcgcgcc tcaacccaat gatccgtac                                   29

<210> SEQ ID NO 11
<211> LENGTH: 2526
<212> TYPE: DNA
<213> ORGANISM: Artificial Sequence
<220> FEATURE:
<221> NAME/KEY: source
<222> LOCATION: 1..2526
<223> OTHER INFORMATION: /organism="Artificial Sequence"
      /note="Nucleotide sequence EIN2, variant 1"
      /mol_type="unassigned DNA"

<400> SEQUENCE: 11
atgctgtggc tggccgccac ccccctgaag agcgccagca acagagccga ggcccagatc    60
tggaacatgg acgccaacaa cgccctgacc taccccagcg tgaacgagga ggagatcgag   120
aagaccgagt gcagaagaaa cgaggacgag agcggcgtga agatcgagag cagagtgaag   180
```

```
gaccagctgg acaccagctg cgccaccagc agcatctacg agggccccga caacgtgctg      240
atgaccgagc aggacatcag aagcagcccc cccgacgaga gagagatgga cgtgcactac      300
accaccagcc aggccacctg catcagagag gactgcgacg tgcacgagca gaccatgctg      360
cagacctgcg gcgtgaacga ggtgagcgac aaggaggtga tcctggagac caagatggcc      420
cacggcgagc ccatgacccc cgccgagaag atcgccagca tggagaacaa ctgcagatac      480
atggacaagg acggcgagat ggtgagctgg gagaccgagg acgccaccaa ggccgccccc      540
accagcaact tcaccgtgat ctgcgacggc ccccccagct tcagaagcct gagcggcgag      600
ggcggcagcg gcagcgccag cctgaccaga atgcagggca tcggcagagc cgccagaaga      660
aagatctgca tgatcctgga cgactactgg ggccacggct acgacttcca cgtgaacgcc      720
ggcgccgagg ccagagccaa gaaggccgac cagctgttca tgaccgagaa ccacagcgcc      780
tgcaccgtga gagccgacag cttcatcaag gacgtgagca gcgcctacac cctgacccc      840 tgcatcaaga tcatggacag ccagatgacc agcagcctgt acgacagcct gaagaaccag      900
agaagccccg gcagcatcga cagcctgtac ggcctgaaca gaggcaccag ccctgcccc      960 ctgctgaaca agggccagat gctgggcgcc tacggccaga ccaccaacaa caaccaggcc     1020
tacgagctga gcgacagaaa gtacagcacc ctgcacgccc cagcagcag cgagctgtgg     1080 gagcaccagc agcccggcac cggccacggc tacaacatga gagctacgt ggagcagctg     1140 gccaaggaga gagtggagat gctgcagagc agaggcgagg cccccagcag cagaagcatg     1200
gccctgggca ccgccagcta caccaaccag gccgccgcca tgctgaagca gaagtgcaac     1260
aacatcctga gccccggccc cgccccctg ttcgagaact cgccatgag cagaagcatg     1320 tgcagacaga ccgaccacag ctactacatg ctgcccagca gcatcaacag cgacaccgtg     1380
ggcgccgccg tggccaacga gaagaagtac tgctgcatcc ccgacatcag cgccctgacc     1440
atgtgcatca gacagatgca cctgcccaac aacagaagcg cctacttcga ccccagcagc     1500
ggcggcggcg gctacggcgc cagctacggc cacgccagca cgagtgcag cgcctactgc     1560 cagctgggca gcagagtggc cgtgcccagc acctacgacg agatcagcaa cagcagaggc     1620
ggctggaagg acgcctggag catccccag accgccacca gcggcaccgg cagcatctgg     1680
agcagacagc cctacgacca gttcggcgtg ccgagaaga acggcctgct gggcgaggac     1740
ctgagaaaca agtgcaaccc cgccaacatc gaccagcagg ccaccagcaa catggacggc     1800
gaggtgagac tgctgaacag cttcagacac agcatgctga agctgatcaa gctggagctg     1860
agcgactggg ccttcatcaa cagcgacggc ctggacgagg aggtgatcga cagagtgggc     1920
gcccacgaga agtggatctg ggaggccgag gcccacgaga tccagcaggt gggcaagatg     1980
ggcgagcccc tgatctgcag cgtgcccaac agcggcgacg gctgcgtgtg gagagccgac     2040
ctgatcggca gcttcggcgt gttctgcatc cacagaggcc tggacatgag cctgatggag     2100
agcagacccg acctgttcgg ccacttcacc tacgtgctga acagactgca gggcatcatc     2160
gaccccgcct acagccacct gagaaccccc atgaccccca gcttctgcgg ccagatgccc     2220
gtgagccacc agagaatgag ccccaccagc gccaacggca tcctgccccc cgccctgcac     2280
cccggcagag gcaagtgcag cagcgccgtg tgcctggccg acctgatcaa ggacggcgag     2340
gtggccatca gcagccacaa gggcagaagc atgagcgccg tgatcgacgt gatctacccc     2400
aaggccaagg agcagctggg cagcgtgctg aagaagtaca agagacacct gagcaacaag     2460
cccatgggca tgcagcagga cgccccatg agcagaaaga acgtgagcgc ctacatgagc     2520
ctgggc                                                                2526
```

<210> SEQ ID NO 12
<211> LENGTH: 842
<212> TYPE: PRT
<213> ORGANISM: Artificial Sequence
<220> FEATURE:
<223> OTHER INFORMATION: Amino acid sequence EIN2, variant 1

<400> SEQUENCE: 12

```
Met Leu Trp Leu Ala Ala Thr Pro Leu Lys Ser Ala Ser Asn Arg Ala
1               5                   10                  15

Glu Ala Gln Ile Trp Asn Met Asp Ala Asn Asn Ala Leu Thr Tyr Pro
            20                  25                  30

Ser Val Asn Glu Glu Ile Glu Lys Thr Glu Cys Arg Arg Asn Glu
        35                  40                  45

Asp Glu Ser Gly Val Lys Ile Glu Ser Arg Val Lys Asp Gln Leu Asp
    50                  55                  60

Thr Ser Cys Ala Thr Ser Ser Ile Tyr Glu Gly Pro Asp Asn Val Leu
65                  70                  75                  80

Met Thr Glu Gln Asp Ile Arg Ser Ser Pro Pro Asp Glu Arg Glu Met
                85                  90                  95

Asp Val His Tyr Thr Thr Ser Gln Ala Thr Cys Ile Arg Glu Asp Cys
            100                 105                 110

Asp Val His Glu Gln Thr Met Leu Gln Thr Cys Gly Val Asn Glu Val
            115                 120                 125

Ser Asp Lys Glu Val Ile Leu Glu Thr Lys Met Ala His Gly Glu Pro
    130                 135                 140

Met Thr Pro Ala Glu Lys Ile Ala Ser Met Glu Asn Asn Cys Arg Tyr
145                 150                 155                 160

Met Asp Lys Asp Gly Glu Met Val Ser Trp Glu Thr Glu Asp Ala Thr
                165                 170                 175

Lys Ala Ala Pro Thr Ser Asn Phe Thr Val Ile Cys Asp Gly Pro Pro
            180                 185                 190

Ser Phe Arg Ser Leu Ser Gly Glu Gly Gly Ser Gly Ser Ala Ser Leu
        195                 200                 205

Thr Arg Met Gln Gly Ile Gly Arg Ala Ala Arg Lys Ile Cys Met
    210                 215                 220

Ile Leu Asp Asp Tyr Trp Gly His Gly Tyr Asp Phe His Val Asn Ala
225                 230                 235                 240

Gly Ala Glu Ala Arg Ala Lys Lys Ala Asp Gln Leu Phe Met Thr Glu
                245                 250                 255

Asn His Ser Ala Cys Thr Val Arg Ala Asp Ser Phe Ile Lys Asp Val
            260                 265                 270

Ser Ser Ala Tyr Thr Leu Thr Pro Cys Ile Lys Ile Met Asp Ser Gln
        275                 280                 285

Met Thr Ser Ser Leu Tyr Asp Ser Leu Lys Asn Gln Arg Ser Pro Gly
    290                 295                 300

Ser Ile Asp Ser Leu Tyr Gly Leu Asn Arg Gly Thr Ser Pro Cys Pro
305                 310                 315                 320

Leu Leu Asn Lys Gly Gln Met Leu Gly Ala Tyr Gly Gln Thr Thr Asn
                325                 330                 335

Asn Asn Gln Ala Tyr Glu Leu Ser Asp Arg Lys Tyr Ser Thr Leu His
            340                 345                 350

Ala Pro Ser Ser Ser Glu Leu Trp Glu His Gln Gln Pro Gly Thr Gly
        355                 360                 365
```

```
His Gly Tyr Asn Met Lys Ser Tyr Val Glu Gln Leu Ala Lys Glu Arg
    370                 375                 380

Val Glu Met Leu Gln Ser Arg Gly Glu Gly Pro Ser Ser Arg Ser Met
385                 390                 395                 400

Ala Leu Gly Thr Ala Ser Tyr Thr Asn Gln Ala Ala Met Leu Lys
                405                 410                 415

Gln Lys Cys Asn Asn Ile Leu Ser Pro Gly Pro Ala Pro Leu Phe Glu
                420                 425                 430

Asn Phe Ala Met Ser Arg Ser Met Cys Arg Gln Thr Asp His Ser Tyr
                435                 440                 445

Tyr Met Leu Pro Ser Ser Ile Asn Ser Asp Thr Val Gly Ala Ala Val
    450                 455                 460

Ala Asn Glu Lys Lys Tyr Cys Cys Ile Pro Asp Ile Ser Ala Leu Thr
465                 470                 475                 480

Met Cys Ile Arg Gln Met His Leu Pro Asn Asn Arg Ser Ala Tyr Phe
                485                 490                 495

Asp Pro Ser Ser Gly Gly Gly Tyr Gly Ser Tyr Gly His Ala
                500                 505                 510

Ser Asn Glu Cys Ser Ala Tyr Cys Gln Leu Gly Ser Arg Val Ala Val
                515                 520                 525

Pro Ser Thr Tyr Asp Glu Ile Ser Asn Ser Arg Gly Gly Trp Lys Asp
    530                 535                 540

Ala Trp Ser Ile Pro Gln Thr Ala Thr Ser Gly Thr Gly Ser Ile Trp
545                 550                 555                 560

Ser Arg Gln Pro Tyr Asp Gln Phe Gly Val Ala Glu Lys Asn Gly Leu
                565                 570                 575

Leu Gly Glu Asp Leu Arg Asn Lys Cys Asn Pro Ala Asn Ile Asp Gln
                580                 585                 590

Gln Ala Thr Ser Asn Met Asp Gly Glu Val Arg Leu Leu Asn Ser Phe
                595                 600                 605

Arg His Ser Met Leu Lys Leu Ile Lys Leu Glu Leu Ser Asp Trp Ala
    610                 615                 620

Phe Ile Asn Ser Asp Gly Leu Asp Glu Val Ile Asp Arg Val Gly
625                 630                 635                 640

Ala His Glu Lys Trp Ile Trp Glu Ala Glu His Glu Ile Gln Gln
                645                 650                 655

Val Gly Lys Met Gly Glu Pro Leu Ile Cys Ser Val Pro Asn Ser Gly
                660                 665                 670

Asp Gly Cys Val Trp Arg Ala Asp Leu Ile Gly Ser Phe Gly Val Phe
                675                 680                 685

Cys Ile His Arg Gly Leu Asp Met Ser Leu Met Glu Ser Arg Pro Asp
    690                 695                 700

Leu Phe Gly His Phe Thr Tyr Val Leu Asn Arg Leu Gln Gly Ile Ile
705                 710                 715                 720

Asp Pro Ala Tyr Ser His Leu Arg Thr Pro Met Thr Pro Ser Phe Cys
                725                 730                 735

Gly Gln Met Pro Val Ser His Gln Arg Met Ser Pro Thr Ser Ala Asn
                740                 745                 750

Gly Ile Leu Pro Pro Ala Leu His Pro Gly Arg Gly Lys Cys Ser Ser
                755                 760                 765

Ala Val Cys Leu Ala Asp Leu Ile Lys Asp Gly Glu Val Ala Ile Ser
    770                 775                 780
```

```
Ser His Lys Gly Arg Ser Met Ser Ala Val Ile Asp Val Ile Tyr Pro
785                 790                 795                 800

Lys Ala Lys Glu Gln Leu Gly Ser Val Leu Lys Tyr Lys Arg His
            805                 810                 815

Leu Ser Asn Lys Pro Met Gly Met Gln Gln Asp Ala Pro Met Ser Arg
            820                 825                 830

Lys Asn Val Ser Ala Tyr Met Ser Leu Gly
            835                 840

<210> SEQ ID NO 13
<211> LENGTH: 2526
<212> TYPE: DNA
<213> ORGANISM: Artificial Sequence
<220> FEATURE:
<221> NAME/KEY: source
<222> LOCATION: 1..2526
<223> OTHER INFORMATION: /organism="Artificial Sequence"
      /note="Nucleotide sequence EIN2, variant 2"
      /mol_type="unassigned DNA"

<400> SEQUENCE: 13
atgctgtggc tggccgccac cccccctgaag agcgccagca acagagccga ggcccagatc     60
tggaacatgg acgcccagaa cgccctgagc taccccagcg tgcaggagga cgagatcgag    120
agaaccgaca ccagaagaca ggacgacgac agcatcggca gactggagag cagagtgaga    180
gagaacctgg agagctgcag cgccaccagc agcggcttcg acctgcccga acatcatc     240 atgtgcgaca cgagggcag aagcagcccc ccgaggaga gagagctgga ggtgaagtac    300
agcaccacca acgtgtgcag cctgaaggag acagcgacg tgaaggagca gagcgtgatc    360
cagagcaccg tgctgcagga gatcagcgag aaggacctga tcgtggagtg caagatggcc    420
aaggccgagc ccatcagccc cgtggagaag atcatgtgca tggagaacaa cagcaagttc    480
ctggaccacg aggtggaggt ggtgagctgg agaccgagg aggccaccag agtggtgccc    540
agcagccagt tcaccatcgg cagcgacggc ccccccagct tcagaagcct gtgcgtggag    600
ggcggcagcg gcagcggcag cctgaccaga ctgaacgtgc tgggcaagat ggccagaaga    660
aagctgagcg ccatcatcga cgagttctac gcccacctgt tcgacttcca catccagctg    720
gtggccgacg ccagaggcca aagctggac caggggcttcg tgtgcgacca gagaagcgcc    780
agcagcggca aggccgacag cttcggcaag gagatcacca cggctacac catgtgcccc    840 accatgaagg ccatggacag caacatgacc agctgcctgt tcgacagcct gaagcagaac    900
agaacccccc tgagcatcga cagcctgtgg gccctgcaga gactgaccag ccccagcccc    960
gtgatgaaca gaatgaacgg catggtggtg ttcggcaaca gcaccaacca gaacaacgcc   1020
ttcgagctga ccgacagaag attctgcagc ctgagagccc ccaccagcag cgagggctac   1080
gagcaccagc agcccggcac cgtgcacggc ttccagatga gagctgggg cgacaacgcc   1140 gccaaggaga gagtggaggc cctgaactgc agaatggagg cccccacctg ccactgcatg   1200 gcccctgggct gcctgagcta cagccagaac ctggccggcg ccctgaagca aagagccag   1260 aacggcctga ccccggccc cgcccccggc ttcgagaact gggtggtgag caagagcatc   1320
accagacaga gcgagagaag ctactacgcc gtgcccacca gcatcaacac cgacaccgtg   1380
ggcgccgccg tggccaacga agaagttc agcagcatgc ccgacatcac cggcctgagc   1440
atgagcgcca gaaacgtgca catcccccag aacaagagcg gctactggga cccccagcagc   1500 ggcggcctgg gctacggcgc cagctacggc agactgagca cgacagcag cctgtacagc   1560 aacctgggca ccagagtgct ggtgcccagc acctacgacg acctgagcca gagcagaggc   1620
```

```
ggctaccacg acgcctacag cctgccccag agcgccacca ccggcaccct gagcctgtgg   1680
agcagaaacc ccttcgagca gttcatcgtg gccgagagaa acggcgccgt gggcgacgac   1740
ctgaagaacc acacccagcc catcaacatc gacaaccaga tcagctgcaa cgtggacgcc   1800
gaggccaccc tggtgcagag cttcagacac tgcggcctga agctgggcaa gctggacggc   1860
agcgagtggc tgttcctgaa cagcgagggc gtggaggagg agctgatcga ccacgtggcc   1920
ggcagagaga agtacatgtt cgacgccgag gccagagaca tgcagcaggt gggccacatg   1980
ggcgagcccc tgatcagcac cgtgccccag tgcggcgacg gctgcctgtg gagagccgac   2040
ctgatcgtgt gcttcggcgt gtggtgcgcc cacaaggtgc tggacctgag cctgatcgag   2100
agcagacccg agctgtgggg cagatacacc tacatgatca acagactgca gggcgtggtg   2160
gacccggcct tcagcaagct gagaaccccc atgaccccca gcttctgcct gcagggcccc   2220
gccagccaca acagagccac ccccaccagc ctgaacggcg ccctgccccc cgccgccaag   2280
cccctgcacg gcaagtgcac caccgccgtg accctgctgg acctgatcag agacgtggag   2340
gtggccggca gcaccaagaa gggcagaacc ggcagcgccg ccggcgacgt ggcctggccc   2400
aagatgagag agaacatggc cagcgtgctg agaagataca agaagagt gagcaacaag   2460 cccatcggca tgaacaacga cggccccggc agcaagaagc aggtgaccgc ctacggcagc   2520
ctgggc                                                             2526

<210> SEQ ID NO 14
<211> LENGTH: 842
<212> TYPE: PRT
<213> ORGANISM: Artificial Sequence
<220> FEATURE:
<223> OTHER INFORMATION: Amino acid sequence EIN2, variant 2

<400> SEQUENCE: 14

Met Leu Trp Leu Ala Ala Thr Pro Leu Lys Ser Ala Ser Asn Arg Ala
1               5                   10                  15

Glu Ala Gln Ile Trp Asn Met Asp Ala Gln Asn Ala Leu Ser Tyr Pro
            20                  25                  30

Ser Val Gln Glu Asp Glu Ile Glu Arg Thr Asp Thr Arg Arg Gln Asp
        35                  40                  45

Asp Asp Ser Ile Gly Arg Leu Glu Ser Arg Val Arg Glu Asn Leu Glu
    50                  55                  60

Ser Cys Ser Ala Thr Ser Ser Gly Phe Asp Leu Pro Glu Asn Ile Ile
65                  70                  75                  80

Met Cys Asp Asn Glu Gly Arg Ser Ser Pro Glu Glu Arg Glu Leu
                85                  90                  95

Glu Val Lys Tyr Ser Thr Thr Asn Val Cys Ser Leu Lys Glu Asp Ser
            100                 105                 110

Asp Val Lys Glu Gln Ser Val Ile Gln Ser Thr Val Leu Gln Glu Ile
        115                 120                 125

Ser Glu Lys Asp Leu Ile Val Glu Cys Lys Met Ala Lys Ala Glu Pro
    130                 135                 140

Ile Ser Pro Val Glu Lys Ile Met Cys Met Glu Asn Asn Ser Lys Phe
145                 150                 155                 160

Leu Asp His Glu Val Glu Val Ser Trp Glu Thr Glu Glu Ala Thr
                165                 170                 175

Arg Val Val Pro Ser Ser Gln Phe Thr Ile Gly Ser Asp Gly Pro Pro
            180                 185                 190
```

-continued

```
Ser Phe Arg Ser Leu Cys Val Glu Gly Gly Ser Gly Ser Leu
            195                 200             205

Thr Arg Leu Asn Val Leu Gly Lys Met Ala Arg Lys Leu Ser Ala
    210                 215                 220

Ile Ile Asp Glu Phe Tyr Ala His Leu Phe Asp Phe His Ile Gln Leu
225                 230                 235                 240

Val Ala Asp Ala Arg Gly His Lys Leu Asp Gln Gly Phe Val Cys Asp
                245                 250                 255

Gln Arg Ser Ala Ser Ser Gly Lys Ala Asp Ser Phe Gly Lys Glu Ile
            260                 265                 270

Thr Ser Gly Tyr Thr Met Cys Pro Thr Met Lys Ala Met Asp Ser Asn
            275                 280                 285

Met Thr Ser Cys Leu Phe Asp Ser Leu Lys Gln Asn Arg Thr Pro Leu
    290                 295                 300

Ser Ile Asp Ser Leu Trp Ala Leu Gln Arg Leu Thr Ser Pro Ser Pro
305                 310                 315                 320

Val Met Asn Arg Met Asn Gly Met Val Val Phe Gly Asn Ser Thr Asn
                325                 330                 335

Gln Asn Asn Ala Phe Glu Leu Thr Asp Arg Arg Phe Cys Ser Leu Arg
            340                 345                 350

Ala Pro Thr Ser Ser Glu Gly Tyr Glu His Gln Gln Pro Gly Thr Val
            355                 360                 365

His Gly Phe Gln Met Lys Ser Trp Gly Asp Asn Ala Ala Lys Glu Arg
            370                 375                 380

Val Glu Ala Leu Asn Cys Arg Met Glu Gly Pro Thr Cys His Cys Met
385                 390                 395                 400

Ala Leu Gly Cys Leu Ser Tyr Ser Gln Asn Leu Ala Gly Ala Leu Lys
                405                 410                 415

Gln Lys Ser Gln Asn Gly Leu Thr Pro Gly Pro Ala Pro Gly Phe Glu
            420                 425                 430

Asn Trp Val Val Ser Lys Ser Ile Thr Arg Gln Ser Glu Arg Ser Tyr
            435                 440                 445

Tyr Ala Val Pro Thr Ser Ile Asn Thr Asp Thr Val Gly Ala Ala Val
    450                 455                 460

Ala Asn Glu Lys Lys Phe Ser Ser Met Pro Asp Ile Thr Gly Leu Ser
465                 470                 475                 480

Met Ser Ala Arg Asn Val His Ile Pro Gln Asn Lys Ser Gly Tyr Trp
                485                 490                 495

Asp Pro Ser Ser Gly Gly Leu Gly Tyr Gly Ala Ser Tyr Gly Arg Leu
            500                 505                 510

Ser Asn Asp Ser Ser Leu Tyr Ser Asn Leu Gly Thr Arg Val Leu Val
            515                 520                 525

Pro Ser Thr Tyr Asp Asp Leu Ser Gln Ser Arg Gly Gly Tyr His Asp
    530                 535                 540

Ala Tyr Ser Leu Pro Gln Ser Ala Thr Thr Gly Thr Leu Ser Leu Trp
545                 550                 555                 560

Ser Arg Asn Pro Phe Glu Gln Phe Ile Val Ala Glu Arg Asn Gly Ala
                565                 570                 575

Val Gly Asp Asp Leu Lys Asn His Thr Gln Pro Ile Asn Ile Asp Asn
            580                 585                 590

Gln Ile Ser Cys Asn Val Asp Ala Glu Ala His Leu Val Gln Ser Phe
            595                 600                 605

Arg His Cys Gly Leu Lys Leu Gly Lys Leu Asp Gly Ser Glu Trp Leu
```

Phe Leu Asn Ser Glu Gly Val Glu Glu Leu Ile Asp His Val Ala
625                 630                 635                 640

Gly Arg Glu Lys Tyr Met Phe Asp Ala Glu Arg Asp Met Gln Gln
            645                 650                 655

Val Gly His Met Gly Glu Pro Leu Ile Ser Thr Val Pro Gln Cys Gly
        660                 665                 670

Asp Gly Cys Leu Trp Arg Ala Asp Leu Ile Val Cys Phe Gly Val Trp
            675                 680                 685

Cys Ala His Lys Val Leu Asp Leu Ser Leu Ile Glu Ser Arg Pro Glu
        690                 695                 700

Leu Trp Gly Arg Tyr Thr Tyr Met Ile Asn Arg Leu Gln Gly Val Val
705                 710                 715                 720

Asp Pro Ala Phe Ser Lys Leu Arg Thr Pro Met Thr Pro Ser Phe Cys
            725                 730                 735

Leu Gln Gly Pro Ala Ser His Asn Arg Ala Thr Pro Thr Ser Leu Asn
            740                 745                 750

Gly Ala Leu Pro Pro Ala Ala Lys Pro Leu His Gly Lys Cys Thr Thr
            755                 760                 765

Ala Val Thr Leu Leu Asp Leu Ile Arg Asp Val Glu Val Ala Gly Ser
        770                 775                 780

Thr Lys Lys Gly Arg Thr Gly Ser Ala Ala Gly Asp Val Ala Trp Pro
785                 790                 795                 800

Lys Met Arg Glu Asn Met Ala Ser Val Leu Arg Arg Tyr Arg Arg
            805                 810                 815

Val Ser Asn Lys Pro Ile Gly Met Asn Asn Asp Gly Pro Gly Ser Lys
            820                 825                 830

Lys Gln Val Thr Ala Tyr Gly Ser Leu Gly
            835                 840

<210> SEQ ID NO 15
<211> LENGTH: 2526
<212> TYPE: DNA
<213> ORGANISM: Artificial Sequence
<220> FEATURE:
<221> NAME/KEY: source
<222> LOCATION: 1..2526
<223> OTHER INFORMATION: /organism="Artificial Sequence"
    /note="Nucleotide sequence EIN2, variant 3"
    /mol_type="unassigned DNA"

<400> SEQUENCE: 15
atgctgtggc tggccgccac ccccctgaag agcgccagca acagagccga ggcccagatc      60
tggaacatgg acgcccagaa cgccctgagc tacccccagcg tgaacgacga ggagatcgac    120
agaagcgaga ccaagagaaa cgaggacgag agcatcatga gactggagag cagagtgaag    180
gagcagctgg agaccaccag cgtgaccacc agcgtgtacg acctgcccga gaacatcgtg    240
ggcaccgagc aggacatcag aaccagcccc cccgaggaga gagagctgga ggtgaagtac    300
agcaccagcc aggtgaccag cctgcacgag gacagcgacg ccacgagca gtgcgtgctg    360 cagaccaccg tgatccagga gggcagcgag agagacctgc tggtggagac caaggtggcc    420
aagatcgagc ccatgagccc cggcgagaga atcgccagca tggacaacca gagcagattc    480
atcgacagag aggtggaggt ggtgagctgg gagaccgagg acgcctgcaa gatcgccccc    540
accagccagt tcagcggcgg cagcgacggc cccccagct tcagaagcct gagcggcgac    600
ggcggcagcg gctgcggcag cctgtgcaga ctgcagggcc tgggccacgc cgccagaaga    660

```
cacatcagcg ccggcctgga ggagttctgg ggccacctgt acgacttcca cggccagctg    720
gtgctggagg ccagaatcag aaagctggac caggtgtacg gcaccgacca gcacagcgcc    780
agcagcatgc acatggagag cttcggcaag gacatcagct gcggcttctg catgagcccc    840
accgccaagg gcatggacag ccagatgagc agcagcctgt acgacagcgg caagcagcag    900 cacaccccg gcagcatcga caccctgtac ggcctgcaga gaggcagcag ccccagcccc    960
ctggccaaca gatgcagat ggtgggcgcc tacggcaaca gcagccagaa caacaacatg   1020
tacgagctga gcgagagaag atacagcagc ctgaaggccc ccagcaccag cgacctgtgg   1080
gagcacaacc agcccgccac cgtgcacggc taccagggca gagctacgg cgacaacctg   1140 gccagagaga gactggaggc cctgcagagc aagatggaga tccccaccag caagagcgtg   1200
ctgctgggct gcctgagcta cacccagcag ctggccctgg ccctgaagca aagagccag   1260 aacggcctga ccccggccc cgccccggc ttcgagaact cgccggcag cagaagcgcc   1320 agcagaaaca gcgacagaag ctactacgtg gtgcccacct gcggcaacac cgacaccgtg   1380
ggcgccgccg tggcccagga agaagtgg agcagcatgc ccgacatcag catgctgagc   1440
atgaccatga gaaacatgca catccccaac aacaagagcg gctactggga ccccagcagc   1500
ggcggcgccg gctacggcgc cagctacggc agactgagca cgagagctg cctgtactgc   1560 cagctgggct gcagagtggg cgtgcccagc acctgggacg acatcagcca gagcagaggc   1620
ctgtacagag acgcctactg catgcccag tgcgccacca ccggcagcct gagcatctac   1680
agcagaaacc ccttcgagaa cttcggcgcc gccgagagaa acggcgccgt gggcgaggag   1740
ctgagaaaca gaagcaaccc cggcaacatc gagaacaacg cctgctgcaa cctggacatg   1800
gaggccagac tgctgaactg cttccaccac tgcatcctga gctgatcca cgtggagggc   1860 tgcgagtggc tgttcggcca gagcgacggc ggcgacgagg agctgatcga gagagtggcc   1920
gccaaggaca agttcatcta cgaggccgag gccagagaga tcaaccagct gggccacatg   1980
ggcgagcccc tggtgagcag cctgcccaac tgcggcgacg gctgcgtgtg gagagccgag   2040
ctggccgtga gcttcggcgt gtggagcatc cacagagtgg tggagggcag cctgctggag   2100
agcagacccg agctgtacgg caagtactgc tacatcctga cagactgca gggcgtgatc   2160 gaccccgcct tcaccaagat cagaaccccc atgaccccct gcttctgcct gcagatcccc   2220
gccagccacc agagagccag ccccaccacc gccaacggca tgctgccccc cgccgccaga   2280
cccgccaagg ccaagtgcac caccgccctg accggcctgg acctggccaa ggaggtggag   2340
atggccatca gctgcaagaa gggcaagagc ggcaccgccg ccggcgacgt ggccttcccc   2400
agagtgaagg agcagctgct gagcgtgctg aagaagtaca agagacacct gagcaacaag   2460
cccgtgggca tgaaccagga cggccccggc agcagaaaga acgtgaccgc ctacggcacc   2520
ctgggc                                                                 2526
```

<210> SEQ ID NO 16
<211> LENGTH: 842
<212> TYPE: PRT
<213> ORGANISM: Artificial Sequence
<220> FEATURE:
<223> OTHER INFORMATION: Amino acid sequence EIN2, variant 3

<400> SEQUENCE: 16

Met Leu Trp Leu Ala Ala Thr Pro Leu Lys Ser Ala Ser Asn Arg Ala
1               5                   10                  15

Glu Ala Gln Ile Trp Asn Met Asp Ala Gln Asn Ala Leu Ser Tyr Pro

```
             20                  25                  30
Ser Val Asn Asp Glu Glu Ile Asp Arg Ser Glu Thr Lys Arg Asn Glu
             35                  40                  45
Asp Glu Ser Ile Met Arg Leu Glu Ser Arg Val Lys Glu Gln Leu Glu
             50                  55                  60
Thr Thr Ser Val Thr Thr Ser Val Tyr Asp Leu Pro Glu Asn Ile Val
 65                  70                  75                  80
Gly Thr Glu Gln Asp Ile Arg Thr Ser Pro Pro Glu Glu Arg Glu Leu
                 85                  90                  95
Glu Val Lys Tyr Ser Thr Ser Gln Val Thr Ser Leu His Glu Asp Ser
                100                 105                 110
Asp Gly His Glu Gln Cys Val Leu Gln Thr Thr Val Ile Gln Glu Gly
                115                 120                 125
Ser Glu Arg Asp Leu Leu Val Glu Thr Lys Val Ala Lys Ile Glu Pro
                130                 135                 140
Met Ser Pro Gly Glu Arg Ile Ala Ser Met Asp Asn Gln Ser Arg Phe
145                 150                 155                 160
Ile Asp Arg Glu Val Glu Val Ser Trp Glu Thr Glu Asp Ala Cys
                165                 170                 175
Lys Ile Ala Pro Thr Ser Gln Phe Ser Gly Ser Asp Gly Pro Pro
                180                 185                 190
Ser Phe Arg Ser Leu Ser Gly Asp Gly Gly Ser Gly Cys Gly Ser Leu
                195                 200                 205
Cys Arg Leu Gln Gly Leu Gly His Ala Ala Arg Arg His Ile Ser Ala
                210                 215                 220
Gly Leu Glu Glu Phe Trp Gly His Leu Tyr Asp Phe His Gly Gln Leu
225                 230                 235                 240
Val Leu Glu Ala Arg Ile Arg Lys Leu Asp Gln Val Tyr Gly Thr Asp
                245                 250                 255
Gln His Ser Ala Ser Ser Met His Met Glu Ser Phe Gly Lys Asp Ile
                260                 265                 270
Ser Cys Gly Phe Cys Met Ser Pro Thr Ala Lys Gly Met Asp Ser Gln
                275                 280                 285
Met Ser Ser Ser Leu Tyr Asp Ser Gly Lys Gln Gln His Thr Pro Gly
                290                 295                 300
Ser Ile Asp Thr Leu Tyr Gly Leu Gln Arg Gly Ser Ser Pro Ser Pro
305                 310                 315                 320
Leu Ala Asn Lys Met Gln Met Val Gly Ala Tyr Gly Asn Ser Ser Gln
                325                 330                 335
Asn Asn Asn Met Tyr Glu Leu Ser Glu Arg Arg Tyr Ser Ser Leu Lys
                340                 345                 350
Ala Pro Ser Thr Ser Asp Leu Trp Glu His Asn Gln Pro Ala Thr Val
                355                 360                 365
His Gly Tyr Gln Gly Lys Ser Tyr Gly Asp Asn Leu Ala Arg Glu Arg
                370                 375                 380
Leu Glu Ala Leu Gln Ser Lys Met Glu Ile Pro Thr Ser Lys Ser Val
385                 390                 395                 400
Leu Leu Gly Cys Leu Ser Tyr Thr Gln Gln Leu Ala Leu Ala Leu Lys
                405                 410                 415
Gln Lys Ser Gln Asn Gly Leu Thr Pro Gly Pro Ala Pro Gly Phe Glu
                420                 425                 430
Asn Phe Ala Gly Ser Arg Ser Ala Ser Arg Asn Ser Asp Arg Ser Tyr
                435                 440                 445
```

Tyr Val Val Pro Thr Cys Gly Asn Thr Asp Thr Val Gly Ala Ala Val
450                 455                 460

Ala Gln Glu Lys Lys Trp Ser Ser Met Pro Asp Ile Ser Met Leu Ser
465                 470                 475                 480

Met Thr Met Arg Asn Met His Ile Pro Asn Asn Lys Ser Gly Tyr Trp
        485                 490                 495

Asp Pro Ser Ser Gly Ala Gly Tyr Gly Ala Ser Tyr Gly Arg Leu
            500                 505                 510

Ser Asn Glu Ser Cys Leu Tyr Cys Gln Leu Gly Cys Arg Val Gly Val
            515                 520                 525

Pro Ser Thr Trp Asp Asp Ile Ser Gln Ser Arg Gly Leu Tyr Arg Asp
    530                 535                 540

Ala Tyr Cys Met Pro Gln Cys Ala Thr Thr Gly Ser Leu Ser Ile Tyr
545                 550                 555                 560

Ser Arg Asn Pro Phe Glu Asn Phe Gly Ala Ala Glu Arg Asn Gly Ala
                565                 570                 575

Val Gly Glu Glu Leu Arg Asn Arg Ser Asn Pro Gly Asn Ile Glu Asn
                580                 585                 590

Asn Ala Cys Cys Asn Leu Asp Met Glu Ala Arg Leu Leu Asn Cys Phe
            595                 600                 605

His His Cys Ile Leu Lys Leu Ile His Val Glu Gly Cys Glu Trp Leu
    610                 615                 620

Phe Gly Gln Ser Asp Gly Gly Asp Glu Glu Leu Ile Glu Arg Val Ala
625                 630                 635                 640

Ala Lys Asp Lys Phe Ile Tyr Glu Ala Glu Ala Arg Glu Ile Asn Gln
                645                 650                 655

Leu Gly His Met Gly Glu Pro Leu Val Ser Ser Leu Pro Asn Cys Gly
            660                 665                 670

Asp Gly Cys Val Trp Arg Ala Glu Leu Ala Val Ser Phe Gly Val Trp
        675                 680                 685

Ser Ile His Arg Val Val Glu Gly Ser Leu Leu Glu Ser Arg Pro Glu
690                 695                 700

Leu Tyr Gly Lys Tyr Cys Tyr Ile Leu Asn Arg Leu Gln Gly Val Ile
705                 710                 715                 720

Asp Pro Ala Phe Thr Lys Ile Arg Thr Pro Met Thr Pro Cys Phe Cys
                725                 730                 735

Leu Gln Ile Pro Ala Ser His Gln Arg Ala Ser Pro Thr Thr Ala Asn
                740                 745                 750

Gly Met Leu Pro Pro Ala Ala Arg Pro Ala Lys Ala Lys Cys Thr Thr
            755                 760                 765

Ala Leu Thr Gly Leu Asp Leu Ala Lys Glu Val Glu Met Ala Ile Ser
770                 775                 780

Cys Lys Lys Gly Lys Ser Gly Thr Ala Ala Gly Asp Val Ala Phe Pro
785                 790                 795                 800

Arg Val Lys Glu Gln Leu Leu Ser Val Leu Lys Lys Tyr Lys Arg His
                805                 810                 815

Leu Ser Asn Lys Pro Val Gly Met Asn Gln Asp Gly Pro Gly Ser Arg
            820                 825                 830

Lys Asn Val Thr Ala Tyr Gly Thr Leu Gly
            835                 840

<210> SEQ ID NO 17
<211> LENGTH: 2526

```
<212> TYPE: DNA
<213> ORGANISM: Artificial Sequence
<220> FEATURE:
<221> NAME/KEY: source
<222> LOCATION: 1..2526
<223> OTHER INFORMATION: /organism="Artificial Sequence"
      /note="Nucleotide sequence EIN2, variant 4"
      /mol_type="unassigned DNA"

<400> SEQUENCE: 17
atgctgtggc tggccgccac cccectgaag agcgccagca acagagccga ggcccagatc    60
tggaacatgg acgcccagaa cgccctgagc ttccccagcg cccaggagga ggagatcgag   120
cacaccgaga cccacagaaa cgacgacgag agcatcgtga gactggacag cagagtgaag   180
gaccagctgg acaccaccag cgtgaccagc agcgtgtacg acctgcccga gaacatcctg   240
atgaccgacc aggagatcag aagcagcccc cccgaggaca gagacatcga cgtgaagtac   300
agcaccaccc agggcagcag cctgcacgag gacagcgacg tgaaggagaa ctgcatgctg   360
cagagcaccg tggtgaacga ggccagcgac aaggacctgg tggtggagac caagatggcc   420
aagatcgagc ccatgtgccc cgtggagaag atcgccagca tggagaacaa cagcaagttc   480
atcgagagag acgtggaggg cgtgagctgg agaccgagg agctgaccag agccgccccc   540
accagcaact ggaccgtggc cagcgacggc ccccccagct ccacagccct gagcggcgag   600
ggcggcagcg gcaccggcag cctgagcaga ctgcaggtgc tgggcaaggc cgccagaaga   660
cacctgagcg ccatcctgga cgagttctgg ggccacgtgt acgagtacca cggccagatc   720
gtggccgagg ccagagccag aagaatcgac cagctgttcg gcaccgacca gaagagcgcc   780
agcagcatga aggccgacag cttcggcaga gacatcagca cggctactg catgagcccc   840 accgccaagg gcatggacag ccagatgtgc agcagcctgt acgacagcct gaagcagaac   900
agaacccccg gcagcatcga cagcatcttc ggcggcaaca gaggcagcag ccccagcccc   960
ctggtgaaca gaatgcaggt gctgggcgcc tacggcaaca ccacccagaa caacaacgcc  1020
tacgaggcca gcgaccacca ctacagcagc ctgagagccc cagcaccag cgagggctgg  1080 gagaagcagc agcccgccac cgtgcacggc taccagggca gagctacgt ggacaacctg  1140 gcccacgaga gactggaggc cgtgcagagc agagccgaga tccccagcag cagatgcatg  1200
atcctgggca ccctgagcta cacccagaac ggcggcatcg ccctgaagca gcacagccag  1260
aacggcgtga cccccggccc cgcccccggc ttcgagaact cgccatgag cagaaccatc  1320 agcagacaga gcgagaagag cttctacggc gtgcccagca gcggcaacac cgacaccgtg  1380
ggcgccgccg tggtgaacga agaagtac agcagcatgc ccgacatctg catcctgagc  1440
atgagcgcca gaaacatgca cctgcccaac aacaagaccg gctactggga ccccagcagc  1500
ggcggcggcg gctacggcgc cagctacggc agaatgagca cgagagcag cctgttcagc  1560 cagctgggca gcagagtggg catgcccagc acctacgagg acatcagcca gtgcagaggc  1620
ggctaccacg acgcctacag cctgcccag agcgccacca ccggcaccgg cagcctgtgg  1680
agcagacagc ccttcgagca gttcggcatc gccgagagaa cggcgccgt gggcgaggag  1740 ctgagaaaca gtgcaaccc catcaacatc gaccagaacg ccagcagcca ggtggacgcc  1800
gaggccagac tgctgcagag cttcagacac tgcatcctga gatcatcaa gctggacctg  1860 agcgagtgga tcttcatcca gagcgacggc gtggacgagg agctgggcga cagagtggcc  1920
gccagagaga agttcatcta cgaggccgac atgaaggaga tccagcaggt gggccacatg  1980
ggcgacccca tgatcagcag cgtgccccag tgcggcgacg gctgcgtgtg gaaggtggag  2040
```

```
ctgatcgtgt gcttcggcgg ctggtgcatc cacagagtgc tggacctgag cctgatggag    2100
agcagacccg agctgtgggg caagtacacc tacgtgctga acagactgca gggcctgatc    2160
gaccccgcct tcagcaagct gcacaccccc atgacccccca gcttctgcct gaacatcccc    2220
```

```
ctgatcgtgt gcttcggcgg ctggtgcatc cacagagtgc tggacctgag cctgatggag    2100
agcagacccg agctgtgggg caagtacacc tacgtgctga acagactgca gggcctgatc    2160
gaccccgcct tcagcaagct gcacaccccc atgacccccca gcttctgcct gaacatcccc    2220
gccagccacc agagagcctg ccccaccagc gccaacggca tgctgccccc catggccaag    2280
cccgccaagg gcaagagcac caccgccatg accctgctgg acggcatcaa ggaggtggag    2340
atggccatca gctgcagaaa gggcagaacc ggcaccgccg ccggcgacgt ggcctggccc    2400
aaggccaagg agcagctggc ctgcgtgctg aagagatgga agagacacct gagcaacaag    2460
cccgtgggca tgaaccagga cggccccctg tgcagaaaga acgtgaccgg ctacggcagc    2520
ctgggc                                                                2526
```

<210> SEQ ID NO 18
<211> LENGTH: 842
<212> TYPE: PRT
<213> ORGANISM: Artificial Sequence
<220> FEATURE:
<223> OTHER INFORMATION: Amino acid sequence EIN2, variant 4

<400> SEQUENCE: 18

```
Met Leu Trp Leu Ala Ala Thr Pro Leu Lys Ser Ala Ser Asn Arg Ala
1               5                   10                  15

Glu Ala Gln Ile Trp Asn Met Asp Ala Gln Asn Ala Leu Ser Phe Pro
            20                  25                  30

Ser Ala Gln Glu Glu Ile Glu His Thr Glu Thr His Arg Asn Asp
        35                  40                  45

Asp Glu Ser Ile Val Arg Leu Asp Ser Arg Val Lys Asp Gln Leu Asp
    50                  55                  60

Thr Thr Ser Val Thr Ser Ser Val Tyr Asp Leu Pro Glu Asn Ile Leu
65                  70                  75                  80

Met Thr Asp Gln Glu Ile Arg Ser Ser Pro Pro Glu Asp Arg Asp Ile
                85                  90                  95

Asp Val Lys Tyr Ser Thr Thr Gln Gly Ser Ser Leu His Glu Asp Ser
            100                 105                 110

Asp Val Lys Glu Asn Cys Met Leu Gln Ser Thr Val Val Asn Glu Ala
        115                 120                 125

Ser Asp Lys Asp Leu Val Val Glu Thr Lys Met Ala Lys Ile Glu Pro
    130                 135                 140

Met Cys Pro Val Glu Lys Ile Ala Ser Met Glu Asn Asn Ser Lys Phe
145                 150                 155                 160

Ile Glu Arg Asp Val Glu Gly Val Ser Trp Glu Thr Glu Glu Leu Thr
                165                 170                 175

Arg Ala Ala Pro Thr Ser Asn Trp Thr Val Ala Ser Asp Gly Pro Pro
            180                 185                 190

Ser Phe His Ser Leu Ser Gly Glu Gly Gly Ser Gly Thr Gly Ser Leu
        195                 200                 205

Ser Arg Leu Gln Val Leu Gly Lys Ala Ala Arg His Leu Ser Ala
    210                 215                 220

Ile Leu Asp Glu Phe Trp Gly His Val Tyr Glu Tyr His Gly Gln Ile
225                 230                 235                 240

Val Ala Glu Ala Arg Ala Arg Arg Ile Asp Gln Leu Phe Gly Thr Asp
                245                 250                 255

Gln Lys Ser Ala Ser Ser Met Lys Ala Asp Ser Phe Gly Arg Asp Ile
            260                 265                 270
```

```
Ser Ser Gly Tyr Cys Met Ser Pro Thr Ala Lys Gly Met Asp Ser Gln
        275                 280                 285

Met Cys Ser Ser Leu Tyr Asp Ser Leu Lys Gln Asn Arg Thr Pro Gly
    290                 295                 300

Ser Ile Asp Ser Ile Phe Gly Gly Asn Arg Gly Ser Ser Pro Ser Pro
305                 310                 315                 320

Leu Val Asn Arg Met Gln Val Leu Gly Ala Tyr Gly Asn Thr Thr Gln
                325                 330                 335

Asn Asn Asn Ala Tyr Glu Ala Ser Asp His His Tyr Ser Ser Leu Arg
            340                 345                 350

Ala Pro Ser Thr Ser Glu Gly Trp Glu Lys Gln Gln Pro Ala Thr Val
        355                 360                 365

His Gly Tyr Gln Gly Lys Ser Tyr Val Asp Asn Leu Ala His Glu Arg
    370                 375                 380

Leu Glu Ala Val Gln Ser Arg Ala Glu Ile Pro Ser Ser Arg Cys Met
385                 390                 395                 400

Ile Leu Gly Thr Leu Ser Tyr Thr Gln Asn Gly Gly Ile Ala Leu Lys
                405                 410                 415

Gln His Ser Gln Asn Gly Val Thr Pro Gly Pro Ala Pro Gly Phe Glu
            420                 425                 430

Asn Phe Ala Met Ser Arg Thr Ile Ser Arg Gln Ser Glu Lys Ser Phe
        435                 440                 445

Tyr Gly Val Pro Ser Ser Gly Asn Thr Asp Thr Val Gly Ala Ala Val
    450                 455                 460

Val Asn Glu Lys Lys Tyr Ser Ser Met Pro Asp Ile Cys Ile Leu Ser
465                 470                 475                 480

Met Ser Ala Arg Asn Met His Leu Pro Asn Asn Lys Thr Gly Tyr Trp
                485                 490                 495

Asp Pro Ser Ser Gly Gly Gly Tyr Gly Ala Ser Tyr Gly Arg Met
            500                 505                 510

Ser Asn Glu Ser Ser Leu Phe Ser Gln Leu Gly Ser Arg Val Gly Met
        515                 520                 525

Pro Ser Thr Tyr Glu Asp Ile Ser Gln Cys Arg Gly Gly Tyr His Asp
    530                 535                 540

Ala Tyr Ser Leu Pro Gln Ser Ala Thr Thr Gly Thr Gly Ser Leu Trp
545                 550                 555                 560

Ser Arg Gln Pro Phe Glu Gln Phe Gly Ile Ala Glu Arg Asn Gly Ala
                565                 570                 575

Val Gly Glu Glu Leu Arg Asn Lys Cys Asn Pro Ile Asn Ile Asp Gln
            580                 585                 590

Asn Ala Ser Ser Gln Val Asp Ala Glu Ala Arg Leu Leu Gln Ser Phe
        595                 600                 605

Arg His Cys Ile Leu Lys Ile Ile Lys Leu Asp Leu Ser Glu Trp Ile
    610                 615                 620

Phe Ile Gln Ser Asp Gly Val Asp Glu Glu Leu Gly Asp Arg Val Ala
625                 630                 635                 640

Ala Arg Glu Lys Phe Ile Tyr Glu Ala Asp Met Lys Glu Ile Gln Gln
                645                 650                 655

Val Gly His Met Gly Asp Pro Met Ile Ser Ser Val Pro Gln Cys Gly
            660                 665                 670

Asp Gly Cys Val Trp Lys Val Glu Leu Ile Val Cys Phe Gly Gly Trp
        675                 680                 685

Cys Ile His Arg Val Leu Asp Leu Ser Leu Met Glu Ser Arg Pro Glu
```

```
                690               695               700
Leu Trp Gly Lys Tyr Thr Tyr Val Leu Asn Arg Leu Gln Gly Leu Ile
705                 710                 715                 720

Asp Pro Ala Phe Ser Lys Leu His Thr Pro Met Thr Pro Ser Phe Cys
                725                 730                 735

Leu Asn Ile Pro Ala Ser His Gln Arg Ala Cys Pro Thr Ser Ala Asn
                740                 745                 750

Gly Met Leu Pro Pro Met Ala Lys Pro Ala Lys Gly Lys Ser Thr Thr
            755                 760                 765

Ala Met Thr Leu Leu Asp Gly Ile Lys Glu Val Glu Met Ala Ile Ser
770                 775                 780

Cys Arg Lys Gly Arg Thr Gly Thr Ala Ala Gly Asp Val Ala Trp Pro
785                 790                 795                 800

Lys Ala Lys Glu Gln Leu Ala Cys Val Leu Lys Arg Trp Lys Arg His
                805                 810                 815

Leu Ser Asn Lys Pro Val Gly Met Asn Gln Asp Gly Pro Leu Cys Arg
            820                 825                 830

Lys Asn Val Thr Gly Tyr Gly Ser Leu Gly
            835                 840

<210> SEQ ID NO 19
<211> LENGTH: 2526
<212> TYPE: DNA
<213> ORGANISM: Artificial Sequence
<220> FEATURE:
<221> NAME/KEY: source
<222> LOCATION: 1..2526
<223> OTHER INFORMATION: /organism="Artificial Sequence"
      /note="Nucleotide sequence EIN2, variant 5"
      /mol_type="unassigned DNA"

<400> SEQUENCE: 19
atgctgtggc tggccgccac ccccctgaag agcgccagca acagagccga ggcccagatc      60
tggaacatgg acgcccagca ggccctgagc taccccagcg tgcaggacga ggagatcgag     120
agaaccgaga ccagaagaca ggaggacgag agcatcgtga gactggagag cagagtgaag     180
gaccagctgg acaccagcag cgtgaccagc agcgtgtacg agctgcccga gaacatcctg     240
atgaccgacc aggagatcaa gagctgcccc ccgaggaga gagagctgga cgtgaagtac      300
agcaccagcc aggtgagcag cctgaaggac gacagcgacg tgaaggagca gagcgtgctg     360
aacagcacca tcgtgaacga ggtgagcgac agagacctga tcgtggagac cagaatggcc     420
aagatcgagc ccatgagccc cgtggagaag atcgtgagca tggagaacaa cagcaagttc     480
atcgacaagg acgtggaggg cgtgagctac gactgcgagg aggccaccaa ggccgccccc     540
accagcaact tcaccgtggg cagcgacgtg cccccagct tcagaaccct gagcggcgac     600
ggcggcagcg gcaccggcag cctgagcaga ctgcagatcc tgctgagagg cgccagaaga     660
aagctgagcg ccatcctgga cgagttctgg ggccacctgt acgacttcca cggccagctg     720
gtggccgagg ccagagccaa gaagctggac cagatcttcg gctgcgacca agagagcgcc     780
agcagcatga aggccgacag cttcggcaag gacatcagca gcggctactg catgagcccc     840
accgtgaagg gcatggacag ccagatgacc agcagcctgt acgacagcct gaagcagcag     900 agaaccccccg gcagcatcga cagcatctgg ggcctgcaga aggcagcag cccagccc      960 atcgtgaaca gaatgcagat cctgggcgcc tacggcaaca ccaccaacaa caaccaggcc    1020
tacgagctga gcgagagaag atacagcagc ctgaaggccc ccagcagcag cgagggcttc    1080
```

```
gagagacagc agcccgccag cggccacggc taccagatga agagcttcgt ggagaacctg    1140
gccaaggaga agctggacgc cctgcagagc agaggcgaga tccccaccag cagaagcatg    1200
gccctgggca ccggctgcta ctgccagcag ctggccctgg ccctgaagca aagagccag     1260 aacggcctga ccccggccc cgccccggc tacgagaact cgccggcag cagaagcatc       1320 agcagacaga gcgagagaag ctacttcggc gtgcccagca gcggcaactg cgacagcgtg    1380
ggcgccgccg tggccaacga gaagcactac agcagcatgc ccgacatcag cggcctgagc    1440
atgagcgcca gaaacatgca cctgcccaac aacaagagcg cctactggga ccccagcagc   1500
gtgggcggcg gctacggcgc cagctacggc aagctgagca cgagagcag cctgtacagc     1560 aacctgggca gcagagtggg cgtgcccagc acctacgacg acatcagcca gaccagaggc    1620
ggctacagag acgcctggag cctgcccag agcgccacca ccggcaccgg cagcctgtgg     1680
agcagacagc ccttcgagca gtggggcgtg gccgagagaa acggcgccgt gggcgaggac    1740
ctgagaaaca gaagcaaccc catcaacatc gacaacaacg ccagcagcaa cgtggacgcc    1800
gaggccaagc tgctgcagag ctacagaaag tgcatcctga agctgatcaa gctggagggc    1860
agcgagtacc tgttcggcca gagcgacggc gtggacgagg agctgatcga cagagtggcc    1920
ctgagagaga agttcatcta cgagctggag gccagagaga tcaaccaggt gggccacatg    1980
ggcgagcccc tggccagcac cgtgcccaac tgcggcgacg gctgcgtgtg gagagtggac    2040
ctgatcgtga gcttcggcgt gtggtgcatc cacagagtgc tggacggcag cgccatggag    2100
agcagacccg acctgtgggg caagtacacc tacgtgctga acagactgca gatggtgatc    2160
gaccccgcct tcagcaagct gagaaccccc gccaccccct gcttctgcct gcagatcccc    2220
gccagccacc agagagtgag ccccaccagc gccaacggca tgctgccccc cggcgccaag    2280
cccgccaagg gcaagtgcac cagcgccgtg accctgctgg acatgatcaa ggacgtggag    2340
atggccatca gcagccacaa gggcagatgc ggcagcgccg ccggcgacgt ggcctggccc    2400
aagggcaagg agaacctggc cagcgtgctg aagagatacc acagaagact gagcaacaga    2460
cccgtgggca tgaaccagga cggcccctg agcagaaaga acgtgaccgc ctacctgagc     2520
ctgggc                                                              2526
```

<210> SEQ ID NO 20
<211> LENGTH: 842
<212> TYPE: PRT
<213> ORGANISM: Artificial Sequence
<220> FEATURE:
<223> OTHER INFORMATION: Amino acid sequence EIN2, variant 5

<400> SEQUENCE: 20

```
Met Leu Trp Leu Ala Ala Thr Pro Leu Lys Ser Ala Ser Asn Arg Ala
1               5                   10                  15

Glu Ala Gln Ile Trp Asn Met Asp Ala Gln Gln Ala Leu Ser Tyr Pro
            20                  25                  30

Ser Val Gln Asp Glu Glu Ile Glu Arg Thr Glu Thr Arg Arg Gln Glu
        35                  40                  45

Asp Glu Ser Ile Val Arg Leu Glu Ser Arg Val Lys Asp Gln Leu Asp
    50                  55                  60

Thr Ser Ser Val Thr Ser Ser Val Tyr Glu Leu Pro Glu Asn Ile Leu
65                  70                  75                  80

Met Thr Asp Gln Glu Ile Lys Ser Cys Pro Pro Glu Glu Arg Glu Leu
                85                  90                  95

Asp Val Lys Tyr Ser Thr Ser Gln Val Ser Ser Leu Lys Asp Asp Ser
```

```
                100                 105                 110
Asp Val Lys Glu Gln Ser Val Leu Asn Ser Thr Ile Val Asn Glu Val
            115                 120                 125

Ser Asp Arg Asp Leu Ile Val Glu Thr Arg Met Ala Lys Ile Glu Pro
130                 135                 140

Met Ser Pro Val Glu Lys Ile Val Ser Met Glu Asn Asn Ser Lys Phe
145                 150                 155                 160

Ile Asp Lys Asp Val Glu Gly Val Ser Tyr Asp Cys Glu Glu Ala Thr
            165                 170                 175

Lys Ala Ala Pro Thr Ser Asn Phe Thr Val Gly Ser Asp Val Pro Pro
            180                 185                 190

Ser Phe Arg Thr Leu Ser Gly Asp Gly Gly Ser Gly Thr Gly Ser Leu
            195                 200                 205

Ser Arg Leu Gln Ile Leu Leu Arg Gly Ala Arg Arg Lys Leu Ser Ala
            210                 215                 220

Ile Leu Asp Glu Phe Trp Gly His Leu Tyr Asp Phe His Gly Gln Leu
225                 230                 235                 240

Val Ala Glu Ala Arg Ala Lys Lys Leu Asp Gln Ile Phe Gly Cys Asp
                245                 250                 255

Gln Lys Ser Ala Ser Ser Met Lys Ala Asp Ser Phe Gly Lys Asp Ile
            260                 265                 270

Ser Ser Gly Tyr Cys Met Ser Pro Thr Val Lys Gly Met Asp Ser Gln
            275                 280                 285

Met Thr Ser Ser Leu Tyr Asp Ser Leu Lys Gln Gln Arg Thr Pro Gly
            290                 295                 300

Ser Ile Asp Ser Ile Trp Gly Leu Gln Arg Gly Ser Ser Pro Ser Pro
305                 310                 315                 320

Ile Val Asn Arg Met Gln Ile Leu Gly Ala Tyr Gly Asn Thr Thr Asn
                325                 330                 335

Asn Asn Gln Ala Tyr Glu Leu Ser Glu Arg Arg Tyr Ser Ser Leu Lys
            340                 345                 350

Ala Pro Ser Ser Ser Glu Gly Phe Glu Arg Gln Gln Pro Ala Ser Gly
            355                 360                 365

His Gly Tyr Gln Met Lys Ser Phe Val Glu Asn Leu Ala Lys Glu Lys
            370                 375                 380

Leu Asp Ala Leu Gln Ser Arg Gly Glu Ile Pro Thr Ser Arg Ser Met
385                 390                 395                 400

Ala Leu Gly Thr Gly Cys Tyr Cys Gln Gln Leu Ala Leu Ala Leu Lys
                405                 410                 415

Gln Lys Ser Gln Asn Gly Leu Thr Pro Gly Pro Ala Pro Gly Tyr Glu
            420                 425                 430

Asn Phe Ala Gly Ser Arg Ser Ile Ser Arg Gln Ser Glu Arg Ser Tyr
            435                 440                 445

Phe Gly Val Pro Ser Ser Gly Asn Cys Asp Ser Val Gly Ala Ala Val
            450                 455                 460

Ala Asn Glu Lys His Tyr Ser Met Pro Asp Ile Ser Gly Leu Ser
465                 470                 475                 480

Met Ser Ala Arg Asn Met His Leu Pro Asn Asn Lys Ser Ala Tyr Trp
                485                 490                 495

Asp Pro Ser Ser Val Gly Gly Tyr Gly Ala Ser Tyr Gly Lys Leu
            500                 505                 510

Ser Asn Glu Ser Ser Leu Tyr Ser Asn Leu Gly Ser Arg Val Gly Val
            515                 520                 525
```

Pro Ser Thr Tyr Asp Asp Ile Ser Gln Thr Arg Gly Gly Tyr Arg Asp
            530                 535                 540

Ala Trp Ser Leu Pro Gln Ser Ala Thr Thr Gly Thr Gly Ser Leu Trp
545                 550                 555                 560

Ser Arg Gln Pro Phe Glu Gln Trp Gly Val Ala Glu Arg Asn Gly Ala
                565                 570                 575

Val Gly Glu Asp Leu Arg Asn Arg Ser Asn Pro Ile Asn Ile Asp Asn
            580                 585                 590

Asn Ala Ser Ser Asn Val Asp Ala Glu Ala Lys Leu Leu Gln Ser Tyr
        595                 600                 605

Arg Lys Cys Ile Leu Lys Leu Ile Lys Leu Glu Gly Ser Glu Tyr Leu
    610                 615                 620

Phe Gly Gln Ser Asp Gly Val Asp Glu Glu Leu Ile Asp Arg Val Ala
625                 630                 635                 640

Leu Arg Glu Lys Phe Ile Tyr Glu Leu Glu Ala Arg Glu Ile Asn Gln
                645                 650                 655

Val Gly His Met Gly Glu Pro Leu Ala Ser Thr Val Pro Asn Cys Gly
            660                 665                 670

Asp Gly Cys Val Trp Arg Val Asp Leu Ile Val Ser Phe Gly Val Trp
        675                 680                 685

Cys Ile His Arg Val Leu Asp Gly Ser Ala Met Glu Ser Arg Pro Asp
    690                 695                 700

Leu Trp Gly Lys Tyr Thr Tyr Val Leu Asn Arg Leu Gln Met Val Ile
705                 710                 715                 720

Asp Pro Ala Phe Ser Lys Leu Arg Thr Pro Ala Thr Pro Cys Phe Cys
                725                 730                 735

Leu Gln Ile Pro Ala Ser His Gln Arg Val Ser Pro Thr Ser Ala Asn
            740                 745                 750

Gly Met Leu Pro Pro Gly Ala Lys Pro Ala Lys Gly Lys Cys Thr Ser
        755                 760                 765

Ala Val Thr Leu Leu Asp Met Ile Lys Asp Val Glu Met Ala Ile Ser
    770                 775                 780

Ser His Lys Gly Arg Cys Gly Ser Ala Ala Gly Asp Val Ala Trp Pro
785                 790                 795                 800

Lys Gly Lys Glu Asn Leu Ala Ser Val Leu Lys Arg Tyr His Arg Arg
                805                 810                 815

Leu Ser Asn Arg Pro Val Gly Met Asn Gln Asp Gly Pro Leu Ser Arg
            820                 825                 830

Lys Asn Val Thr Ala Tyr Leu Ser Leu Gly
        835                 840

<210> SEQ ID NO 21
<211> LENGTH: 2526
<212> TYPE: DNA
<213> ORGANISM: Artificial Sequence
<220> FEATURE:
<221> NAME/KEY: source
<222> LOCATION: 1..2526
<223> OTHER INFORMATION: /organism="Artificial Sequence"
      /note="Nucleotide sequence EIN2, variant 6"
      /mol_type="unassigned DNA"

<400> SEQUENCE: 21
atgctgtggc tggccgccac ccccctgaag agcgccagca acagagccga ggcccagatc    60
tggaacatgg acgcccagaa cgccctgagc taccccagcg tgcaggagga ggagatcgac   120

```
agatgcgaga ccagaaagaa cgaggacgag agcatcgtga gactggacag ccacgtgaag      180
gaccagctgg acaccaccag cgtgaccagc agcgtgtacg acctgcccga gaacatcctg      240
atgaccgacc aggagatcag aagcagcccc cccgaggaga aggagctgga cgtgaagtac      300
agcaccagcc aggtgagcag cctgaaggag acagcgagg tgaaggagca gagcgtgctg       360
cagaccaccg tggtgaacga ggtgagcgac aaggacctga tcgtggacac caagatggcc      420
aagatcgagc ccatgagccc cgtggagaag atcgtgagca tggacaacaa cagcaagttc      480
atcgagagag acgtggaggg cgtgagctgg acaccgagg aggccaccaa ggccgccccc       540
accagcaact tcaccgtggg cagcgacggc cccccagct tcagaagcat ctgcggcgag       600
ctgggcagcg gcaccggcag cgtgagcaga ctgcagggcc tgggcagagc cggcagaaga      660
cacctgagcc tgatcctgga cgagttctgg ggccacctgt acgactggca cggccagctg      720
gtggccgagg ccagagccaa gaagctggac cagctgttcg gctgcgacca gaagagcgcc      780
agcagcggca aggccgacag cttcggcaag gacatcagca gcggctactg catgagcccc      840
accatcaagg gcatggacag ccagatcacc agcagcctgt acgacagcct gagacagcag      900 aagaccccg gcagcatcga cagcctgtac ggcctgcaga gaggcagcag ccccagcccc       960
ctggtgaaca gactgcagat gctgggcgcc tacggcaaca cctgcaacaa caacaacgcc     1020
tacgacctga gcgagagaag atacagcagc ctgagagccc ccagcagcag cgagggctgg     1080
gagcaccagc agcccgccac cgtgaagggc taccagatga gagctacgt ggacaacctg      1140 gccaaggaga gactggaggc cctgcagacc agaggcgaga tccccaccag cagaagcatg     1200
gccctgggca ccctgagcta cacccagaac ctggccctgg ccctgaagca aagagccag     1260 aacatgctga ccccccggccc cgccccggc ttcgagaact tcatcggcag cagaagcatc     1320
agcagacaga gcgagagaag ctactacggc gtgcccagca ccgcaacac cgacaccatg     1380 ggcgccgccg tggccaacga agaagtac agcagcatgc ccgacatcag cggcctgacc      1440
atgagcgcca gaaacatgca cctgcccaac aacaagagcg ctactggga ccccagcagc     1500 ggcggcggcg gctacggcgc cagctacggc aagctgagca cgagagcac cctgtacagc     1560 aacctgggca gcaaggtggg cgtgcccagc acctacgacg acatcagcca gagcagggc      1620 ggctacagag acgcctggac cctgcccag agcgccacca ccggcaccgg cacctgtgg     1680 agcagacagc ccttcgagca gttcggcgtg gccgagagaa acggcgccgt gggcgaggag     1740
ctgagaaaca gaagcaaccc catcaacatc gacaacaacg ccagcagcaa cgtggacgcc     1800
gaggtgaagc tgctgcagag cttcagacac tgcatcctga agctgatcaa gctggacggc     1860
agcgagtggg gcttcggcca gagcgacctg gtggacgagg agctgatcga cagagtggcc     1920
gccagagaga agttcatcta cgaggccgag gccagagaga tcaaccaggt gggccacggc     1980
ggcgagcccc tgatcagcac cgtgcccaac tgcggcgacg gctgcgtgtg gagagccgac     2040
ctgatcgtga gcttcggcgt gtggagcatc acagagtgc tggagctgag cctgatggac     2100
agcagacccg agctgtgggg caagtggacc tacgtgctgc agagactgca gggcgtgatc     2160
gaccccgcct ggagcaagct gagaaccccc atgacccccct gctggtgcct gcagatcccc     2220
gccagccaca cagagccag ccccaccacc gccaacggca tgctgccccc cgccgccaag     2280
cccgccaagg gcaagtgcac caccatcgtg accctgctgg acatcatcaa ggacgtggag     2340
atggccatca gcaccagaaa ggccagaacc ggctgcgccg ccggcgacgt ggccttcccc     2400
aagggccacg agaacctggc cagcgtgctg aagagataca agaagagact gagcaacaag     2460
cccgtgggca tgaaccagga cggccccggc agcagaaaga acgtgaccgc ctacatcagc     2520
```

```
                                                                   ctgggc                                                                2526
```

\<210\> SEQ ID NO 22
\<211\> LENGTH: 842
\<212\> TYPE: PRT
\<213\> ORGANISM: Artificial Sequence
\<220\> FEATURE:
\<223\> OTHER INFORMATION: Amino acid sequence EIN2, variant 6

\<400\> SEQUENCE: 22

```
Met Leu Trp Leu Ala Ala Thr Pro Leu Lys Ser Ala Ser Asn Arg Ala
1               5                   10                  15

Glu Ala Gln Ile Trp Asn Met Asp Ala Gln Asn Ala Leu Ser Tyr Pro
            20                  25                  30

Ser Val Gln Glu Glu Ile Asp Arg Cys Glu Thr Arg Lys Asn Glu
        35                  40                  45

Asp Glu Ser Ile Val Arg Leu Asp Ser His Val Lys Asp Gln Leu Asp
    50                  55                  60

Thr Thr Ser Val Thr Ser Ser Val Tyr Asp Leu Pro Glu Asn Ile Leu
65                  70                  75                  80

Met Thr Asp Gln Glu Ile Arg Ser Ser Pro Pro Glu Glu Lys Glu Leu
                85                  90                  95

Asp Val Lys Tyr Ser Thr Ser Gln Val Ser Ser Leu Lys Glu Asp Ser
            100                 105                 110

Glu Val Lys Glu Gln Ser Val Leu Gln Thr Thr Val Asn Glu Val
        115                 120                 125

Ser Asp Lys Asp Leu Ile Val Asp Thr Lys Met Ala Lys Ile Glu Pro
    130                 135                 140

Met Ser Pro Val Glu Lys Ile Val Ser Met Asp Asn Asn Ser Lys Phe
145                 150                 155                 160

Ile Glu Arg Asp Val Glu Gly Val Ser Trp Asp Thr Glu Glu Ala Thr
                165                 170                 175

Lys Ala Ala Pro Thr Ser Asn Phe Thr Val Gly Ser Asp Gly Pro Pro
            180                 185                 190

Ser Phe Arg Ser Ile Cys Gly Glu Leu Gly Ser Gly Thr Gly Ser Val
        195                 200                 205

Ser Arg Leu Gln Gly Leu Gly Arg Ala Gly Arg Arg His Leu Ser Leu
    210                 215                 220

Ile Leu Asp Glu Phe Trp Gly His Leu Tyr Asp Trp His Gly Gln Leu
225                 230                 235                 240

Val Ala Glu Ala Arg Ala Lys Lys Leu Asp Gln Leu Phe Gly Cys Asp
                245                 250                 255

Gln Lys Ser Ala Ser Ser Gly Lys Ala Asp Ser Phe Gly Lys Asp Ile
            260                 265                 270

Ser Ser Gly Tyr Cys Met Ser Pro Thr Ile Lys Gly Met Asp Ser Gln
        275                 280                 285

Ile Thr Ser Ser Leu Tyr Asp Ser Leu Arg Gln Gln Lys Thr Pro Gly
    290                 295                 300

Ser Ile Asp Ser Leu Tyr Gly Leu Gln Arg Gly Ser Ser Pro Ser Pro
305                 310                 315                 320

Leu Val Asn Arg Leu Gln Met Leu Gly Ala Tyr Gly Asn Thr Cys Asn
                325                 330                 335

Asn Asn Asn Ala Tyr Asp Leu Ser Glu Arg Arg Tyr Ser Ser Leu Arg
            340                 345                 350
```

```
Ala Pro Ser Ser Ser Glu Gly Trp Glu His Gln Gln Pro Ala Thr Val
            355                 360                 365

Lys Gly Tyr Gln Met Lys Ser Tyr Val Asp Asn Leu Ala Lys Glu Arg
370                 375                 380

Leu Glu Ala Leu Gln Thr Arg Gly Glu Ile Pro Thr Ser Arg Ser Met
385                 390                 395                 400

Ala Leu Gly Thr Leu Ser Tyr Thr Gln Asn Leu Ala Leu Ala Leu Lys
                405                 410                 415

Gln Lys Ser Gln Asn Met Leu Thr Gly Pro Ala Pro Gly Phe Glu
            420                 425                 430

Asn Phe Ile Gly Ser Arg Ser Ile Ser Arg Gln Ser Glu Arg Ser Tyr
            435                 440                 445

Tyr Gly Val Pro Ser Thr Gly Asn Thr Asp Thr Met Gly Ala Ala Val
        450                 455                 460

Ala Asn Glu Lys Lys Tyr Ser Ser Met Pro Asp Ile Ser Gly Leu Thr
465                 470                 475                 480

Met Ser Ala Arg Asn Met His Leu Pro Asn Asn Lys Ser Gly Tyr Trp
            485                 490                 495

Asp Pro Ser Ser Gly Gly Gly Tyr Gly Ala Ser Tyr Gly Lys Leu
            500                 505                 510

Ser Asn Glu Ser Thr Leu Tyr Ser Asn Leu Gly Ser Lys Val Gly Val
        515                 520                 525

Pro Ser Thr Tyr Asp Asp Ile Ser Gln Ser Arg Gly Gly Tyr Arg Asp
        530                 535                 540

Ala Trp Thr Leu Pro Gln Ser Ala Thr Thr Gly Thr Gly Thr Leu Trp
545                 550                 555                 560

Ser Arg Gln Pro Phe Glu Gln Phe Gly Val Ala Glu Arg Asn Gly Ala
                565                 570                 575

Val Gly Glu Glu Leu Arg Asn Arg Ser Asn Pro Ile Asn Ile Asp Asn
            580                 585                 590

Asn Ala Ser Ser Asn Val Asp Ala Glu Val Lys Leu Leu Gln Ser Phe
        595                 600                 605

Arg His Cys Ile Leu Lys Leu Ile Lys Leu Asp Gly Ser Glu Trp Gly
    610                 615                 620

Phe Gly Gln Ser Asp Leu Val Asp Glu Glu Leu Ile Asp Arg Val Ala
625                 630                 635                 640

Ala Arg Glu Lys Phe Ile Tyr Glu Ala Glu Arg Glu Ile Asn Gln
                645                 650                 655

Val Gly His Gly Gly Glu Pro Leu Ile Ser Thr Val Pro Asn Cys Gly
            660                 665                 670

Asp Gly Cys Val Trp Arg Ala Asp Leu Ile Val Ser Phe Gly Val Trp
        675                 680                 685

Ser Ile His Arg Val Leu Glu Leu Ser Leu Met Asp Ser Arg Pro Glu
    690                 695                 700

Leu Trp Gly Lys Trp Thr Tyr Val Leu Gln Arg Leu Gln Gly Val Ile
705                 710                 715                 720

Asp Pro Ala Trp Ser Lys Leu Arg Thr Pro Met Thr Pro Cys Trp Cys
                725                 730                 735

Leu Gln Ile Pro Ala Ser His Asn Arg Ala Ser Pro Thr Thr Ala Asn
            740                 745                 750

Gly Met Leu Pro Pro Ala Ala Lys Pro Ala Lys Gly Lys Cys Thr Thr
        755                 760                 765

Ile Val Thr Leu Leu Asp Ile Ile Lys Asp Val Glu Met Ala Ile Ser
```

```
                770             775             780
Thr Arg Lys Ala Arg Thr Gly Cys Ala Ala Gly Asp Val Ala Phe Pro
785                 790             795                 800

Lys Gly His Glu Asn Leu Ala Ser Val Leu Lys Arg Tyr Lys Lys Arg
            805                 810                 815

Leu Ser Asn Lys Pro Val Gly Met Asn Gln Asp Gly Pro Gly Ser Arg
            820                 825             830

Lys Asn Val Thr Ala Tyr Ile Ser Leu Gly
            835                 840

<210> SEQ ID NO 23
<211> LENGTH: 2526
<212> TYPE: DNA
<213> ORGANISM: Artificial Sequence
<220> FEATURE:
<221> NAME/KEY: source
<222> LOCATION: 1..2526
<223> OTHER INFORMATION: /organism="Artificial Sequence"
      /note="Nucleotide sequence EIN2, variant 7"
      /mol_type="unassigned DNA"

<400> SEQUENCE: 23
atgctgtggc tggccgccac cccctgaag agcgccagca acagagccga ggcccagatc      60
tggaacatgg acgcccagaa cgccctgagc taccccagcg tgcaggagga ggagatcgag    120
agaaccgaga ccagaagaaa cgaggacgag agcatcgtga actggagag cagagtgaag    180 gaccagctgg acaccaccag cgtgaccagc agcgtgtacg acctgcccga gaacatcctg    240
atgaccgacc aggagatcag aaccagcccc cccgaggaga gagctgga cgtgaagtac      300 agcaccagcc aggtgagcag cctgaaggag gacagcgacg tgaaggagca gagcgtgctg    360
cagagcaccg tggtgaacga ggtgagcgac aaggacctga tcctggagac caagatggcc    420
aagatcgagc ccatgagccc cgtggagaag atcgtgagca tggagaacaa cagcaagttc    480
atcgagaagg acgtggaggg cgtgagctgg agaccgagg aggccaccaa gccgccccc     540 accagcaact tcaccgtggg cagcgacggc ccccccagct tcagaagcct gagcggcgag    600
ggcggcagcg gcaccggcag cctgagcaga atccagggca tgggcagagc cgccagaaga    660
cacctgagcg ccatcctgga ggagttctgg ggccacctgt acgacttcca cggccagctg    720
gtggccgacg ccagagccaa gaaggccgac cagctgttcg gcaccgacca agagcgcc     780 agcagcatga aggccgacag cttcatcaag gacatcagca gcggctactg catgagcccc    840
accgccaagg gcatggacag ccagatgacc agcagcctgt acgacagcct gagacagcag    900 agaaccccg gcagcatcga cagcctgtac ggcctgcaga gaggcagcag ccccagcccc    960
ctggtgaaca gaatgcagat gctgggcgcc tacggccaga ccaccaacaa caacaacggc   1020
ttcgagctga gcgacagaag atacagcagc ctgagagccc cagcagcag cgagggctgg    1080 gagcaccagc agcccgcctg cgtgcacggc tggcagatga agtgctacgt ggacaacctg   1140
gccaaggaga gactggaggc cctgcagagc agaggcgaga tccccaccag caagagcatg   1200
gccctgggca ccctgagcta cacccagcag ctggccctgg ccctgaagca agagagccag   1260 caggggcctga ccccggccc cggccccggc ttcgagaact cgccggcag cagaagcatc    1320 agcagacaga gcgagagaag ctactacggc gtgcccagca gcggcaacac cgacaccgtg    1380
ggcgccctgg tggccaacga gaagaagtac agcagcatgc ccgacgtgag cggcctgagc    1440
atgagcgcca gaaacatgca cctgcccaac aacaagagcg cctactacga cccccagcag    1500
ggcggcggcg gctacggcgc cagctacggc agactgagca acgagagcag cctgtacagc    1560
```

```
aacctgggca gcagagtggg cgtgcccagc acctacgacg acatcagcaa cagcagaggc    1620
ggctacagag acgcctggag cctgcccag agcgccacca ccggcaccgg cagcctgtgg     1680
agcagacagc ccttcgagca gttcggcgtg ccgagagaa acggcgccgt gggcgaggag    1740
gcccacaaca gaagcaaccc catcaacatc gacaacaacg ccagcaccaa cgtggacgcc    1800
gaggccaagc tgctgcagag cttcagaaga tgcatcctga agctgatcaa gctggagggc    1860
agcgagttcc tgttcggcca gagcgacggc gtggacgagg agctgatcga cagagtggcc    1920
ggcagagaga agttcatcta cgaggccgag gccagagaga tcaaccaggt gggccacatg    1980
ggcgagcccc tgatcagcag cgtgcccaac tgcggcgagg gctgcatgtg gagagccgac    2040
ctgatcgtga gcttcggcgt gtggtgcatc cacagagtgc tggacctgag cctgatggag    2100
agcagacccg agctgtgggg caagtacacc tacgtgctga acagactgca gggcgtgatc    2160
gaccccgcct tcagcagact gagaaccccc atgaccccct gcttctgcct gcagatcccc    2220
gccagccacc agagagccag ccccaccagc gccaacggca tgctgccccc cgccgccaag    2280
cccgccaagg gcaagtgcac caccgccggc accctgctgg acctgatcaa ggacgtggac    2340
atggccatca gcaccagaaa gggcagaacc ggcaccgccg ccggcgaggt ggccttcccc    2400
cacatcaagg agaacctgat cagcgtgctg aagagataca agaagact gagcaacaag    2460 cccatgggca tgaaccagga cggcccatc agcagaaaga acgtgaccgc ctacggcagc    2520
ctgggc                                                               2526
```

<210> SEQ ID NO 24
<211> LENGTH: 842
<212> TYPE: PRT
<213> ORGANISM: Artificial Sequence
<220> FEATURE:
<223> OTHER INFORMATION: Amino acid sequence EIN2, variant 7

<400> SEQUENCE: 24

```
Met Leu Trp Leu Ala Ala Thr Pro Leu Lys Ser Ala Ser Asn Arg Ala
1               5                   10                  15

Glu Ala Gln Ile Trp Asn Met Asp Ala Gln Asn Ala Leu Ser Tyr Pro
            20                  25                  30

Ser Val Gln Glu Glu Ile Glu Arg Thr Glu Thr Arg Arg Asn Glu
        35                  40                  45

Asp Glu Ser Ile Val Arg Leu Glu Ser Arg Val Lys Asp Gln Leu Asp
    50                  55                  60

Thr Thr Ser Val Thr Ser Ser Val Tyr Asp Leu Pro Glu Asn Ile Leu
65                  70                  75                  80

Met Thr Asp Gln Glu Ile Arg Thr Ser Pro Pro Glu Glu Arg Glu Leu
                85                  90                  95

Asp Val Lys Tyr Ser Thr Ser Gln Val Ser Ser Leu Lys Glu Asp Ser
            100                 105                 110

Asp Val Lys Glu Gln Ser Val Leu Gln Ser Thr Val Val Asn Glu Val
        115                 120                 125

Ser Asp Lys Asp Leu Ile Leu Glu Thr Lys Met Ala Lys Ile Glu Pro
    130                 135                 140

Met Ser Pro Val Glu Lys Ile Val Ser Met Glu Asn Asn Ser Lys Phe
145                 150                 155                 160

Ile Glu Lys Asp Val Glu Gly Val Ser Trp Glu Thr Glu Glu Ala Thr
                165                 170                 175

Lys Ala Ala Pro Thr Ser Asn Phe Thr Val Gly Ser Asp Gly Pro Pro
```

```
                180                 185                 190
Ser Phe Arg Ser Leu Ser Gly Glu Gly Gly Ser Gly Thr Gly Ser Leu
            195                 200                 205

Ser Arg Ile Gln Gly Met Gly Arg Ala Ala Arg His Leu Ser Ala
    210                 215                 220

Ile Leu Glu Glu Phe Trp Gly His Leu Tyr Asp Phe His Gly Gln Leu
225                 230                 235                 240

Val Ala Asp Ala Arg Ala Lys Lys Ala Asp Gln Leu Phe Gly Thr Asp
                245                 250                 255

Gln Lys Ser Ala Ser Ser Met Lys Ala Asp Ser Phe Ile Lys Asp Ile
            260                 265                 270

Ser Ser Gly Tyr Cys Met Ser Pro Thr Ala Lys Gly Met Asp Ser Gln
        275                 280                 285

Met Thr Ser Ser Leu Tyr Asp Ser Leu Arg Gln Arg Thr Pro Gly
    290                 295                 300

Ser Ile Asp Ser Leu Tyr Gly Leu Gln Arg Gly Ser Pro Ser Pro
305                 310                 315                 320

Leu Val Asn Arg Met Gln Met Leu Gly Ala Tyr Gly Gln Thr Thr Asn
                325                 330                 335

Asn Asn Asn Gly Phe Glu Leu Ser Asp Arg Arg Tyr Ser Ser Leu Arg
            340                 345                 350

Ala Pro Ser Ser Ser Gly Trp Glu His Gln Gln Pro Ala Cys Val
        355                 360                 365

His Gly Trp Gln Met Lys Cys Tyr Val Asp Asn Leu Ala Lys Glu Arg
    370                 375                 380

Leu Glu Ala Leu Gln Ser Arg Gly Glu Ile Pro Thr Ser Lys Ser Met
385                 390                 395                 400

Ala Leu Gly Thr Leu Ser Tyr Thr Gln Gln Leu Ala Leu Ala Leu Lys
                405                 410                 415

Gln Lys Ser Gln Gln Gly Leu Thr Pro Gly Pro Gly Pro Gly Phe Glu
            420                 425                 430

Asn Phe Ala Gly Ser Arg Ser Ile Ser Arg Gln Ser Glu Arg Ser Tyr
        435                 440                 445

Tyr Gly Val Pro Ser Ser Gly Asn Thr Asp Thr Val Gly Ala Leu Val
    450                 455                 460

Ala Asn Glu Lys Lys Tyr Ser Ser Met Pro Asp Val Ser Gly Leu Ser
465                 470                 475                 480

Met Ser Ala Arg Asn Met His Leu Pro Asn Asn Lys Ser Gly Tyr Tyr
                485                 490                 495

Asp Pro Ser Ser Gly Gly Gly Tyr Gly Ala Ser Tyr Gly Arg Leu
            500                 505                 510

Ser Asn Glu Ser Ser Leu Tyr Ser Asn Leu Gly Ser Arg Val Gly Val
        515                 520                 525

Pro Ser Thr Tyr Asp Asp Ile Ser Asn Ser Arg Gly Gly Tyr Arg Asp
    530                 535                 540

Ala Trp Ser Leu Pro Gln Ser Ala Thr Thr Gly Thr Gly Ser Leu Trp
545                 550                 555                 560

Ser Arg Gln Pro Phe Glu Gln Phe Gly Val Ala Glu Arg Asn Gly Ala
                565                 570                 575

Val Gly Glu Glu Ala His Asn Arg Ser Asn Pro Ile Asn Ile Asp Asn
            580                 585                 590

Asn Ala Ser Thr Asn Val Asp Ala Glu Ala Lys Leu Leu Gln Ser Phe
        595                 600                 605
```

Arg Arg Cys Ile Leu Lys Leu Ile Lys Leu Glu Gly Ser Glu Phe Leu
                610                 615                 620

Phe Gly Gln Ser Asp Gly Val Asp Glu Glu Leu Ile Asp Arg Val Ala
625                 630                 635                 640

Gly Arg Glu Lys Phe Ile Tyr Glu Ala Glu Ala Arg Glu Ile Asn Gln
                645                 650                 655

Val Gly His Met Gly Glu Pro Leu Ile Ser Ser Val Pro Asn Cys Gly
                660                 665                 670

Glu Gly Cys Met Trp Arg Ala Asp Leu Ile Val Ser Phe Gly Val Trp
            675                 680                 685

Cys Ile His Arg Val Leu Asp Leu Ser Leu Met Glu Ser Arg Pro Glu
            690                 695                 700

Leu Trp Gly Lys Tyr Thr Tyr Val Leu Asn Arg Leu Gln Gly Val Ile
705                 710                 715                 720

Asp Pro Ala Phe Ser Arg Leu Arg Thr Pro Met Thr Pro Cys Phe Cys
                725                 730                 735

Leu Gln Ile Pro Ala Ser His Gln Arg Ala Ser Pro Thr Ser Ala Asn
                740                 745                 750

Gly Met Leu Pro Pro Ala Ala Lys Pro Ala Lys Gly Lys Cys Thr Thr
            755                 760                 765

Ala Gly Thr Leu Leu Asp Leu Ile Lys Asp Val Asp Met Ala Ile Ser
770                 775                 780

Thr Arg Lys Gly Arg Thr Gly Thr Ala Ala Gly Glu Val Ala Phe Pro
785                 790                 795                 800

His Ile Lys Glu Asn Leu Ile Ser Val Leu Lys Arg Tyr Lys Arg Arg
                805                 810                 815

Leu Ser Asn Lys Pro Met Gly Met Asn Gln Asp Gly Pro Ile Ser Arg
                820                 825                 830

Lys Asn Val Thr Ala Tyr Gly Ser Leu Gly
            835                 840

<210> SEQ ID NO 25
<211> LENGTH: 2526
<212> TYPE: DNA
<213> ORGANISM: Artificial Sequence
<220> FEATURE:
<221> NAME/KEY: source
<222> LOCATION: 1..2526
<223> OTHER INFORMATION: /organism="Artificial Sequence"
      /note="Nucleotide sequence EIN2, variant 8"
      /mol_type="unassigned DNA"

<400> SEQUENCE: 25
atgctgtggc tggccgccac ccccctgaag agcgccagca acagagccga ggcccagatc      60
tggaacatgg acgcccagaa cgccctgagc taccccagcg tgcaggagga ggagatcgag     120
agaaccgagt gcagaagaaa cgaggacgag agcatcgtga gactggagag cagagtgaag     180
gaccagctgg acaccaccag cgtgaccagc agcgtgtacg acctgcccga gaacatcctg     240
ctgaccgacc aggagatcag aagcagcccc ccgaggagag agagctgga cgtgaagtac     300 agcaccagcc aggtgagcag cctgaaggag gacagcgacg tgaaggagca gagcgtgctg     360
cagagcaccg gcgtgaacga ggtgagcgac aaggacctga tcgtggagtg caagatggcc     420
aagatcgagc ccatgagccc cgtggagaag atcgtgagca tggagaacaa cagcaagttc     480
atcgagaagg acgtggacgg cgtgagctgg gagaccgacg aggccaccaa ggccgccccc     540
accagcaact tcaccgtggg ctgcgacggc ccccccagct tcagaagcct gagcggcgag     600

| | | |
|---|---|---|
| ggcggcagcg gcaccggcag cctgagcaga ctgcagggcc tgggcagagc cgccagaaga | 660 | |
| cacctgagcg ccatcctgga cgagttctgg ggccacctgt acgacttcca cggccagctg | 720 | |
| gtggccgagg ccagagccaa gagactggac cagctgttcg gcaccgacca aagagcgcc | 780 | |
| agcagcatga aggccgacag cttcggcaag gacatcagca cggctactg catgagcccc | 840 | |
| accgccaagg gcatggacag ccagatgacc agcaccctgt acgacagcct gaagcagcag | 900 | |
| agaaccccg gcagcatcga cagcctgtac ggcctgcaga gaggcagcag ccccagcccc | 960 | |
| ctggtgaaca gaatgcagat gctgggcgcc tacggcaaca ccaccaacaa caacaacgcc | 1020 | |
| tacgagctga gcgagagaag atacagcagc ctgagcccc cagcagcag cgagggctgg | 1080 | |
| gagcaccagc agcccgccac cgtgcacggc taccagatga agtgctacgt ggacaacctg | 1140 | |
| gccaaggaga gactggagat gctgcagagc agaggcgaga tccccacctg cagaagcatg | 1200 | |
| gccctgggca ccctgagcta cacccagcag ctggccctgg ccctgagaca aagagccag | 1260 | |
| aacggcctga ccccggccc cgccccggc ttcgagaact cgccggcag cagaagcatc | 1320 | |
| agcagacaga gcgagagaag ctactacggc gtgcccagca gcggcaacac cgagaccgtg | 1380 | |
| ggcgccgccg tggccaacga gaagaagtac agcagcatgc ccgacatcag cggcctgagc | 1440 | |
| atgagcgcca gaaacatgca cctgcccaac cagaagagcg gctactggga ccccagcagc | 1500 | |
| ggcggcggcg gctacggcgc cagctacggc agactgagca cgagagcag cctgtacagc | 1560 | |
| aacctgggca gcagagtggg cgtgcccagc acctacgacg acatcagcca gagcagagtg | 1620 | |
| ggctacagag acgcctacag cctgcccag agcgccacca ccggcaccgg cagcctgtgg | 1680 | |
| agcagacagc ccttcgagca gttcggcgtg gccgagagaa acggcgccgt gggcgaggag | 1740 | |
| ctgagaaaca gaagcaaccc catcaacatc gagaaccagg ccagcagcaa cgtggacgtg | 1800 | |
| gaggccaagc tgctgcagag cttcagacac tgcatcctga gctgatcaa gctggagggc | 1860 | |
| agcgagtggc tgttcggcca gagcgacggc gtggacgagg agctgatcga cagagtggcc | 1920 | |
| gccagagaga agttcatcta cgaggccgag gccagagaga tcaaccaggt gggccacatg | 1980 | |
| ggcgagcccc tgatcagcag cgtgcccaac tgcggcgacg gctgcgtgtg gagagccgac | 2040 | |
| ctgatcgtga gcttcggcgt gtggtgcatc cacagagtgc tggacctgag cctgatggag | 2100 | |
| agcagaccg agctgtgggg caagtacacc tacgtgctga acagactgca gggcgtgatc | 2160 | |
| gaccccgcct ctgcaagct gagaaccccc atgacccct gcttctgcct gcagatcccc | 2220 | |
| gccagccacc agagagccag ccccaccagc gccaacggca tgctgccccc gccgccaga | 2280 | |
| cccgccaagg gcaagagcac caccgccgtg accctggtgg acctgatcaa ggacgtggag | 2340 | |
| atggccatca gctgcagaaa gggcagaacc ggcaccgccg ccggcgacgt ggccttcccc | 2400 | |
| aagggcaagg agaacctggc cagcgtgctg aagagataca agagaagact gagcaacaag | 2460 | |
| cccgtgggca tgaaccagga cggccccggc agcagaaaga acgtgaccgc ctacctgagc | 2520 | |
| ctgggc | 2526 | |

<210> SEQ ID NO 26
<211> LENGTH: 842
<212> TYPE: PRT
<213> ORGANISM: Artificial Sequence
<220> FEATURE:
<223> OTHER INFORMATION: Amino acid sequence EIN2, variant 8

<400> SEQUENCE: 26

Met Leu Trp Leu Ala Ala Thr Pro Leu Lys Ser Ala Ser Asn Arg Ala
1               5                   10                  15

```
Glu Ala Gln Ile Trp Asn Met Asp Ala Gln Asn Ala Leu Ser Tyr Pro
                20                  25                  30

Ser Val Gln Glu Glu Ile Glu Arg Thr Glu Cys Arg Arg Asn Glu
        35                  40                  45

Asp Glu Ser Ile Val Arg Leu Glu Ser Arg Val Lys Asp Gln Leu Asp
    50                  55                  60

Thr Thr Ser Val Thr Ser Ser Val Tyr Asp Leu Pro Glu Asn Ile Leu
65                  70                  75                  80

Leu Thr Asp Gln Glu Ile Arg Ser Ser Pro Pro Glu Glu Arg Glu Leu
                85                  90                  95

Asp Val Lys Tyr Ser Thr Ser Gln Val Ser Ser Leu Lys Glu Asp Ser
                100                 105                 110

Asp Val Lys Glu Gln Ser Val Leu Gln Ser Thr Gly Val Asn Glu Val
                115                 120                 125

Ser Asp Lys Asp Leu Ile Val Glu Cys Lys Met Ala Lys Ile Glu Pro
    130                 135                 140

Met Ser Pro Val Glu Lys Ile Val Ser Met Glu Asn Asn Ser Lys Phe
145                 150                 155                 160

Ile Glu Lys Asp Val Asp Gly Val Ser Trp Glu Thr Asp Glu Ala Thr
                165                 170                 175

Lys Ala Ala Pro Thr Ser Asn Phe Thr Val Gly Cys Asp Gly Pro Pro
                180                 185                 190

Ser Phe Arg Ser Leu Ser Gly Glu Gly Gly Ser Gly Thr Gly Ser Leu
            195                 200                 205

Ser Arg Leu Gln Gly Leu Gly Arg Ala Ala Arg Arg His Leu Ser Ala
            210                 215                 220

Ile Leu Asp Glu Phe Trp Gly His Leu Tyr Asp Phe His Gly Gln Leu
225                 230                 235                 240

Val Ala Glu Ala Arg Ala Lys Arg Leu Asp Gln Leu Phe Gly Thr Asp
                245                 250                 255

Gln Lys Ser Ala Ser Ser Met Lys Ala Asp Ser Phe Gly Lys Asp Ile
                260                 265                 270

Ser Ser Gly Tyr Cys Met Ser Pro Thr Ala Lys Gly Met Asp Ser Gln
            275                 280                 285

Met Thr Ser Thr Leu Tyr Asp Ser Leu Lys Gln Gln Arg Thr Pro Gly
            290                 295                 300

Ser Ile Asp Ser Leu Tyr Gly Leu Gln Arg Gly Ser Ser Pro Ser Pro
305                 310                 315                 320

Leu Val Asn Arg Met Gln Met Leu Gly Ala Tyr Gly Asn Thr Thr Asn
                325                 330                 335

Asn Asn Asn Ala Tyr Glu Leu Ser Glu Arg Arg Tyr Ser Ser Leu Arg
                340                 345                 350

Ala Pro Ser Ser Ser Glu Gly Trp Glu His Gln Gln Pro Ala Thr Val
            355                 360                 365

His Gly Tyr Gln Met Lys Cys Tyr Val Asp Asn Leu Ala Lys Glu Arg
            370                 375                 380

Leu Glu Met Leu Gln Ser Arg Gly Glu Ile Pro Thr Cys Arg Ser Met
385                 390                 395                 400

Ala Leu Gly Thr Leu Ser Tyr Thr Gln Gln Leu Ala Leu Ala Leu Arg
                405                 410                 415

Gln Lys Ser Gln Asn Gly Leu Thr Pro Gly Pro Ala Pro Gly Phe Glu
                420                 425                 430
```

```
Asn Phe Ala Gly Ser Arg Ser Ile Ser Arg Gln Ser Glu Arg Ser Tyr
            435                 440                 445

Tyr Gly Val Pro Ser Ser Gly Asn Thr Glu Thr Val Gly Ala Ala Val
450                 455                 460

Ala Asn Glu Lys Lys Tyr Ser Ser Met Pro Asp Ile Ser Gly Leu Ser
465                 470                 475                 480

Met Ser Ala Arg Asn Met His Leu Pro Asn Gln Lys Ser Gly Tyr Trp
            485                 490                 495

Asp Pro Ser Ser Gly Gly Gly Tyr Gly Ala Ser Tyr Gly Arg Leu
            500                 505                 510

Ser Asn Glu Ser Ser Leu Tyr Ser Asn Leu Gly Ser Arg Val Gly Val
            515                 520                 525

Pro Ser Thr Tyr Asp Asp Ile Ser Gln Ser Arg Val Gly Tyr Arg Asp
            530                 535                 540

Ala Tyr Ser Leu Pro Gln Ser Ala Thr Thr Gly Thr Gly Ser Leu Trp
545                 550                 555                 560

Ser Arg Gln Pro Phe Glu Gln Phe Gly Val Ala Glu Arg Asn Gly Ala
                565                 570                 575

Val Gly Glu Glu Leu Arg Asn Arg Ser Asn Pro Ile Asn Ile Glu Asn
            580                 585                 590

Gln Ala Ser Ser Asn Val Asp Val Glu Ala Lys Leu Leu Gln Ser Phe
            595                 600                 605

Arg His Cys Ile Leu Lys Leu Ile Lys Leu Glu Gly Ser Glu Trp Leu
            610                 615                 620

Phe Gly Gln Ser Asp Gly Val Asp Glu Glu Leu Ile Asp Arg Val Ala
625                 630                 635                 640

Ala Arg Glu Lys Phe Ile Tyr Glu Ala Glu Ala Arg Glu Ile Asn Gln
                645                 650                 655

Val Gly His Met Gly Glu Pro Leu Ile Ser Ser Val Pro Asn Cys Gly
            660                 665                 670

Asp Gly Cys Val Trp Arg Ala Asp Leu Ile Val Ser Phe Gly Val Trp
            675                 680                 685

Cys Ile His Arg Val Leu Asp Leu Ser Leu Met Glu Ser Arg Pro Glu
            690                 695                 700

Leu Trp Gly Lys Tyr Thr Tyr Val Leu Asn Arg Leu Gln Gly Val Ile
705                 710                 715                 720

Asp Pro Ala Phe Cys Lys Leu Arg Thr Pro Met Thr Pro Cys Phe Cys
                725                 730                 735

Leu Gln Ile Pro Ala Ser His Gln Arg Ala Ser Pro Thr Ser Ala Asn
            740                 745                 750

Gly Met Leu Pro Pro Ala Ala Arg Pro Ala Lys Gly Lys Ser Thr Thr
            755                 760                 765

Ala Val Thr Leu Val Asp Leu Ile Lys Asp Val Glu Met Ala Ile Ser
            770                 775                 780

Cys Arg Lys Gly Arg Thr Gly Thr Ala Ala Gly Asp Val Ala Phe Pro
785                 790                 795                 800

Lys Gly Lys Glu Asn Leu Ala Ser Val Leu Arg Tyr Lys Arg Arg
                805                 810                 815

Leu Ser Asn Lys Pro Val Gly Met Asn Gln Asp Gly Pro Gly Ser Arg
            820                 825                 830

Lys Asn Val Thr Ala Tyr Leu Ser Leu Gly
            835                 840
```

```
<210> SEQ ID NO 27
<211> LENGTH: 2529
<212> TYPE: DNA
<213> ORGANISM: Artificial Sequence
<220> FEATURE:
<221> NAME/KEY: source
<222> LOCATION: 1..2529
<223> OTHER INFORMATION: /organism="Artificial Sequence"
      /note="Nucleotide sequence EIN2, variant 9"
      /mol_type="unassigned DNA"

<400> SEQUENCE: 27
atgctttggc tggctgctac ccccatgaag tccgcgtcaa accgagctga ggcgcagatc      60
tggaatatgg acgcccagaa cgcattgtca taccctttctg tccaggagga agagatagag     120
cggactgaga ctcgccgtaa tgaggatgag agtatcgtgc gcatggagag tcgcgttaaa     180
gaccaaatgg acaccacatc agttacatcc agcgtatacg acatgcctga aaatatctta     240
atgacagacc aggagataag atcatctccc cccgaagagc gcgaattgga cgttaaatat     300
tcaacgtctc aggtatcctc gctcaaagag gattccgacg tgaaagagca atcagtgatg     360
caaagcacgg tagtgaacga agtaagcgac aaagacatga tcgtagagac caaaatggca     420
aagatcgagc ccatgtcccc tgtcgaaaaa atagtgagta tggaaaacaa ttccaaattc     480
atagagaaag acgtagaagg agtctcatgg gagactgagg aggcgacgaa ggcggcccca     540
accagtaatt tcacagttgg cagcgacggc cccccctctt ttcggtccct atctggcgag     600
ggaggtagcg aacggggtc tctgtcgaga atgcagggga tgggcagagc agcaagaagg     660
catctcagtg ctatactcga cgagttctgg gggcacttgt acgacttcca cggacagatg     720
gtcgcggagg cacgggctaa aaagttggac caactgttcg gcacagacca gaaaagcgcg     780
tcaagtatga aggctgactc gttcggtaag gatatatcgt ccggctactg tatgtcgcct     840
acggccaaag gcatggacag tcaaatgact agttccttgt acgactctat gaaacaacaa     900
cgtaccccag gtagcattga ctctatgtac ggcttgcagc gcggcagctc tccttctcct     960
atggtgaatc gaatgcaaat gatgggcgcg tacggaaata ctaccaacaa caacaacgcc    1020
tatgagatgt ccgaaaggcg ctattcgtca atgcgtgccc cgtctagctc tgaagggtgg    1080
gagcatcagc agccggcaac ggtccatggg tatcaaatga agtcgtacgt tgacaacatg    1140
gccaaggagc gtctggaggc gttacagagt aggggtgaaa tccccacgtc tcggtcgatg    1200
gctctcggaa cgatgtcgta cacgcaacag ttagccctcg caatgaagca aaaaagccaa    1260
aacgggttga ctccgggccc ggctcccggc ttcgaaaact cgccggttc acgatcgatc    1320 tctcgccaga gtgagcggag ctactatggg gtcccttcat cagggaacac agatacagtc    1380
ggagctgcgg ttgctaacga aaagaagtat tcctccatgc cagacataag tggcatgtca    1440
atgtctgcca gaaatatgca ccttccgaat aataaatccg ggtattggga cccgtcgtca    1500
gggggtggcg gatacggggc tagctacggc cgactgtcca acgagtcgtc actctacagc    1560
aatatgggtt cccgagtagg tgtgccaagt acctacgacg atatatccca gtctcgaggc    1620
ggataccgcg acgcgtattc tatgccgcaa tcagcgacaa cgggaacggg cagtctatgg    1680
agccgccaac ctttcgaaca attcggagtt gcagaacgta acggcgcggt aggggaagag    1740
ttgcgtaata ggtcaaaccc aatcaacatc gataataatg cgtcaagcaa cgtggacgcg    1800
gaagccaaac tcctacaatc ctttcggcat tgcatattga agctcataaa gctcgagggt    1860
tcggagtgga tgttcggtca gtcagacggt gtagacgagg agatgatcga tcgtgtggcg    1920
gccagggaaa aattcatata cgaggcagag gcacgagaga tcaatcaggt aggacatatg    1980
```

| | | |
|---|---|---|
| ggagaaccgc tcatctctag cgtcccaaat tgcggcgacg gatgtgtctg gcgtgccgat | 2040 |
| atgatcgtga gcttcggcgt ctggtgcata catcgagtgt tagatatgtc gctgatggaa | 2100 |
| tcccgtccgg aactatgggg caaatatacg tatgtgttga atagactgca aggggtcata | 2160 |
| gaccccgctt tttctaaaat gcggacgcct atgacgccat gtttctgtct tcaaattccc | 2220 |
| gcttcgcatc aaagggccag cccaaccagc gccaatggca tgttaccgcc cgcggcgaaa | 2280 |
| cctgccaagg ggaagtgtac tacggctgtt accctactgg atctcatcaa ggatgtagag | 2340 |
| atggctataa gctgccgaaa gggtcgaacg ggcaccgcag ccggagacgt tgcatttcca | 2400 |
| aaaggaaagg aaaacatggc aagcgtgatg aaacgataca agagaaggct gtcgaataag | 2460 |
| ccggttggaa tgaaccaaga cgggccaggc tcgaggaaga atgtcacggc ctatgggagc | 2520 |
| atggggtaa | 2529 |

<210> SEQ ID NO 28
<211> LENGTH: 2529
<212> TYPE: DNA
<213> ORGANISM: Artificial Sequence
<220> FEATURE:
<221> NAME/KEY: source
<222> LOCATION: 1..2529
<223> OTHER INFORMATION: /organism="Artificial Sequence"
    /note="Nucleotide sequence EIN2, variant 10"
    /mol_type="unassigned DNA"

<400> SEQUENCE: 28

| | | |
|---|---|---|
| atgctctgga tggcggcaac accaatgaaa agcgcttcca accgcgcaga ggcccagatt | 60 |
| tggaacatgg acgctcagaa tgctttgagc taccctagtg tacaggagga agagattgag | 120 |
| agaaccgaga caaggcggaa tgaggatgag tcgatcgttc ggatggagtc gagagtaaaa | 180 |
| gaccaaatgg acacgacatc ggtgacgtca agtgtgtacg acttgcctga aaacatccta | 240 |
| atgacggacc aagagatacg ttcgtccccg ccagaagagc gcgaaatgga tgttaagtac | 300 |
| tctacctccc aggtaagctc gctgaaagag gatagtgatg tcaaagagca gtccgtaatg | 360 |
| caatcgaccg ttgtaaacga ggtcagtgac aaagacatga ttgtggagac taaaatggca | 420 |
| aagatagaac cgatgtcccc agtcgaaaaa atcgtcagta tggaaaacaa ttcgaagttc | 480 |
| atagagaaag acgtcgaagg agtgagttgg agactgagg aggcgaccaa agccgcgcca | 540 |
| actagtaact tcaccgtggg ttctgacggg ccaccctcct ttcgatccct ctcaggggag | 600 |
| ggaggctctg gaaccggcag cctatcacga atgcagggca tggggcgtgc ggcaagacga | 660 |
| catctgtctg ccattcttga cgagttctgg ggacacctgt acgacttcca tggacagatg | 720 |
| gttgcggaag ctcgagccaa aaaactcgat cagatgtttg gtacagacca aagagcgca | 780 |
| tcctcgatga agctgactc gttcggtaag gatatatcaa gtggatactg tatgtctcca | 840 |
| acggcgaaag ggatggacag ccaaatgact tcgagcctat acgactctat gaaacagcaa | 900 |
| cgcaccccgg ggagtattga ttcgatgtat gggctacagc gagggtcgtc tccttcccct | 960 |
| ttggtgaatc gcatgcagat gatgggcgca tacggcaaca ccacaaacaa caacaacgct | 1020 |
| tatgagatgt ccgaacggag gtattcgtcg atgcgagcgc cgtctagctc agaaggatgg | 1080 |
| gagcatcagc agcccgccac tgtccacggg tatcagatga agtcttacgt cgataacatg | 1140 |
| gcaaaggagc gactggaggc cttgcagtcc cgaggtgaaa tccccacttc tagatcgatg | 1200 |
| gccctaggaa cgatgtcata cacacaacag ttggcgcttg cgatgaagca gaagagtcag | 1260 |
| aacggactga cgccaggccc cgctcctggc ttcgaaaact cgcgggatc gcggtctatc | 1320 |
| agccgccagt ctgagcgatc gtattacggt gtgccttcgt ctggcaacac ggataccgtt | 1380 |

```
ggggccgcgg tcgccaatga gaagaagtac tcttctatgc ctgacatatc aggcatgagt   1440
atgtccgcgc gcaatatgca cctgcctaat aataaatcag gatattggga cccatcttcg   1500
gggggaggcg gatacggggc aagctacggt cgtctgtcga atgagagctc tctgtactcc   1560
aacatggggt ctcgggttgg cgtcccctca acatacgacg atatcagcca gagcagaggc   1620
gggtatcgcg acgcctattc gatgccacag tcagcgacca caggcaccgg ttcccttt gg   1680 tcgcgtcaac cgttcgagca attcggcgtc gcggagcgaa acggggccgt cggggaagaa   1740
ctcaggaaca gatcgaatcc cattaacatt gataataatg cgtctagcaa cgtcgatgct   1800
gaagcgaaac tcttacaaag ctttagacac tgcatcctaa agttaataaa gcttgaaggc   1860
tctgaatgga tgttcggtca gagtgacgga gtggatgaag atgatagacc gtgttgcg    1920 gcacgtgaaa aatttattta cgaggccgag gctagagaaa tcaatcaagt aggccacatg   1980
ggggaacctc tcatatcatc cgttccgaac tgcggtgatg ggtgtgtttg gcgggccgac   2040
atgatagttt ccttcggtgt atggtgcatc cataggggtac tggatatgag tttaatggaa   2100
agcaggcctg aattgtgggg gaaatatacg tatgtcctga atcgactgca aggcgtaata   2160
gaccctgcct ttagtaaaat gcgtaccccg atgacaccct gtttctgttt gcaaatacc    2220 gcatcccatc aacgggcaag tccgacatcg gcaaatggaa tgttacccc c agcggcaaag  2280 ccagcgaaag ggaagtgtac aactgcagtc acccttctag atctaataaa agatgttgaa   2340
atggctatta gctgtaggaa gggcagaact ggaactgcgg ctggtgacgt ggcctttcct   2400
aaaggtaagg aaaacatggc atcggtcatg aaacgttaca agcggagact cagtaacaag   2460
ccagtgggga tgaaccaaga cggtcccggg agtcgtaaaa atgttactgc ctacggttca   2520
atgggataa                                                          2529
```

<210> SEQ ID NO 29
<211> LENGTH: 2529
<212> TYPE: DNA
<213> ORGANISM: Artificial Sequence
<220> FEATURE:
<221> NAME/KEY: source
<222> LOCATION: 1..2529
<223> OTHER INFORMATION: /organism="Artificial Sequence"
    /note="Nucleotide sequence EIN2, variant 11"
    /mol_type="unassigned DNA"

<400> SEQUENCE: 29

```
atgctatgga tggcagccac cccactgaag tctgcatcca acagggcgga ggctcaaata    60
tggaatatgg acgcccagaa cgctcttagc taccctcgg tacaagaaga agaaatagag    120
agaaccgaga ctcgacggaa tgaggacgag tcgatagtac gcatggaatc gagggtcaag    180
gatcagatgg ataccacgtc cgtgacttcg tctgtatatg acttgcccga gaatatcctt    240
atgacagatc aagagattcg atctagtcca cccgaggaga gagaaatgga cgtaaaatat    300
tcaacttctc aggtttcgag tcttaaggag gattccgatg taaaggaaca atctgtaatg    360
caatctacag tcgtgaacga agtcagtgat aaggacctga ttgtcgagac aaagatggcg    420
aagattgagc caatgagtcc tgttgaaaaa atcgtgtcca tggaaaataa cagcaaattt    480
atagagaaag acgtcgaagg cgtttcctgg gaaacggagg aagctactaa agcagcaccc    540
acctctaatt tcactgtagg gtcagacgga cctccttcat tcaggagctt aagcggggag    600
gggggaagcg ggacgggtag cctttcccgt atgcagggaa tggggcgtgc agcaaggcgg    660
catctctctg cgatactaga cgagttctgg ggacatttat atgacttcca tggtcaaatg    720
```

```
gttgcggaag ctcgtgcaaa aaaactggat cagctgtttg gcacagatca gaaatcagcg    780
tcaagcatga aggctgactc gtttggcaaa gatatctcaa gtggctactg catgagcccg    840
acggccaaag ggatggactc acaaatgaca agttctctat acgattcaat gaagcaacag    900
agaacgcctg ggtccatcga cagcatgtac ggactgcaaa ggggtagttc accatccccc    960
atggtgaatc gtatgcaaat gatgggtgca tacggtaata caactaataa caacaatgct   1020
tatgagatga gtgaaagaag atatagcagc ctgcgtgcgc cgtcgtcatc cgaaggctgg   1080
gagcaccagc agccagccac cgttcatggc tatcaaatga atcctatgt cgataatttg    1140 gcgaaggaaa ggctggaagc attgcagtcc cgcggtgaaa ttcccacgtc gcgatcaatg   1200
gctcttggaa ccttgtctta cactcaacag cttgccctgg cgttgaaaca gaagtcccaa   1260
aacggcttga ctccagggcc tgctcctggc tttgagaatt cgcggggag taggagcata    1320 agtcgtcagt ctgaaagaag ttactatggt gtaccctctt ctggtaacac ggacacagtt   1380
ggggcagcag tagccaacga aaagaagtat tcaagcatgc ccgatatatc ggggttgtct   1440
atgtcagcaa ggaatatgca ccttccgaat aacaaaagtg ggtattggga cccgtcatcg   1500
ggtggaggag gttatggagc atcttatggt aggttgtcta atgaatcttc gctttactcc   1560
aacatgggta gccgagtggg cgttccatcg acatatgacg acatttcaca gagtcgtgga   1620
ggctacagag atgcttacag tatgccccag tccgcgacca cggggaccgg tagcttgtgg   1680
tcgaggcaac ccttcgaaca atttggagtt gcagaaagga acggtgccgt tggtgaagaa   1740
ctccgcaaca ggtctaaccc tattaacata gacaataacg cgtccagcaa cgttgatgct   1800
gaagcgaagc tattacaaag ctttcgtcat tgtattctaa agctcattaa gctggaaggc   1860
tcggagtgga tgttcggaca gagcgacggc gttgacgaag agatgatcga tcgggtcgcg   1920
gcacgcgaga aatttatcta tgaggcagag gctcgggaaa taaatcaagt tgggcatatg   1980
ggtgaaccat tgatctccag cgtccctaac tgcggagacg gctgtgtatg gagagctgac   2040
atgatagtaa gttccggagt ttggtgtatc caccgtgtcc tcgacatgtc actcatggag   2100
agtcgccctg aactgtgggg aaaatataca tatgttttaa atcgcttaca aggggtgatc   2160
gacccagcgt tttcgaagat gagaacaccc atgacccct gttttttgttt gcaaattccg    2220 gcgagccacc aaagggcgag tcccacgagt gctaaccgca tgttaccgcc agcagcaaag   2280
ccggcaaaag gcaagtgtac aacggcagtc acacttttag atcttataaa ggatgtcgaa   2340
atggcgatct cttgcaggaa gggccggacc ggtaccgctg ctggagacgt cgctttcccg   2400
aaaggcaagg aaaatatggc aagtgtgttg aaacgttaca agagacggtt atccaataaa   2460
cctgtcggca tgaaccagga tggacccggc tcaagaaaaa atgtcacggc atatggttca   2520
ttgggttaa                                                            2529
```

<210> SEQ ID NO 30
<211> LENGTH: 2529
<212> TYPE: DNA
<213> ORGANISM: Artificial Sequence
<220> FEATURE:
<221> NAME/KEY: source
<222> LOCATION: 1..2529
<223> OTHER INFORMATION: /organism="Artificial Sequence"
     /note="Nucleotide sequence EIN2, variant 12"
     /mol_type="unassigned DNA"

<400> SEQUENCE: 30

```
atgctctgga tggcagccac accgctgaag tctgcaagta acagagcgga ggcgcagata     60
tggaatatgg atgctcaaaa cgcgctatct taccccctcgg ttcaagagga agaaatagaa    120
```

```
cgaacagaga caaggcggaa cgaagatgaa tcgatagtgc ggatggagtc gagggtgaag      180
gaccaattgg acactacgtc cgtaacttct tcggtctatg acttgccaga aaatattcta      240
atgacggatc aagaaatcag gagctcccca ccagaggagc gagaaatgga cgttaagtac      300
tcaacctctc aagttagttc cctgaaggaa gactcggacg tgaaggagca gtctgtgatg      360
caaagcacag tggttaatga agtgagtgac aaggatatga ttgtagaaac aaaaatggcg      420
aaaattgagc ctatgtcgcc ggtggagaag attgtatcaa tggaaaacaa cagcaaattt      480
attgaaaagg atgttgaagg cgtttcatgg gagacagagg aggctaccaa ggctgctcct      540
acctctaact tcacggtcgg ctctgacggt cctccctcat ttcgcagtct gagtggggag      600
gggggctctg gcactggaag ccttttcacgg ttgcagggtt gggaagagc tgcgcggagg      660 cacttatccg ctatacttga tgagttctgg ggacatttat acgacttcca cggtcagatg      720
gtggccgaag cgagggctaa aaaattggac cagatgtttg gcactgatca aaagtcagca      780
tcttctatga aagcggactc gttcggaaaa gatattagca gtggatactg tatgtcgcca      840
acagcgaagg gaatggactc acaaatgact agcagcctgt atgactctat gaagcagcag      900
aggacaccgg gcagtataga tagtttgtac ggccttcaga gaggatcttc accgagcccc      960
ttggttaacc gtatgcagat gttggggggcc tatggaaata ccactaataa caacaatgca     1020
tatgaattga gtgagcgaag gtactctagc ctgcgtgctc catcatctag tgagggatgg     1080
gagcatcagc agccagctac ggtgcacggg tatcagatga agtcgtacgt agataatttg     1140
gccaaagaaa ggctggaggc ccttcagtcc agaggagaga tccccacaag cagatcaatg     1200
gcgcttggga cattgagcta cacccagcag cttgctttag ccatgaagca gaaatcacag     1260
aacggcttaa ccccctggacc ggccccaggg ttcgagaatt ttgctgggtc gaggagcata     1320
agccgacagt ccgagagatc gtattatggt gttccgtctt ccggcaacac cgatactgtg     1380
ggcgccgcag tagccaatga aagaagtac tctagcatgc ctgatatttc gggtatgagc     1440
atgagtgcaa ggaacatgca cttaccgaat aacaagagtg gttattggga cccgtcatcc     1500
ggagggggtg gttacggcgc ctcttatggt cggttatcaa atgagtcatc gttatactct     1560
aatttggggt cccgggttgg agtgccaagc acatatgacg acatttccca gtcaagagga     1620
ggctatagag acgcctatag tatgccacaa agtgcaacaa caggcaccgg cagtttgtgg     1680
tcacgtcagc cctttgaaca gttcggtgta gcggagagga atggtgcggt tggagaagaa     1740
ctccgaaaca gatccaaccc tataaatatt gacaataacg cttcttctaa tgttgatgca     1800
gaggccaaac ttcttcagtc gttccgacac tgcattctta agcttattaa attagaggga     1860
tcggaatggt tgttcggcca gtcggacgga gttgacgagg agctgattga tcgggtggct     1920 gccccgagaaa aatttatcta cgaagctgaa gcccgagaga ttaatcaagt tggtcacatg     1980
ggcgagccac taatttcatc ggttccgaac tgtggcgacg ggtgtgtatg gagagctgac     2040
atgattgtga gcttcggagt ttggtgtata caccgtgtac ttgacttgtc tctgatggaa     2100
agccggcccg agctttgggg aaagtatacg tatgttctca acaggctaca aggcgtgata     2160
gacccggctt tcagcaaact gcggacaccc atgacgccat gcttttgcct ccagatccca     2220
gcctctcacc aaagagcgtc gcctacctca gctaacggaa tgcttcctcc ggccgctaaa     2280
ccggccaagg gcaagtgcac gaccgcagta acccttcttg atcttataaa ggacgtcgaa     2340
atggcgatct cctgtcgaaa gggccgaacc gggacagctg cggagacgt agctttttcct     2400 aaagggaagg aaaatatggc gtcggtaatg aagcggtata acgtcggtt gtcgaacaag     2460
```

| cccgtaggca tgaaccaaga tggaccaggt tcacgtaaaa atgtaactgc gtatggatct | 2520 |
| atgggatag | 2529 |

<210> SEQ ID NO 31
<211> LENGTH: 2529
<212> TYPE: DNA
<213> ORGANISM: Artificial Sequence
<220> FEATURE:
<221> NAME/KEY: source
<222> LOCATION: 1..2529
<223> OTHER INFORMATION: /organism="Artificial Sequence"
      /note="Nucleotide sequence EIN2, variant 13"
      /mol_type="unassigned DNA"

<400> SEQUENCE: 31

| atgctctggc tggcagccac cccaatgaaa tctgcgagta atagagcgga ggcgcagata | 60 |
| tggaatatgg acgctcaaaa tgctctctct tatccatctg tgcaggaaga ggagattgag | 120 |
| agaacagaaa caaggaggaa tgaggacgag agcatagtcc ggatggagag ccgagttaag | 180 |
| gatcagttgg atactacgtc tgttacttcc tcggtctatg acttgccaga gaatattcta | 240 |
| atgacggacc aagaaatacg aagttctcct ccagaagaaa gagaattgga cgtgaagtat | 300 |
| tctaccagtc aagtttcaag tcttaaagag gattctgacg taaaagagca gtctgtattg | 360 |
| cagtcaacag tagtcaatga ggttagtgac aaggatctga ttgttgaaac caagatggcg | 420 |
| aaaattgaac cgatgagtcc tgtggaaaag attgtttcga tggagaataa cagcaagttt | 480 |
| attgagaagg atgttgaagg agttagctgg gagacagagg aagctaccaa ggctgcccct | 540 |
| acaagcaact ttacggtcgg atcagatggg cctcctagct tccgcagcct atcaggtgaa | 600 |
| ggaggaagtg ggactggaag cctttcacgg ttgcaagggt tgggacgagc tgccaggaga | 660 |
| catttatctg cgatccttga tgaattttgg ggacatttat atgattttca tgggcaattg | 720 |
| gttgcggaag ctcgagccaa gaaactagac cagctgttcg gcaccgatca aaagtcagct | 780 |
| tccagtatga aagcagactc gtttggaaag gacatcagta gtgggtactg catgagtcct | 840 |
| actgcgaaag ggatggactc acaaatgact tcatctttat acgattcaat gaagcagcaa | 900 |
| cggactccgg gtagtatcga ttcgttgtat ggattacaac gcgggtcgag tccgtcaccg | 960 |
| atggtgaatc gtatgcagat gttgggtgca tatgggaata ccacaaacaa taataatgcg | 1020 |
| tatgagttgt cagagcgccg atatagctcc atgcgtgctc catcatctag tgaaggttgg | 1080 |
| gaacatcaac aaccagctac agtccatgga taccagatga atcctatgt agataatttg | 1140 |
| gcaaaagaac gactcgaagc cctacaatct cgtggagaga tcccaacatc gagatctatg | 1200 |
| gcgcttggta ccttgagcta cactcaacag cttgctttag ccttgaaaca aaagtctcaa | 1260 |
| aatggtctta cgccaggacc agctccaggc ttcgagaatt ttgctggctc tagaagcatc | 1320 |
| tctcgacaaa gcgagagaag ctattatggt gttccttctt ctgggaatac tgatactgtt | 1380 |
| ggcgcagcag tagctaatga agaaaatat agtagcatgc cagatatctc tggattgtct | 1440 |
| atgtccgcaa ggaacatgca tttaccaaac aataaaagtg gatactggga tccgagcagt | 1500 |
| ggtggaggag ggtatggtgc gtcttatggt cgcctttcta atgaaagttc gctttatagt | 1560 |
| aacatgggat cacgggttgg agtaccctcg acttatgatg acatttctca gtcacgcgga | 1620 |
| ggctacagag atgcctacag tttgccacag agcgcaacaa cagggaccgg atcgctttgg | 1680 |
| tccagacagc cctttgaaca atttggtgta gcggagcgaa acggtgctgt tggtgaggag | 1740 |
| ctccgcaata gatcgaatcc gattaacatc gacaacaacg cctcgagtaa tgttgatgct | 1800 |
| gaggcgaaac tcctccagtc gttccggcat tgcatcctca agttgatcaa acttgaagga | 1860 |

```
tccgagtggt tgtttggaca atccgatgga gttgatgaag aactgattga ccgcgttgcc   1920
gcgcgagaga agtttatcta tgaggctgaa gctcgtgaaa tcaaccaggt gggtcacatg   1980
ggggaaccac taatttcatc ggtgcctaac tgtggagatg gttgtgtttg gagagctgat   2040
ttgatcgtga gctttggagt ttggtgcatt caccgtgtcc ttgacttgtc tctcatggag   2100
agtcggcctg agctctgggg aaaatacacc tacgttttga accgcctaca gggagtgatt   2160
gatccggcat tctcgaaact gcggacacca atgactccgt gcttttgcct gcagattcct   2220
gcgagtcacc aacgagcgag tccgacttca gctaatggaa tgttaccgcc ggctgcaaag   2280
ccagccaagg ggaagtgcac aaccgcagtc acacttctgg acctaatcaa agacgttgaa   2340
atggcaatca gttgtagaaa aggccgaaca ggtacagcag ccggtgatgt cgctttccca   2400
aaggggaaag agaatttggc cagtgttttg aagcggtaca agcgtcggtt atcaaataaa   2460
cccgtaggta tgaatcaaga tggacccggt tcgcgcaaga atgtgacagc gtacggatca   2520
atgggctga                                                           2529
```

<210> SEQ ID NO 32
<211> LENGTH: 2529
<212> TYPE: DNA
<213> ORGANISM: Artificial Sequence
<220> FEATURE:
<221> NAME/KEY: source
<222> LOCATION: 1..2529
<223> OTHER INFORMATION: /organism="Artificial Sequence"
    /note="Nucleotide sequence EIN2, variant 14"
    /mol_type="unassigned DNA"

<400> SEQUENCE: 32

```
atgctctggc tggcagcgac gccgctgaaa tctgcgagta acagagcgga agctcagata     60
tggaacatgg atgctcagaa tgcttttatca tatccatcag ttcaagaaga agaaattgaa    120
agaacagaaa caaggaggaa tgaggacgaa tccattgtgc gcttggagtc cagggtgaag    180
gatcagttgg atactacgtc tgttacgagc tcggtgtatg atttgccaga gaacattcta    240
atgacggatc aggaaatccg ttcgagtcct cccgaggagc gggagttgga cgtcaagtat    300
tctacctctc aagtttccag tttaaaagaa gactctgacg taaaggagca atctgtattg    360
cagtcaacag tggtgaatga ggtaagtgat aaggatctga ttgtggagac taagatggcc    420
aaaatcgaac caatgagtcc tgtggagaag attgtctcca tggaaaataa cagcaagttt    480
attgaaaagg atgttgaagg ggttagctgg gaaacagaag aagctaccaa agctgctcct    540
acaagcaatt tcactgtcgg atctgatggt cctccttcat tccgctcatt aagtggggaa    600
ggggaagtg ggacgggatc attgtcacgg atgcagggtt tgggacgtgc tgcgcggaga    660
cacttatctg caatcttgga tgagttctgg ggacatttat atgatttcca cggtcaattg    720
gttgcagaag cccgcgcaaa gaaactagat cagctgttcg gcacagatca aaagtcagct    780
tctagcatga agcggattc gtttggaaaa gacattagca gtggatattg tatgtcacca    840
actgcgaagg gaatggatag tcagatgact tcaagcctat atgattcaat gaaacaacag    900
aggacaccgg gaagtatcga ttcgttgtac ggattacaac gggggtcctc accgtcaccg    960
ttggtcaacc gtatgcagat gttgggtgct tatggtaaca ccactaataa taacaatgct   1020
tacgagttga gtgaaagaag atattctagc atgcgagcac catcatccag cgagggttgg   1080
gagcatcaac agccagcgac cgttcatgga taccagatga agtcatatgt agacaatttg   1140
gccaaagagc ggcttgaagc gttacaatcc cgtgggggaga tcccgacatc aagatcaatg   1200
```

```
gcccttggta ccttgagcta tacacagcaa ttagctcttg ccttgaaaca aaaaagccag    1260
aatggtctaa cccctggacc agcgcctggg tttgagaatt ttgctggatc acggagcata    1320
tcgagacaat ctgaaagatc ttattacggt gttccatcat cgggcaatac tgatactgtt    1380
ggcgcagcag ttgccaatga gaaaaaatat agtagtatgc cagacatttc aggattgtct    1440
atgagtgcaa ggaacatgca tttaccaaac aacaaaagcg gatactggga cccgtcaagt    1500
ggagggggtg ggtacggcgc atcttacggt cggttatcga atgaatcatc gttgtattct    1560
aacatggggt cacgggtggg agttccctcg acttatgatg acatttctca gtcaagagga    1620
ggttacagag atgcctacag tttgccacag tccgcgacaa caggcaccgg atcgctgtgg    1680
tccagacaac cctttgagca atttggtgta gcggagagga atggagctgt tggtgaggag    1740
ctcaggaaca gaagcaaccc aatcaatata gacaacaatg cttcttctaa tgtggatgcc    1800
gaggctaaac ttcttcagtc gttcaggcac tgtattctga gttaattaa acttgaagga    1860 tccgagtgga tgtttggaca aagcgatgga gttgatgagg aactgattga ccgggtagct    1920
gcacgagaga agtttatcta tgaagctgaa gctcgagaaa taaaccaggt gggtcacatg    1980
ggggagccgc taatttcatc tgttcctaac tgtggagatg gatgcgtttg gagagctgat    2040
atgatagtct ctttcggagt ttggtgtatt catcgtgtct tggacttgtc tttgatggag    2100
agtcggcccg agctttgggg aaaatacaca tatgttctca accgcctaca gggagtgatc    2160
gacccagcgt tctcaaagat gcggacacca atgacgccgt gcttttgcct tcagattcca    2220
gcatcacacc agagagcgag tccaacttcc gcaaacggaa tgttacctcc ggctgcaaag    2280
ccggcaaaag gcaaatgtac aacagcagta acacttcttg atctcatcaa agacgtcgaa    2340
atggcaatat cttgtcgtaa aggccgaacc gggacagccg ctggagatgt ggcttttcca    2400
aaggggaagg agaatatggc ttcagttttg aagcggtaca acggcgattt atcgaataaa    2460
ccagtgggta tgaatcagga tggacctggt agccgaaaaa acgtgactgc ttacggatca    2520
ttgggttga                                                            2529
```

<210> SEQ ID NO 33
<211> LENGTH: 2529
<212> TYPE: DNA
<213> ORGANISM: Artificial Sequence
<220> FEATURE:
<221> NAME/KEY: source
<222> LOCATION: 1..2529
<223> OTHER INFORMATION: /organism="Artificial Sequence"
    /note="Nucleotide sequence EIN2, variant 15"
    /mol_type="unassigned DNA"

<400> SEQUENCE: 33

```
atgttatggc tggcagccac gccgatgaaa tctgcgagta acagagcgga agctcaaata      60
tggaacatgg atgctcaaaa tgctttatct tatccatctg ttcaagaaga ggagattgag     120
agaacagaaa caagaaggaa cgaggacgaa tcaatagtac ggatggaaag cagggtaaag     180
gatcaattgg atacaacgtc tgttacttcg tcggtctatg atttgccaga gaacattcta     240
atgacggatc aggaaatccg ctccagccct ccagaagaga gagttgga cgtaaagtac       300 tctacatctc aggtaagtag tcttaaggag gactctgacg taaaggaaca gtctgtattg     360
cagtcaacag tggttaatga agtcagtgat aaggatctga ttgttgaaac aaagatggcg     420 aaaaattgaac caatgagtcc tgtggagaag attgttagca tggagaataa cagcaagttt    480
attgaaaagg acgttgaagg ggtttcatgg gaaacagaag aagctacaaa agctgctcct    540
acatccaact ttacggtcgg atccgatggt cctccttcat tccgcagctt aagtggggag    600
```

```
gggggaagtg ggactggatc actttcaaga ttgcagggtt tgggacgtgc tgcccggaga      660
cacctgtctg cgatcctcga tgaattttgg ggtcatttat atgattttca tgggcagttg      720
gttgctgaag ccagggctaa gaagctagat cagctgtttg gcacagatca aaaatcagcc      780
tcttctatga aagcagattc gtttggaaaa gacattagca gtggatattg catgtcacca      840
actgcgaagg gtatggattc acagatgact tcaagtttat atgattcact gaagcagcag      900
aggaccccgg gaagtatcga ttcgatgtac gggttacaga gaggttcctc accgagtccg      960
atggtcaacc gtatgcagat gttgggtgca tatggtaaca ccactaacaa taataatgct     1020
tacgaattgt ccgagagaag atattctagc ctgcgtgctc cctcatcttc agagggttgg     1080
gaacatcaac aaccagctac tgttcacgga taccagatga agtcatatgt agacaatttg     1140
gctaaagaaa ggcttgaagc cttacaatcc cgtggtgaga tcccgacaag tagatctatg     1200
gcgcttggta cattgagtta tacacaacaa cttgctttag ccttgaaaca gaagtcccag     1260
aatggtctta cccctggacc agcccctggg tttgaaaatt ttgctgggtc tagaagcatt     1320
tcgcgacaaa gtgaaagatc ttattacgga gttccatcta gtggcaatac tgacactgtt     1380
ggcgccgcag ttgccaatga gaaaaaatat agtagcatgc ccgatatttc aggattgtct     1440
atgtccgcaa ggaatatgca tttacctaac aacaagagtg gatattggga tccttcaagt     1500
ggaggaggag ggtatggtgc gtcttatggt cggttaagca atgaatcatc gttgtattct     1560
aatttgggct cacgagtggg agtcccctcg acgtatgatg acatttctca atcacgaggc     1620
ggctacagag atgcctacag tttgccacaa agtgccacaa cagggaccgg atcactttgg     1680
tcaagacagc ccttcgaaca gtttggtgtt gcggagagga atggtgctgt gggtgaggag     1740
ctaaggaatc ggtcgaatcc gatcaatata gataacaacg cttcttctaa tgttgatgcc     1800
gaggctaagc ttttgcagtc gtttaggcac tgtattctaa agttaattaa gctcgaggga     1860
tccgagtggt tgtttggaca aagcgatgga gttgacgaag aaatgatcga ccgggtagcg     1920
gcacgagaga agtttatata cgaagctgaa gctcgagaaa taaaccaggt gggtcacatg     1980
ggggagccac taatatcatc ggttcctaac tgtggagatg gttgcgtttg gagagcggat     2040
ttgattgtga gctttggagt ttggtgcatt caccgtgtcc ttgacttgtc tctcatggag     2100
agtcggcctg aactttgggg aaagtacact tacgttctca acagactaca gggagtgatt     2160
gatccggcgt tcagtaaact gcggacacca atgacaccgt gcttttgcct tcaaatccca     2220
gcgagccacc aacgtgcgag tccgacgtca gctaacggaa tgttaccccc ggctgcaaaa     2280
ccggctaaag gcaaatgcac aaccgcagtc acacttcttg atctaatcaa agacgttgag     2340
atggcaatct cttgtagaaa gggccgaacc ggcacagctg caggtgatgt agctttcccg     2400
aaggggaaag agaatttggc ttcggttttg aagcggtata acgtcggtt atcgaataaa      2460 ccagtaggta tgaatcagga tggacctggt tcaagaaaaa acgtgactgc gtacggatcc     2520
ttgggctga                                                             2529
```

<210> SEQ ID NO 34
<211> LENGTH: 2529
<212> TYPE: DNA
<213> ORGANISM: Artificial Sequence
<220> FEATURE:
<221> NAME/KEY: source
<222> LOCATION: 1..2529
<223> OTHER INFORMATION: /organism="Artificial Sequence"
    /note="Nucleotide sequence EIN2, variant 16"
    /mol_type="unassigned DNA"

```
<400> SEQUENCE: 34
atgctctggc tggcagccac gcctctgaag tctgcgtcta acagagcgga agctcaaatt      60
tggaacatgg atgctcaaaa cgctttatct tatccatctg ttcaagaaga ggaaattgaa     120
agaacagaaa caaggaggaa cgaagatgaa tcaattgtga gattggagag cagggtaaag     180
gatcagttgg atactacgtc tgttactagc tcggtctatg atttgccaga gaacattcta     240
atgacggatc aagagatccg ttcgagccct ccagaagaaa gagagttgga tgtaaagtac     300
tctacgtctc aagttagtag tcttaaggaa gactctgatg taaaggaaca gtctgtattg     360
cagtctacag tggttaatga ggtcagtgat aaggatatga ttgttgaaac aaagatggcg     420
aaaattgaac caatgagtcc tgtggagaag atcgttagca tggagaataa cagcaagttt     480
attgaaaagg atgttgaagg ggtttcatgg gaaacggaag aagcaaccaa ggctgcacct     540
actagcaact ttactgtagg atctgatggt cctccttcat tccgcagctt aagtggtgaa     600 ggggaagtg gactggaag cctttcacgg ttgcaaggtt tgggccgtgc tgcccggaga     660
cacttatctg cgatccttga tgagttttgg ggacattat atgattttca tgggcaattg     720
gttgctgaag ccagggcaaa gaaactagat cagctgtttg gcactgatca aaagtcagcc     780
tcttctatga aagcagattc gtttggaaaa gacattagca gtggatattg catgtcacca     840
actgcgaagg ggatggattc acagatgact tcaagtttat atgattcact gaagcaacag     900
aggacaccgg aagtatcga ctcgttgtat ggattacaaa gaggttcgtc accgtcaccg     960
ttggtcaatc gtatgcagat gttgggtgca tatggaaaca ccactaacaa caataatgct    1020
tacgagttga gtgagagaag atactctagc ctgcgtgctc catcatcttc agagggttgg    1080
gaacaccaac aaccagctac agttcacggt taccagatga agtcatatgt agacaatttg    1140
gctaaggaac gtcttgaagc cttacaatcc cgtggagaga tcccgacatc gagatctatg    1200
gcgcttggta cattgagcta tacacagcaa cttgctttag ccttgaaaca gaagtcccag    1260
aacggtctaa cacctggacc agctcctgga tttgagaatt ttgcagggtc tagaagcata    1320
tcgcgacaat ctgaaagatc ttattacggt gttccatctt ctggcaatac tgatactgtt    1380
ggcgcagcag tagccaatga aagaaatat agtagtatgc cagatatctc aggcttgtct    1440
atgtccgcaa ggaacatgca tttaccaaat aacaagagtg gatactggga tccgtcaagt    1500
ggaggaggag ctatggtgc gtcttatggc cggttaagca atgaatcatc gttatattct    1560
aatttggggt cacgggtggg agtaccctcg acttatgatg acatttctca atcacgcgga    1620
ggctacagag atgcctactc tttgccacag agtgcaacaa cagggaccgg atcgctttgg    1680
tcccggcagc cctttgagca gtttggtgta gcggagagga atggtgctgt tggtgaggag    1740
ctcaggaaca gatcgaatcc gatcaatatt gataacaacg cctcctctaa tgttgatgca    1800
gaggctaagc ttcttcagtc ctttcgtcac tgtattctaa aacttattaa acttgaagga    1860
tccgagtggt tgtttggtca atctgatgga gttgatgagg aactgattga ccgggtagct    1920
gcacgagaga agtttatcta tgaagctgaa gcgcgagaaa taaatcaagt gggtcacatg    1980
ggggaaccac tcatttcatc ggttcctaac tgtggagatg gttgcgtttg gagagctgat    2040
ttgattgtga gctttggagt ttggtgcatt caccgtgttc ttgacttgtc tctcatggag    2100
agtcggcctg agctttgggg aaagtacact tacgttctca accgcctaca gggagtgatt    2160
gatccggcgt tctcaaagct gcggacacca atgacaccgt gtttttgcct tcagattcca    2220
gcgtcccacc agagagcgag tccgacttca gctaacggaa tgttacctcc ggctgcaaaa    2280
ccggctaaag gcaaatgcac aaccgcagtt acacttcttg atctaatcaa agacgttgaa    2340
```

```
atggcaatct cttgtagaaa aggccgaacc ggtacagctg caggtgatgt ggctttccca    2400
aaagggaaag agaatttggc ttcggttttg aagcggtaca aacgtcgctt gtcgaataaa    2460
ccagtaggta tgaatcaaga tggccccggt tcaagaaaaa acgtgactgc gtacggatca    2520
ttgggttga                                                            2529
```

FUNGAL RESISTANT PLANTS EXPRESSING EIN2

This application is a National Stage application of International Application No. PCT/EP2014/050879, filed Jan. 17, 2014, which claims priority under 35 U.S.C. § 119 to European Patent Application No. 13152968.7, filed Jan. 29, 2013, the entire contents of which are incorporated herein by reference.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "74750_SeqListing.txt" created on Jul. 8, 2015, and is 153,355 bytes in size. The sequence listing contained in this .txt file is part of the specification and is hereby incorporated by reference herein in its entirety.

SUMMARY OF THE INVENTION

The present invention relates to a method of increasing resistance against fungal pathogens, in particular, pathogens of the family Phacopsoraceae, for example soybean rust, in plants, plant parts, and/or plant cells. This is achieved by increasing the expression and/or activity of an EIN2 protein in a plant, plant part and/or plant cell in comparison to wild type plants, wild type plant parts and/or wild type plant cells.

Furthermore, the invention relates to transgenic plants, plant parts, and/or plant cells having an increased resistance against fungal pathogens, in particular, pathogens of the family Phacopsoraceae, for example soybean rust, and to recombinant expression vectors comprising a sequence that is identical or homologous to a sequence encoding an EIN2 protein.

BACKGROUND OF THE INVENTION

The cultivation of agricultural crop plants serves mainly for the production of foodstuffs for humans and animals. Monocultures in particular, which are the rule nowadays, are highly susceptible to an epidemic-like spreading of diseases. The result is markedly reduced yields. To date, the pathogenic organisms have been controlled mainly by using pesticides. Nowadays, the possibility of directly modifying the genetic disposition of a plant or pathogen is also open to man.

Resistance generally describes the ability of a plant to prevent, or at least curtail the infestation and colonization by a harmful pathogen. Different mechanisms can be discerned in the naturally occurring resistance, with which the plants fend off colonization by phytopathogenic organisms. These specific interactions between the pathogen and the host determine the course of infection (Schopfer and Brennicke (1999) Pflanzenphysiologie, Springer Verlag, Berlin-Heidelberg, Germany).

With regard to the race specific resistance, also called host resistance, a differentiation is made between compatible and incompatible interactions. In the compatible interaction, an interaction occurs between a virulent pathogen and a susceptible plant. The pathogen survives, and may build up reproduction structures, while the host mostly dies off. An incompatible interaction occurs on the other hand when the pathogen infects the plant but is inhibited in its growth before or after weak development of symptoms (mostly by the presence of R genes of the NBS-LRR family, see below). In the latter case, the plant is resistant to the respective pathogen (Schopfer and Brennicke, vide supra). However, this type of resistance is specific for a certain strain or pathogen.

In both compatible and incompatible interactions a defensive and specific reaction of the host to the pathogen occurs. In nature, however, this resistance is often overcome because of the rapid evolutionary development of new virulent races of the pathogens (Neu et al. (2003) American Cytopathol. Society, MPMI 16 No. 7: 626-633).

Most pathogens are plant-species specific. This means that a pathogen can induce a disease in a certain plant species, but not in other plant species (Heath (2002) Can. J. Plant Pathol. 24: 259-264). The resistance against a pathogen in certain plant species is called non-host resistance. The non-host resistance offers strong, broad, and permanent protection from phytopathogens. Genes providing non-host resistance provide the opportunity of a strong, broad and permanent protection against certain diseases in non-host plants. In particular, such a resistance works for different strains of the pathogen.

Fungi are distributed worldwide. Approximately 100 000 different fungal species are known to date. Thereof rusts are of great importance. They can have a complicated development cycle with up to five different spore stages (spermatium, aecidiospore, uredospore, teleutospore and basidiospore).

During the infection of plants by pathogenic fungi, different phases are usually observed. The first phases of the interaction between phytopathogenic fungi and their potential host plants are decisive for the colonization of the plant by the fungus. During the first stage of the infection, the spores become attached to the surface of the plants, germinate, and the fungus penetrates the plant. Fungi may penetrate the plant via existing ports such as stomata, lenticels, hydatodes and wounds, or else they penetrate the plant epidermis directly as the result of the mechanical force and with the aid of cell-wall-digesting enzymes. Specific infection structures are developed for penetration of the plant.

Immediately after recognition of a potential pathogen the plant starts to elicit defense reactions. Mostly the presence of the pathogen is sensed via so called PAMP receptors, a class of trans-membrane receptor like kinases recognizing conserved pathogen associated molecules (e.g. flagellin or chitin). Downstream of the PAMP receptors, the phytohormones salicylic acid (SA), jasmonate (JA) and ethylene (ET) play a critical role in the regulation of the different defense reactions. Depending on the ratio of the different phytohormones, different defense reactions are elicited by the host cell. Generally SA dependent defense is linked with resistance against biotrophic pathogens, whereas JA/ET dependent defense reactions are in most cases directed against necrotrophic pathogens (and insects).

Another more specific resistance mechanism is based on the presence of so called resistance genes (R-genes). Most R genes belong to the nucleotide-binding site-leucine-rich repeat (NBS-LRR) gene family and function in monitoring the presence of pathogen effector proteins (virulence factors; avirulence factors). After recognizing the pathogen derived proteins a strong defense reaction (mostly accompanied by a programmed cell death) is elicited.

The soybean rust *Phakopsora pachyrhizi* directly penetrates the plant epidermis. After crossing the epidermal cell, the fungus reaches the intercellular space of the mesophyll, where the fungus starts to spread through the leaves. To acquire nutrients the fungus penetrates mesophyll cells and develops haustoria inside the mesophyl cell. During the penetration process the plasmamembrane of the penetrated mesophyll cell stays intact. Therefore the soybean rust fungus establishes a biotrophic interaction with soybean.

The biotrophic phytopathogenic fungi, such as soybean rust and all other rust fungi, depend for their nutrition on the metabolism of living cells of the plants. This type of fungi belong to the group of biotrophic fungi, like other rust fungi, powdery mildew fungi or oomycete pathogens like the genus *Phytophthora* or *Peronospora* The necrotrophic phytopathogenic fungi depend for their nutrition on dead cells of the plants, e.g. species from the genus *Fusarium, Rhizoctonia* or *Mycospaerella* Soybean rust has occupied an intermediate position, since it penetrates the epidermis directly, whereupon the penetrated cell becomes necrotic. After the penetration, the fungus changes over to an obligatory-biotrophic lifestyle. The subgroup of the biotrophic fungal pathogens which follows essentially such an infection strategy is heminecrotrohic. In contrast to a heminecrotrophic pathogen, a hemibiotrophic pathogen lives for a short period of time in a biotrophic manner and subsequently starts killing the host cell and/or host organism, i.e., changes for the rest of its life-cycle to a necrotrophic life-style.

Soybean rust has become increasingly important in recent times. The disease may be caused by the biotrophic rusts *Phakopsora pachyrhizi* and *Phakopsora meibomiae*. They belong to the class Basidiomycota, order Uredinales, family Phakopsoraceae. Both rusts infect a wide spectrum of leguminosic host plants. *P. pachyrhizi*, also referred to as Asian rust, is the more aggressive pathogen on soy (*Glycine max*), and is therefore, at least currently, of great importance for agriculture. *P. pachyrhizi* can be found in nearly all tropical and subtropical soy growing regions of the world. *P. pachyrhizi* is capable of infecting 31 species from 17 families of the Leguminosae under natural conditions and is capable of growing on further 60 species under controlled conditions (Sinclair et al. (eds.), Proceedings of the rust workshop (1995), National SoyaResearch Laboratory, Publication No. 1 (1996); Rytter J. L. et al., Plant Dis. 87, 818 (1984)). *P. meibomiae* has been found in the Caribbean Basin and in Puerto Rico, and has not caused substantial damage as yet.

*P. pachyrhizi* can currently be controlled in the field only by means of fungicides. Soy plants with resistance to the entire spectrum of the isolates are not available. When searching for resistant soybean accessions, six dominant R-genes of the NBS-LRR family, named Rpp1-5 and Rpp? (Hyuuga), which mediate resistance of soy to *P. pachyrhizi*, were discovered by screening thousands of soybean varieties. As the R-genes are derived from a host (soybean), the resistance was lost rapidly, as *P. pachyrhizi* develops new virulent races. Therefore there is a strong need to discover R-genes that are derived from non-hosts plants (e.g. *Arabidopsis*) as they are thought to be more durable.

In recent years, fungal diseases, e.g. soybean rust, has gained in importance as pest in agricultural production. There was therefore a demand in the prior art for developing methods to control fungi and to provide fungal resistant plants.

Much research has been performed on the field of powdery and downy mildew infecting the epidermal layer of plants. However, the problem to cope with soybean rust which infects the mesophyll remains unsolved.

The object of the present invention is inter alia to provide a method of increasing resistance against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* and *Phakopsora meibomiae*, also known as soybean rust.

Surprisingly, we found that fungal pathogens, in particular of the family Phacopsoraceae, for example soybean rust, can be controlled by increasing the expression of an EIN2 protein.

The present invention therefore provides a method of increasing resistance against fungal pathogens, preferably against rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* and *Phakopsora meibomiae*, also known as soybean rust, in transgenic plants, transgenic plant parts, or transgenic plant cells by overexpressing one or more EIN2 nucleic acids.

A further object is to provide transgenic plants resistant against fungal pathogens, preferably rust pathogens (i.e., fungal pathogens of the order Pucciniales), preferably of the family Phacopsoraceae, more preferably against fungal pathogens of the genus *Phacopsora*, most preferably against *Phakopsora pachyrhizi* and *Phakopsora meibomiae*, also known as soybean rust, a method for producing such plants as well as a vector construct useful for the above methods.

Therefore, the present invention also refers to a recombinant vector construct and a transgenic plant, transgenic plant part, or transgenic plant cell comprising an exogenous EIN2 nucleic acid. Furthermore, a method for the production of a transgenic plant, transgenic plant part or transgenic plant cell using the nucleic acid of the present invention is claimed herein. In addition, the use of a nucleic acid or the recombinant vector of the present invention for the transformation of a plant, plant part, or plant cell is claimed herein.

The objects of the present invention, as outlined above, are achieved by the subject-matter of the main claims. Preferred embodiments of the invention are defined by the subject matter of the dependent claims.

BRIEF SUMMARY OF THE INVENTION

The object of the present invention is inter alia to provide a method of increasing resistance against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* and *Phakopsora meibomiae*, also known as soybean rust.

Surprisingly, we found that resistance against fungal pathogens, in particular of the family Phacopsoraceae, for example soybean rust, can be enhanced by increasing the expression of an EIN2 protein.

The present invention therefore provides a method of increasing resistance against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* and *Phakopsora meibomiae*, also known as soybean rust, in transgenic plants, transgenic plant parts, or transgenic plant cells by overexpressing one or more EIN2 nucleic acids.

A further object is to provide transgenic plants resistant against fungal pathogens, preferably rust pathogens (i.e., fungal pathogens of the order Pucciniales), preferably of the family Phacopsoraceae, more preferably against fungal pathogens of the genus *Phacopsora*, most preferably against *Phakopsora pachyrhizi* and *Phakopsora meibomiae*, also known as soybean rust, a method for producing such plants as well as a vector construct useful for the above methods.

Therefore, the present invention also refers to a recombinant vector construct and a transgenic plant, transgenic plant part, or transgenic plant cell comprising an exogenous EIN2 nucleic acid. Furthermore, a method for the production of a transgenic plant, transgenic plant part or transgenic plant cell using the nucleic acid of the present invention is claimed herein. In addition, the use of a nucleic acid or the recombinant vector of the present invention for the transformation of a plant, plant part, or plant cell is claimed herein.

The objects of the present invention, as outlined above, are achieved by the subject-matter of the main claims. Preferred embodiments of the invention are defined by the subject matter of the dependent claims.

BRIEF DESCRIPTION OF THE SEVERAL VIEWS OF THE DRAWINGS

FIG. 1 shows the scoring system used to determine the level of diseased leaf area of wildtype and transgenic soy plants against the rust fungus *P. pachyrhizi* (as described in GODOY, C. V., KOGA, L. J. & CANTERI, M. G. Diagrammatic scale for assessment of soybean rust severity. Fitopatologia Brasileira 31:063-068. 2006).

FIG. 2 shows the schematic illustration of the plant transformation vector harboring the EIN2 fragment DNA under control of the parsley ubiquitine promoter.

FIG. 3 shows the alignment of the *Arabidopsis* EIN2 genomic sequence (AT5G03280, TAIR accession No 4515110756, SEQ ID NO: 6), the putative CDS of EIN2 (derived from the genomic sequence; accession NM_120406, SEQ ID NO: 4), the CDS of the C-terminal fragment of EIN2 (Alonso et al. (1999) Science 284(5423): 2148-52, SEQ ID NO: 2) and the sequence of the EIN2 fragment (SEQ ID NO: 1) as used in the Examples.

FIG. 4 shows the alignment of the *Arabidopsis* EIN2 full-length protein (accession No. NP_195948, SEQ ID NO: 5) and the EIN2 fragment protein (SEQ ID NO: 3).

FIG. 5 shows the nucleotide sequence of the EIN2 fragment gene from *Arabidopsis thaliana* having SEQ ID NO: 1.

FIG. 6 shows the sequence of the EIN2 fragment protein (SEQ ID NO: 3) as derived from EIN2 fragment nucleotide sequence as shown in SEQ ID NO: 1.

FIG. 7 shows the nucleotide sequence of the full-length EIN2 sequence (accession No. NM_120406), having SEQ ID NO: 4.

FIG. 8 shows the amino acid sequence of the full-length EIN2 protein having SEQ ID NO: 5.

FIG. 9 shows the result of the scoring of 36 transgenic soy plants (derived from 5 independent events, 6-9 plants per event) expressing the EIN2 fragment overexpression vector construct. $T_1$ soybean plants expressing EIN2 fragment protein (SEQ ID NO: 3) were inoculated with spores of *Phakopsora pachyrhizi*. The evaluation of the diseased leaf area on all leaves was performed 14 days after inoculation. The average of the percentage of the leaf area showing fungal colonies or strong yellowing/browning on all leaves was considered as diseased leaf area. At all 36 soybean $T_1$ plants expressing the EIN2 fragment (expression checked by RT-PCR) were evaluated in parallel to non-transgenic control plants. The average of the diseased leaf area is shown in FIG. 9. Overexpression of EIN2 fragment protein significantly (**: $p<0.01$) reduces the diseased leaf area in comparison to non-transgenic control plants by 38.8%.

FIG. 10 contains a brief description of the sequences of the sequence listing.

DETAILED DESCRIPTION OF THE INVENTION

The present invention may be understood more readily by reference to the following detailed description of the preferred embodiments of the invention and the examples included herein.

Definitions

Unless otherwise noted, the terms used herein are to be understood according to conventional usage by those of ordinary skill in the relevant art. In addition to the definitions of terms provided herein, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement).

It is to be understood that as used in the specification and in the claims, “a” or “an” can mean one or more, depending upon the context in which it is used. Thus, for example, reference to “a cell” can mean that at least one cell can be utilized. It is to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

“Homologues” of a protein encompass peptides, oligopeptides, polypeptides, proteins and/or enzymes having amino acid substitutions, deletions and/or insertions relative to the unmodified protein in question and having similar functional activity as the unmodified protein from which they are derived.

"Homologues" of a nucleic acid encompass nucleotides and/or polynucleotides having nucleic acid substitutions, deletions and/or insertions relative to the unmodified nucleic acid in question, wherein the protein coded by such nucleic acids has similar functional activity as the unmodified protein coded by the unmodified nucleic acid from which they are derived. In particular, homologues of a nucleic acid may encompass substitutions on the basis of the degenerative amino acid code.

The terms "identity", "homology" and "similarity" are used herein interchangeably. "Identity" or "homology" or "similarity" between two nucleic acids sequences or amino acid sequences refers in each case over the entire length of the respective EIN2 nucleic acid sequence or EIN2 amino acid sequence.

Preferably, "percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the region being compared and multiplying the result by 100.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity or similarity or homology and performs a statistical analysis of the identity or similarity or homology between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity/homology/identity may also be determined using one of the methods available in the MatGAT software package (Campanella et al., BMC Bioinformatics. 2003 Jul. 10; 4:29. MatGAT: an application that generates similarity/homology/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

The sequence identity may also be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 April; 5(2):151-1) with the following settings:

Multiple alignment parameter:
Gap opening penalty 10
Gap extension penalty 10
Gap separation penalty range 8
Gap separation penalty off
% identity for alignment delay 40
Residue specific gaps off
Hydrophilic residue gap off
Transition weighing 0
Pairwise alignment parameter:
FAST algorithm on
K-tuple size 1
Gap penalty 3
Window size 5
Number of best diagonals 5

Alternatively the identity may be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, the web page: http://www.ebi.ac.uk/Tools/clustalw/index.html# and the following settings
DNA Gap Open Penalty 15.0
DNA Gap Extension Penalty 6.66
DNA Matrix Identity
Protein Gap Open Penalty 10.0
Protein Gap Extension Penalty 0.2
Protein matrix Gonnet
Protein/DNA ENDGAP −1
Protein/DNA GAPDIST 4

Sequence identity between the nucleic acid or protein useful according to the present invention and the EIN2 nucleic acids or EIN2 proteins may be optimized by sequence comparison and alignment algorithms known in the art (see Gribskov and Devereux, Sequence Analysis Primer, Stockton Press, 1991, and references cited therein) and calculating the percent difference between the nucleotide or protein sequences by, for example, the Smith-Waterman algorithm as implemented in the BESTFIT software program using default parameters (e.g., University of Wisconsin Genetic Computing Group).

A "deletion" refers to removal of one or more amino acids from a protein or to the removal of one or more nucleic acids from DNA, ssRNA and/or dsRNA.

An "insertion" refers to one or more amino acid residues or nucleic acid residues being introduced into a predetermined site in a protein or the nucleic acid.

A "substitution" refers to replacement of amino acids of the protein with other amino acids having similar properties (such as similar hydrophobicity, hydrophilicity, antigenicity, propensity to form or break α-helical structures or beta-sheet structures).

On the nucleic acid level a substitution refers to a replacement of one or more nucleotides with other nucleotides within a nucleic acid, wherein the protein coded by the modified nucleic acid has a similar function. In particular homologues of a nucleic acid encompass substitutions on the basis of the degenerative amino acid code.

Amino acid substitutions are typically of single residues, but may be clustered depending upon functional constraints placed upon the protein and may range from 1 to 10 amino acids; insertions or deletion will usually be of the order of about 1 to 10 amino acid residues. The amino acid substitutions are preferably conservative amino acid substitutions. Conservative substitution tables are well known in the art (see for example Taylor W. R. (1986)

The classification of amino acid conservation J Theor Biol., 119:205-18 and Table 1 below).

TABLE 1

Examples of conserved amino acid substitutions

| Residue | Conservative Substitutions |
|---|---|
| A | G, V, I, L, M |
| C | S, T |
| E | D |
| D | E |
| G | A, V, I, L, M |
| F | Y, W |
| I | V, A, G, L, M |
| H | R, K |
| K | R, H |
| M | L, I, V, A, G |
| L | M, I, V, A, G |
| N | Q |
| Q | N |
| P | |
| S | T, C |
| R | K, H |
| T | S, C |
| W | Y, F |
| V | I, A, G, L, M |
| Y | F, W |

Amino acid substitutions, deletions and/or insertions may readily be made using peptide synthetic techniques well known in the art, such as solid phase peptide synthesis and the like, or by recombinant DNA manipulation.

Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gene in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

The terms "encode" or "coding for" is used for the capability of a nucleic acid to contain the information for the amino acid sequence of a protein via the genetic code, i.e., the succession of codons each being a sequence of three nucleotides, which specify which amino acid will be added next during protein synthesis. The terms "encode" or "coding for" therefore includes all possible reading frames of a nucleic acid. Furthermore, the terms "encode" or "coding for" also applies to a nucleic acid, which coding sequence is interrupted by noncoding nucleic acid sequences, which are removed prior translation, e.g., a nucleic acid sequence comprising introns.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein.

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

As used herein the terms "fungal-resistance", "resistant to a fungus" and/or "fungal-resistant" mean reducing, preventing, or delaying an infection by fungi. The term "resistance" refers to fungal resistance. Resistance does not imply that the plant necessarily has 100% resistance to infection. In preferred embodiments, enhancing or increasing fungal resistance means that resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant.

As used herein the terms "soybean rust-resistance", "resistant to a soybean rust", "soybean rust-resistant", "rust-resistance", "resistant to a rust", or "rust-resistant" mean reducing or preventing or delaying an infection of a plant, plant part, or plant cell by Phacopsoracea, in particular *Phakopsora pachyrhizi* and *Phakopsora meibomiae*—also known as soybean rust or Asian Soybean Rust (ASR), as compared to a wild type plant, wild type plant part, or wild type plant cell. Resistance does not imply that the plant necessarily has 100% resistance to infection. In preferred embodiments, enhancing or increasing rust resistance means that rust resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant that is not resistant to soybean rust. Preferably the wild type plant is a plant of a similar, more preferably identical, genotype as the plant having increased resistance to the soybean rust, but does not comprise an exogenous EIN2 nucleic acid, functional fragments thereof and/or an exogenous nucleic acid capable of hybridizing with an EIN2 nucleic acid.

The level of fungal resistance of a plant can be determined in various ways, e.g. by scoring/measuring the infected leaf area in relation to the overall leaf area. Another possibility to determine the level of resistance is to count the number of soybean rust colonies on the plant or to measure the amount of spores produced by these colonies. Another way to resolve the degree of fungal infestation is to specifically measure the amount of rust DNA by quantitative (q) PCR. Specific probes and primer sequences for most fungal pathogens are available in the literature (Frederick R D, Snyder C L, Peterson G L, et al. 2002 Polymerase chain reaction assays for the detection and discrimination of the rust pathogens *Phakopsora pachyrhizi* and *P. meibomiae*, Phytopathology 92(2) 217-227).

The term "hybridization" as used herein includes "any process by which a strand of nucleic acid molecule joins with a complementary strand through base pairing" (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules.

As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41 (% G+C), when a nucleic acid molecule is in aqueous solution at 1 M NaCl (see e.g., Anderson and Young, Quantitative Filter Hybridization, in Nucleic Acid Hybridization (1985). Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term "stringency conditions" refers to conditions, wherein 100 contiguous nucleotides or more, 150 contiguous nucleotides or more, 200 contiguous nucleotides or more or 250 contiguous nucleotides or more which are a fragment or identical to the complementary nucleic acid molecule (DNA, RNA, ssDNA or ssRNA) hybridizes under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably at 65° C., with a specific nucleic acid molecule (DNA; RNA, ssDNA or ss RNA). Preferably, the hybridizing conditions are equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C., more preferably the hybridizing conditions are equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. Preferably, the complementary nucleotides hybridize with a fragment or the whole EIN2 nucleic acids. Alternatively, preferred hybridization conditions encompass hybridisation at 65° C. in 1×SSC or at 42° C. in 1×SSC and 50% formamide, followed by washing at 65° C. in 0.3×SSC or hybridisation at 50° C. in 4×SSC or at 40° C. in 6×SSC and 50% formamide, followed by washing at 50° C. in 2×SSC. Further preferred hybridization conditions are 0.1% SDS, 0.1 SSD and 65° C.

The term "plant" is intended to encompass plants at any stage of maturity or development, as well as any tissues or organs (plant parts) taken or derived from any such plant unless otherwise clearly indicated by context. Plant parts include, but are not limited to, plant cells, stems, roots, flowers, ovules, stamens, seeds, leaves, embryos, meristematic regions, callus tissue, anther cultures, gametophytes, sporophytes, pollen, microspores, protoplasts, hairy root cultures, and/or the like. The present invention also includes seeds produced by the plants of the present invention. Preferably, the seeds comprise the exogenous EIN2 nucleic acids. In one embodiment, the seeds can develop into plants with increased resistance to fungal infection as compared to a wild-type variety of the plant seed. As used herein, a "plant cell" includes, but is not limited to, a protoplast, gamete producing cell, and a cell that regenerates into a whole plant. Tissue culture of various tissues of plants and regeneration of plants therefrom is well known in the art and is widely published.

Reference herein to an "endogenous" nucleic acid and/or protein refers to the nucleic acid and/or protein in question as found in a plant in its natural form (i.e., without there being any human intervention).

The term "exogenous" nucleic acid refers to a nucleic acid that has been introduced in a plant by means of genetechnology. An "exogenous" nucleic acid can either not occur in a plant in its natural form, be different from the nucleic acid in question as found in a plant in its natural form, or can be identical to a nucleic acid found in a plant in its natural form, but integrated not within their natural genetic environment. The corresponding meaning of "exogenous" is applied in the context of protein expression. For example, a transgenic plant containing a transgene, i.e., an exogenous nucleic acid, may, when compared to the expression of the endogenous gene, encounter a substantial increase of the expression of the respective gene or protein in total. A transgenic plant according to the present invention includes an exogenous EIN2 nucleic acid integrated at any genetic loci and optionally the plant may also include the endogenous gene within the natural genetic background.

For the purposes of the invention, "recombinant" means with regard to, for example, a nucleic acid sequence, a nucleic acid molecule, an expression cassette or a vector construct comprising any one or more EIN2 nucleic acids, all those constructions brought about by man by genetechnological methods in which either (a) the sequences of the EIN2 nucleic acids or a part thereof, or (b) genetic control sequence(s) which is operably linked with the EIN2 nucleic acid sequence according to the invention, for example a promoter, or (c) a) and b)

are not located in their natural genetic environment or have been modified by man by genetechnological methods. The modification may take the form of, for example, a substitution, addition, deletion, inversion or insertion of one or more nucleotide residues. The natural genetic environment is understood as meaning the natural genomic or chromosomal locus in the original plant or the presence in a genomic library or the combination with the natural promoter.

For instance, a naturally occurring expression cassette— for example the naturally occurring combination of the natural promoter of the nucleic acid sequences with the corresponding nucleic acid sequence encoding a protein useful in the methods of the present invention, as defined above—becomes a recombinant expression cassette when this expression cassette is modified by man by non-natural, synthetic ("artificial") methods such as, for example, mutagenic treatment. Suitable methods are described, for example, in U.S. Pat. No. 5,565,350, WO 00/15815 or US200405323. Furthermore, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is not integrated in the natural genetic environment but in a different genetic environment.

For instance, a naturally occurring expression cassette— for example the naturally occurring combination of the natural promoter of the nucleic acid sequences with the corresponding nucleic acid sequence encoding a protein useful in the methods of the present invention, as defined above—becomes a recombinant expression cassette when this expression cassette is modified by man by non-natural, synthetic ("artificial") methods such as, for example, mutagenic treatment. Suitable methods are described, for example, in U.S. Pat. No. 5,565,350, WO 00/15815 or US200405323. Furthermore, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is not integrated in the natural genetic environment but in a different genetic environment.

The term "isolated nucleic acid" or "isolated protein" refers to a nucleic acid or protein that is not located in its natural environment, in particular its natural cellular environment. Thus, an isolated nucleic acid or isolated protein is essentially separated from other components of its natural environment. However, the skilled person in the art is aware that preparations of an isolated nucleic acid or an isolated protein can display a certain degree of impurity depending on the isolation procedure used. Methods for purifying nucleic acids and proteins are well known in the art. The isolated gene may be isolated from an organism or may be manmade, for example by chemical synthesis. In this regard, a recombinant nucleic acid may also be in an isolated form.

As used herein, the term "transgenic" refers to an organism, e.g., a plant, plant cell, callus, plant tissue, or plant part that exogenously contains the nucleic acid, recombinant construct, vector or expression cassette described herein or a part thereof which is preferably introduced by non-essentially biological processes, preferably by *Agrobacteria* transformation. The recombinant construct or a part thereof is stably integrated into a chromosome, so that it is passed on to successive generations by clonal propagation, vegetative propagation or sexual propagation. Preferred successive generations are transgenic too. Essentially biological processes may be crossing of plants and/or natural recombination.

A transgenic plant, plants cell or tissue for the purposes of the invention is thus understood as meaning that an exogenous EIN2 nucleic acid, recombinant construct, vector or expression cassette including one or more EIN2 nucleic acids is integrated into the genome by means of genetechnology.

A "wild type" plant, "wild type" plant part, or "wild type" plant cell means that said plant, plant part, or plant cell does not express exogenous EIN2 nucleic acid or exogenous EIN2 protein.

Natural locus means the location on a specific chromosome, preferably the location between certain genes, more preferably the same sequence background as in the original plant which is transformed.

Preferably, the transgenic plant, plant cell or tissue thereof expresses the EIN2 nucleic acids, EIN2 constructs or EIN2 expression cassettes described herein.

The term "expression" or "gene expression" means the transcription of a specific gene or specific genes or specific genetic vector construct. The term "expression" or "gene expression" in particular means the transcription of a gene or genes or genetic vector construct into structural RNA (rRNA, tRNA), or mRNA with or without subsequent translation of the latter into a protein. The process includes transcription of DNA and processing of the resulting RNA product. The term "expression" or "gene expression" can also include the translation of the mRNA and therewith the synthesis of the encoded protein, i.e., protein expression.

The term "increased expression" or "enhanced expression" or "overexpression" or "increase of content" as used herein means any form of expression that is additional to the original wild-type expression level. For the purposes of this invention, the original wild-type expression level might also be zero (absence of expression).

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the protein of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

The term "functional fragment" refers to any nucleic acid or protein which comprises merely a part of the fulllength nucleic acid or fulllength protein, respectively, but still provides the same function, e.g., fungal resistance, when expressed or repressed in a plant, respectively. Preferably, the fragment comprises at least 50%, at least 60%, at least 70%, at least 80%, at least 90% at least 95%, at least 98%, at least 99% of the original sequence. Preferably, the functional fragment comprises contiguous nucleic acids or amino acids as in the original nucleic acid or original protein, respectively. In one embodiment the fragment of any of the EIN2 nucleic acids has an identity as defined above over a length of at least 20%, at least 30%, at least 50%, at least 75%, at least 90% of the nucleotides of the respective EIN2 nucleic acid.

The term "splice variant" as used herein encompasses variants of a nucleic acid sequence in which selected introns and/or exons have been excised, replaced, displaced or added, or in which introns have been shortened or lengthened. Thus, a splice variant can have one or more or even all introns removed or added. According to this definition, a cDNA is considered as a splice variant of the respective intron-containing genomic sequence and vice versa. Such splice variants may be found in nature or may be manmade. Methods for predicting and isolating such splice variants are well known in the art (see for example Foissac and Schiex (2005) BMC Bioinformatics 6: 25).

In cases where overexpression of nucleic acid is desired, the term "similar functional activity" or "similar function" means that any homologue and/or fragment provide fungal resistance when expressed in a plant. Preferably similar functional activity means at least 50%, at least 60%, at least 70%, at least 80%, at least 90%, at least 95%, at least 98%, at least 99% or 100% or higher fungal resistance compared with functional activity provided by the exogenous expression of the EIN2 nucleotide sequence as defined by SEQ ID NO: 1 or 2 or 4.

The term "increased activity" or "enhanced activity" as used herein means any protein having increased activity and which provides an increased fungal resistance compared with the wildtype plant merely expressing the respective endogenous EIN2 nucleic acid. As far as overexpression is concerned, for the purposes of this invention, the original wild-type expression level might also be zero (absence of expression).

With respect to a vector construct and/or the recombinant nucleic acid molecules, the term "operatively linked" is intended to mean that the nucleic acid to be expressed is linked to the regulatory sequence, including promoters, terminators, enhancers and/or other expression control elements (e.g., polyadenylation signals), in a manner which allows for expression of the nucleic acid (e.g., in a host plant cell when the vector is introduced into the host plant cell). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, Eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the vector can depend on such factors as the choice of the host cell to be transformed, the level of expression of nucleic acid desired, and the like.

The term "introduction" or "transformation" as referred to herein encompass the transfer of an exogenous polynucleotide into a host cell, irrespective of the method used for transfer. Plant tissue capable of subsequent clonal propagation, whether by organogenesis or embryogenesis, may be transformed with a vector construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The host genome includes the nucleic acid contained in the nucleus as well as the nucleic acid contained in the plastids, e.g., chloroplasts, and/or mitochondria. The resulting transformed plant cell may then be used to regenerate a transformed plant in a manner known to persons skilled in the art.

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

DETAILED DESCRIPTION

EIN2 Nucleic Acids

The EIN2 nucleic acid to be overexpressed in order to achieve increased resistance to fungal pathogens, e.g., of the family Phacopsoraceae, for example soybean rust, is preferably a nucleic acid coding for an EIN2 protein, and is preferably as defined by SEQ ID NO: 1, 2, 4, 6, 11, 13, 15, 17, 19, 21, 23, 25, 27, 28, 29, 30, 31, 32, 33, or 34, or a fragment, homolog, derivative, orthologue or paralogue thereof, or a splice variant thereof. Preferably, the nucleic acid coding for an EIN2 protein of the present invention has at least 60% identity, preferably at least 70% sequence identity, at least 80%, at least 90%, at least 92%, at least 95%, at least 97%, at least 98%, at least 99% sequence identity, or even 100% sequence identity with SEQ ID NO: 1, 2, 4, 6, 11, 13, 15, 17, 19, 21, 23, 25, 27, 28, 29, 30, 31, 32, 33, or 34, or is a functional fragment thereof, or a splice variant thereof. Most preferred is at least 90% identity, at least 92%, at least 95%, at least 97%, more preferred is at least 98% or at least 99% identity with SEQ ID NO: 1, 2, 4, 6, 11, 13, 15, 17, 19, 21, 23, 25, 27, 28, 29, 30, 31, 32, 33, or 34.

Preferably, the EIN2 nucleic acid to be overexpressed in order to achieve increased resistance to fungal pathogens, e.g., of the family Phacopsoraceae, for example soybean rust, is preferably a nucleic acid coding for an EIN2 protein, and is preferably as defined by SEQ ID NO: 2, or a fragment, homolog, derivative, orthologue or paralogue thereof, or a splice variant thereof. Preferably, the nucleic acid coding for an EIN2 protein of the present invention has at least 60% identity, preferably at least 70% sequence identity, at least 80%, at least 90%, at least 92%, at least 95%, at least 97%, at least 98%, at least 99% sequence identity, or even 100% sequence identity with SEQ ID NO: 2 or is a functional fragment thereof, or a splice variant thereof. Most preferred is at least 90% identity, at least 92%, at least 95%, at least 97% identity, more preferred is at least 98% or at least 99% identity with SEQ ID NO: 2.

More preferably, the EIN2 nucleic acid to be overexpressed in order to achieve increased resistance to fungal pathogens, e.g., of the family Phacopsoraceae, for example soybean rust, is preferably a nucleic acid coding for an EIN2 protein, and is preferably as defined by SEQ ID NO: 1, or a fragment, homolog, derivative, orthologue or paralogue thereof, or a splice variant thereof. Preferably, the nucleic acid coding for an EIN2 protein of the present invention has at least 60% identity, preferably at least 70% sequence identity, at least 80%, at least 90%, at least 92%, at least 95%, at least 97%, at least 98%, at least 99% sequence identity, or even 100% sequence identity with SEQ ID NO: 1 or is a functional fragment thereof, or a splice variant thereof. Most preferred is at least 92%, at least 95%, at least 97% identity, more preferred is at least 98% or at least 99% identity with SEQ ID NO: 1.

Preferably, the EIN2 nucleic acid to be overexpressed in order to achieve increased resistance to fungal pathogens, e.g., of the family Phacopsoraceae, for example soybean rust, is preferably a nucleic acid coding for an EIN2 protein, and is preferably as defined by SEQ ID NO: 4, or a fragment, homolog, derivative, orthologue or paralogue thereof, or a splice variant thereof. Preferably, the nucleic acid coding for an EIN2 protein of the present invention has at least 60% identity, preferably at least 70% sequence identity, at least 80%, at least 90%, at least 92%, at least 95%, at least 97%, at least 98%, at least 99% sequence identity, or even 100% sequence identity with SEQ ID NO: 4 or is a functional fragment thereof, or a splice variant thereof. Most preferred is at least 90% identity, at least 92%, at least 95%, at least 97% identity, more preferred is at least 98% or at least 99% identity with SEQ ID NO: 4.

Preferably the EIN2 nucleic acid is an isolated nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, 2, 4, 6, 11, 13, 15, 17, 19, 21, 23, 25, 27, 28, 29, 30, 31, 32, 33, or 34, or a functional fragment, derivative, orthologue, or paralogue thereof, or a splice variant thereof, wherein overexpression of the sequence confers enhanced fungal resistance in the plant relative to a control plant;

(ii) a nucleic acid encoding an EIN2 protein comprising an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 3, 5, 12, 14, 16, 18, 20, 22, 24, or 26, or a functional fragment, derivative, orthologue, or paralogue thereof, wherein overexpression of the sequence confers enhanced fungal resistance in the plant relative to a control plant; preferably the EIN2 protein has essentially the same biological activity as an EIN2 protein encoded by SEQ ID NO: 1, 2, 4, or 6; preferably the EIN2 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding an EIN2 protein; preferably wherein the nucleic acid molecule codes for a polypeptide which has essentially identical properties to the polypeptide described in SEQ ID NO: 3 or 5; preferably the encoded protein confers enhanced fungal resistance relative to control plants; and (iv) a nucleic acid encoding the same EIN2 protein as the EIN2 nucleic acids of (i) to (iii) above, but differing from the EIN2 nucleic acids of (i) to (iii) above due to the degeneracy of the genetic code.

Preferably the EIN2 nucleic acid is an isolated nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, or a functional fragment, derivative, orthologue, or paralogue thereof, or a splice variant thereof, wherein overexpression of the sequence confers enhanced fungal resistance in the plant relative to a control plant;

(ii) a nucleic acid encoding an EIN2 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 3, or a functional fragment, derivative, orthologue, or paralogue thereof, wherein overexpression of the sequence confers enhanced fungal resistance in the plant relative to a control plant; preferably the EIN2 protein has essentially the same biological activity as an EIN2 protein encoded by SEQ ID NO: 1, preferably the EIN2 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding an EIN2 protein; preferably wherein the nucleic acid molecule codes for a polypeptide which has essentially identical properties to the polypeptide described in SEQ ID NO: 3 or 5; preferably the encoded protein confers enhanced fungal resistance relative to control plants; and (iv) a nucleic acid encoding the same EIN2 protein as the EIN2 nucleic acids of (i) to (iii) above, but differing from the EIN2 nucleic acids of (i) to (iii) above due to the degeneracy of the genetic code.

Preferably the EIN2 nucleic acid is an isolated nucleic acid molecule consisting of the coding sequence for the EIN2 C-terminal fragment or a fragment thereof comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1 or 2, or a functional fragment, derivative, orthologue, or paralogue thereof, or a splice variant thereof, wherein overexpression of the sequence confers enhanced fungal resistance in the plant relative to a control plant;

(ii) a nucleic acid encoding an EIN2 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 3, or a functional fragment, derivative, orthologue, or paralogue thereof, wherein overexpression of the sequence confers enhanced fungal resistance in the plant relative to a control plant; preferably the EIN2 protein has essentially the same biological activity as an EIN2 protein encoded by SEQ ID NO: 1, preferably the EIN2 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding an EIN2 protein; preferably wherein the nucleic acid molecule codes for a polypeptide which has essentially identical properties to the polypeptide described in SEQ ID NO: 3 or 5; preferably the encoded protein confers enhanced fungal resistance relative to control plants; and (iv) a nucleic acid encoding the same EIN2 protein as the EIN2 nucleic acids of (i) to (iii) above, but differing from the EIN2 nucleic acids of (i) to (iii) above due to the degeneracy of the genetic code.

Preferably the EIN2 nucleic acid is an isolated nucleic acid molecule comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 2 or 4, or a functional fragment, derivative, orthologue, or paralogue thereof, or a splice variant thereof;

(ii) a nucleic acid encoding an EIN2 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 3 or 5, or a functional fragment, derivative, orthologue, or paralogue thereof; preferably the EIN2 protein has essentially the same biological activity as an EIN2 protein encoded by SEQ ID NO: 2 or 4, preferably the EIN2 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding an EIN2 protein; preferably wherein the nucleic acid molecule codes for a polypeptide which has essentially identical properties to the polypeptide described in SEQ ID NO: 3 or 5; preferably the encoded protein confers enhanced fungal resistance relative to control plants; and (iv) a nucleic acid encoding the same EIN2 protein as the EIN2 nucleic acids of (i) to (iii) above, but differing from the EIN2 nucleic acids of (i) to (iii) above due to the degeneracy of the genetic code.

Percentages of identity of a nucleic acid are indicated with reference to the entire nucleotide region given in a sequence specifically disclosed herein.

Preferably the portion of the EIN2 nucleic acid is about 1000-2000, about 2000-2500, about 2500-3000, about 3000-3500, about 3500-4000, about 4000-4500, about 4500-5000, about 5000-5500, or about 5500-5900 nucleotides, preferably consecutive nucleotides, preferably counted from the 5' or 3' end of the nucleic acid, in length, of the nucleic acid sequences given in SEQ ID NO: 1, 2, 4, 6, 11, 13, 15, 17, 19, 21, 23, 25, 27, 28, 29, 30, 31, 32, 33, or 34.

Preferably, the EIN2 nucleic acid comprises at least about 1000, at least about 2000, at least about 3000, at least about 4000, at least about 4500, at least about 5000, at least about 5500, or at least about 5900, nucleotides, preferably continuous nucleotides, preferably counted from the 5' or 3' end of the nucleic acid or up to the full length of the nucleic acid sequence set out in SEQ ID NO: 1, 2, 4, 6, 11, 13, 15, 17, 19, 21, 23, 25, 27, 28, 29, 30, 31, 32, 33, or 34.

Preferably, the EIN2 nucleic acid comprises at least about 1000, at least about 1500, at least about 2000, at least about 2100, at least about 2200, at least about 2300, at least about 2400, at least about 2500, or at least about 2600 nucleotides, preferably continuous nucleotides, preferably counted from the 5' or 3' end of the nucleic acid or up to the full length of the nucleic acid sequence set out in SEQ ID NO: 1, 2, 11, 13, 15, 17, 19, 21, 23, 25, 27, 28, 29, 30, 31, 32, 33, or 34.

Preferably the portion of the EIN2 nucleic acid is about 1000-1500, about 1500-2000, about 2000-2100, about 2100-2200, about 2200-2300, about 2300-2400, about 2400-2500, about 2500-2600, or about 2600-2606 nucleotides, preferably consecutive nucleotides, preferably counted from the 5' or 3' end of the nucleic acid, in length, of the nucleic acid sequences given in SEQ ID NO: 1, 2, 11, 13, 15, 17, 19, 21, 23, 25, 27, 28, 29, 30, 31, 32, 33, or 34.

Preferably, the EIN2 nucleic acid comprises at least about 2000, at least about 2500, at least about 3000, at least about 3100, at least about 3200, at least about 3300, at least about 3400, at least about 3500, at least about 3600, at least 3700, or at least about 3800 nucleotides, preferably continuous nucleotides, preferably counted from the 5' or 3' end of the nucleic acid or up to the full length of the nucleic acid sequence set out in SEQ ID NO: 4.

Preferably the portion of the EIN2 nucleic acid is about 2000-2500, about 2500-3000, about 3000-3100, about 3100-3200, about 3200-3300, about 3300-3400, about 3400-3500, about 3500-3600, about 3600-3700, or 3700-3800, or about 3800-3885 nucleotides, preferably consecutive nucleotides, preferably counted from the 5' or 3' end of the nucleic acid, in length, of the nucleic acid sequences given in SEQ ID NO: 4.

Figure 3:
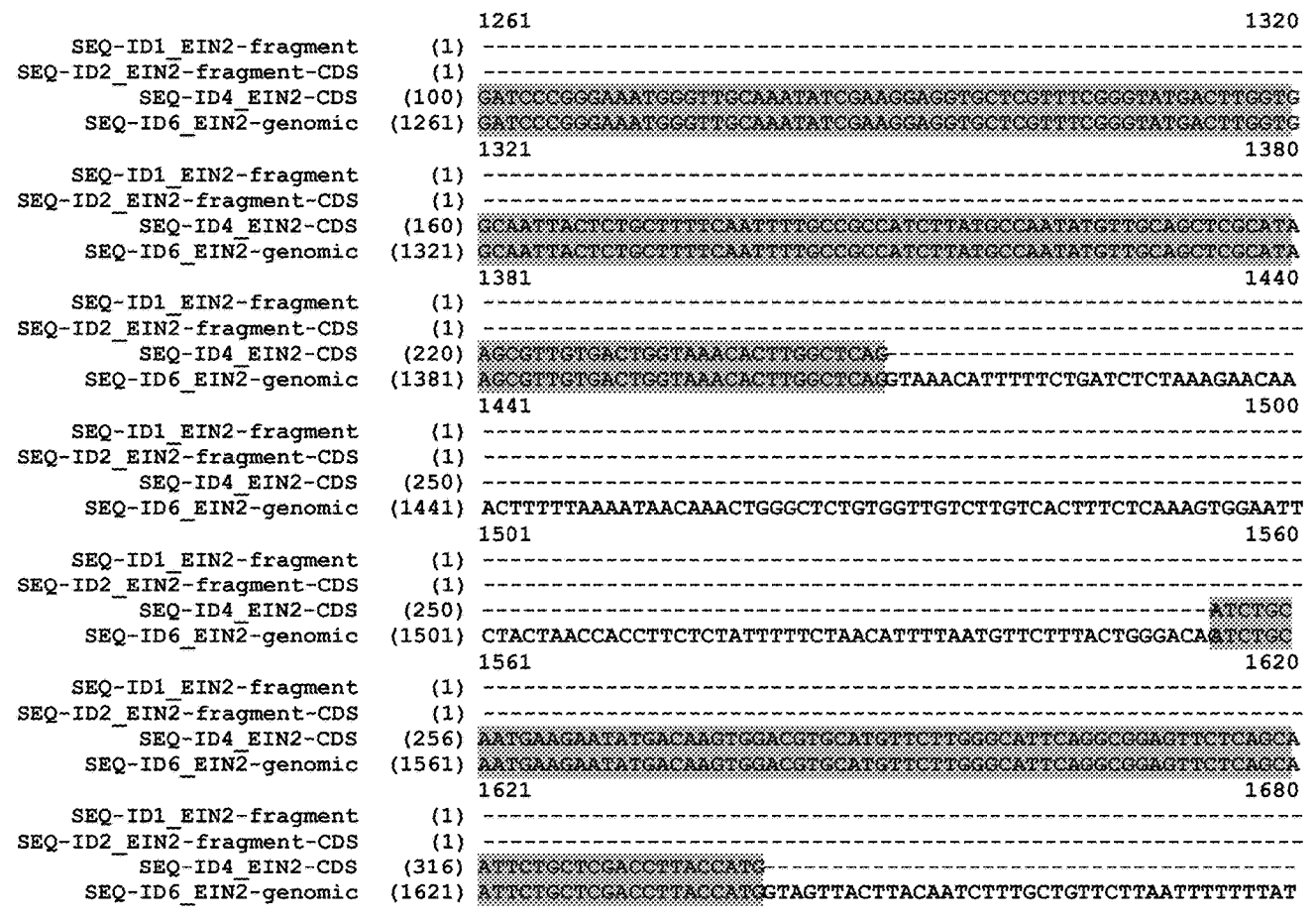
Figure 3:
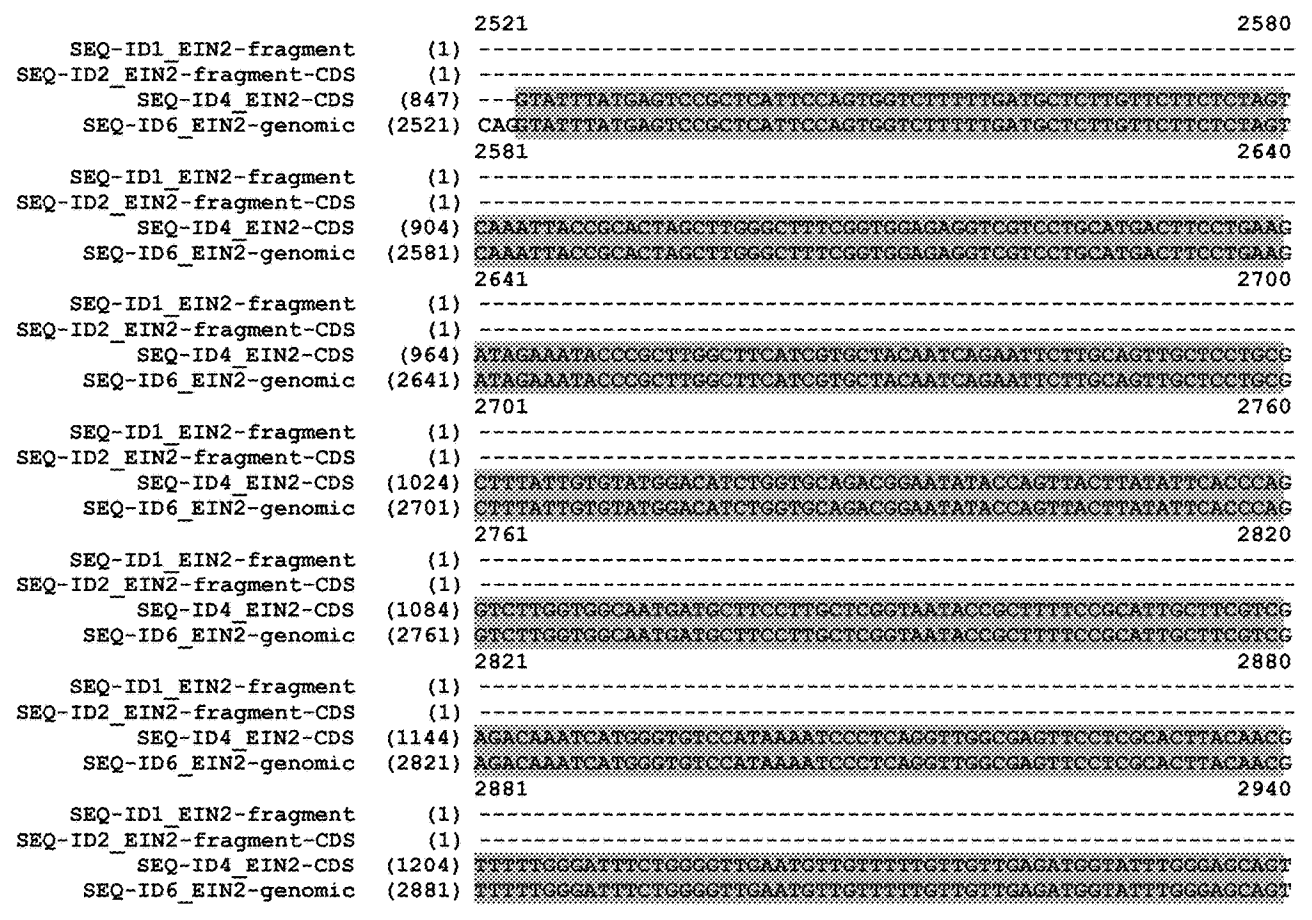
Figure 3:
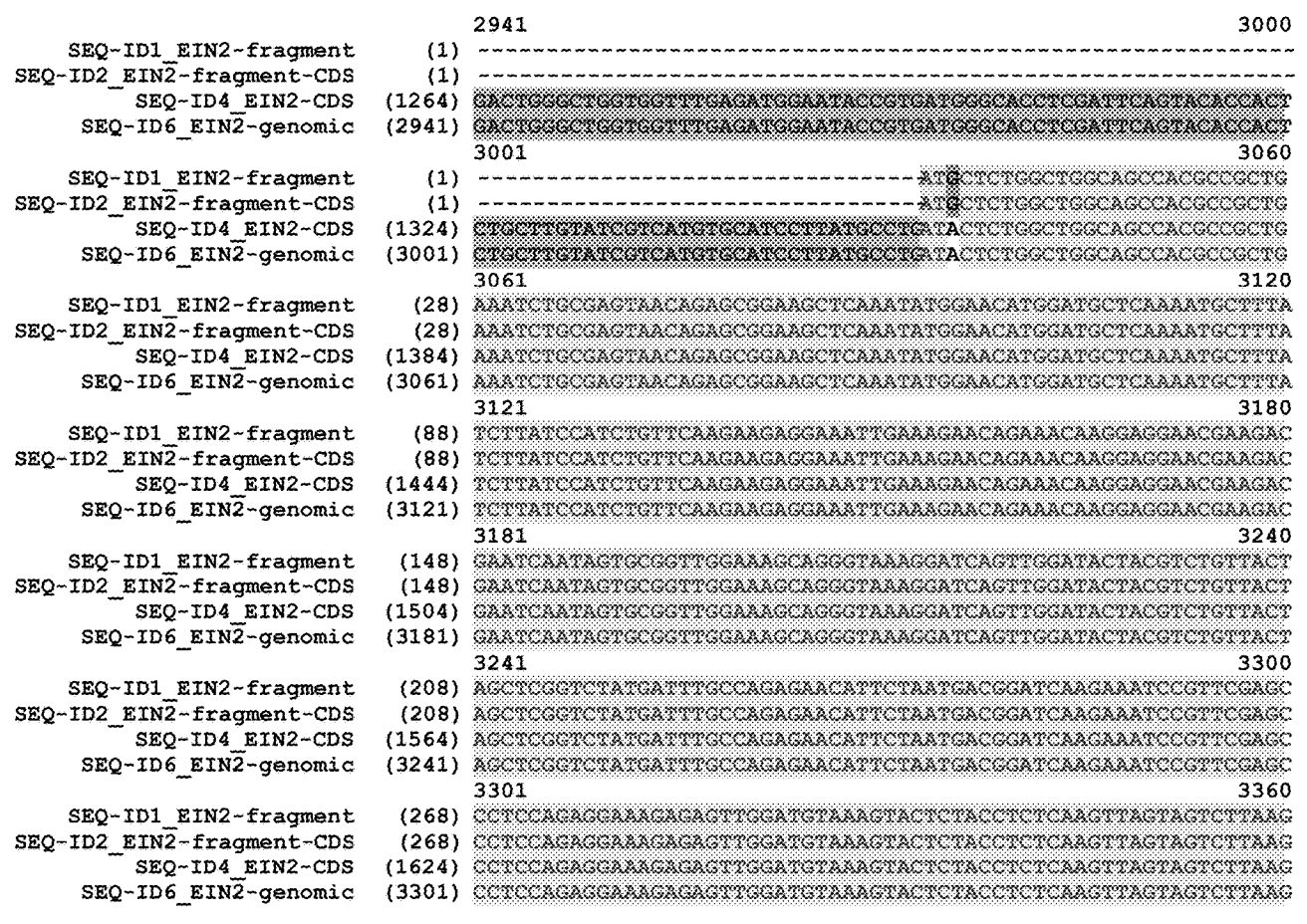
Figure 3:
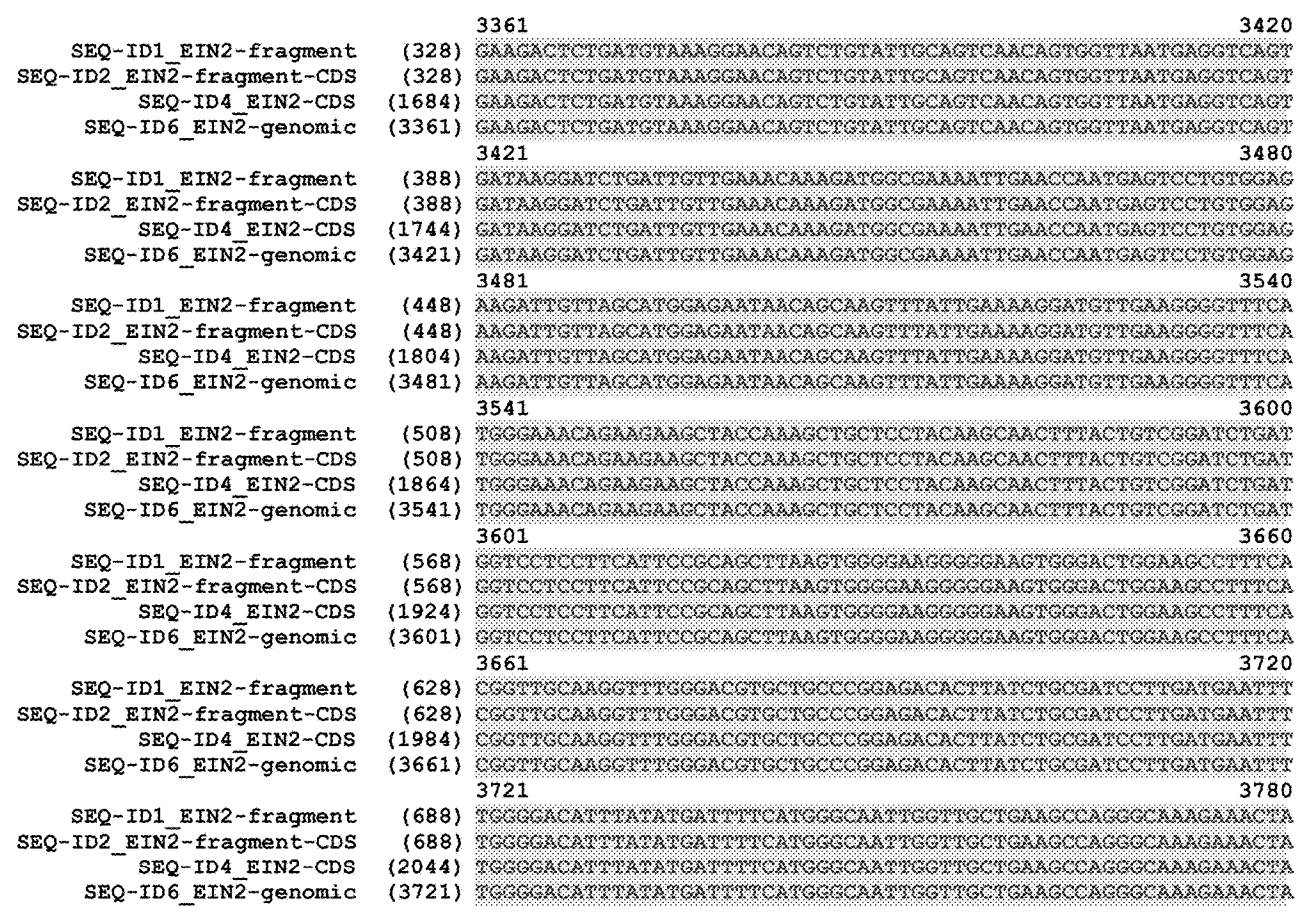
Figure 3:
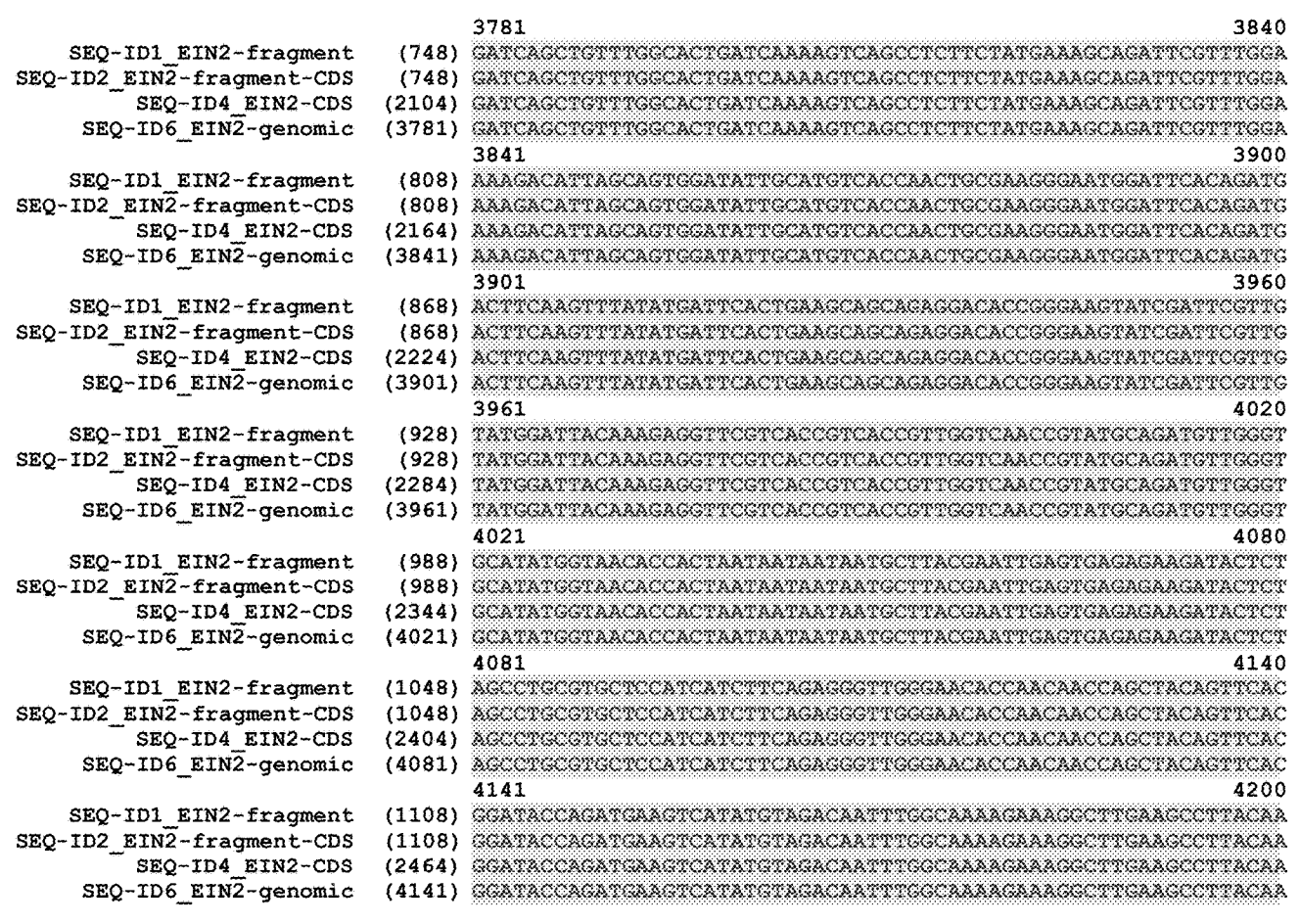
Figure 3:
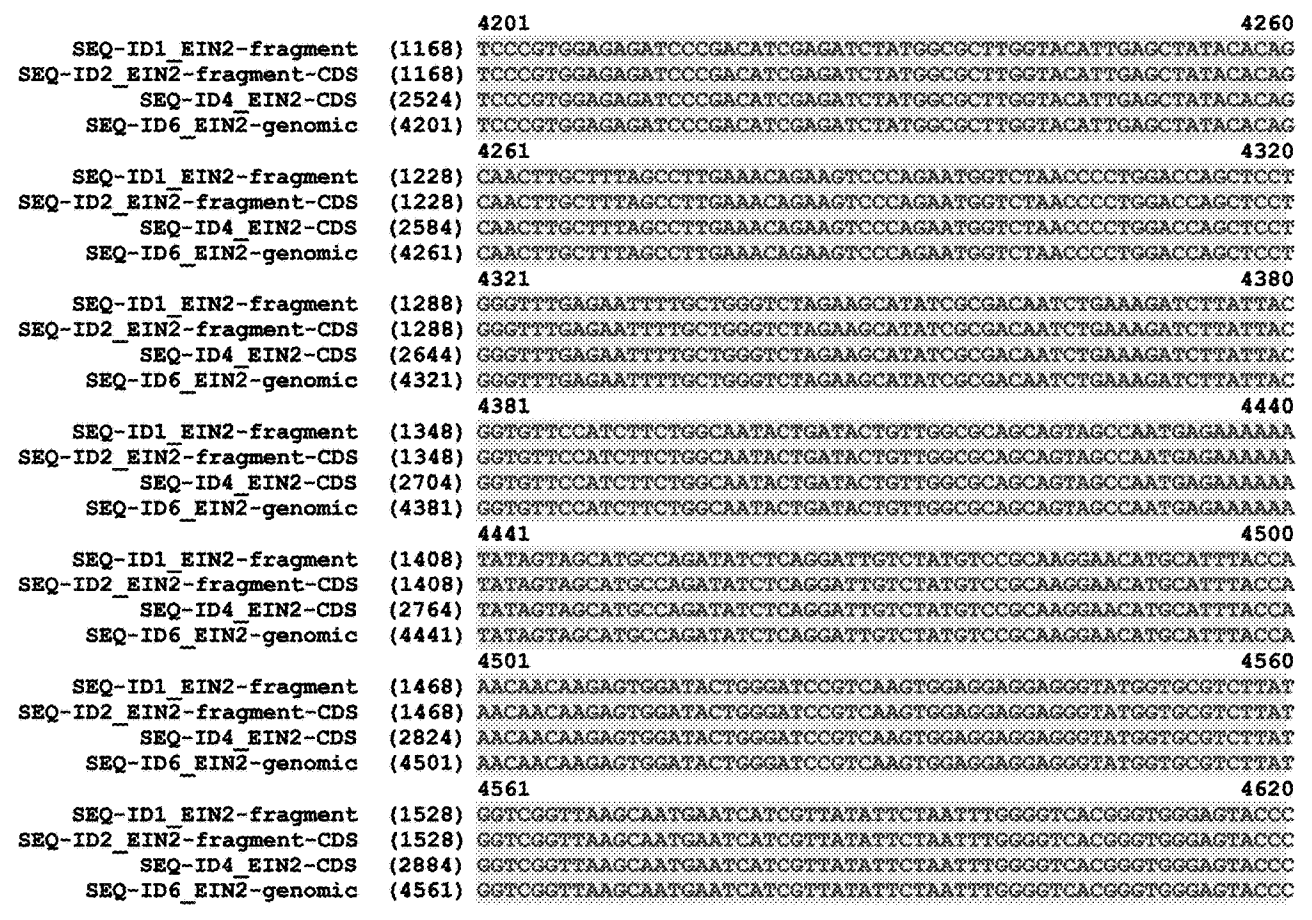
Figure 3:
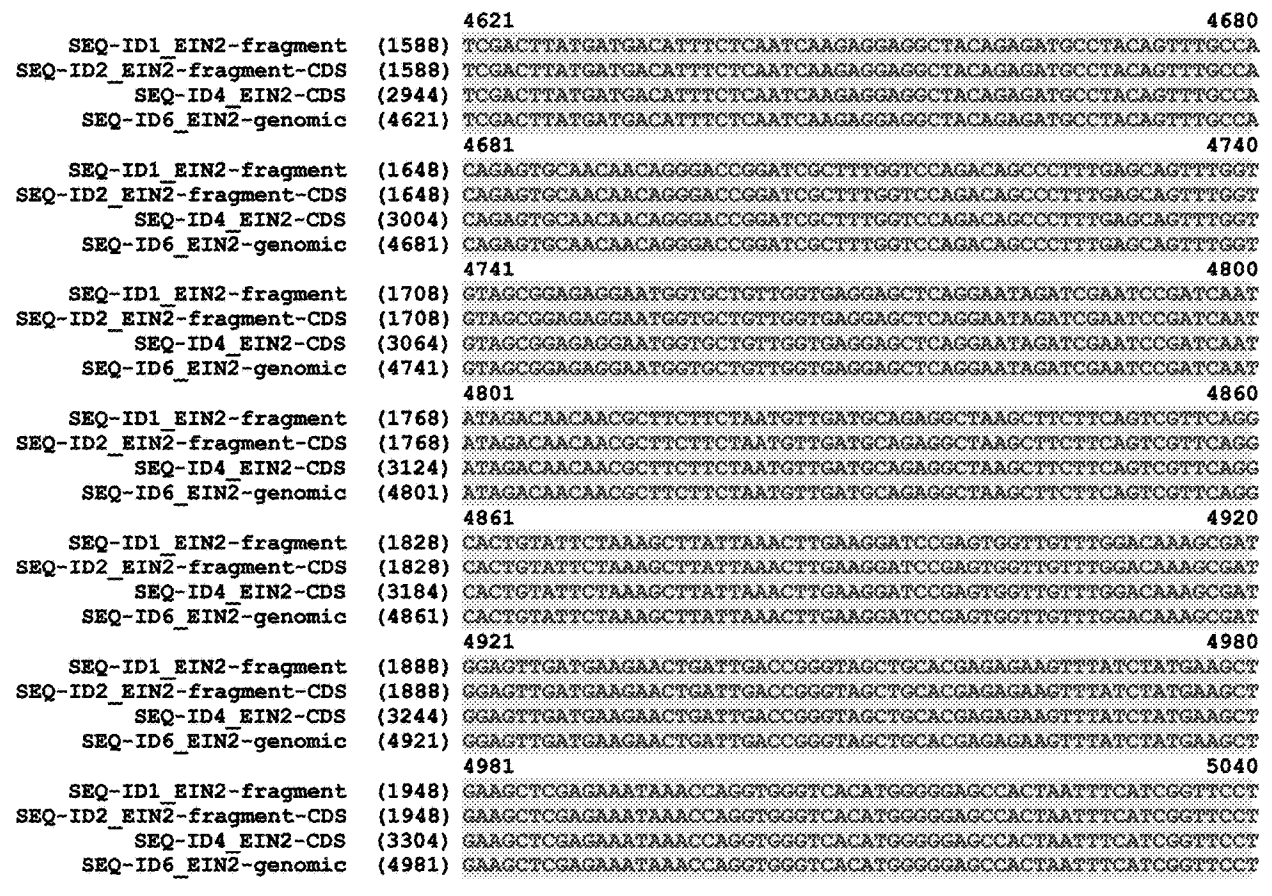
Figure 3:
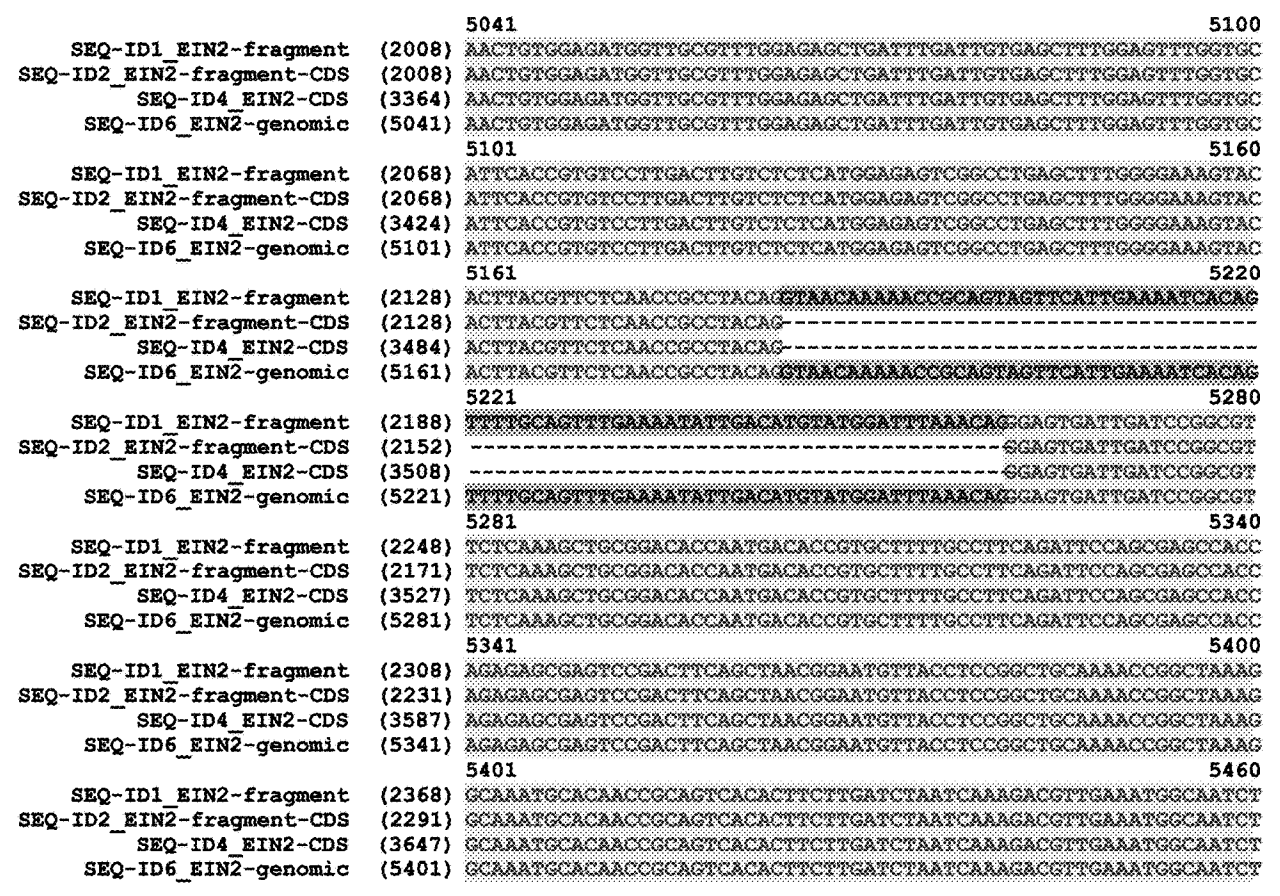

Preferably, the EIN2 nucleic acid is an EIN2 nucleic acid splice variant. Preferred splice variants are splice variants of a nucleic acid represented by SEQ ID NO: 6. Preferred EIN2 nucleic acids being a splice variant of SEQ ID NO: 6 are shown in FIG. 3.

Preferably, the EIN2 nucleic acid is an isolated nucleic acid molecule comprising a splice variant of SEQ ID NO: 6, wherein the splice variant is selected from the group consisting of:
(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, 2, or 4, or a functional fragment, derivative, orthologue, or paralogue thereof, wherein overexpression of the sequence confers enhanced fungal resistance in the plant relative to a control plant;
(ii) a nucleic acid encoding an EIN2 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 3 or 5, or a functional fragment, derivative, orthologue, or paralogue thereof, wherein overexpression of the sequence confers enhanced fungal resistance in the plant relative to a control plant; preferably the EIN2 protein has essentially the same biological activity as an EIN2 protein encoded by SEQ ID NO: 1, 2, or 4; preferably the EIN2 protein confers enhanced fungal resistance relative to control plants;
(iii) a nucleic acid molecule which hybridizes with a complementary sequence of any of the nucleic acid molecules of (i) or (ii) under high stringency hybridization conditions; preferably encoding an EIN2 protein; preferably wherein the nucleic acid molecule codes for a polypeptide which has essentially identical properties to the polypeptide described in SEQ ID NO: 3 or 5; preferably the encoded protein confers enhanced fungal resistance relative to control plants; and
(iv) a nucleic acid encoding the same EIN2 protein as the EIN2 nucleic acids of (i) to (iii) above, but differing from the EIN2 nucleic acids of (i) to (iii) above due to the degeneracy of the genetic code.

Preferred splice variants of SEQ ID NO: 6 consist of or comprise anyone of the nucleotide sequences shown in SEQ ID NO: 1, 2, or 4. Most preferred is the EIN2 nucleic acid splice variant as shown in SEQ ID NO: 1.

Preferably the EIN2 nucleic acid is an isolated nucleic acid molecule comprising a nucleic acid selected from the group consisting of:
(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 6, or a splice variant thereof, wherein overexpression of the sequence confers enhanced fungal resistance in the plant relative to a control plant;
(ii) a nucleic acid molecule which hybridizes with a complementary sequence of any of the nucleic acid molecules of (i) under high stringency hybridization conditions; preferably encoding an EIN2 protein; preferably wherein the nucleic acid molecule codes for a polypeptide which has essentially identical properties to the polypeptide described in SEQ ID NO: 3 or 5; preferably the encoded protein confers enhanced fungal resistance relative to control plants; and
(iii) a nucleic acid encoding the same EIN2 protein as the EIN2 nucleic acids of (i) to (ii) above, but differing from the EIN2 nucleic acids of (i) to (ii) above due to the degeneracy of the genetic code;
wherein the splice variant thereof is selected from the group consisting of:
(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, 2, or 4, or a functional fragment, derivative, orthologue, or paralogue thereof;
(ii) a nucleic acid encoding an EIN2 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 3 or 5, or a functional fragment, derivative, orthologue, or paralogue thereof; preferably the EIN2 protein has essentially the same biological activity as an EIN2 protein encoded by SEQ ID NO: 1, 2, 4, or 6; preferably the EIN2 protein confers enhanced fungal resistance relative to control plants;
(iii) a nucleic acid molecule which hybridizes with a complementary sequence of any of the nucleic acid molecules of (i) or (ii) under high stringency hybridization conditions; preferably encoding an EIN2 protein; preferably wherein the nucleic acid molecule codes for a polypeptide which has essentially identical properties to the polypeptide described in SEQ ID NO: 3 or 5; preferably the encoded protein confers enhanced fungal resistance relative to control plants; and (iv) a nucleic acid encoding the same EIN2 protein as the EIN2 nucleic acids of (i) to (iii) above, but differing from the EIN2 nucleic acids of (i) to (iii) above due to the degeneracy of the genetic code.

More preferably the EIN2 nucleic acid is an isolated nucleic acid molecule comprising a nucleic acid selected from the group consisting of:

a nucleic acid having in increasing order of preference least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 6, or a splice variant thereof;

wherein the splice variant thereof is selected from the group consisting of:

a nucleic acid having in increasing order of preference at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, 2, or 4; preferably SEQ ID NO: 1.

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The EIN2 nucleic acids described herein are useful in the constructs, methods, plants, harvestable parts and products of the invention.

EIN2 Proteins

The EIN2 protein is preferably defined by SEQ ID NO: 3, 5, 12, 14, 16, 18, 20, 22, 24, or 26, or a fragment, homolog, derivative, orthologue or paralogue thereof. Preferably, the EIN2 protein of the present invention is encoded by a nucleic acid, which has at least 60% identity, preferably at least 70% sequence identity, at least 80%, at least 90%, at least 92%, at least 95%, at least 97%, at least 98%, at least 99% sequence identity, or even 100% sequence identity with SEQ ID NO: 1, 2, 4, 6, 11, 13, 15, 17, 19, 21, 23, 25, 27, 28, 29, 30, 31, 32, 33, or 34, or a functional fragment thereof. More preferably, the EIN2 protein of the present invention has at least 60%, preferably at least 70% sequence identity, at least 80%, at least 90%, at least 92%, at least 95%, at least 97%, at least 98%, at least 99% sequence identity, or even 100% sequence identity with SEQ ID NO: 3, 5, 12, 14, 16, 18, 20, 22, 24, or 26, or is a functional fragment thereof, an orthologue or a paralogue thereof. Most preferred is at least 90% identity, at least 92%, at least 95%, at least 97% identity, more preferred is at least 98% or at least 99% identity with SEQ ID NO: 3, 5, 12, 14, 16, 18, 20, 22, 24, or 26.

More preferably, the EIN2 protein of the present invention has at least 60%, preferably at least 70% sequence identity, at least 80%, at least 90%, at least 92%, at least 95%, at least 97%, at least 98%, at least 99% sequence identity, or even 100% sequence identity with SEQ ID NO: 3 or is a functional fragment thereof, an orthologue or a paralogue thereof.

More preferably, the EIN2 protein of the present invention has at least 60%, preferably at least 70% sequence identity, at least 80%, at least 90%, at least 92%, at least 95%, at least 97%, at least 98%, at least 99% sequence identity, or even 100% sequence identity with SEQ ID NO: 5, or is a functional fragment thereof, an orthologue or a paralogue thereof.

The EIN2 protein is preferably defined by SEQ ID NO: 3, 5, 12, 14, 16, 18, 20, 22, 24, or 26, or a fragment, homolog, derivative, orthologue or paralogue thereof. Preferably, the EIN2 protein of the present invention is encoded by a nucleic acid, which has at least 60% identity, preferably at least 70% sequence identity, at least 80%, at least 90%, at least 92%, at least 95%, at least 97%, at least 98%, at least 99% sequence identity, or even 100% sequence identity with SEQ ID NO: 1, 2, 4, 6, 11, 13, 15, 17, 19, 21, 23, 25, 27, 28, 29, 30, 31, 32, 33, or 34 or a functional fragment thereof. More preferably, the EIN2 protein of the present invention has at least 60%, preferably at least 70% sequence identity, at least 80%, at least 90%, at least 92%, at least 95%, at least 97%, at least 98%, at least 99% sequence identity, or even 100% sequence identity with SEQ ID NO: 3, 5, 12, 14, 16, 18, 20, 22, 24, or 26, or is a functional fragment thereof, an orthologue or a paralogue thereof. Most preferred is at least 92%, at least 95%, at least 97% identity, more preferred is at least 98% or at least 99% identity with SEQ ID NO: 3, 5, 12, 14, 16, 18, 20, 22, 24, or 26.

Preferably, the EIN2 protein is a protein consisting of or comprising an amino acid sequence selected from the group consisting of:

(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 3, 5, 12, 14, 16, 18, 20, 22, 24, or 26, or a functional fragment, derivative, orthologue, or paralogue thereof, wherein overexpression of the sequence confers enhanced fungal resistance in the plant relative to a control plant; preferably the EIN2 protein has essentially the same biological activity as an EIN2 protein encoded by SEQ ID NO: 1, 2, 4, or 6; preferably the EIN2 protein confers enhanced fungal resistance relative to control plants; or (ii) an amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, 2, 4, 6, 11, 13, 15, 17, 19, 21, 23, 25, 27, 28, 29, 30, 31, 32, 33, or 34, or a functional fragment, derivative, orthologue, or paralogue thereof, or a splice variant thereof, wherein overexpression of the sequence confers enhanced fungal resistance in the plant relative to a control plant; preferably the EIN2 protein confers enhanced fungal resistance relative to control plants.

Preferably, the EIN2 protein is a protein consisting of the EIN2 C-terminal fragment or fragment thereof comprising an amino acid sequence selected from the group consisting of:
(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 3, or a functional fragment, derivative, orthologue, or paralogue thereof, wherein overexpression of the sequence confers enhanced fungal resistance in the plant relative to a control plant; preferably the EIN2 protein has essentially the same biological activity as an EIN2 protein encoded by SEQ ID NO: 1 or 2; preferably the EIN2 protein confers enhanced fungal resistance relative to control plants; or
(ii) an amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1 or 2, or a functional fragment, derivative, orthologue, or paralogue thereof, or a splice variant thereof, wherein overexpression of the sequence confers enhanced fungal resistance in the plant relative to a control plant; preferably the EIN2 protein confers enhanced fungal resistance relative to control plants.

Preferably, the EIN2 protein is a protein comprising an amino acid sequence selected from the group consisting of:
(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 3, or a functional fragment, derivative, orthologue, or paralogue thereof, wherein overexpression of the sequence confers enhanced fungal resistance in the plant relative to a control plant; preferably the EIN2 protein has essentially the same biological activity as an EIN2 protein encoded by SEQ ID NO: 1 or 2; preferably the EIN2 protein confers enhanced fungal resistance relative to control plants; or
(ii) an amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1 or 2, or a functional fragment, derivative, orthologue, or paralogue thereof, or a splice variant thereof, wherein overexpression of the sequence confers enhanced fungal resistance in the plant relative to a control plant; preferably the EIN2 protein confers enhanced fungal resistance relative to control plants.

Preferably, the EIN2 protein is a protein comprising an amino acid sequence selected from the group consisting of:
(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 5, or a functional fragment, derivative, orthologue, or paralogue thereof; preferably the EIN2 protein has essentially the same biological activity as an EIN2 protein encoded by SEQ ID NO: 4; preferably the EIN2 protein confers enhanced fungal resistance relative to control plants; or
(ii) an amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 4, or a functional fragment, derivative, orthologue, or paralogue thereof, or a splice variant thereof; preferably the EIN2 protein confers enhanced fungal resistance relative to control plants.

A preferred derivative of an EIN2 protein is an EIN2 protein consisting of or comprising an amino acid sequence selected from the group consisting of:
an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence represented by SEQ ID NO: 3, 5, 12, 14, 16, 18, 20, 22, 24, or 26, wherein the non-identical amino acid residues are conservative amino acid substitutions, preferably as shown in Table 1, of the corresponding amino acid residue of SEQ ID NO: 3, 5, 12, 14, 16, 18, 20, 22, 24, or 26; preferably the EIN2 protein has essentially the same biological activity as SEQ ID NO: 3 or 5, or as an EIN2 protein encoded by SEQ ID NO: 1, 2, 4, or 6; preferably the EIN2 protein confers enhanced fungal resistance relative to control plants.

Preferably, the EIN2 protein consists of or comprises an amino acid sequence represented by SEQ ID NO: 3, 5, 12, 14, 16, 18, 20, 22, 24, or 26 with one or more conservative amino acid substitutions, preferably as shown in Table 1, of the corresponding amino acid residues of SEQ ID NO: 3, 5, 12, 14, 16, 18, 20, 22, 24, or 26. Preferably 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 1-10, 10-20, 20-30, 40-50, 50-60, 60-70, 70-80, 80-90, 90-100, 100-110, 110-120, 120-130, 130-140, 140-150, 150-160, 60-170, 170-180, 180-190, 190-200, 200-210, or 210-220 amino acid residues of SEQ ID NO: 3, 5, 12, 14, 16, 18, 20, 22, 24, or 26 are conservative amino acid substitutions, preferably as shown in Table 1, of the corresponding amino acid residue of SEQ ID NO: 3, 5, 12, 14, 16, 18, 20, 22, 24, or 26.

More preferably, the EIN2 protein consists of or comprises an amino acid sequence having at least 80%, at least 85%, at least 90%, at least 95%, at least 98% or at least 99% sequence identity with an amino acid sequence as represented by SEQ ID NO: 3, 5, 12, 14, 16, 18, 20, 22, 24, or 26, wherein at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, or at least 120 of the non-identical amino acid residues, or wherein 1-10, 10-20, 20-30, 40-50, 50-60, 60-70, 70-80, 80-90, 90-100, 100-110, 110-120, 120-130, 130-140, 140-150, 150-160, 60-170, 170-180, 180-190, 190-200, 200-210, or 210-220 or even all of the non-identical amino acid residues are conservative amino acid substitutions, preferably as shown in Table 1, of the corresponding amino acid residue of SEQ ID NO: 3, 5, 12, 14, 16, 18, 20, 22, 24, or 26.

Percentages of identity of a polypeptide or protein are indicated with reference to the entire amino acid sequence specifically disclosed herein.

Preferably, the EIN2 protein comprises at least about 500, at least about 600, at least about 700, at least about 800, at least about 900, at least about 1000, at least about 1050, at least about 1100, at least about 1150, at least about 1200, at least about 1250, or at least about 1290 amino acid residues, preferably continuous amino acid residues, preferably counted from the N-terminus or the C-terminus of the amino acid sequence, or up to the full length of the amino acid sequence set out in SEQ ID NO: 5.

Preferably, the EIN2 polypeptide comprises about 500-600, about 600-700, about 700-800, about 800-900, about 900-1000, about 1050-1100, about 1100-1150, about 1150-1200, or about 1250-1294, preferably consecutive amino acid residues, preferably counted from the N-terminus or C-terminus of the amino acid sequence, or up to the full length of any of the amino acid sequences encoded by the nucleic acid sequences set out in SEQ ID NO: 5.

Preferably, the EIN2 protein comprises at least about 500, at least about 550, at least about 600, at least about 650, at least about 700, at least about 750, at least about 800, or at least about 840 amino acid residues, preferably continuous amino acid residues, preferably counted from the N-terminus or the C-terminus of the amino acid sequence, or up to the full length of the amino acid sequence set out in SEQ ID NO: 3, 12, 14, 16, 18, 20, 22, 24, or 26.

Preferably, the EIN2 polypeptide comprises about 500-550, about 550-600, about 600-650, about 650-700, about 700-750, about 750-800, or about 800-842 amino acid residues, preferably consecutive amino acid residues, preferably counted from the N-terminus or C-terminus of the amino acid sequence, or up to the full length of any of the amino acid sequences encoded by the nucleic acid sequences set out in SEQ ID NO: 3, 12, 14, 16, 18, 20, 22, 24, or 26.

The EIN2 proteins described herein are useful in the constructs, methods, plants, harvestable parts and products of the invention.

Methods for Increasing Fungal Resistance; Methods for Modulating Gene Expression One embodiment of the invention is a method for increasing fungal resistance, preferably resistance to Phacopsoracea, for example soy bean rust, in a plant, plant part, or plant cell by increasing the expression of an EIN2 protein or a functional fragment, orthologue, paralogue or homologue thereof in comparison to wild-type plants, wild-type plant parts or wild-type plant cells.

The present invention also provides a method for increasing resistance to fungal pathogens, in particular a heminecrotrophic pathogen, in particular to rust pathogens (i.e., fungal pathogens of the order Pucciniales), preferably fungal pathogens of the family Phacopsoraceae, preferably against fungal pathogens of the genus *Phacopsora*, most preferably against *Phakopsora pachyrhizi* and *Phakopsora meibomiae*, also known as soy bean rust in plants or plant cells, wherein in comparison to wild type plants, wild type plant parts, or wild type plant cells an EIN2 protein is overexpressed.

The present invention further provides a method for increasing resistance to fungal pathogens of the genus *Phacopsora*, most preferably against *Phakopsora pachyrhizi* and *Phakopsora meibomiae*, also known as soy bean rust in plants or plant cells by overexpression of an EIN2 protein.

In preferred embodiments, the protein amount and/or function of the EIN2 protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the EIN2 nucleic acid.

In one embodiment of the invention, the EIN2 protein is encoded by a nucleic acid comprising (i) an exogenous nucleic acid having at least 60%, preferably at least 70%, for example at least 75%, more preferably at least 80%, for example at least 85%, even more preferably at least 90%, for example at least 95% or at least 96% or at least 97% or at least 98% most preferably 99% identity with SEQ ID NO: 1, 2, 4, 6, 11, 13, 15, 17, 19, 21, 23, 25, 27, 28, 29, 30, 31, 32, 33, or 34, a functional fragment thereof, or an orthologue or a paralogue thereof, or a splice variant thereof; or by (ii) an exogenous nucleic acid encoding a protein comprising an amino acid sequence having at least 60% identity, preferably at least 70%, for example at least 75%, more preferably at least 80%, for example at least 85%, even more preferably at least 90%, for example at least 95% or at least 96% or at least 97% or at least 98% most preferably 99% homology with SEQ ID NO: 3, 5, 12, 14, 16, 18, 20, 22, 24, or 26, a functional fragment thereof, an orthologue or a paralogue thereof, preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 3 or 5; preferably the encoded protein confers enhanced fungal resistance relative to control plants; or by (iv) an exogenous nucleic acid encoding the same EIN2 protein as the nucleic acids of (i) to (iii) above, but differing from the nucleic acids of (i) to (iii) above due to the degeneracy of the genetic code.

A method for increasing fungal resistance, preferably resistance to Phacopsoracea, for example soy bean rust, in a plant, plant part, or plant cell, by increasing the expression of an EIN2 protein or a functional fragment, orthologue, paralogue or homologue thereof, or a splice variant thereof, wherein the EIN2 protein is encoded by a nucleic acid comprising (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 1, 2, 4, 6, 11, 13, 15, 17, 19, 21, 23, 25, 27, 28, 29, 30, 31, 32, 33, or 34, or a functional fragment thereof, an orthologue or a paralogue thereof, or a splice variant thereof;

(ii) an exogenous nucleic acid encoding a protein comprising an amino acid sequence having at least 60%, preferably at least 70% sequence identity, at least 80%, at least 90%, at least 95%, at least 98%, at least 99% sequence identity, or even 100% sequence identity with SEQ ID NO: 3, 5, 12, 14, 16, 18, 20, 22, 24, or 26, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 3 or 5; preferably the encoded protein confers enhanced fungal resistance relative to control plants; and/or by (iv) an exogenous nucleic acid encoding the same EIN2 protein as the nucleic acids of (i) to (iii) above, but differing from the nucleic acids of (i) to (iii) above due to the degeneracy of the genetic code;

is a further embodiment of the invention.

A method for increasing fungal resistance, preferably resistance to Phacopsoracea, for example soy bean rust, in a plant, plant part, or plant cell, by increasing the expression of an EIN2 protein or a functional fragment, orthologue, paralogue or homologue thereof, or a splice variant thereof, wherein the EIN2 protein is encoded by (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 1 or a functional fragment thereof, an orthologue or a paralogue thereof, or a splice variant thereof;

(ii) an exogenous nucleic acid encoding a protein having at least 60%, preferably at least 70% sequence identity, at least 80%, at least 90%, at least 95%, at least 98%, at least 99% sequence identity, or even 100% sequence identity with SEQ ID NO: 3, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 3; preferably the encoded protein confers enhanced fungal resistance relative to control plants; and/or by (iv) an exogenous nucleic acid encoding the same EIN2 protein as the nucleic acids of (i) to (iii) above, but differing from the nucleic acids of (i) to (iii) above due to the degeneracy of the genetic code is a further embodiment of the invention.

A method for increasing fungal resistance, preferably resistance to Phacopsoracea, for example soy bean rust, in a plant, plant part, or plant cell, by increasing the expression of an EIN2 protein or a functional fragment, orthologue, paralogue or homologue thereof, or a splice variant thereof, wherein the EIN2 protein is encoded by (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 4 or a functional fragment thereof, an orthologue or a paralogue thereof, or a splice variant thereof;

(ii) an exogenous nucleic acid encoding a protein having at least 60%, preferably at least 70% sequence identity, at least 80%, at least 90%, at least 95%, at least 98%, at least 99% sequence identity, or even 100% sequence identity with SEQ ID NO: 5, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 3 or 5; preferably the encoded protein confers enhanced fungal resistance relative to control plants; and/or by (iv) an exogenous nucleic acid encoding the same EIN2 protein as the nucleic acids of (i) to (iii) above, but differing from the nucleic acids of (i) to (iii) above due to the degeneracy of the genetic code is a further embodiment of the invention.

In a further method of the invention, the method comprises the steps of
(a) stably transforming a plant cell with a recombinant expression cassette comprising
  (i) a nucleic acid having at least 60% identity, preferably at least 70% sequence identity, at least 80%, at least 90%, at least 95%, at least 98%, at least 99% sequence identity, or even 100% sequence identity with SEQ ID NO: 1, 2, 4, 6, 11, 13, 15, 17, 19, 21, 23, 25, 27, 28, 29, 30, 31, 32, 33, or 34, or a functional fragment thereof, or an orthologue or a paralogue thereof, or a splice variant thereof;
  (ii) a nucleic acid coding for a protein comprising an amino acid sequence having at least 60% identity, preferably at least 70% sequence identity, at least 80%, at least 90%, at least 95%, at least 98%, at least 99% sequence identity, or even 100% sequence identity with SEQ ID NO: 3, 5, 12, 14, 16, 18, 20, 22, 24, or 26, a functional fragment thereof, an orthologue or a paralogue thereof; preferably the encoded protein confers enhanced fungal resistance relative to control plants;
  (iii) a nucleic acid capable of hybridizing under stringent conditions with a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 3 or 5; preferably the encoded protein confers enhanced fungal resistance relative to control plants; and/or
  (iv) a nucleic acid encoding the same EIN2 polypeptide as the nucleic acids of (i) to (iii) above, but differing from the nucleic acids of (i) to (iii) above due to the degeneracy of the genetic code,
  in functional linkage with a promoter;
(b) regenerating the plant from the plant cell; and
(c) expressing said nucleic acid, optionally wherein the nucleic acid which codes for an EIN2 protein is expressed in an amount and for a period sufficient to generate or to increase soybean rust resistance in said plant.

Preferably, the method comprises the steps of
(a) stably transforming a plant cell with a recombinant expression cassette comprising
  (i) a nucleic acid having at least 60% identity, preferably at least 70% sequence identity, at least 80%, at least 90%, at least 95%, at least 98%, at least 99% sequence identity, or even 100% sequence identity with SEQ ID NO: 1, or a functional fragment thereof, or an orthologue or a paralogue thereof, or a splice variant thereof;
  (ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 3, a functional fragment thereof, an orthologue or a paralogue thereof; preferably the encoded protein confers enhanced fungal resistance relative to control plants;
  (iii) a nucleic acid capable of hybridizing under stringent conditions with a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 3; preferably the encoded protein confers enhanced fungal resistance relative to control plants; and/or
  (iv) a nucleic acid encoding the same EIN2 polypeptide as the nucleic acids of (i) to (iii) above, but differing from the nucleic acids of (i) to (iii) above due to the degeneracy of the genetic code,
  in functional linkage with a promoter;
(b) regenerating the plant from the plant cell; and
(c) expressing said nucleic acid, optionally wherein the nucleic acid which codes for an EIN2 protein is expressed in an amount and for a period sufficient to generate or to increase soybean rust resistance in said plant.

Preferably, the method comprises the steps of
(a) stably transforming a plant cell with a recombinant expression cassette comprising
  (i) a nucleic acid having at least 60% identity, preferably at least 70% sequence identity, at least 80%, at least 90%, at least 95%, at least 98%, at least 99% sequence identity, or even 100% sequence identity with SEQ ID NO: 4, or a functional fragment thereof, or an orthologue or a paralogue thereof, or a splice variant thereof;
  (ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 5, a functional fragment thereof, an orthologue or a paralogue thereof; preferably the encoded protein confers enhanced fungal resistance relative to control plants;
  (iii) a nucleic acid capable of hybridizing under stringent conditions with a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 5; preferably the encoded protein confers enhanced fungal resistance relative to control plants; and/or
  (iv) a nucleic acid encoding the same EIN2 polypeptide as the nucleic acids of (i) to (iii) above, but differing from the nucleic acids of (i) to (iii) above due to the degeneracy of the genetic code,
  in functional linkage with a promoter;
(b) regenerating the plant from the plant cell; and
(c) expressing said nucleic acid, optionally wherein the nucleic acid which codes for an EIN2 protein is expressed in an amount and for a period sufficient to generate or to increase soybean rust resistance in said plant.

Preferably, the promoter is a rust induced and/or mesophyll-specific promoter, preferably the rust induced mesophyll specific promoter 820.

Preferably, the method for increasing fungal resistance, preferably resistance to Phacopsoracea, for example soy bean rust, in a plant, plant part, or plant cell further comprises the step of selecting a transgenic plant expressing
(i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 1, 2, 4, 6, 11, 13, 15, 17, 19, 21, 23, 25, 27, 28, 29, 30, 31, 32, 33, or 34, or a functional fragment thereof, or an orthologue or a paralogue thereof, or a splice variant thereof;
(ii) an exogenous nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 3, 5, 12, 14, 16, 18, 20, 22, 24, or 26, a functional fragment thereof, an orthologue or a paralogue thereof; preferably the encoded protein confers enhanced fungal resistance relative to control plants;

(iii) an exogenous nucleic acid capable of hybridizing under stringent conditions a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 3 or 5; preferably the encoded protein confers enhanced fungal resistance relative to control plants; and/or (iv) an exogenous nucleic acid encoding the same EIN2 polypeptide as the nucleic acids of (i) to (iii) above, but differing from the nucleic acids of (i) to (iii) above due to the degeneracy of the genetic code.

A preferred embodiment is a method for increasing resistance to soy bean rust in a soy bean plant, soy bean plant part, or soy bean plant cell, by increasing the expression of an EIN2 protein, wherein the EIN2 protein is encoded by a nucleic acid comprising (i) an exogenous nucleic acid having at least 80%, at least 90%, at least 95%, at least 98%, at least 99% sequence identity, or even 100% sequence identity with SEQ ID NO: 1, 2, 4, 6, 11, 13, 15, 17, 19, 21, 23, 25, 27, 28, 29, 30, 31, 32, 33, or 34;

(ii) an exogenous nucleic acid encoding a protein comprising an amino acid sequence having at least 80%, at least 90%, at least 95%, at least 98%, at least 99% sequence identity, or even 100% sequence identity with SEQ ID NO: 3, 5, 12, 14, 16, 18, 20, 22, 24, or 26; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 3 or 5; preferably the encoded protein confers enhanced fungal resistance relative to control plants; and/or by (iv) an exogenous nucleic acid encoding the same EIN2 protein as the nucleic acids of (i) to (iii) above, but differing from the nucleic acids of (i) to (iii) above due to the degeneracy of the genetic code, wherein increasing the expression of the EIN2 protein is achieved by transforming the soy bean plant, plant part or plant cell with a nucleic acid comprising the nucleic acid set out under item (i) or (ii) or (iii) or (iv).

Also a preferred embodiment is a method for increasing resistance to soy bean rust in a soy bean plant, soy bean plant part, or soy bean plant cell, by increasing the expression of an EIN2 protein, wherein the EIN2 protein is encoded by a nucleic acid comprising (i) an exogenous nucleic acid having at least 80%, at least 90%, at least 95%, at least 98%, at least 99% sequence identity, or even 100% sequence identity with SEQ ID NO: 1, 2, 4, 6, 11, 13, 15, 17, 19, 21, 23, 25, 27, 28, 29, 30, 31, 32, 33, or 34;

(ii) an exogenous nucleic acid encoding a protein comprising an amino acid sequence having at least 80%, at least 90%, at least 95%, at least 98%, at least 99% sequence identity, or even 100% sequence identity with SEQ ID NO: 3, 5, 12, 14, 16, 18, 20, 22, 24, or 26; preferably the encoded protein confers enhanced fungal resistance relative to control plants; or (iii) an exogenous nucleic acid encoding the same EIN2 protein as the nucleic acids of (i) to (ii) above, but differing from the nucleic acids of (i) to (ii) above due to the degeneracy of the genetic code, wherein increasing the expression of the EIN2 protein is achieved by transforming the soy bean plant, plant part or plant cell with a nucleic acid comprising the nucleic acid set out under item (i) or (ii) or (iii).

The fungal pathogens or fungus-like pathogens (such as, for example, Chromista) can belong to the group comprising Plasmodiophoramycota, Oomycota, Ascomycota, Chytridiomycetes, Zygomycetes, Basidiomycota or Deuteromycetes (Fungi imperfecti). Pathogens which may be mentioned by way of example, but not by limitation, are those detailed in Tables 2 and 3, and the diseases which are associated with them.

TABLE 2

Diseases caused by biotrophic and/or heminecrotrophic phytopathogenic fungi

| Disease | Pathogen |
| --- | --- |
| Leaf rust | *Puccinia recondita* |
| Yellow rust | *P. striiformis* |
| Powdery mildew | *Erysiphe graminis/Blumeria grarrinis* |
| Rust (common corn) | *Puccinia sorghi* |
| Rust (Southern corn) | *Puccinia polysora* |
| Tobacco leaf spot | *Cercospora nicotianae* |
| Rust (soybean) | *Phakopsora pachyrhizi, P. meibomiae* |
| Rust (tropical corn) | *Physopella pallescens, P. zeae = Angiopsora zeae* |

TABLE 3

Diseases caused by necrotrophic and/or hemibiotrophic fungi and Oomycetes

| Disease | Pathogen |
| --- | --- |
| Plume blotch | *Septoria (Stagonospora) nodorum* |
| Leaf blotch | *Septoria tritici* |
| Ear fusarioses | *Fusarium* spp. |
| Late blight | *Phytophthora infestans* |
| Anthrocnose leaf blight | *Colletotrichum graminicola* (teleomorph: *Glomerella graminicola Politis*); *Glomerella tucumanensis* (anamorph: *Glomerella falcatum* Went) |
| Anthracnose stalk rot | |
| Curvularia leaf spot | *Curvularia clavata, C. eragrostidis, = C. maculans* (teleomorph: *Cochliobolus eragrostidis*),*Curvularia inaequalis,C. intermedia* (teleomorph: *Cochliobolus intermedius*),*Curvularia lunata* (teleomorph: *Cochli-* |

TABLE 3-continued

Diseases caused by necrotrophic and/or hemibiotrophic fungi and Oomycetes

| Disease | Pathogen |
| --- | --- |
|  | *obolus lunatus*),*Curvularia pallescens* (teleomorph: *Cochliobolus pallescens*), *Curvularia senegalensis*, *C. tuberculata* (teleomorph: *Cochliobolus tuberculatus*) |
| Didymella leaf spot | *Didymella exitalis* |
| Diplodia leaf spot or streak | *Stenocarpella macrospora* = *Diplodialeaf macrospora* |
| Brown stripe downy mildew | *Sclerophthora rayssiae* var. *zeae* |
| Crazy top downy mildew | *Sclerophthora macrospora* = *Sclerospora macrospora* |
| Green ear downy mildew (gramiricola downy mildew) | *Sclerospora graminicola* |
| Leaf spots, minor | *Alternaria alternata*, *Ascochyta maydis*, *A. tritici*, *A. zeicola*, *Bipolaris victoriae* = *Helminthosporium victoriae* (teleomorph: *Cochliobolus victoriae*),*C. sativus* (anamorph: *Bipolaris sorokiniana* = *H. sorokinianum* = *H. sativum*), *Epicoccum nigrum*, *Exserohilum prolatum* = *Drechslera prolata* (teleomorph: *Setosphaeria prolata*) *Graphium penicillioides*, *Leptosphaeria maydis*, *Leptothyrium zeae*, *Ophiosphaerella herpotricha*, (anamorph: *Scolecosporiella* sp.), *Paraphaeosphaeria michotii*, *Phoma* sp., *Septoria zeae*, *S. zeicola*, *S. zeina* |
| Northern corn leaf blight (white blast, crown stalk rot, stripe) | *Setosphaeria turcica* (anamorph: *Exserohilum turdcum* = *Helminthosporium turcicum*) |
| Northern corn leaf spot Helminthosporium ear rot (race 1) | *Cochliobolus carbonum* (anamorph: *Bipolaris zeicola* = *Helminthosporium carbonum*) |
| Phaeosphaeria leaf spot | *Phaeosphaeria maydis* = *Sphaerulina maydis* |
| Rostratum leaf spot (Helminthosporium leaf disease, ear and stalk rot) | *Setosphaeria rostrata*, (anamorph: *xserohilum rostratum* = *Helminthosporium rostratum*) |
| Java downy mildew | *Peronosclerospora maydis* = *Sclerospora maydis* |
| Philippine downy mildew | *Peronosclerospora philippinensis* = *Sclerospora phlippinensis* |
| Sorghum downy mildew | *Peronosclerospora sorghi* = *Sclerospora sorghi* |
| Spontaneum downy mildew | *Peronosclerospora spontanea* = *Sclerospora spontanea* |
| Sugarcane downy mildew | *Peronosclerospora sacchari* = *Sclerospora sacchari* |
| Sclerotium ear rot (southern blight) | *Sclerotium rolfsii* Sacc. (teleomorph: *Athelia rolfsii*) |
| Seed rot-seedling blight | *Bipolaris sorokiniana*, *B. zeicola* = *Helmnthosporium carbonum*, *Diplodia maydis*, *Exserohilum pedicillatum*, *Exserohilum turcicum* = *Helminthosporium turcicum*, *Fusarium avenaceum*, *F. culmorum*, *F. rroniliforme*, *Gibberella zeae* (anamorph: *F. graminearum*), *Macrophomina phaseolina*, *Penicillium* spp., *Phomopsis* sp., *Pythium* spp., *Rhizoctonia solani*, *R. zeae*, *Sclerotium rolfsii*, *Spicaria* sp. |
| Selenophoma leaf spot | *Selenophoma* sp. |
| Yellow leaf blight | *Ascochyta ischaemi*, *Phyllosticta maydis* (teleomorph: *Mycosphaerella zeae-maydis*) |
| Zonate leaf spot | *Gloeocercospora sorghi* |

The following are especially preferred:

Plasmodiophoromycota such as *Plasmodiophora brassicae* (clubroot of crucifers), *Spongospora subterranea*, *Polymyxa graminis*, Oomycota such as *Bremia lactucae* (downy mildew of lettuce), *Peronospora* (downy mildew) in snapdragon (*P. antirrhini*), onion (*P. destructor*), spinach (*P. effusa*), soybean (*P. manchurica*), tobacco ("blue mold"; *P. tabacina*) alfalfa and clover (*P. trifolium*), *Pseudoperonospora humuli* (downy mildew of hops), *Plasmopara* (downy mildew in grapevines) (*P. viticola*) and sunflower (*P. halstedii*), *Sclerophthora macrospora* (downy mildew in cereals and grasses), *Pythium* (for example damping-off of Beta beet caused by *P. debaryanum*), *Phytophthora infestans* (late blight in potato and in tomato and the like), *Albugo* spec.

Ascomycota such as *Microdochium nivale* (snow mold of rye and wheat), *Fusarium*, *Fusarium graminearum*, *Fusarium culmorum* (partial ear sterility mainly in wheat), *Fusarium oxysporum* (*Fusarium* wilt of tomato), *Blumeria graminis* (powdery mildew of barley (f. sp. *hordei*) and wheat (f. sp. *tritici*)), *Erysiphe pisi* (powdery mildew of pea), *Nectria galligena* (*Nectria* canker of fruit trees), *Uncinula necator* (powdery mildew of grapevine), *Pseudopeziza tracheiphila* (red fire disease of grapevine), *Claviceps purpurea* (ergot on, for example, rye and grasses), *Gaeumannomyces graminis* (take-all on wheat, rye and other grasses), *Magnaporthe grisea*, *Pyrenophora graminea* (leaf stripe of barley), *Pyrenophora teres* (net blotch of barley), *Pyrenophora tritici-repentis* (leaf blight of wheat), *Venturia inaequalis* (apple scab), *Sclerotinia sclerotium* (stalk break, stem rot), *Pseudopeziza medicaginis* (leaf spot of alfalfa, white and red clover).

Basidiomycetes such as *Typhula incarnata* (*typhula* blight on barley, rye, wheat), *Ustilago maydis* (blister smut on maize), *Ustilago nuda* (loose smut on barley), *Ustilago tritici* (loose smut on wheat, spelt), *Ustilago avenae* (loose smut on oats), *Rhizoctonia solani* (*rhizoctonia* root rot of potato), *Sphacelotheca* spp. (head smut of sorghum), *Melampsora lini* (rust of flax), *Puccinia graminis* (stem rust of wheat, barley, rye, oats), *Puccinia recondita* (leaf rust on wheat), *Puccinia dispersa* (brown rust on rye), *Puccinia hordei* (leaf rust of barley), *Puccinia coronata* (crown rust of oats), *Puccinia striiformis* (yellow rust of wheat, barley, rye and a large number of grasses), *Uromyces appendiculatus* (brown rust of bean), *Sclerotium rolfsii* (root and stem rots of many plants).

Deuteromycetes (Fungi imperfecti) such as *Septoria* (*Stagonospora*) *nodorum* (glume blotch) of wheat (*Septoria tritici*), *Pseudocercosporella herpotrichoides* (eyespot of wheat, barley, rye), *Rynchosporium secalis* (leaf spot on rye and barley), *Alternaria solani* (early blight of potato, tomato), *Phoma betae* (blackleg on Beta beet), *Cercospora beticola* (leaf spot on Beta beet), *Alternaria brassicae* (black spot on oilseed rape, cabbage and other crucifers), *Verticillium dahliae* (*verticillium* wilt), *Colletotrichum*, *Colletotrichum lindemuthianum* (bean anthracnose), *Phoma lingam* (blackleg of cabbage and oilseed rape), *Botrytis cinerea* (grey mold of grapevine, strawberry, tomato, hops and the like).

Especially preferred are biotrophic pathogens, e.g., *Phakopsora pachyrhizi* and/or those pathogens which have essentially a similar infection mechanism as *Phakopsora pachyrhizi*, as described herein. Particularly preferred are pathogens from the subclass Pucciniomycetes, preferably from the order Pucciniales (rust), previously known as Uredinales, among which in particular the Melompsoraceae. Preferred are Phakopsoraceae, more preferably *Phakopsora*. Especially preferred are *Phakopsora pachyrhizi* and/or *Phakopsora meibomiae*.

Also preferred rust fungi are selected from the group of *Puccinia*, *Gymnosporangium*, *Juniperus*, *Cronartium*, *Hemileia*, and *Uromyces*, preferably *Puccinia sorghi*, *Gymnosporangium juniperi-virginianae*, *Juniperus virginiana*, *Cronartium ribicola*, *Hemileia vastatrix*, *Puccinia graminis*, *Puccinia coronata*, *Uromyces phaseoli Puccinia hemerocallidis*, *Puccinia persistens* subsp. *Triticina*, *Puccinia striiformis*, *Puccinia graminis* causes, and/or *Uromyces appendeculatus*.

Further preferred pathogens, preferably pathogens of maize, are pathogens causing stalk rot diseases, in particular *Fusarium* stalk rot, *Gibberella* stalk rot, *Diplodia* stalk rot, and Charcoal rot and pathogens causing anthracnose. Preferred pathogens causing *Fusarium* stalk rot are *Fusarium verticillioides*, *Fusarium proliferatum* or *Fusarium subglutinans*. A preferred pathogen causing *Gibberella* stalk rot is *Fusarium graminearum*. A preferred pathogen causing *Diplodia* stalk rot is *Diplodia maydis*. A preferred pathogen causing Charcoal rot is *Macrophomina phaseolina*. A preferred pathogen causing anthracnose is *Colletotrichum graminicola*.

EIN2 Expression Constructs and Vector Constructs

A recombinant vector construct comprising:

(a) (i) a nucleic acid having at least 60% identity, preferably at least 70% sequence identity, at least 80%, at least 90%, at least 95%, at least 98%, at least 99% sequence identity, or even 100% sequence identity with SEQ ID NO: 1, 2, 4, 6, 11, 13, 15, 17, 19, 21, 23, 25, 27, 28, 29, 30, 31, 32, 33, or 34, or a functional fragment thereof, or an orthologue or a paralogue thereof, or a splice variant thereof;

(ii) a nucleic acid coding for a protein comprising an amino acid sequence having at least 60% identity, preferably at least 70% sequence identity, at least 80%, at least 90%, at least 95%, at least 98%, at least 99% sequence identity, or even 100% sequence identity with SEQ ID NO: 3, 5, 12, 14, 16, 18, 20, 22, 24, or 26, a functional fragment thereof, an orthologue or a paralogue thereof; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 3 or 5; preferably the encoded protein confers enhanced fungal resistance relative to control plants; and/or (iv) a nucleic acid encoding the same EIN2 protein as the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Furthermore, a recombinant vector construct is provided comprising:

(a) (i) a nucleic acid having at least 80%, at least 90%, at least 95%, at least 98%, at least 99% sequence identity, or even 100% sequence identity with SEQ ID NO: 1, 2, 4, 6, 11, 13, 15, 17, 19, 21, 23, 25, 27, 28, 29, 30, 31, 32, 33, or 34;

(ii) a nucleic acid coding for a protein comprising an amino acid sequence having at least 80%, at least 90%, at least 95%, at least 98%, at least 99% sequence identity, or even 100% sequence identity with SEQ ID NO: 3, 5, 12, 14, 16, 18, 20, 22, 24, or 26; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 3 or 5; preferably the encoded protein confers enhanced fungal resistance relative to control plants; and/or (iv) a nucleic acid encoding the same EIN2 protein as the nucleic acids of (i) to (iii) above, but differing from the nucleic acids of (i) to (iii) above due to the degeneracy of the genetic code, operably linked with
(b) a promoter and
(c) a transcription termination sequence is a further embodiment of the invention.

Furthermore, a recombinant vector construct is provided comprising:
(a) (i) a nucleic acid having at least 80%, at least 90%, at least 95%, at least 98%, at least 99% sequence identity, or even 100% sequence identity with SEQ ID NO: 1;
(ii) a nucleic acid coding for a protein having at least 80%, at least 90%, at least 95%, at least 98%, at least 99% sequence identity, or even 100% sequence identity with SEQ ID NO: 3; preferably the encoded protein confers enhanced fungal resistance relative to control plants;
(iii) a nucleic acid capable of hybridizing under stringent conditions with a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 3; preferably the encoded protein confers enhanced fungal resistance relative to control plants; and/or
(iv) a nucleic acid encoding the same EIN2 protein as the nucleic acids of (i) to (iii) above, but differing from the nucleic acids of (i) to (iii) above due to the degeneracy of the genetic code,
operably linked with
(b) a promoter and
(c) a transcription termination sequence is a further embodiment of the invention.

Furthermore, a recombinant vector construct is provided comprising:
(a) (i) a nucleic acid having at least 80%, at least 90%, at least 95%, at least 98%, at least 99% sequence identity, or even 100% sequence identity with SEQ ID NO: 4;
(ii) a nucleic acid coding for a protein having at least 80%, at least 90%, at least 95%, at least 98%, at least 99% sequence identity, or even 100% sequence identity with SEQ ID NO: 5; preferably the encoded protein confers enhanced fungal resistance relative to control plants;
(iii) a nucleic acid capable of hybridizing under stringent conditions with a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 5; preferably the encoded protein confers enhanced fungal resistance relative to control plants; and/or
(iv) a nucleic acid encoding the same EIN2 protein as the nucleic acids of (i) to (iii) above, but differing from the nucleic acids of (i) to (iii) above due to the degeneracy of the genetic code,
operably linked with
(b) a promoter and
(c) a transcription termination sequence is a further embodiment of the invention.

In the case of a genomic library, the natural genetic environment of the nucleic acid sequence is preferably retained, at least in part. The environment preferably flanks the nucleic acid sequence at least on one side and has a sequence length of at least 50 bp, preferably at least 500 bp, especially preferably at least 1000 bp, most preferably at least 5000 bp.

Promoters according to the present invention may be constitutive, inducible, in particular pathogen-inducible, developmental stage-preferred, cell type-preferred, tissue-preferred or organ-preferred. Constitutive promoters are active under most conditions. Non-limiting examples of constitutive promoters include the CaMV 19S and 35S promoters (Odell et al., 1985, Nature 313:810-812), the sX CaMV 35S promoter (Kay et al., 1987, Science 236:1299-1302), the Sep1 promoter, the rice actin promoter (McElroy et al., 1990, Plant Cell 2:163-171), the *Arabidopsis* actin promoter, the ubiquitin promoter (Christensen et al., 1989, Plant Molec. Biol. 18:675-689); pEmu (Last et al., 1991, Theor. Appl. Genet. 81:581-588), the figwort mosaic virus 35S promoter, the Smas promoter (Velten et al., 1984, EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and/or the like.

Preferably, the expression vector of the invention comprises a constitutive promoter, mesophyll-specific promoter, epidermis-specific promoter, root-specific promoter, a pathogen inducible promoter, or a fungal-inducible promoter.

A promoter is inducible, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in its induced state, than in its un-induced state. A promoter is cell-, tissue- or organ-specific, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in a particular cell-type, tissue or organ, then in other cell-types or tissues of the same plant, preferably the other cell-types or tissues are cell types or tissues of the same plant organ, e.g. a root. In the case of organ specific promoters, the promoter activity has to be compared to the promoter activity in other plant organs, e.g. leaves, stems, flowers or seeds. Preferably, the promoter is a constitutive promoter, mesophyll-specific promoter, or epidermis-specific promoter.

In preferred embodiments, the increase in the protein amount and/or activity of the EIN2 protein takes place in a constitutive or tissue-specific manner. In especially preferred embodiments, an essentially pathogen-induced increase in the protein amount and/or protein activity takes place, for example by recombinant expression of the EIN2 nucleic acid under the control of a fungal-inducable promoter. In particular, the expression of the EIN2 nucleic acid takes place on fungal infected sites, where, however, preferably the expression of the EIN2 nucleic acid remains essentially unchanged in tissues not infected by fungus.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, leaf-preferred, stigma-preferred, pollen-preferred, anther-preferred, a petal-preferred, sepal-preferred, pedicel-preferred, silique-preferred, stem-preferred, root-preferred promoters and/or the like. Seed preferred promoters are preferentially expressed during seed development and/or germination. For example, seed preferred promoters can be embryo-preferred, endosperm preferred and seed coat-preferred. See Thompson et al., 1989, BioEssays 10:108. Examples of seed preferred promoters include, but are not limited to cellulose synthase (celA), Cim1, gamma-zein, globulin-1, maize 19 kD zein (cZ19B1) and/or the like.

Other suitable tissue-preferred or organ-preferred promoters include, but are not limited to, the napin-gene promoter from rapeseed (U.S. Pat. No. 5,608,152), the USP-promoter from *Vicia faba* (Baeumlein et al., 1991, Mol Gen Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2):233-9), as well as promoters conferring seed specific expression in monocot plants like maize, barley, wheat, rye, rice, etc. Suitable promoters to note are the Ipt2 or Ipt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and/or rye secalin gene).

Promoters useful according to the invention include, but are not limited to, are the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, bronze promoters, the Zm13 promoter (U.S. Pat. No. 5,086,169), the maize polygalacturonase promoters (PG) (U.S. Pat. Nos. 5,412,085 and 5,545,546), the SGB6 promoter (U.S. Pat. No. 5,470,359), as well as synthetic or other natural promoters.

Epidermis-specific promoters may be selected from the group consisting of:
WIR5 (=GstA1); acc. X56012; Dudler & Schweizer,
GLP4, acc. AJ310534; Wei Y., Zhang Z., Andersen C. H., Schmelzer E., Gregersen P. L., Collinge D. B., Smedegaard-Petersen V. and Thordal-Christensen H., Plant Molecular Biology 36, 101 (1998);
GLP2a, acc. AJ237942, Schweizer P., Christoffel A. and Dudler R., Plant J. 20, 541 (1999);
Prx7, acc. AJ003141, Kristensen B. K., Ammitzböll H., Rasmussen S. K. and Nielsen K. A., Molecular Plant Pathology, 2(6), 311 (2001);
GerA, acc. AF250933; Wu S., Druka A., Horvath H., Kleinhofs A., Kannangara G. and von Wettstein D., Plant Phys Biochem 38, 685 (2000);
OsROC1, acc. AP004656
RTBV, acc. AAV62708, AAV62707; Klöti A., Henrich C., Bieri S., He X., Chen G., Burkhardt P. K., Wünn J., Lucca P., Hohn T., Potrykus I. and Fütterer J., PMB 40, 249 (1999);
Chitinase ChtC2-Promoter from potato (Ancillo et al., Planta. 217(4), 566, (2003));
AtProT3 Promoter (Grallath et al., Plant Physiology. 137(1), 117 (2005));
SHN-Promoters from *Arabidopsis* (AP2/EREBP transcription factors involved in cutin and wax production) (Aarón et al., Plant Cell. 16(9), 2463 (2004)); and/or
GSTA1 from wheat (Dudler et al., WP2005306368 and Altpeter et al., Plant Molecular Biology. 57(2), 271 (2005)).

Mesophyll-specific promoters may be selected from the group consisting of:
PPCZm1 (=PEPC); Kausch A. P., Owen T. P., Zachwieja S. J., Flynn A. R. and Sheen J., Plant Mol. Biol. 45, 1 (2001);
OsrbcS, Kyozuka et al., PlaNT Phys 102, 991 (1993); Kyozuka J., McElroy D., Hayakawa T., Xie Y., Wu R. and Shimamoto K., Plant Phys. 102, 991 (1993);
OsPPDK, acc. AC099041;
TaGF-2.8, acc. M63223; Schweizer P., Christoffel A. and Dudler R., Plant J. 20, 541 (1999);
TaFBPase, acc. X53957;
TaWIS1, acc. AF467542; US 200220115849;
HvBIS1, acc. AF467539; US 200220115849;
ZmMIS1, acc. AF467514; US 200220115849;
HvPR1a, acc. X74939; Bryngelsson et al., Mol. Plant Microbe Interacti. 7 (2), 267 (1994);
HvPR1b, acc. X74940; Bryngelsson et al., Mol. Plant Microbe Interact. 7(2), 267 (1994);
HvB1,3gluc; acc. AF479647;
HvPrx8, acc. AJ276227; Kristensen et al., Molecular Plant Pathology, 2(6), 311 (2001); and/or
HvPAL, acc. X97313; Wei Y., Zhang Z., Andersen C. H., Schmelzer E., Gregersen P. L., Collinge D. B., Smedegaard-Petersen V. and Thordal-Christensen H. Plant Molecular Biology 36, 101 (1998).

Constitutive promoters may be selected from the group consisting of
PcUbi promoter from parsley (WO 03/102198)
CaMV 35S promoter: Cauliflower Mosaic Virus 35S promoter (Benfey et al. 1989 EMBO J. 8(8): 2195-2202),
STPT promoter: *Arabidopsis thaliana* Short Triose phosphate translocator promoter (Accession NM_123979)
Act1 promoter: *Oryza sativa* actin 1 gene promoter (McElroy et al. 1990 PLANT CELL 2(2) 163-171 a) and/or
EF1A2 promoter: *Glycine max* translation elongation factor EF1 alpha (US 20090133159).

In preferred embodiments, the increase in the protein quantity or function of the EIN2 protein takes place in a constitutive or tissue-specific manner. In especially preferred embodiments, an essentially pathogen-induced increase in the protein quantity or protein function takes place, for example by exogenous expression of the EIN2 nucleic acid under the con-trot of a fungal-inducible promoter, preferably a rust-inducible promoter. In particular, the expression of the EIN2 nucleic acid takes place on fungal infected sites, where, however, preferably the expression of the EIN2 nucleic acid sequence remains essentially unchanged in tissues not infected by fungus.

Preferably, the EIN2 nucleic acid is under the control of a rust induced mesophyll specific promoter. More preferably, the promoter is the rust induced mesophyll specific promoter 820.

A preferred terminator is the terminator of the cathepsin D inhibitor gene from *Solanum tuberosum*.

Preferred promoter-terminator combinations with the gene of interest in between are a promoter from parsley, preferably, the parsley ubiquitine promoter or the maize ubiquitin promoter, in combination with the terminator of the cathepsin D inhibitor gene from *Solanum tuberosum*. Another preferred promoter-terminator combination is the rust induced mesophyll specific promoter 820 in combination with the terminator of the cathepsin D inhibitor gene from *Solanum tuberosum*.

An intron sequence may also be added to the 5' untranslated region (UTR) and/or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

One type of vector construct is a "plasmid," which refers to a circular double stranded DNA loop into which additional DNA segments can be ligated. Another type of vector is a viral vector, wherein additional DNA segments can be ligated into the viral genome. Certain vector constructs are capable of autonomous replication in a host plant cell into which they are introduced. Other vector constructs are integrated into the genome of a host plant cell upon introduction into the host cell, and thereby are replicated along with the host genome. In particular the vector construct is capable of directing the expression of gene to which the vectors is operatively linked. However, the invention is intended to include such other forms of expression vector constructs, such as viral vectors (e.g., potato virus X, tobacco rattle virus, and/or Gemini virus), which serve equivalent functions.

Transgenic Organisms; Transgenic Plants, Plant Parts, and Plant Cells

A preferred embodiment is a transgenic plant, transgenic plant part, or transgenic plant cell overexpressing an exogenous EIN2 protein. Preferably, the EIN2 protein overexpressed in the plant, plant part or plant cell is encoded by a nucleic acid comprising
(i) an exogenous nucleic acid having at least 60% identity with SEQ ID NO: 1, 2, 4, 6, 11, 13, 15, 17, 19, 21, 23, 25, 27, 28, 29, 30, 31, 32, 33, or 34, or a functional fragment, thereof, an orthologue or a paralogue thereof, or a splice variant thereof; or by
(ii) an exogenous nucleic acid encoding a protein comprising an amino acid sequence having at least 60% identity with SEQ ID NO: 3, 5, 12, 14, 16, 18, 20, 22, 24, or 26, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 3 or 5; preferably the encoded protein confers enhanced fungal resistance relative to control plants; and/or by
(iv) an exogenous nucleic acid encoding the same EIN2 protein as the nucleic acids of (i) to (iii) above, but differing from the nucleic acids of (i) to (iii) above due to the degeneracy of the genetic code.

Most preferably, the exogenous nucleic acid has at least 80%, at least 90%, at least 95%, at least 98%, at least 99% sequence identity, or even 100% sequence identity with SEQ ID NO: 1, 2, 4, 6, 11, 13, 15, 17, 19, 21, 23, 25, 27, 28, 29, 30, 31, 32, 33, or 34; or comprises an exogenous nucleic acid encoding a protein having at least 80%, at least 90%, at least 95%, at least 98%, at least 99% sequence identity, or even 100% sequence identity with SEQ ID NO: 3, 5, 12, 14, 16, 18, 20, 22, 24, or 26.

A preferred embodiment is a transgenic plant, transgenic plant part, or transgenic plant cell overexpressing an exogenous EIN2 protein. Preferably, the EIN2 protein overexpressed in the plant, plant part or plant cell is encoded by
(i) an exogenous nucleic acid having at least 60% identity with SEQ ID NO: 1 or a functional fragment, thereof, an orthologue or a paralogue thereof, or a splice variant thereof; or by
(ii) an exogenous nucleic acid encoding a protein having at least 60% identity with SEQ ID NO: 3, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 3; preferably the encoded protein confers enhanced fungal resistance relative to control plants; and/or by
(iv) an exogenous nucleic acid encoding the same EIN2 protein as the nucleic acids of (i) to (iii) above, but differing from the nucleic acids of (i) to (iii) above due to the degeneracy of the genetic code.

A preferred embodiment is a transgenic plant, transgenic plant part, or transgenic plant cell overexpressing an exogenous EIN2 protein. Preferably, the EIN2 protein overexpressed in the plant, plant part or plant cell is encoded by
(i) an exogenous nucleic acid having at least 60% identity with SEQ ID NO: 4 or a functional fragment, thereof, an orthologue or a paralogue thereof, or a splice variant thereof; or by
(ii) an exogenous nucleic acid encoding a protein having at least 60% identity with SEQ ID NO: 5, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 5; preferably the encoded protein confers enhanced fungal resistance relative to control plants; and/or by
(iv) an exogenous nucleic acid encoding the same EIN2 protein as the nucleic acids of (i) to (iii) above, but differing from the nucleic acids of (i) to (iii) above due to the degeneracy of the genetic code.

Most preferably, the exogenous nucleic acid has at least 80%, at least 90%, at least 95%, at least 98%, at least 99% sequence identity, or even 100% sequence identity with SEQ ID NO: 1; or comprises an exogenous nucleic acid encoding a protein having at least 80%, at least 90%, at least 95%, at least 98%, at least 99% sequence identity, or even 100% sequence identity with SEQ ID NO: 3.

Most preferably, the exogenous nucleic acid has at least 80%, at least 90%, at least 95%, at least 98%, at least 99% sequence identity, or even 100% sequence identity with SEQ ID NO: 2; or comprises an exogenous nucleic acid encoding a protein having at least 80%, at least 90%, at least 95%, at least 98%, at least 99% sequence identity, or even 100% sequence identity with SEQ ID NO: 3.

Most preferably, the exogenous nucleic acid has at least 80%, at least 90%, at least 95%, at least 98%, at least 99% sequence identity, or even 100% sequence identity with SEQ ID NO: 4; or comprises an exogenous nucleic acid encoding a protein having at least 80%, at least 90%, at least 95%, at least 98%, at least 99% sequence identity, or even 100% sequence identity with SEQ ID NO: 5.

In preferred embodiments, the protein amount of an EIN2 protein in the transgenic plant is increased by at least 10%, at least 20%, at least 30%, at least 40%, at least 50%, at least 60%, at least 70%, at least 80%, at least 90%, or at least 95% or more in comparison to a wild type plant that is not transformed with the EIN2 nucleic acid.

More preferably, the transgenic plant, transgenic plant part, or transgenic plant cell according to the present invention has been obtained by transformation with a recombinant vector described herein.

Suitable methods for transforming or transfecting host cells including plant cells are well known in the art of plant biotechnology. Any method may be used to transform the recombinant expression vector into plant cells to yield the transgenic plants of the invention. General methods for transforming dicotyledonous plants are disclosed, for example, in U.S. Pat. Nos. 4,940,838; 5,464,763, and the like. Methods for transforming specific dicotyledonous plants, for example, cotton, are set forth in U.S. Pat. Nos. 5,004,863; 5,159,135; and 5,846,797. Soy transformation methods are set forth in U.S. Pat. Nos. 4,992,375; 5,416,011; 5,569,834; 5,824,877; 6,384,301 and in EP 0301749B1 may be used. Transformation methods may include direct and indirect methods of transformation. Suitable direct methods include polyethylene glycol induced DNA uptake, liposome-mediated transformation (U.S. Pat. No. 4,536,475), biolistic methods using the gene gun (Fromm M E et al., Bio/Technology. 8(9):833-9, 1990; Gordon-Kamm et al. Plant Cell 2:603, 1990), electroporation, incubation of dry embryos in DNA-comprising solution, and microinjection. In the case of these direct transformation methods, the plasmids used need not meet any particular requirements. Simple plasmids, such as those of the pUC series, pBR322, M13mp series, pACYC184 and the like can be used. If intact plants are to be regenerated from the transformed cells, an additional selectable marker gene is preferably located on the plasmid. The direct transformation techniques are equally suitable for dicotyledonous and monocotyledonous plants.

Transformation can also be carried out by bacterial infection by means of *Agrobacterium* (for example EP 0 116 718), viral infection by means of viral vectors (EP 0 067 553; U.S. Pat. No. 4,407,956; WO 95/34668; WO 93/03161) or by means of pollen (EP 0 270 356; WO 85/01856; U.S. Pat. No. 4,684,611). *Agrobacterium* based transformation techniques (especially for dicotyledonous plants) are well known in the art. The *Agrobacterium* strain (e.g., *Agrobacterium tumefaciens* or *Agrobacterium rhizogenes*) comprises a plasmid (Ti or Ri plasmid) and a T-DNA element which is transferred to the plant following infection with *Agrobacterium*. The T-DNA (transferred DNA) is integrated into the genome of the plant cell. The T-DNA may be localized on the Ri- or Ti-plasmid or is separately comprised in a so-called binary vector. Methods for the *Agrobacterium*-mediated transformation are described, for example, in Horsch R B et al. (1985) Science 225:1229. The *Agrobacterium*-mediated transformation is best suited to dicotyledonous plants but has also been adapted to monocotyledonous plants. The transformation of plants by *Agrobacteria* is described in, for example, White F F, Vectors for Gene Transfer in Higher Plants, Transgenic Plants, Vol. 1, Engineering and Utilization, edited by S. D. Kung and R. Wu, Academic Press, 1993, pp. 15-38; Jenes B et al. Techniques for Gene Transfer, Transgenic Plants, Vol. 1, Engineering and Utilization, edited by S. D. Kung and R. Wu, Academic Press, 1993, pp. 128-143; Potrykus (1991) Annu Rev Plant Physiol Plant Molec Biol 42:205-225. Transformation may result in transient or stable transformation and expression. Although a nucleotide sequence of the present invention can be inserted into any plant and plant cell falling within these broad classes, it is particularly useful in crop plant cells.

The genetically modified plant cells can be regenerated via all methods with which the skilled worker is familiar. Suitable methods can be found in the abovementioned publications by S. D. Kung and R. Wu, Potrykus or Höfgen and Willmitzer.

After transformation, plant cells or cell groupings may be selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above. The transformed plants may also be directly selected by screening for the presence of the EIN2 nucleic acid.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, constructs or vectors or expression cassettes are not present in the genome of the original plant or are present in the genome of the transgenic plant not at their natural locus of the genome of the original plant.

Preferably, the transgenic plant of the present invention or the plant obtained by the method of the present invention has increased resistance against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* and *Phakopsora meibomiae*, also known as soybean rust. Preferably, resistance against *Phakopsora pachyrhizi* and/or *Phakopsora meibomiae* is increased.

Preferably, the plant, plant part, or plant cell is a plant or derived from a plant selected from the group consisting of beans, soya, pea, clover, kudzu, lucerne, lentils, lupins, vetches, groundnut, rice, wheat, barley, *arabidopsis*, lentil, banana, canola, cotton, potatoe, corn, sugar cane, alfalfa, and sugar beet.

In one embodiment of the present invention the plant is selected from the group consisting of beans, soya, pea, clover, kudzu, lucerne, lentils, lupins, vetches, and/or groundnut. Preferably, the plant is a legume, comprising plants of the genus *Phaseolus* (comprising French bean, dwarf bean, climbing bean (*Phaseolus vulgaris*), Lima bean (*Phaseolus lunatus* L.), Tepary bean (*Phaseolus acutifolius* A. Gray), runner bean (*Phaseolus coccineus*)); the genus *Glycine* (comprising *Glycine soja*, soybeans (*Glycine max* (L.) Merill)); pea (*Pisum*) (comprising shelling peas (*Pisum sativum* L. convar. *sativum*), also called smooth or round-seeded peas; marrowfat pea (*Pisum sativum* L. convar. medullare Alef. emend. C. O. Lehm), sugar pea (*Pisum sativum* L. convar. axiphium Alef emend. C. O. Lehm), also called snow pea, edible-podded pea or mangetout, (*Pisum granda sneida* L. convar. sneidulo p. shneiderium)); peanut (*Arachis hypogaea*), clover (*Trifolium* spec.), medick (*Medicago*), kudzu vine (*Pueraria lobata*), common lucerne, alfalfa (*M. sativa* L.), chickpea (*Cicer*), lentils (Lens) (*Lens culinaris* Medik.), lupins (*Lupinus*); vetches (*Vicia*), field bean, broad bean (*Vicia faba*), vetchling (*Lathyrus*) (comprising chickling pea (*Lathyrus sativus*), heath pea (*Lathyrus tuberosus*)); genus *Vigna* (comprising moth bean (*Vigna aconitifolia* (Jacq.) Maréchal), adzuki bean (*Vigna angularis* (Willd.) Ohwi & H. Ohashi), urd bean (*Vigna mungo* (L.) Hepper), mung bean (*Vigna radiata* (L.) R. Wilczek), bambara groundnut (*Vigna subterrane* (L.) Verdc.), rice bean (*Vigna umbellata* (Thunb.) Ohwi & H. Ohashi), *Vigna vexillata* (L.) A. Rich., *Vigna unguiculata* (L.) Walp., in the three subspecies asparagus bean, cowpea, catjang bean)); pigeonpea (*Cajanus cajan* (L.) Millsp.), the genus *Macrotyloma* (comprising geocarpa groundnut (*Macrotyloma geocarpum* (Harms) Maréchal & Baudet), horse bean (*Macrotyloma uniflorum* (Lam.) Verdc.); goa bean (*Psophocarpus tetragonolobus* (L.) DC.), African yam bean (*Sphenostylis stenocarpa* (Hochst. ex A. Rich.) Harms), Egyptian black bean, *dolichos* bean, lablab bean (*Lablab purpureus* (L.) Sweet), yam bean (*Pachyrhizus*), guar bean (*Cyamopsis tetragonolobus* (L.) Taub.); and/or the genus *Canavalia* (comprising jack bean (*Canavalia ensiformis* (L.) DC.), sword bean (*Canavalia gladiata* (Jacq.) DC.).

Further preferred is a plant selected from the group consisting of beans, soya, pea, clover, kudzu, lucerne, lentils, lupins, vetches, and groundnut. Most preferably, the plant, plant part, or plant cell is or is derived from soy.

Preferably, the transgenic plant of the present invention or the plant obtained by the method of the present invention is a soybean plant and has increased resistance against fungal pathogens of the order Pucciniales (rust), preferably, of the family Phacopsoraceae, more preferably against fungal pathogens of the genus *Phacopsora*, most preferably against *Phakopsora pachyrhizi* and *Phakopsora meibomiae*, also known as soybean rust. Preferably, resistance against *Phakopsora pachyrhizi* and/or *Phakopsora meibomiae* is increased.

Methods for the Production of Transgenic Plants

One embodiment according to the present invention provides a method for producing a transgenic plant, a transgenic plant part, or a transgenic plant cell resistant to a fungal pathogen, preferably of the family Phacopsoraceae, for example soybean rust, wherein the recombinant nucleic acid used to generate a transgenic plant comprises a promoter that is functional in the plant cell, operably linked to an EIN2 nucleic acid, which is preferably SEQ ID NO: 1, and a terminator regulatory sequence.

In one embodiment, the present invention refers to a method for the production of a transgenic plant, transgenic plant part, or transgenic plant cell having increased fungal resistance, comprising
(a) introducing a recombinant vector construct according to the present invention into a plant, a plant part or a plant cell and
(b) generating a transgenic plant from the plant, plant part or plant cell.

Preferably, the method for the production of the transgenic plant, transgenic plant part, or transgenic plant cell further comprises the step
(c) expressing the EIN2 protein, preferably encoded by a nucleic acid comprising
 (i) an exogenous nucleic acid having at least 60% identity with SEQ ID NO: 1, 2, 4, 6, 11, 13, 15, 17, 19, 21, 23, 25, 27, 28, 29, 30, 31, 32, 33, or 34, a functional fragment thereof, an orthologue or a paralogue thereof, or a splice variant thereof;
 (ii) an exogenous nucleic acid encoding a protein comprising an amino acid sequence having at least 60% identity with SEQ ID NO: 3, 5, 12, 14, 16, 18, 20, 22, 24, or 26, or a functional fragment thereof, an orthologue or a paralogue thereof; preferably the encoded protein confers enhanced fungal resistance relative to control plants;
 (iii) an exogenous nucleic acid capable of hybridizing under stringent conditions with a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 3 or 5; preferably the encoded protein confers enhanced fungal resistance relative to control plants; and/or by
 (iv) an exogenous nucleic acid encoding the same EIN2 protein as the nucleic acids of (i) to (iii) above, but differing from the nucleic acids of (i) to (iii) above due to the degeneracy of the genetic code.

Preferably, said introducing and expressing does not comprise an essentially biological process.

More preferably, the method for the production of the transgenic plant, transgenic plant part, or transgenic plant cell further comprises the step
(c) expressing the EIN2 protein, preferably encoded by
 (i) an exogenous nucleic acid having at least 60% identity with SEQ ID NO: 1, a functional fragment thereof, an orthologue or a paralogue thereof, or a splice variant thereof;
 (ii) an exogenous nucleic acid encoding a protein having at least 60% identity with SEQ ID NO: 3, or a functional fragment thereof, an orthologue or a paralogue thereof; preferably the encoded protein confers enhanced fungal resistance relative to control plants;
 (iii) an exogenous nucleic acid capable of hybridizing under stringent conditions with a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 3; preferably the encoded protein confers enhanced fungal resistance relative to control plants; and/or by
(iv) an exogenous nucleic acid encoding the same EIN2 protein as the nucleic acids of (i) to (iii) above, but differing from the nucleic acids of (i) to (iii) above due to the degeneracy of the genetic code.

More preferably, the method for the production of the transgenic plant, transgenic plant part, or transgenic plant cell further comprises the step
(c) expressing the EIN2 protein, preferably encoded by
   (i) an exogenous nucleic acid having at least 60% identity with SEQ ID NO: 4, a functional fragment thereof, an orthologue or a paralogue thereof, or a splice variant thereof;
   (ii) an exogenous nucleic acid encoding a protein having at least 60% identity with SEQ ID NO: 5, or a functional fragment thereof, an orthologue or a paralogue thereof; preferably the encoded protein confers enhanced fungal resistance relative to control plants;
   (iii) an exogenous nucleic acid capable of hybridizing under stringent conditions with a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 5; preferably the encoded protein confers enhanced fungal resistance relative to control plants; and/or by
   (iv) an exogenous nucleic acid encoding the same EIN2 protein as the nucleic acids of (i) to (iii) above, but differing from the nucleic acids of (i) to (iii) above due to the degeneracy of the genetic code.

Preferably, the method for the production of the transgenic plant, transgenic plant part, or transgenic plant cell further comprises the step of selecting a transgenic plant expressing
   (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 1, 2, 4, 6, 11, 13, 15, 17, 19, 21, 23, 25, 27, 28, 29, 30, 31, 32, 33, or 34, or a functional fragment thereof, or an orthologue or a paralogue thereof, or a splice variant thereof;
   (ii) an exogenous nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 3, 5, 12, 14, 16, 18, 20, 22, 24, or 26, a functional fragment thereof, an orthologue or a paralogue thereof; preferably the encoded protein confers enhanced fungal resistance relative to control plants;
   (iii) an exogenous nucleic acid capable of hybridizing under stringent conditions with a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 3 or 5; preferably the encoded protein confers enhanced fungal resistance relative to control plants; and/or
   (iv) an exogenous nucleic acid encoding the same EIN2 polypeptide as the nucleic acids of (i) to (iii) above, but differing from the nucleic acids of (i) to (iii) above due to the degeneracy of the genetic code.

Preferably, the method for the production of the transgenic plant, transgenic plant part, or transgenic plant cell additionally comprises the step of harvesting the seeds of the transgenic plant and planting the seeds and growing the seeds to plants, wherein the grown plant(s) comprises
   (i) the exogenous nucleic acid having at least 60% identity with SEQ ID NO: 1, 2, 4, 6, 11, 13, 15, 17, 19, 21, 23, 25, 27, 28, 29, 30, 31, 32, 33, or 34, a functional fragment thereof, an orthologue or a paralogue thereof, or a splice variant thereof;
   (ii) the exogenous nucleic acid encoding a protein comprising an amino acid sequence having at least 60% identity with SEQ ID NO: 3, 5, 12, 14, 16, 18, 20, 22, 24, or 26, or a functional fragment thereof, an orthologue or a paralogue thereof; preferably the encoded protein confers enhanced fungal resistance relative to control plants;
   (iii) the exogenous nucleic acid capable of hybridizing under stringent conditions with a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 3 or 5; preferably the encoded protein confers enhanced fungal resistance relative to control plants; and/or
   (iv) the exogenous nucleic acid encoding the same EIN2 protein as the nucleic acids of (i) to (iii) above, but differing from the nucleic acids of (i) to (iii) above due to the degeneracy of the genetic code;

preferably, the step of harvesting the seeds of the transgenic plant and planting the seeds and growing the seeds to plants, wherein the grown plant(s) comprises
   (i) the exogenous nucleic acid having at least 60% identity with SEQ ID NO: 1, 2, 4, 6, 11, 13, 15, 17, 19, 21, 23, 25, 27, 28, 29, 30, 31, 32, 33, or 34, a functional fragment thereof, an orthologue or a paralogue thereof, or a splice variant thereof;
   (ii) the exogenous nucleic acid encoding a protein comprising an amino acid sequence having at least 60% identity with SEQ ID NO: 3, 5, 12, 14, 16, 18, 20, 22, 24, or 26, or a functional fragment thereof, an orthologue or a paralogue thereof; preferably the encoded protein confers enhanced fungal resistance relative to control plants;
   (iii) the exogenous nucleic acid capable of hybridizing under stringent conditions with a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 3 or 5; preferably the encoded protein confers enhanced fungal resistance relative to control plants; and/or
   (iv) the exogenous nucleic acid encoding the same EIN2 protein as the nucleic acids of (i) to (iii) above, but differing from the nucleic acids of (i) to (iii) above due to the degeneracy of the genetic code;

is repeated more than one time, preferably, 1, 2, 3, 4, 5, 6, 8, 9, 10, 15, 20, 25, 30, 35, 40, 45, or 50 times.

The transgenic plants may be selected by known methods as described above (e.g., by screening for the presence of one or more markers which are encoded by plant-expressible genes co-transferred with the EIN2 gene or by directly screening for the EIN2 nucleic acid).

Furthermore, the use of the exogenous EIN2 nucleic acid or the recombinant vector construct comprising the EIN2 nucleic acid for the transformation of a plant, plant part, or plant cell to provide a fungal resistant plant, plant part, or plant cell is provided.

Harvestable Parts and Products

Harvestable parts of the transgenic plant according to the present invention are part of the invention. Preferably, the harvestable parts comprise the EIN2 nucleic acid or EIN2 protein. The harvestable parts may be seeds, roots, leaves and/or flowers comprising the EIN2 nucleic acid or EIN2 protein or parts thereof. Preferred parts of soy plants are soy beans comprising the EIN2 nucleic acid or EIN2 protein.

Products derived from a transgenic plant according to the present invention, parts thereof or harvestable parts thereof are part of the invention. A preferred product is meal or oil, preferably, soybean meal or soybean oil. Preferably, the soybean meal and/or oil comprises the EIN2 nucleic acid or EIN2 protein.

Methods for Manufacturing a Product

In one embodiment the method for the production of a product comprises
a) growing the plants of the invention or obtainable by the methods of invention and
b) producing said product from or by the plants of the invention and/or parts, e.g. seeds, of these plants.

In a further embodiment the method comprises the steps a) growing the plants of the invention, b) removing the harvestable parts as defined above from the plants and c) producing said product from or by the harvestable parts of the invention.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

Methods for Breeding/Methods for Plant Improvement/ Methods Plant Variety Production The transgenic plants of the invention may be crossed with similar transgenic plants or with transgenic plants lacking the nucleic acids of the invention or with non-transgenic plants, using known methods of plant breeding, to prepare seeds. Further, the transgenic plant cells or plants of the present invention may comprise, and/or be crossed to another transgenic plant that comprises one or more exogenous nucleic acids, thus creating a "stack" of transgenes in the plant and/or its progeny. The seed is then planted to obtain a crossed fertile transgenic plant comprising the EIN2 nucleic acid. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the exogenous nucleic acid.

Thus, one embodiment of the present invention is a method for breeding a fungal resistant plant comprising the steps of
(a) crossing a transgenic plant described herein or a plant obtainable by a method described herein with a second plant;
(b) obtaining a seed or seeds resulting from the crossing step described in (a);
(c) planting said seed or seeds and growing the seed or seeds to plants; and
(d) selecting from said plants the plants expressing an EIN2 protein, preferably encoded by a nucleic acid comprising
  (i) an exogenous nucleic acid having at least 60% identity with SEQ ID NO: 1, 2, 4, 6, 11, 13, 15, 17, 19, 21, 23, 25, 27, 28, 29, 30, 31, 32, 33, or 34, a functional fragment thereof, an orthologue or a paralogue thereof, or a splice variant thereof;
  (ii) an exogenous nucleic acid encoding a protein comprising an amino acid sequence having at least 60% identity with SEQ ID NO: 3, 5, 12, 14, 16, 18, 20, 22, 24, or 26, or a functional fragment thereof, an orthologue or a paralogue thereof; preferably the encoded protein confers enhanced fungal resistance relative to control plants;
  (iii) an exogenous nucleic acid capable of hybridizing under stringent conditions with a complementary sequence of any of the nucleic acids according to (i) or (ii); preferably encoding an EIN2 protein; preferably wherein the nucleic acid molecule codes for a polypeptide which has essentially identical properties to the polypeptide described in SEQ ID NO: 3 or 5; preferably the encoded protein confers enhanced fungal resistance relative to control plants; and/or by
  (iv) an exogenous nucleic acid encoding the same EIN2 protein as the nucleic acids of (i) to (iii) above, but differing from the nucleic acids of (i) to (iii) above due to the degeneracy of the genetic code.

Another preferred embodiment is a method for plant improvement comprising
(a) obtaining a transgenic plant by any of the methods of the present invention;
(b) combining within one plant cell the genetic material of at least one plant cell of the plant of (a) with the genetic material of at least one cell differing in one or more gene from the plant cells of the plants of (a) or crossing the transgenic plant of (a) with a second plant;
(c) obtaining seed from at least one plant generated from the one plant cell of (b) or the plant of the cross of step (b);
(d) planting said seeds and growing the seeds to plants; and (e) selecting from said plants, plants expressing the nucleic acid encoding the EIN2 protein; and optionally (f) producing propagation material from the plants expressing the nucleic acid encoding the EIN2 protein.

The transgenic plants may be selected by known methods as described above (e.g., by screening for the presence of one or more markers which are encoded by plant-expressible genes co-transferred with the EIN2 gene or screening for the EIN2 nucleic acid itself).

According to the present invention, the introduced EIN2 nucleic acid may be maintained in the plant cell stably if it is incorporated into a non-chromosomal autonomous replicon or integrated into the plant chromosomes. Whether present in an extra-chromosomal nonreplicating or replicating vector construct or a vector construct that is integrated into a chromosome, the exogenous EIN2 nucleic acid preferably resides in a plant expression cassette. A plant expression cassette preferably contains regulatory sequences capable of driving gene expression in plant cells that are functional linked so that each sequence can fulfill its function, for example, termination of transcription by polyadenylation signals. Preferred polyadenylation signals are those originating from *Agrobacterium tumefacienst*-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other functional linked sequences like translational enhancers such as the overdrive-sequence containing the 5'-untranslated leader sequence from tobacco mosaic virus increasing the polypeptide per RNA ratio (Gallie et al., 1987, Nucl. Acids Research 15:8693-8711). Examples of plant expression vectors include those detailed in: Becker, D. et al., 1992, New plant binary vectors with selectable markers located proximal to the left border, Plant Mol. Biol. 20:1195-1197; Bevan, M. W., 1984, Binary *Agrobacterium* vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

EXAMPLES

The following examples are not intended to limit the scope of the claims to the invention, but are rather intended to be exemplary of certain embodiments. Any variations in the exemplified methods that occur to the skilled artisan are intended to fall within the scope of the present invention.

Example 1: General Methods

The chemical synthesis of oligonucleotides can be affected, for example, in the known fashion using the phosphoamidite method (Voet, Voet, 2nd Edition, Wiley Press New York, pages 896-897). The cloning steps carried out for the purposes of the present invention such as, for example, restriction cleavages, agarose gel electrophoresis, purification of DNA fragments, transfer of nucleic acids to nitrocellulose and nylon membranes, linking DNA fragments, transformation of *E. coli* cells, bacterial cultures, phage multiplication and sequence analysis of recombinant DNA, are carried out as described by Sambrook et al. Cold Spring Harbor Laboratory Press (1989), ISBN 0-87969-309-6. The sequencing of recombinant DNA molecules is carried out with an MWG-Licor laser fluorescence DNA sequencer following the method of Sanger (Sanger et al., Proc. Natl. Acad. Sci. USA 74, 5463 (1977)).

Example 2: Cloning of Overexpression Vector Constructs

The genomic DNA was produced from *Arabidopsis thaliana* (ecotype Col-0) by using the DNeasy Plant Mini Kit von Qiagen (Invitrogen). All steps of DNA preparation and purification were performed according as described in the manual.

First, the C-terminal fragment of EIN2 was specifically amplified from the genomic DNA by PCR as described in the protocol of the Phusion hot-start, Pfu Ultra, Pfu Turbo or Herculase DNA polymerase (Stratagene).

The composition for the protocol of the Pfu Ultra, Pfu Turbo or Herculase DNA polymerase was as follows: 1×PCR buffer, 0.2 mM of each dNTP, 100-1000 ng genomic DNA of *Arabidopsis thaliana* (var Columbia-0), 20 pmol forward primer, 20 pmol reverse primer, 0.5 µl Phusion hot-start, Pfu Ultra, Pfu Turbo or Herculase DNA polymerase.

The amplification cycles were as follows: 1 cycle of 30 seconds at 98° C., followed by 36 cycles of in each case 10 seconds at 98° C., 20 seconds at 66° C. and 120 seconds at 72° C., followed by 1 cycle of 7 minutes at 72° C., then 4° C.

The primers (as shown in SEQ ID NO: 7 and 8) were designed in a way that the specifically bind to sequences in the EIN2 coding sequence and 3'UTR downstream of the stop codon of the EIN2 coding sequence. The forward primer (SEQ ID NO: 7) is designed in a way that a NotI restriction site (bold) is located upstream of a novel ATG (underlined), which is introduced to facilitate the translation of the C-terminal fragment into a protein. The reverse primer (SEQ ID NO: 8) is designed in a way that an AscI restriction site (bold) is located downstream of the stop-codon (underlined)

```
i) forward primer:
                                       (SEQ ID NO: 7)
5'-CCTATGCGGCCGCCCATGCTCTGGCTGGCAGCC-3' ii) reverse primer:
                                       (SEQ ID NO: 8)
5'-CCTATGGCGCGCCCTTCTTCTTCAACCCAATGATCCGTAC-3'
```

The amplified fragment (2642 bp) was eluted and purified from an 1% agarose gel by using the GFX PCR DNA Gel Band Purification Kit (GE Healthcare Europe GmbH, Freiburg, Germany).

The amplified fragment was digested using the restriction enzymes NotI and AscI (NEB Biolabs) and ligated in a NotI/AscI digested Gateway pENTRY-B vector (Invitrogen, Life Technologies, Carlsbad, Calif., USA) in a way that the EIN2 fragment is located in sense direction between the attL1 and attL2 recombination sites.

As the EIN2-fragment should be used in several other downstream experiments, the EIN2-fragment was subsequently sub-cloned into a GATEWAY ENTRY-B (Invitrogen, Life Technologies, Carlsbad, Calif., USA) in a way that the EIN2 fragment is located in sense direction between the parsley ubiquitin (PcUbi) promoter and an *Agrobacterium tumefaciens* derived nopaline synthase terminator (NOS) terminator. The PcUbi promoter regulates constitutive expression of the ubi4-2 gene (accession number X64345)

of *Petroselinum crispum* (Kawalleck et al. 1993 Plant Molecular Biology 21(4): 673-684).

Therefore the EIN2 fragment containing pENTRY-B vector, as described above, was used as template for a PCR reaction to specifically amplify the EIN2-fragment as described in the protocol of the Phusion hot-start, Pfu Ultra, Pfu Turbo or Herculase DNA polymerase (Stratagene).

The composition for the protocol of the Pfu Ultra, Pfu Turbo or Herculase DNA polymerase was as follows: 1×PCR buffer, 0.2 mM of each dNTP, 100 ng template DNA derived from the previous PCR of, 20 pmol forward primer, 20 pmol reverse primer, 1 mM MgCl2, 0.5 µl Phusion hot-start, Pfu Ultra, Pfu Turbo or Herculase DNA polymerase.

The amplification cycles were as follows:
1 cycle of 30 seconds at 98° C., followed by 35 cycles of in each case 10 seconds at 98° C., 10 seconds at 64° C. and 70 seconds at 72° C., followed by 1 cycle of 10 minutes at 72° C., then 4° C.

The primers (as shown in SEQ ID 9 and 10) were designed in a way to specifically amplify the EIN2 fragment and to introduce a PacI-site in front of the start-ATG and a AscI restriction site downstream of the stop-codon.

```
i) forward primer:
                                    (SEQ ID NO: 9)
5'-AATTAATTAACCATGCTCTGGCTGGCAGC-3' ii) reverse primer:
                                    (SEQ ID NO: 10)
5'-TTGGCGCGCCTCAACCCAATGATCCGTAC-3'
```

The amplified fragment (2628 bp) was eluted and purified from an 1% agarose gel by using the GFX PCR DNA Gel Band Purification Kit (GE Healthcare Europe GmbH, Freiburg, Germany).

The eluted fragment was digested using the restriction enzymes PacI and AscI (NEB Biolabs) and ligated in a PacI/AscI GATEWAY ENTRY-B (Invitrogen, Life Technologies, Carlsbad, Calif., USA) in a way that the EIN2 fragment is located in sense direction between the parsley ubiquitin (PcUbi) promoter and an *Agrobacterium tumefaciens* derived nopaline synthase terminator (NOS) terminator.

It is also possible to generate all DNA fragments mentioned in this invention by DNA synthesis (Geneart, Regensburg, Germany).

Figure 2:
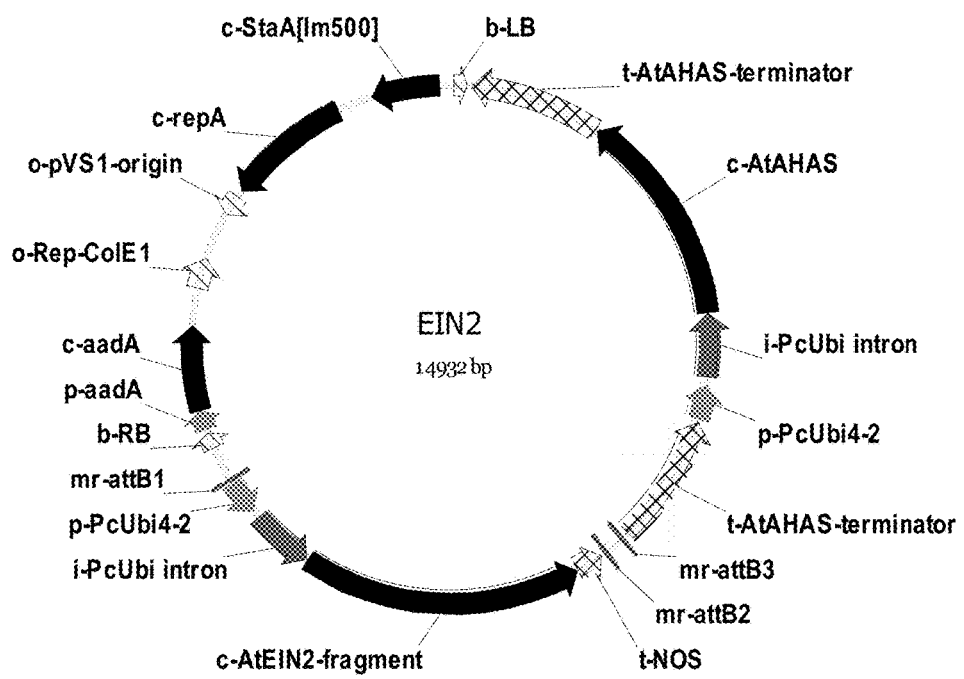

To obtain the binary plant transformation vector, a triple LR reaction (Gateway system, Invitrogen, Life Technologies, Carlsbad, Calif., USA) was performed according to manufacturer's protocol by using an empty pENTRY-A vector, the PcUbi promoter::EIN2-fragement::nos-terminator in the above described pENTRY-B vector and an empty pENTRY-C. As target a binary pDEST vector was used which is composed of: (1) a Spectinomycin/Streptomycin resistance cassette for bacterial selection (2) a pVS1 origin for replication in *Agrobacteria* (3) a ColE1 origin of replication for stable maintenance in *E. coli* and (4) between the right and left border an AHAS selection under control of a PcUbi-promoter (see FIG. 2). The recombination reaction was transformed into *E. coli* (DH5alpha), mini-prepped and screened by specific restriction digestions. A positive clone from each vector construct was sequenced and submitted soy transformation.

Example 3: Soy Transformation

The expression vector constructs (see example 2) were transformed into soy.

3.1 Sterilization and Germination of Soy Seeds

Virtually any seed of any soy variety can be employed in the method of the invention. A variety of soybean cultivar (including Jack, Williams 82, Jake, Stoddard and Resnik) is appropriate for soy transformation. Soy seeds were sterilized in a chamber with a chlorine gas produced by adding 3.5 ml 12N HCl drop wise into 100 ml bleach (5.25% sodium hypo-chlorite) in a desiccator with a tightly fitting lid. After 24 to 48 hours in the chamber, seeds were removed and approximately 18 to 20 seeds were plated on solid GM medium with or without 5 µM 6-benzyl-aminopurine (BAP) in 100 mm Petri dishes. Seedlings without BAP are more elongated and roots develop, especially secondary and lateral root formation. BAP strengthens the seedling by forming a shorter and stockier seedling.

Seven-day-old seedlings grown in the light (>100 µEinstein/m$^2$s) at 25° C. were used for explant material for the three-explant types. At this time, the seed coat was split, and the epicotyl with the unifoliate leaves have grown to, at minimum, the length of the cotyledons. The epicotyl should be at least 0.5 cm to avoid the cotyledonary-node tissue (since soycultivars and seed lots may vary in the developmental time a description of the germination stage is more accurate than a specific germination time).

For inoculation of entire seedlings, see Method A (example 3.3.1 and 3.3.2) or leaf explants, see Method B (example 3.3.3).

For method C (see example 3.3.4), the hypocotyl and one and a half or part of both cotyledons were removed from each seedling. The seedlings were then placed on propagation media for 2 to 4 weeks. The seedlings produce several branched shoots to obtain explants from. The majority of the explants originated from the plantlet growing from the apical bud. These explants were preferably used as target tissue.

3.2—Growth and Preparation of *Agrobacterium* Culture

*Agrobacterium* cultures were prepared by streaking *Agrobacterium* (e.g., *A. tumefaciens* or *A. rhizogenes*) carrying the desired binary vector (e.g. H. Klee. R. Horsch and S. Rogers 1987 *Agrobacterium*-Mediated Plant Transformation and its further Applications to Plant Biology; Annual Review of Plant Physiology Vol. 38: 467-486) onto solid YEP growth medium (YEP media: 10 g yeast extract, 10 g Bacto Peptone, 5 g NaCl, Adjust pH to 7.0, and bring final volume to 1 liter with H2O, for YEP agar plates add 20 g Agar, autoclave) and incubating at 25° C. until colonies appeared (about 2 days). Depending on the selectable marker genes present on the Ti or Ri plasmid, the binary vector, and the bacterial chromosomes, different selection compounds were be used for *A. tumefaciens* and *A. rhizogenes* selection in the YEP solid and liquid media. Various *Agrobacterium* strains can be used for the transformation method.

After approximately two days, a single colony (with a sterile toothpick) was picked and 50 ml of liquid YEP was inoculated with antibiotics and shaken at 175 rpm (25° C.) until an OD$_{600}$ between 0.8-1.0 is reached (approximately 2 d). Working glycerol stocks (15%) for transformation are prepared and one-ml of *Agrobacterium* stock aliquoted into 1.5 ml Eppendorf tubes then stored at −80° C.

The day before explant inoculation, 200 ml of YEP were inoculated with 5 µl to 3 ml of working *Agrobacterium* stock in a 500 ml Erlenmeyer flask. The flask was shaken overnight at 25° C. until the $OD_{600}$ was between 0.8 and 1.0. Before preparing the soy explants, the *Agrobacteria* were pelleted by centrifugation for 10 min at 5,500×g at 20° C. The pellet was resuspended in liquid CCM to the desired density ($OD_{600}$ 0.5-0.8) and placed at room temperature at least 30 min before use.

3.3—Explant Preparation and Co-Cultivation (Inoculation)

3.3.1 Method A: Explant Preparation on the Day of Transformation.

Seedlings at this time had elongated epicotyls from at least 0.5 cm but generally between 0.5 and 2 cm. Elongated epicotyls up to 4 cm in length had been successfully employed. Explants were then prepared with: i) with or without some roots, ii) with a partial, one or both cotyledons, all preformed leaves were removed including apical meristem, and the node located at the first set of leaves was injured with several cuts using a sharp scalpel.

This cutting at the node not only induced *Agrobacterium* infection but also distributed the axillary meristem cells and damaged pre-formed shoots. After wounding and preparation, the explants were set aside in a Petri dish and subsequently co-cultivated with the liquid CCM/*Agrobacterium* mixture for 30 minutes. The explants were then removed from the liquid medium and plated on top of a sterile filter paper on 15×100 mm Petri plates with solid co-cultivation medium. The wounded target tissues were placed such that they are in direct contact with the medium.

3.3.2 Modified Method A: Epicotyl Explant Preparation

Soyepicotyl segments prepared from 4 to 8 d old seedlings were used as explants for regeneration and transformation. Seeds of soya cv. L00106CN, 93-41131 and Jack were germinated in ⅒ MS salts or a similar composition medium with or without cytokinins for 4 to 8 d. Epicotyl explants were prepared by removing the cotyledonary node and stem node from the stem section. The epicotyl was cut into 2 to 5 segments. Especially preferred are segments attached to the primary or higher node comprising axillary meristematic tissue.

The explants were used for *Agrobacterium* infection. *Agrobacterium* AGL1 harboring a plasmid with the gene of interest (GOI) and the AHAS, bar or dsdA selectable marker gene was cultured in LB medium with appropriate antibiotics overnight, harvested and resuspended in a inoculation medium with acetosyringone. Freshly prepared epicotyl segments were soaked in the *Agrobacterium* suspension for 30 to 60 min and then the explants were blotted dry on sterile filter papers. The inoculated explants were then cultured on a co-culture medium with L-cysteine and TTD and other chemicals such as acetosyringone for increasing T-DNA delivery for 2 to 4 d. The infected epicotyl explants were then placed on a shoot induction medium with selection agents such as imazapyr (for AHAS gene), glufosinate (for bar gene), or D-serine (for dsdA gene). The regenerated shoots were sub-cultured on elongation medium with the selective agent.

For regeneration of transgenic plants the segments were then cultured on a medium with cytokinins such as BAP, TDZ and/or Kinetin for shoot induction. After 4 to 8 weeks, the cultured tissues were transferred to a medium with lower concentration of cytokinin for shoot elongation. Elongated shoots were transferred to a medium with auxin for rooting and plant development. Multiple shoots were regenerated.

Many stable transformed sectors showing strong cDNA expression were recovered. Soy-plants were regenerated from epicotyl explants. Efficient T-DNA delivery and stable transformed sectors were demonstrated.

3.3.3 Method B: Leaf Explants

For the preparation of the leaf explant the cotyledon was removed from the hypocotyl. The cotyledons were separated from one another and the epicotyl is removed. The primary leaves, which consist of the lamina, the petiole, and the stipules, were removed from the epicotyl by carefully cutting at the base of the stipules such that the axillary meristems were included on the explant. To wound the explant as well as to stimulate de novo shoot formation, any preformed shoots were removed and the area between the stipules was cut with a sharp scalpel 3 to 5 times.

The explants are either completely immersed or the wounded petiole end dipped into the *Agrobacterium* suspension immediately after explant preparation. After inoculation, the explants are blotted onto sterile filter paper to remove excess *Agrobacterium* culture and place explants with the wounded side in contact with a round 7 cm Whatman paper overlaying the solid CCM medium (see above). This filter paper prevents *A. tumefaciens* overgrowth on the soy-explants. Wrap five plates with Parafilm™ "M" (American National Can, Chicago, Ill., USA) and incubate for three to five days in the dark or light at 25° C.

3.3.4 Method C: Propagated Axillary Meristem

For the preparation of the propagated axillary meristem explant propagated 3-4 week-old plantlets were used. Axillary meristem explants can be pre-pared from the first to the fourth node. An average of three to four explants could be obtained from each seedling. The explants were prepared from plantlets by cutting 0.5 to 1.0 cm below the axillary node on the internode and removing the petiole and leaf from the explant. The tip where the axillary meristems lie was cut with a scalpel to induce de novo shoot growth and allow access of target cells to the *Agrobacterium*. Therefore, a 0.5 cm explant included the stem and a bud.

Once cut, the explants were immediately placed in the *Agrobacterium* suspension for 20 to 30 minutes. After inoculation, the explants were blotted onto sterile filter paper to remove excess *Agrobacterium* culture then placed almost completely immersed in solid CCM or on top of a round 7 cm filter paper overlaying the solid CCM, depending on the *Agrobacterium* strain. This filter paper prevents *Agrobacterium* overgrowth on the soy-explants. Plates were wrapped with Parafilm™ "M" (American National Can, Chicago, Ill., USA) and incubated for two to three days in the dark at 25° C.

3.4—Shoot Induction

After 3 to 5 days co-cultivation in the dark at 25° C., the explants were rinsed in liquid SIM medium (to remove excess *Agrobacterium*) (SIM, see Olhoft et al 2007 A novel *Agrobacterium rhizogenes*-mediated transformation method of soy using primary-node explants from seedlings In Vitro Cell. Dev. Biol. Plant (2007) 43:536-549; to remove excess *Agrobacterium*) or Modwash medium (1×B5 major salts, 1×B5 minor salts, 1×MSIII iron, 3% Sucrose, 1×B5 vitamins, 30 mM MES, 350 mg/L Timentin™ pH 5.6, WO 2005/121345) and blotted dry on sterile filter paper (to prevent damage especially on the lamina) before placing on the solid SIM medium. The approximately 5 explants (Method A) or 10 to 20 (Methods B and C) explants were placed such that the target tissue was in direct contact with the medium. During the first 2 weeks, the explants could be cultured with or without selective medium. Preferably, explants were transferred onto SIM without selection for one week.

For leaf explants (Method B), the explant should be placed into the medium such that it is perpendicular to the surface of the medium with the petiole imbedded into the medium and the lamina out of the medium.

For propagated axillary meristem (Method C), the explant was placed into the medium such that it was parallel to the surface of the medium (basipetal) with the explant partially embedded into the medium.

Wrap plates with Scotch 394 venting tape (3M, St. Paul, Minn., USA) were placed in a growth chamber for two weeks with a temperature averaging 25° C. under 18 h light/6 h dark cycle at 70-100 µE/m²s. The explants remained on the SIM medium with or without selection until de novo shoot growth occurred at the target area (e.g., axillary meristems at the first node above the epicotyl). Transfers to fresh medium can occur during this time. Explants were transferred from the SIM with or without selection to SIM with selection after about one week. At this time, there was considerable de novo shoot development at the base of the petiole of the leaf explants in a variety of SIM (Method B), at the primary node for seedling explants (Method A), and at the axillary nodes of propagated explants (Method C).

Preferably, all shoots formed before transformation were removed up to 2 weeks after co-cultivation to stimulate new growth from the meristems. This helped to reduce chimerism in the primary transformant and increase amplification of transgenic meristematic cells. During this time the explant may or may not be cut into smaller pieces (i.e. detaching the node from the explant by cutting the epicotyl).

3.5—Shoot Elongation

After 2 to 4 weeks (or until a mass of shoots was formed) on SIM medium (preferably with selection), the explants were transferred to SEM medium (shoot elongation medium, see Olhoft et al 2007 A novel *Agrobacterium rhizogenes*-mediated transformation method of soy using primary-node explants from seedlings. In Vitro Cell. Dev. Biol. Plant (2007) 43:536-549) that stimulates shoot elongation of the shoot primordia. This medium may or may not contain a selection compound.

After every 2 to 3 weeks, the explants were transferred to fresh SEM medium (preferably containing selection) after carefully removing dead tissue. The explants should hold together and not fragment into pieces and retain somewhat healthy. The explants were continued to be transferred until the explant dies or shoots elongate. Elongated shoots >3 cm were removed and placed into RM medium for about 1 week (Method A and B), or about 2 to 4 weeks depending on the cultivar (Method C) at which time roots began to form. In the case of explants with roots, they were transferred directly into soil. Rooted shoots were transferred to soil and hardened in a growth chamber for 2 to 3 weeks before transferring to the greenhouse. Regenerated plants obtained using this method were fertile and produced on average 500 seeds per plant.

After 5 days of co-cultivation with *Agrobacterium tumefaciens* transient expression of the gene of interest (GOI) was widespread on the seedling axillary meristem explants especially in the regions wounding during explant preparation (Method A). Explants were placed into shoot induction medium without selection to see how the primary-node responds to shoot induction and regeneration. Thus far, greater than 70% of the explants were formed new shoots at this region. Expression of the GOI was stable after 14 days on SIM, implying integration of the T-DNA into the soy genome. In addition, preliminary experiments resulted in the formation of cDNA expressing shoots forming after 3 weeks on SIM.

For Method C, the average regeneration time of a soy plantlet using the propagated axillary meristem protocol was 14 weeks from explant inoculation. Therefore, this method has a quick regeneration time that leads to fertile, healthy soy plants.

Example 4: Pathogen Assay 4.1. Growth of Plants

10 $T_1$ plants per event were potted and grown for 3-4 weeks in the phytochamber (16 h-day-und 8 h-night-Rhythm at a temperature of 16 and 22° C. and a humidity of 75%) till the first 2 trifoliate leaves were fully expanded.

4.2 Inoculation

The plants were inoculated with spores of *P. pachyrhizi*.

In order to obtain appropriate spore material for the inoculation, soybean leaves which had been infected with rust 15-20 days ago, were taken 2-3 days before the inoculation and transferred to agar plates (1% agar in H2O). The leaves were placed with their upper side onto the agar, which allowed the fungus to grow through the tissue and to produce very young spores. For the inoculation solution, the spores were knocked off the leaves and were added to a Tween-H2O solution. The counting of spores was performed under a light microscope by means of a Thoma counting chamber. For the inoculation of the plants, the spore suspension was added into a compressed-air operated spray flask and applied uniformly onto the plants or the leaves until the leaf surface is well moisturized. For macroscopic assays we used a spore density of $1-5 \times 10^5$ spores/ml. For the microscopy, a density of $>5 \times 10^5$ spores/ml is used. The inoculated plants were placed for 24 hours in a greenhouse chamber with an average of 22° C. and >90% of air humidity. The following cultivation was performed in a chamber with an average of 25° C. and 70% of air humidity.

Example 5: Microscopical Screening

For the evaluation of the pathogen development, the inoculated leaves of plants were stained with aniline blue 48 hours after infection.

The aniline blue staining serves for the detection of fluorescent substances. During the defense reactions in host interactions and non-host interactions, substances such as phenols, callose or lignin accumulated or were produced and were incorporated at the cell wall either locally in papillae or in the whole cell (hypersensitive reaction, HR). Complexes were formed in association with aniline blue, which lead e.g. in the case of callose to yellow fluorescence. The leaf material was transferred to falcon tubes or dishes containing destaining solution II (ethanol/acetic acid 6/1) and was incubated in a water bath at 90° C. for 10-15 minutes. The destaining solution II was removed immediately thereafter, and the leaves were washed 2× with water. For the staining, the leaves were incubated for 1.5-2 hours in staining solution II (0.05% aniline blue=methyl blue, 0.067 M di-potassium hydrogen phosphate) and analyzed by microscopy immediately thereafter.

The different interaction types were evaluated (counted) by microscopy. An Olympus UV microscope BX61 (incident light) and a UV Longpath filter (excitation: 375/15, Beam splitter: 405 LP) are used. After aniline blue staining, the spores appeared blue under UV light. The papillae could be recognized beneath the fungal appressorium by a green/yellow staining. The hypersensitive reaction (HR) was characterized by a whole cell fluorescence.

Example 6: Evaluating the Susceptibility to Soybean Rust

The progression of the soybean rust disease was scored by the estimation of the diseased area (area which was covered by sporulating uredinia) on the backside (abaxial side) of the leaf. Additionally the yellowing of the leaf was taken into account (for scheme see FIG. 1).

At all 36 $T_1$ soybean plants (5 independent events, 6-9 plants per event) expressing EIN2 fragment protein were inoculated with spores of Phakopsora pachyrhizi. The macroscopic disease symptoms of soy against P. pachyrhizi of the inoculated soybean plants were scored 14 days after inoculation.

The average of the percentage of the leaf area showing fungal colonies or strong yellowing/browning on all leaves was considered as diseased leaf area. At all 36 soybean $T_1$ plants expressing EIN2 fragment (expression checked by RT-PCR) were evaluated in parallel to non-transgenic control plants. Non-transgenic soy plants grown in parallel to the transgenic plants were used as control. The average of the diseased leaf area is shown in FIG. 9 for plants expressing recombinant EIN2 fragment compared with wildtype plants. Overexpression of the EIN2 fragment reduces the diseased leaf area in comparison to non-transgenic control plants by 38.8% in average over all events and plants generated. This data clearly indicates that the in-planta expression of the EIN2 fragment expression vector construct (see FIG. 2) lead to a lower disease scoring of transgenic plants compared to non-transgenic controls. So, the expression of EIN2 fragment protein (as shown in SEQ ID NO: 3) in soybean significantly ($p<0.01$) increases the resistance of soy against soybean rust.

Example 7: Construction of Maize Expression Cassettes

The nucleic acid sequence encoding EIN2 c-terminus (as shown in SEQ ID NO:2) was synthesized in a way that enables further cloning. The expression cassettes were then assembled in a vector by cloning the synthesized DNA encoding the EIN2 c-terminus gene from *Arabidopsis thaliana* downstream of a SCBV254 promoter (Sugarcane Baciliform Virus promoter fragment ScBV-254) and upstream of a t-nos terminator (3'UTR of Nopaline Synthase from *Agrobacterium tumefaciens*). An intron from the rice Met1 gene was also cloned in between of the promoter and the EIN2 c-terminus sequence.

Plant transformation binary vectors such as pBi-nAR were used (Hofgen & Willmitzer 1990, Plant Sci. 66:221-230). Further examples for plant binary vectors are the pSUN300 or pSUN2-GW vectors and the pPZP vectors (Hajdukiewicz et al., Plant Molecular Biology 25: 989-994, 1994). As target a binary plant transformation vector was used which is composed of: (1) a Kanamycin resistance cassette for bacterial selection (2) a pVS1 origin for replication in *Agrobacteria* (3) a ColE1 origin of replication for stable maintenance in *E. coli* and (4) between the right and left border an ZmAHAS gene as selectable marker under control of a ZmAHAS-promoter.

Construction of the binary vectors was performed by ligation of the expression cassette, as described above, into the binary vector. The recombinant vector containing the expression cassette was transformed into Top10 cells (Invitrogen) using standard conditions. Transformed cells were selected on LB agar containing 50 μg/ml kanamycin grown overnight at 37° C. Plasmid DNA was extracted using the QIAprep Spin Miniprep Kit (Qiagen) following manufacturer's instructions. Analysis of subsequent clones and restriction mapping was performed according to standard molecular biology techniques (Sambrook et al., 1989, "Molecular Cloning: A Laboratory Manual," 2nd Edition, Cold Spring Harbor Laboratory Press, Cold Spring Harbor, N.Y.).

Example 8: Maize Transformation

*Agrobacterium* cells harboring a plasmid containing the gene of interest and the mutated maize AHAS gene were grown in YP medium supplemented with appropriate antibiotics for 1-2 days. One loop of *Agrobacterium* cells was collected and suspended in 1.8 ml M-LS-002 medium (LS-inf). The cultures were incubated while shaking at 1,200 rpm for 5 min-3 hrs. Corn cobs were harvested at 8-11 days after pollination. The cobs were sterilized in 20% Clorox solution for 5 min, followed by spraying with 70% Ethanol and then thoroughly rinsed with sterile water. Immature embryos 0.8-2.0 mm in size were dissected into the tube containing *Agrobacterium* cells in LS-inf solution.

The constructs were transformed into immature embryos by a protocol modified from Japan Tobacco *Agrobacterium* mediated plant transformation method (U.S. Pat. Nos. 5,591,616; 5,731,179; 6,653,529; and U.S. Patent Application Publication No. 2009/0249514). Two types of plasmid vectors were used for transformation. One type had only one T-DNA border on each of left and right side of the border, and selectable marker gene and gene of interest were between the left and right T-DNA borders. The other type was so called "two T-DNA constructs" as described in Japan Tobacco U.S. Pat. No. 5,731,179. In the two DNA constructs, the selectable marker gene was located between one set of T-DNA borders and the gene of interest was included in between the second set of T-DNA borders. Either plasmid vector can be used. The plasmid vector was electroporated into *Agrobacterium*.

*Agrobacterium* infection of the embryos was carried out by inverting the tube several times. The mixture was poured onto a filter paper disk on the surface of a plate containing co-cultivation medium (M-LS-011). The liquid agro-solution was removed and the embryos were checked under a microscope and placed scutellum side up. Embryos were cultured in the dark at 22° C. for 2-4 days, and transferred to M-MS-101 medium without selection and incubated for four to seven days. Embryos were then transferred to M-LS-202 medium containing 0.75 μM imazethapyr and grown for three weeks at 27° C. to select for transformed callus cells.

Plant regeneration was initiated by transferring resistant calli to M-LS-504 medium supplemented with 0.75 μM imazethapyr and growing under light at 26° C. for two to three weeks. Regenerated shoots were then transferred to a rooting box with M-MS-618 medium (0.5 μM imazethapyr). Plantlets with roots were transferred to soil-less potting mixture and grown in a growth chamber for a week, then transplanted to larger pots and maintained in a greenhouse until maturity.

Transgenic maize plant production is also described, for example, in U.S. Pat. Nos. 5,591,616 and 6,653,529; U.S. Patent Application Publication No. 2009/0249514; and WO/2006136596, each of which are hereby incorporated by reference in their entirety. Transformation of maize may be made using *Agrobacterium* transformation, as described in U.S. Pat. Nos. 5,591,616; 5,731,179; U.S. Patent Application Publication No. 2002/0104132, and the like. Transformation of maize (*Zea mays* L.) can also be performed with a modification of the method described by Ishida et al. (Nature Biotech., 1996, 14:745-750). The inbred line A188 (University of Minnesota) or hybrids with A188 as a parent are good sources of donor material for transformation (Fromm et al., Biotech, 1990, 8:833), but other genotypes can be used successfully as well. Ears are harvested from corn plants at approximately 11 days after pollination (DAP) when the length of immature embryos is about 1 to 1.2 mm. Immature embryos are co-cultivated with *Agrobacterium tumefaciens* that carry "super binary" vectors and transgenic plants are recovered through organogenesis. The super binary vector system is described in WO 94/00977 and WO 95/06722. Vectors are constructed as described. Various selection marker genes are used including the maize gene encoding a mutated acetohydroxy acid synthase (AHAS) enzyme (U.S. Pat. No. 6,025,541). Similarly, various promoters are used to regulate the trait gene to provide constitutive, developmental, inducible, tissue or environmental regulation of gene transcription.

Excised embryos can be used and can be grown on callus induction medium, then maize regeneration medium, containing imidazolinone as a selection agent. The Petri dishes are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the imidazolinone herbicides and which are PCR positive for the transgenes.

Example 9: *Fusarium* and *Colletotrichum* Resistance Screening

Transgenic plants are grown in greenhouse or phytochamber under standard growing conditions in a controlled environment (20-25° C., 60-90% humidity). Shortly after plants enter the reproductive phase the transgenic plants are inoculated near the base of the stalk using a fungal suspension of spores (105 spores in PBS solution) of *Fusarium* ssp. or *Colletotrichum graminicola*. Plants are incubated for 2-4 weeks at 20-25° C. and 60-90% humidity.

For scoring the disease, stalks are split and the progression of the disease is scored by observation of the characteristic brown to black color of the fungus as it grows up the stalk. Disease ratings are conducted by assigning a visual score. Per experiment the diseased leaf area of more than 10 transgenic plants (and wild-type plants as control) is scored. For analysis the average of the diseased leaf area of the non-transgenic mother plant is set to 100% to calculate the relative diseased leaf area of the transgenic lines The expression of the EIN2 c-terminus gene will lead to enhanced resistance of corn against *Fusarium* ssp. And *Colletotrichum graminicola*.

The invention claimed is:

1. A method for increasing resistance against *Phakopsora* in a soybean plant, a soybean plant part, or a soybean plant cell, said method comprising increasing the expression and/or activity of an Ethylene-Insensitive 2 (EIN2) protein in the soybean plant, soybean plant part, or soybean plant cell in comparison to a wild type soybean plant, wild type soybean plant part or wild type soybean plant cell, wherein the EIN2 protein is encoded by an exogenous nucleic acid encoding a protein having an amino acid sequence with at least 85% identity to SEQ ID NO: 3, wherein the EIN2 protein confers increased resistance against a pathogen of the genus *Phakopsora* to the soybean plant, soybean plant part, or soybean plant cell in comparison to a wild type soybean plant, wild type soybean plant part or wild type soybean plant cell.

2. The method of claim 1, comprising
(a) stably transforming a soybean plant cell with an expression cassette comprising an exogenous nucleic acid encoding an EIN2 protein having an amino acid sequence with at least 85% identity to SEQ ID NO: 3 in functional linkage with a promoter; and
(b) regenerating the plant from the plant cell.

3. A recombinant vector construct comprising:
(a) a nucleic acid encoding an EIN2 protein having an amino acid sequence with at least 85% identity to SEQ ID NO: 3 operably linked with
(b) a heterologous rust-inducible promoter and
(c) a transcription termination sequence,
wherein expression of said nucleic acid in a transgenic soybean plant, transgenic soybean plant part, or transgenic soybean plant cell confers increased resistance against a pathogen of the genus *Phakopsora* thereto in comparison to a wild type soybean plant, wild type soybean plant part, or wild type soybean plant cell.

4. The method of claim 2, wherein the promoter is a constitutive promoter, pathogen-inducible promoter, a mesophyll-specific promoter or an epidermis specific-promoter.

5. A transgenic soybean plant, transgenic soybean plant part, or transgenic soybean plant cell comprising an exogenous nucleic acid encoding an EIN2 protein comprising an amino acid sequence with at least 85% identity with SEQ ID NO: 3 operably linked to a rust-inducible promoter, wherein expression of said exogenous nucleic acid in the transgenic soybean plant, transgenic soybean plant part, or transgenic soybean plant cell confers increased resistance against a pathogen of the genus *Phakopsora* thereto in comparison to a wild type soybean plant, wild type soybean plant part, or wild type soybean plant cell.

6. A method for the production of a transgenic soybean plant, transgenic soybean plant part, or transgenic soybean plant cell having increased resistance against *Phakopsora*, comprising:

(a) introducing the recombinant vector construct of claim 5 into a soybean plant, a soybean plant part, or a soybean plant cell; and
(b) generating a transgenic soybean plant, transgenic soybean plant part, or transgenic soybean plant cell from the plant, plant part or plant cell.

7. The method of claim 6, further comprising the step of harvesting the seeds of the transgenic soybean plant and planting the seeds and growing the seeds to plants, wherein the grown plants comprise the exogenous nucleic acid encoding a protein having an amino acid sequence with at least 85% identity with SEQ ID NO: 3.

8. A harvestable part of the transgenic soybean plant of claim 5, wherein the part comprises the exogenous nucleic acid encoding a protein having an amino acid sequence with at least 85% identity with SEQ ID NO: 3.

9. A product derived from the transgenic soybean plant of claim 5, wherein the product comprises the exogenous nucleic acid encoding a protein having an amino acid sequence with at least 85% identity with SEQ ID NO: 3.

10. A method for the production of a product comprising
a) growing the transgenic soybean plant of claim 5; and
b) producing said product from or by the plant or a part of the plant.

11. The method of claim 10 comprising
a) growing the plant and removing the harvestable parts from the plant; and
b) producing said product from or by the harvestable parts of the plant.

12. The method of claim 10, wherein the product is meal or oil.

13. The method of claim 1, wherein the resistance against *Phakopsora* is resistance against *Phakopsora meibomiae*, *Phakopsora pachyrhizi*, or a combination thereof.

14. The method of claim 1, wherein the plant is selected from the group consisting of beans, soya, pea, clover, kudzu, lucerne, lentils, lupins, vetches, groundnut, rice, wheat, barley, *arabidopsis*, lentil, banana, canola, cotton, potatoe, corn, sugar cane, alfalfa, and sugar beet.

15. A method for breeding a *Phakopsora* resistant soybean plant comprising
(a) crossing the transgenic soybean plant of claim 5 with a second soybean plant;
(b) obtaining seed from the cross of step (a);
(c) planting said seeds and growing the seeds to plants; and
(d) selecting from the plants produced in step (c) plants expressing the EIN2 protein.

16. The method of claim 1, wherein the EIN2 protein encoded by the exogenous nucleic acid has an amino acid sequence with at least 90% identity to SEQ ID NO:3.

17. The method of claim 1, wherein the EIN2 protein encoded by the exogenous nucleic acid has an amino acid sequence with at least 95% identity to SEQ ID NO:3.

18. The recombinant vector construct of claim 3, wherein the nucleic acid encodes an EIN2 protein having an amino acid sequence with at least 90% identity to SEQ ID NO:3.

19. The recombinant vector construct of claim 3, wherein the nucleic acid encodes an EIN2 protein having an amino acid sequence with at least 95% identity to SEQ ID NO:3.

20. The transgenic plant, transgenic plant part, or transgenic plant cell of claim 5, wherein the EIN2 protein encoded by the exogenous nucleic acid has an amino acid sequence with at least 90% identity to SEQ ID NO: 3.

21. The transgenic plant, transgenic plant part, or transgenic plant cell of claim 5, wherein the EIN2 protein encoded by the exogenous nucleic acid has an amino acid sequence with at least 95% identity to SEQ ID NO: 3.

22. A method for preventing, reducing, or delaying *Phakopsora* infection in a transgenic soybean plant, a transgenic soybean plant part, or a transgenic soybean plant cell, the method comprising:

providing a transgenic soybean plant, a transgenic soybean plant part, or a transgenic soybean plant cell with an exogenous nucleic acid encoding an EIN2 protein comprising an amino acid sequence with at least 85% identity to SEQ ID NO: 3, wherein the EIN2 protein confers increased resistance against *Phakopsora* thereto in comparison to a wild type soybean plant, wild type soybean plant part, or wild type soybean plant cell, and growing the transgenic soybean plant, transgenic soybean plant part, or transgenic soybean plant cell in the presence of a fungal pathogen of the genus *Phakopsora*, wherein *Phakopsora* infection is prevented, reduced, or delayed in the transgenic soybean plant, transgenic soybean plant part, or transgenic soybean plant cell as compared to a wild type soybean plant, wild type soybean plant part, or wild type soybean plant cell.

23. The method of claim 22, wherein the EIN2 protein encoded by the exogenous nucleic acid has an amino acid sequence with at least 90% identity to SEQ ID NO:3.

24. The method of claim 22, wherein the EIN2 protein encoded by the exogenous nucleic acid has an amino acid sequence with at least 95% identity to SEQ ID NO:3.

* * * * *